United States Patent
Johnston

(10) Patent No.: US 11,168,121 B2
(45) Date of Patent: *Nov. 9, 2021

(54) IDENTIFICATION AND USE OF NOVOPEPTIDES FOR THE TREATMENT OF CANCER

(71) Applicant: Calviri, Inc., Tempe, AZ (US)

(72) Inventor: Stephen Albert Johnston, Tempe, AZ (US)

(73) Assignee: CALVIRI, INC., Tempe, AZ (US)

( * ) Notice: Subject to any disclaimer, the term of this patent is extended or adjusted under 35 U.S.C. 154(b) by 104 days.

This patent is subject to a terminal disclaimer.

(21) Appl. No.: 15/669,666

(22) Filed: Aug. 4, 2017

(65) Prior Publication Data

US 2017/0334963 A1    Nov. 23, 2017

Related U.S. Application Data

(60) Continuation of application No. 14/451,374, filed on Aug. 4, 2014, now Pat. No. 9,732,131, which is a continuation-in-part of application No. 13/052,490, filed on Mar. 21, 2011, now Pat. No. 8,796,414, which is a division of application No. 12/280,389, filed as application No. PCT/US2007/062920 on Feb. 27, 2007, now abandoned.

(60) Provisional application No. 60/777,534, filed on Feb. 27, 2006.

(51) Int. Cl.
| | |
|---|---|
| G01N 33/50 | (2006.01) |
| A61K 39/00 | (2006.01) |
| A61K 48/00 | (2006.01) |
| C07K 14/47 | (2006.01) |
| C12Q 1/6886 | (2018.01) |

(52) U.S. Cl.
CPC ...... *C07K 14/4748* (2013.01); *A61K 39/0011* (2013.01); *C12Q 1/6886* (2013.01); *G01N 33/5011* (2013.01); *G01N 33/5047* (2013.01); *A61K 48/00* (2013.01); *A61K 2039/53* (2013.01); *A61K 2039/55522* (2013.01); *C12Q 2600/118* (2013.01); *C12Q 2600/136* (2013.01)

(58) Field of Classification Search
CPC .................................................. C12Q 1/6886
See application file for complete search history.

(56) References Cited

U.S. PATENT DOCUMENTS

| | | |
|---|---|---|
| 5,601,989 A | 2/1997 | Cheever et al. |
| 5,840,839 A | 11/1998 | Wang et al. |
| 5,961,978 A | 10/1999 | Gaudernack et al. |
| 6,759,046 B1 | 7/2004 | Gaudernack et al. |
| 6,861,057 B2 | 3/2005 | Gaudernack et al. |
| 7,078,416 B2 | 7/2006 | Gaudernack et al. |
| 7,192,927 B2 | 3/2007 | Gaudernack et al. |
| 7,375,117 B2 | 5/2008 | Gaudernack et al. |
| 7,794,723 B2 | 9/2010 | Gaudernack et al. |
| 7,863,244 B2 | 1/2011 | Gaudernack et al. |
| 8,053,552 B2 | 11/2011 | Von Knebel-Doeberitz et al. |
| 8,193,326 B2 | 6/2012 | Gaudernack et al. |
| 8,614,177 B2 | 12/2013 | Gaudernack et al. |
| 8,796,414 B2 | 8/2014 | Johnston et al. |
| 8,821,864 B2 | 9/2014 | Von Knebel-Doeberitz et al. |
| 9,115,402 B2 | 8/2015 | Hacohen et al. |
| 9,205,140 B2 | 12/2015 | Kloor et al. |
| 9,254,311 B2 | 2/2016 | Bancel et al. |
| 9,265,816 B2 | 2/2016 | Scheinberg et al. |
| 9,284,349 B2 | 3/2016 | Tsunoda et al. |
| 9,340,830 B2 | 5/2016 | Downing et al. |
| 2004/0265803 A1 | 12/2004 | Doeberitz |
| 2005/0239070 A1 | 10/2005 | Von Knebel-Doeberitz et al. |
| 2005/0244421 A1 | 11/2005 | Strittmatter et al. |
| 2006/0194731 A1 | 8/2006 | Gaudernack et al. |
| 2008/0207483 A1 | 8/2008 | Volinia |
| 2009/0186042 A1 | 7/2009 | Johnston et al. |
| 2010/0111993 A1 | 5/2010 | Tuereci et al. |
| 2011/0105721 A1 | 5/2011 | Gaudernack et al. |
| 2012/0269858 A1 | 10/2012 | Gaudernack et al. |
| 2013/0072660 A1 | 3/2013 | Johnston et al. |
| 2013/0129760 A1 | 5/2013 | Gaudernack et al. |
| 2013/0236490 A1 | 9/2013 | Kalyanasundaram |
| 2013/0273002 A1 | 10/2013 | Tuohy |
| 2014/0087963 A1 | 3/2014 | Johnston et al. |
| 2014/0113286 A1 | 4/2014 | Chan et al. |
| 2014/0170178 A1 | 6/2014 | Kloor et al. |
| 2016/0051654 A1 | 2/2016 | Singh et al. |
| 2016/0051657 A1 | 2/2016 | Varga et al. |

(Continued)

FOREIGN PATENT DOCUMENTS

| | | |
|---|---|---|
| AU | 2007220042 A1 | 9/2007 |
| CA | 2486738 A1 | 12/2003 |
| CA | 2651796 A1 | 9/2007 |

(Continued)

OTHER PUBLICATIONS

Lennertz et al, PNAS, 102:16013-16018, 2005.*
Rammensee et al, Immunol Rev, 188:164-176, 2002.*
Sette et al, J Immunol, 153:5586-5592, 1994.*
Cancer Facts and Figures 2016 Special Section: Cancer in Asian Americans, Native Hawaiians, and Pacific Islanders. American Cancer Society pp. 1-72.
Chan, TA et al. 5-day dosing schedule of temozolomide in relapsed sensitive or refractory small cell lung cancer (SCLC) and methylguanine-DNA methyltransferase (MGMT) analysis in a phase II trial. Journal of Clinical Oncology, 2012 ASCO Annual Meeting Abstracts. 30(15 Suppl) (May 20, 2012) Abstract No. 7052.

(Continued)

*Primary Examiner* — Mark Halvorson
(74) *Attorney, Agent, or Firm* — Knobbe, Martens, Olson & Bear LLP

(57) ABSTRACT

Compositions, methods, systems, apparatus and/or articles of manufacture are disclosed for reducing the susceptibility of a population and/or members thereof to cancer, which may include anti-cancer vaccines, components thereof which may include novopeptides, and methods relating thereto.

26 Claims, 15 Drawing Sheets

Specification includes a Sequence Listing.

(56) References Cited

U.S. PATENT DOCUMENTS

2016/0069895 A1    3/2016    Delamarre et al.

FOREIGN PATENT DOCUMENTS

| EP | 1354895 A1 | 10/2003 |
|---|---|---|
| EP | 1369126 A1 | 12/2003 |
| EP | 1994181 A2 | 11/2008 |
| JP | 2009532664 A | 9/2009 |
| WO | WO-9532731 A2 | 12/1995 |
| WO | WO-9958552 A2 | 11/1999 |
| WO | WO-02051994 A2 | 7/2002 |
| WO | WO-03084467 A2 | 10/2003 |
| WO | WO-2004111075 A2 | 12/2004 |
| WO | WO-2005076009 A2 | 8/2005 |
| WO | WO-2005076099 A1 | 8/2005 |
| WO | WO-2007101227 A2 | 9/2007 |
| WO | WO-2010037395 A2 | 4/2010 |
| WO | WO-2015103037 A2 | 7/2015 |
| WO | WO-2015171747 A1 | 11/2015 |

OTHER PUBLICATIONS

Chan, TA et al. Phase II Trial of Temozolomide in Patients with Relapsed Sensitive or Refractory Small Cell Lung Cancer, with Assessment of Methyl-guanine-DNA Methyltransferase as a Potential Biomarker. Clinical Cancer Research, 18(4):1138-1145 (Feb. 15, 2012).
Chen, W. et al. Modification of Cysteine Residues In Vitro and In Vivo Affects the Immunogenicity and Antigenicity of Major Histocompatibility Complex Class I restricted Viral Determinants. The Journal of Experimental Medicine, 189(11):1757-1764 (Jun. 7, 1999).
Combination Vaccines and Multiple Vaccinations—Vaccine Knowledge Project University of Oxford.(http://vk.ovg.ox.ac.uk/combination-vaccines-and-multiple-vaccinations) Website Accessed Oct. 4, 2013.
Englehard, VH, Structure of peptides associated with class I and class II MHC molecules. Annu Rev Immunol. 12:181-207 (1994).
European Application No. 07757589 Supplementary Search Report dated Apr. 20, 2010.
Hellmann, M. et al. Genomic profile, smoking, and response to anti-PD-1 therapy in non-small cell lung carcinoma, Molecular & Cellular Oncology, 3(1):e1048929 (3 pages) (2016).
International Application No. PCT/US2007/062920 International Search Report and Written Opinion dated May 16, 2008.
Kirovski, D. et al. Combinatorics of The Vaccine Design Problem: Definition and An Algorithm. Technical Report MSR-TR-2007-148. Microsoft Research (http://research.microsoft.com) (Nov. 2007).
Kloor, M. et al. The Imune Biology of Microsatellite-Unstable Cancer. CellPress Trends in Cancer 2(3):121-133 (Mar. 2016).
Korber, B. et al. Immunoinformatics Comes of Age. PLoS Computation Biology, 2(6):e71(9pages) (Jun. 2006).
Lee, HoJoon. Identification of Neo-antigens for a Cancer Vaccine by Transcriptome Analysis. A Dissertation Presented in Partial Fulfillment of the Requirements for the Degree Doctor of Philosophy, Arizona State University. p. 1-168 (May 2012).
Lin, Hong Huang et al. Evaluation of MHC class I peptide binding prediction servers: Application for vaccine research. BMC Immunology 9(8):1-13 (Mar. 16, 2008).
Linnebacher, M. et al. Frameshift Peptide-Derived T-Cell Epitopes: A Source of Novel Tumor-Specific Antigens, International Journal of Cancer, 93; 6-11 (2001).
Rammenesee, H.G. et al. Peptides naturally presented by MHC class I molecules, Annu. Rev. Immunol. 11:213-244 (1993).
Rappuoli, Rino et al. New Approaches to Vaccine Design, from Vaccine Design Innovative Approaches and Novel Strategedies Eds: Rino Rappuoli and Fabio Bagnoli (2011) Caister Academic Press.
Schultze JL et al. From cancer genomics to cancer immunotherapy: toward second-generation tumor antigens. Trends Immunol. 22(9):516-23 (Sep. 1, 2001).
Shen, Luhui. Investigation of Tumor Frame Shift Antigens for Prophylactic Cancer Vaccine, Cancer Detection and Tumorigenicity. A Thesis Presented in Partial Fulfillment of the Requirements for the Degree of Doctor of Philosophy. Arizona State University. pp. 1-256 (Dec. 2012).
Snyder, Alexandra et al. Genetics and Immunology: reinvigorated, OncoImmunology, 4(10);e1029705 (2 pages) Oct. 2015.
U.S. Appl. No. 14/451,374 Final Office Action dated Dec. 27, 2016.
U.S. Appl. No. 10/509,930 File History.
U.S. Appl. No. 11/333,076 File History.
U.S. Appl. No. 13/578,969 File History.
Weinschenk, Toni et al. Integrated Functional Genomics Approach for the Design of Patient-Individual Antitumor Vaccines, Cancer Research 62(20):5818-5827 (2002).
Woerner, SM et al. Systematic Identification of Genes with Coding Microsatellites Mutated in DNA Mismatch Repair-Deficient Cancer Cells, International Journal of Cancer, 93(1); 12-19 (2001).
Berzofsky, J., et al. Progress on new vaccine strategies for the immunotherapy and prevention of cancer. J. Clin. Invest. 113(11):1515-1525 (Jun. 2004).
Gite, S. et al. A high-throughput nonisotopic protein truncation test. Nature Biotechnology, 21(2):194-197 (2003) [Abstract Only].
Kerr, C. Huntington's disease provides cancer clues. The Lancet, Oncology, 3(9):518 (2002).
Leaf, C. Why we're losing the war on cancer. Fortune, 149(6):76-82 (2004).
Lewis, J. Therapeutic cancer vaccines: using unique antigens. PNAS: 101 Supplement 2:14653-14656 (2004).
Saeterdal, I., et al. Frameshift-mutation-derived peptides as tumor-specific antigens in inherited and spontaneous colorectal cancer. PNAS 98(23):13255-13260 (2001).
Sorensen, S.A., et al. Significantly lower incidence of cancer among patients with Huntington disease. Cancer, 86(7):355-359 (1999) [Abstract Only].
Sykes, K.F. et al., Linear expression elements: a rapid, in vivo, method to screen for gene functions. Nat. Biotechnology, 17(4):355-359 (1999).
Wang, R. et al. Utilization of an alternative open reading frame of a normal gene in generation a novel human cancer antigen. The Journal of Experimental Medicine 183:1131-1140 (1996).
Bellone et al., Relevance of the Tumor Antigen in the Validation of Three Vaccination Strategies for Melanoma. J Immunol , 165 (5), 2651-6 (2000).
Disis et al., HER-2/neu Oncogenic Protein: Issues in Vaccine Development. Critical Reviews in Immunology. 18(1-2): 37-45 (1998).
Donnelly et al., Technical and Regulatory Hurdles for DNA Vaccines. Int J Parasitol , 33 (5-6), 457-67 (2003).
Emens et al., Toward a Breast Cancer Vaccine: Work in Progress. Oncology (Williston Park) , 17 (9), 1200-11; discussion 1214, 1217-8 (2003).
Fidler, Selection of Successive Tumour Lines for Metastasis. Nature New Biology 242:148-149 (1973).
Finn, Cancer Vaccines: Between the Idea and the Reality. Nat Rev Immunol, 3 (8), 630-41 (2003).
Finn, Premalignant Lesions as Targets for Cancer Vaccines. J Exp Med 198 (11): 1623-1626 (2003).
Jaffe, Vax Facts. The Scientist (2004).
Konig, Interactions Between MHC Molecules and Co-Receptors of the TCR. Curr Opin Immunol , 14 (1), 75-83 (2002).
Krieg, CpG Motifs: The Active Ingredient in Bacterial Extracts? Nat Med , 9 (7), 831-5 (2003).
Leyssen et al., Prospects for Antiviral Therapy. Adv Virus Res , 61, 511-53 (2003).
Lindahl, DNA Repair. DNA Surveillance Defect in Cancer Cells. Curr Biol , 4 (3), 249-51 (1994).
Minev, Melanoma Vaccines. Semin Oncol, 29 (5), 479-93 (2002).
Nestle et al., Vaccines and melanoma. Clinical and Experimental Dermatology 27: 597-601 (2002).
Pawlik et al., Malignant Melanoma: Current State of Primary and Adjuvant Treatment. Crit Rev Oncol Hematol , 45 (3), 245-64 (2003).

(56) References Cited

OTHER PUBLICATIONS

Renno et al., What's new in the field of cancer vaccines? Cellular and Molecular Life Sciences CMLS 60(7): 1296-1310 (2003).
Saeterdal et al., Frameshift-mutation-derived Peptides as Tumor-Specific Antigens in Inherited and Spontaneous Colorectal Cancer. Proc Natl Acad Sci U S A , 98 (23), 13255-60 (2001).
Sussman, Personalized Cancer Vaccine Promises Remission. Drug Discov Today , 8 (15), 657-8 (2003).
Sykes et al., Genetic Live Vaccines Mimic the Antigenicity but not Pathogenicity of Live Viruses. DNA and Cell Biology 18(7): 521-531 (1999).
Tang et al., Genetic Immunization Is a Simple Method for Eliciting an Immune Response. Nature , 356 (6365), 152-4 (1992).
Timares et al., Quantitative analysis of the immunopotency of genetically transfected dendritic cells. PNAS 95(22): 13147-13152 (1998).
Usmani, Genomic Instability and Metastatic Progression. Pathobiology 61: 109-116 (1993).
Wolchok et al., Phase I Trial of High Dose Paracetamol and Carmustine in Patients With Metastatic Melanoma. Melanoma Res, 13 (2), 189-96 (2003).

\* cited by examiner

1. PCR FS seq between Promoter and Terminator

2. Assembly by PCR

3. PCR Splicing by Overlap Exptension

B16 mouse tumor cells stained with anti-6-21 sera

Pre-immune sera on B16 mouse tumor cells

4T1 mouse breast tumor cells stained with anti-621

IDENTIFICATION AND USE OF NOVOPEPTIDES FOR THE TREATMENT OF CANCER

CROSS-REFERENCE

This application is a continuation of U.S. non-provisional application Ser. No. 14/451,374, filed Aug. 4, 2014, issued as U.S. Pat. No. 9,732,131 on Aug. 15, 2017, which is a continuation-in-part of U.S. non-provisional application Ser. No. 13/052,490, filed Mar. 21, 2011, issued as U.S. Pat. No. 8,796,414 on Aug. 5, 2014, which is a division of U.S. non-provisional application Ser. No. 12/280,389, filed Jan. 15, 2009, which is a U.S. national phase application of PCT international application No. PCT/US2007/062920 filed Feb. 27, 2007, which claims the benefit of U.S. Provisional Application No. 60/777,534, filed on Feb. 27, 2006; this application claims the benefit of each of the foregoing and each is incorporated herein by reference in its entirety.

SEQUENCE LISTING

The instant application contains a sequence listing which has been submitted in ASCII format via EFS-Web and is hereby incorporated by reference in its entirety. Said ASCII copy, created on Aug. 3, 2012, is named 51187-701_301.txt and is 237,551 bytes in size.

BACKGROUND

It is estimated that in 2004 more than 2.4 million new cancer cases will be diagnosed in the U.S. and more than 1 million are expected to be skin cancers. Of those individuals with skin cancer, ~96,000 will be diagnosed with melanoma (4% of newly diagnosed cancers), the most deadly form of skin cancer. Furthermore, the incidence of melanoma continues to increase faster than any other cancer. The stochastic nature of 90 to 95% of all cancers means that everyone is at risk of developing a cancer. In the United States, men have a 50% lifetime risk of developing cancer, while women have a 33% chance (ACS, 2004). With an annual mortality rate of ~563,700 per year, cancer is the second leading cause of death in the United States.

Vaccination against cancer has been proposed for treatment, and occasionally prevention, of cancer, and considerable research effort has been devoted to the exploration of a variety of cancer vaccination strategies. The goal of finding vaccine compositions and treatment methods that are capable of reliably and predictably overcoming tolerance and setting in motion an immune response against tumor cells without inducing autoimmunity has, until now, proved elusive. It is nevertheless clear that cancerous cells have characteristics that can be recognized by the immune system, as demonstrated by experiments in which mice vaccinated with various kinds of tumor cell preparations show protection from tumor challenge. Antigens that are expressed in or by tumor cells are referred to as "tumor associated antigens" ("TAA's"). A particular TAA may or may not also be expressed in non-cancerous cells; TAA's that are not expressed or rarely expressed in non-cancerous cells, or whose expression in non-cancerous cells is sufficiently reduced in comparison to that in cancerous cells that an immune response induced upon vaccination is reasonably specific to cancerous cells, are referred to as "tumor specific antigens" ("TSA's").

Over the past two decades, many labs have devised numerous techniques which aim to turn the patient's immune system against a pre-existing tumor (Berzofsky et al., 2004). These include the use of whole cells, peptides, genetically modified tumor cells, heat-shock proteins or apoptotic tumor cells to stimulate the host's immune system to respond to antigens that are characteristic of cancer cells. Arguably the most elegant approach to cancer vaccination is to use vaccine formulations composed of known and defined TAA's, since this will maximize specificity. Functionally, TAA's may be classed as self and non-self. Self TAA's are derived from non-mutated genes whose expression is limited to selected normal tissues or to overexpressed proteins. While most TAA's identified to date belong to this self class, there are two large potential problems associated with such antigens: autoimmunity and tolerance. Non-self TAA's are expressed exclusively or predominantly by cancer cells, and can be thought of as tumor-specific antigens (TSA's). TSA's can originate either exogenously (such as those derived from viral proteins in virally-associated tumors) or endogenously. Mutation-derived TSA's can arise from point mutations, translocations, and exon mis-splicing. Unlike self TAA's, TSA's pose greatly reduced risk of autoimmunity and tolerance.

SUMMARY

In general, disclosed herein are embodiments of methods, systems, apparatus, compositions, and/or articles of manufacture for reducing the susceptibility of a population and/or members thereof to cancer. Disclosed are methods for identifying and immunologically screening candidate antigens for inclusion in a prophylactic and/or therapeutic cancer vaccine. Further disclosed is a general class of antigens, referred to herein as novopeptides, as well as several specific embodiments and/or examples thereof, including non-MS novopeptides and FS-novopeptides and others. Disclosed are methods and compositions related to novopeptides for use in diagnosing, preventing and treating cancer. Also disclosed are embodiments of methods of using novopeptides to induce an immune response against cancer. Disclosed are vaccines having one or more novopeptide components, which may be used, in various embodiments, for example, prophylactically, or as a therapeutic treatment against existing cancerous cells.

In a first aspect, disclosed are embodiments of synthetic or recombinant peptide components, which may include novopeptides, for use in anti-cancer vaccines.

In a second aspect, disclosed are embodiments of anti-cancer vaccines for prophylactic or therapeutic administration or both, including, for example, anti-cancer vaccines including peptide components and/or novopeptides and anti-cancer vaccines including nucleic acids that encode peptide components and/or novopeptides.

In other aspects, disclosed are embodiments of methods including administration of an anti-cancer vaccine to a population and/or member thereof.

The foregoing summary is intended to provide a brief introduction to the subject matter of this disclosure and does not in any way limit or circumscribe the scope of the invention(s) disclosed herein, which scope is defined by the claims currently appended or as they may be amended, and as interpreted in the light of the entire disclosure, including the detailed description and drawing figures.

BRIEF DESCRIPTION OF THE DRAWING FIGURES

The accompanying drawing figures, which are incorporated in and constitute a part of this specification, illustrate several embodiments and together with the description illustrate various embodiments of the disclosed compositions and methods.

FIGS. 1a and 1b show PCR amplification of novopeptides FS 1-78 (SEQ ID NO: 2) and FS 6-21 (SEQ ID NO: 4), respectively, from various cancerous and non-cancerous cell types.

FIG. 2 demonstrates an embodiment of a method of determining frameshift frequency in tumor cells.

DETAILED DESCRIPTION

Figure 1A:
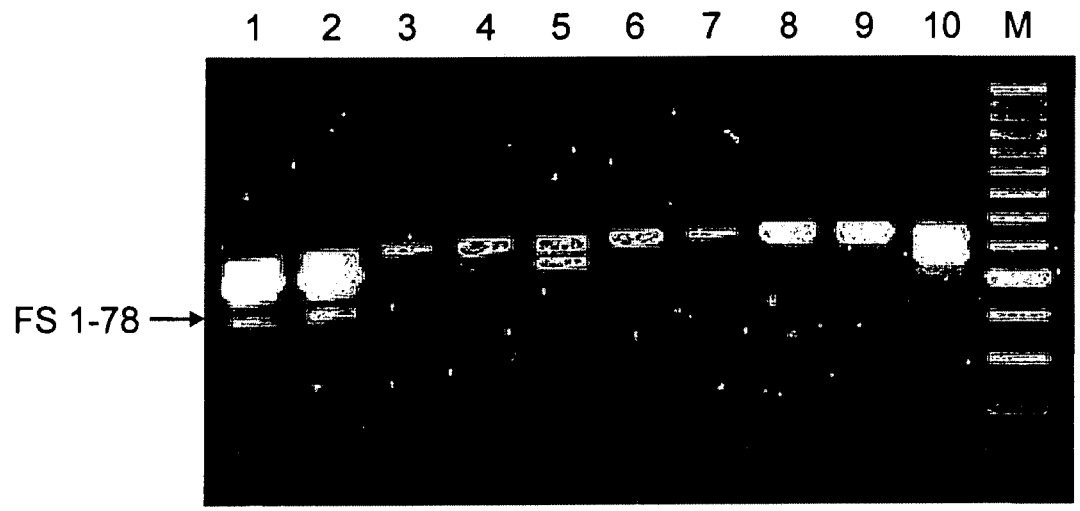

Before the present compounds, compositions, articles, devices, and/or methods are disclosed and described, it is to be understood that they are not limited to specific synthetic methods or specific recombinant biotechnology methods unless otherwise specified, or to particular reagents unless otherwise specified, as such may, of course, vary. It is also to be understood that the terminology used herein is for the purpose of describing particular embodiments only and is not intended to be limiting.

As used in the specification and the appended claims, the singular forms "a," "an" and "the" include plural referents unless the context clearly dictates otherwise. Thus, for example, reference to "a pharmaceutical carrier" includes mixtures of two or more such carriers, and the like.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed the "less than or equal to 10" as well as "greater than or equal to 10" is also disclosed. It is also understood that the throughout the application, data is provided in a number of different formats, and that this data, represents endpoints and starting points, and ranges for any combination of the data points. For example, if a particular data point "10" and a particular data point 15 are disclosed, it is understood that greater than, greater than or equal to, less than, less than or equal to, and equal to 10 and 15 are considered disclosed as well as between 10 and 15.

In this specification and in the claims which follow, reference will be made to a number of terms which shall be defined to have the following meanings:

"Optional" or "optionally" means that the subsequently described event or circumstance may or may not occur, and that the description includes instances where said event or circumstance occurs and instances where it does not.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon.

The methods and compositions disclosed herein pertain in part to a class of compositions, referred to herein as novopeptides, which are useful as candidates for cancer vaccines. Herein, "novopeptide" refers to any composition, such as, for example, a TSA, comprising a polypeptide having at least 8 and no more than 40 amino acids, whose amino acid sequence is encoded by all or part of at least one novopeptide nucleic acid sequence. Thus, for example, a "novopeptide can comprise a TSA having 8, 9, 10, 11, 12, 13, 14, 15, 16, 17, 18, 19, 20, 25, 30, 35, or 40 amino acids or any number of amino acid residues in between. A "novopeptide nucleic acid sequence" means any nucleic acid sequence that can be generated from any non-cancerous reference sequence by a novopeptide associated mutation or variation. "Novopeptide" includes any such polypeptide regardless of how produced or obtained, whether naturally occurring, engineered, produced by in vitro translation, synthesized, or produced in any of the many other ways of generating polypeptides known to one having ordinary skill in the art. A "novopeptide associated mutation or variation" means one or a combination of any one or more point mutations, frame shift mutations, in-frame insertions or deletions, translocations, improper splicing, post-transcriptional events, variations, or other alterations in a nucleic acid sequence from a non-cancerous reference sequence, regardless of whether heritable or not, the effect of which is to cause the amino acid sequence or composition of a polypeptide encoded thereby to differ from that of the non-cancerous reference sequence; "novopeptide associated mutation or variation" expressly includes, without limitation, deviations from non-cancerous reference sequences occurring as a result of mis-translation, mis-splicing, or other events occurring at the RNA level. A "non-cancerous reference sequence" means and includes any nucleic acid sequence occurring in any non-cancerous cell of the organism of interest, whether or not expressed therein. The terms "cancerous cell" and "cancer cell" mean and include any cell exhibiting cancerous, precancerous, dysplagic or other changes characteristic of the transformation of a normal cell into a tumor cell, whether or not malignant and whether or not immediately tumorigenic. It will be recognized that the ontogeny of cancer typically entails a succession of cellular events, and that treatment, whether prophylactic or therapeutic, is optimally applied at the earliest possible stage of that succession. The methods and compositions disclosed herein are intended to apply not only to conditions that have progressed to the point where they are diagnosable as cancer but also to any and all conditions associated with the expression of novopeptides by cells in a manner immunologically distinguishable from normal cells. "Tumor cell" means a cell obtained from or associated with a tumor. "Noncancerous cell" means and includes any cell that is not a cancerous cell or tumor cell. Typically, a novopeptide is a linear polypeptide sequence comprising naturally occurring amino acids; however, "novopeptide" also includes any other polypeptide composition including a sequence that can be expressed by a cancerous cell as a result of a novopeptide associated mutation or variation of a noncancerous reference sequence, whether occurring in DNA or RNA, whether or not comprising one or more amino acids that differ from the naturally occurring amino acids, whether or not post-translationally modified, and whether or not bonded to or associated with any one or more other moieties. A FS-novopeptide is a novopeptide whose sequence differs from that of a noncancerous reference sequence in a manner attributable to one or more novopeptide associated mutations or variations wherein the mutation or variation is a frame shift mutation or variation. A non-MS novopeptide is a novopeptide encoded by a novopeptide nucleic acid sequence that can be generated by a novopeptide associated mutation or variation from a non-cancerous reference sequence that is not a microsatellite sequence.

One interesting technology that has been developed to identify frameshifts without having to sequence genes is the high-throughput solid-phase protein truncation test (HTS-PTT) (Gite et al., 2003). However, a problem with this approach is that the user must have one or a few candidate proteins in mind at the outset, which reintroduces the problem of requiring knowledge about gene function or mechanism. In the present method, high-throughput sequencing capabilities and bioinformatics may be used to identify FS cancer vaccine candidates. In contrast to prior methodology, various embodiments of the methods disclosed herein 1) do not require knowledge about gene function or immunological mechanism, 2) are systematic and amenable to high-throughput, and 3) are generalizable to all types of cancer. No other approach has all three of these characteristics. Furthermore, testing in the melanoma mouse model confirms that these novopeptides are effective therapeutic vaccines and prophylactic vaccines.

The least explored and potentially most useful subclass of TSA is arguably that caused by frameshifts (FS). One of the consequences of transformation from a normal cell to a cancer cell is that DNA replication and RNA processing become more error prone, while DNA repair becomes less robust. This causes an increase in the frequency of FS mutations or variants where 1 or 2 (or other non-multiple of three) new bases are inserted into or deleted from a gene. When such mutations occur in the coding regions of proteins, the resulting shift in reading frames gives rise to the synthesis of truncated genes that have lost their function. On average at least 20% of the FS variants would encode a new peptide of 9 or more amino acids. Since ~9 amino acids are required to bind in the MHC I pocket for presentation to T cells (e.g., 8, 9, 10, or 11 residues), many of the FS variants could be presented. It will be seen that even short FS variants will present new 9-residue peptides by virtue of the fusion of wild-type and FS sequences. Furthermore, as these nonsense proteins tend to be very immunogenic and are expressed predominantly (if not exclusively) in tumor cells, FS-derived antigens are ideal vaccine candidates. In addition to frameshifts, an insertion or deletion of a nucleic acid sequence that is a multiple of three will produce an in-frame deletion or insertion. These will also lead to the production of novopeptides since the junction points will be new peptide sequence.

Relative to oncogenesis, there are at least two classes of mutated proteins to consider, whether produced by frameshifts or other mechanisms: the first class, oncogenic-related variants, are those that result in or contribute to tumor formation or progression. The second class, bystander variants, are those that are not involved in oncogenesis but that happen to be altered simply because the cellular machinery is operating inefficiently or for other reasons. From the point of view of developing a vaccine, both are viable as vaccine candidates.

Disclosed herein are embodiments of methods of screening for a tumor-specific antigen, comprising obtaining a tumor cell, extracting RNA from the cell, and assaying for frameshifts. It is understood and herein contemplated that the tumor-specific antigen can be a peptide or protein.

Disclosed are embodiments of methods of identifying components for a prophylactic cancer vaccine, comprising: identifying novopeptides by informatics, genomics, proteomics or immunological screens; and detecting an immune response to the novopeptide that differentiates between tumor and normal cells. The novopeptide so identified can be used to induce a primary immune response.

Disclosed herein are embodiments of methods of identifying a novopeptide that produces an anti-cancer immune response, comprising identifying a novopeptide by informatics, genomics, proteomics, or immunological screens; and determining that the novopeptide induces an immune response that differentiates between tumor cells and normal cells. It is understood that the novopeptide of the method can be identified by any of the methods disclosed herein. Thus, for example, disclosed herein are embodiments of methods, wherein the novopeptide is identified using cancer genome and expression databases to detect novopeptides preferentially expressed in tumor cells versus normal cells. Alternatively, disclosed are methods, wherein the novopeptide is identified using nucleic acid sequencing methods to detect alterations in DNA and or RNA that lead to the novopeptide. Also disclosed are methods wherein the novopeptide is identified using mass spectrometry to detect novopeptides that are on the tumor cell surface.

It is understood and contemplated herein that any immunoassay that can measure a T cell response can be used in the disclosed methods. Thus, for example, disclosed herein are embodiments of methods of identifying a novopeptide that produces an anti-cancer immune response comprising determining that the novopeptide induces an immune response, wherein the novopeptide is identified using immune assays of human cancer patient serum or animal tumor model serum to detect reactivity to the novopeptide. Also disclosed are methods, wherein the novopeptide is identified using immune assays of human cancer patient peripheral blood mononuclear cells (PBMCs) or animal tumor model (PBMCs) to detect reactivity to the novopeptide. As noted above, the immune assay can be any assay known in the art that measures T cell activity. Thus, for example, the immune assay can be a cytolytic assay such as a 51Cr release assay, or the assay can measure cytokine production in response to the peptide such as ELISPOT, ELISA, and Intracellular Cytokine Staining. Thus, disclosed herein are embodiments of methods wherein the immune assay is selected from the group consisting of ELISPOT, ELISA, and Intracellular Cytokine Staining. Antibodies may also be used to identify T cell activity by binding to T cells specific for a novopeptide. For example, MHC class I and II tetramers, dimers, and trimers can be used to mark novopeptide specific T cells.

Also disclosed are methods of identifying a novopeptide that induces a protective immune response to cancer, comprising identifying a novopeptide by informatics (odds ratios of tumor to normals); sequencing candidate DNA or RNA; performing mass spectrometry on peptides eluted from MHCI of tumor cells and normal cells, and detecting the peptides that are expressed by tumor cells; and determining whether T-cells reactive to the novopeptide peptide react with MHCI matched tumor cells but not normal cells. It is understood that additional steps may be needed to identify novopeptides. Thus, disclosed herein are embodiments of methods, further comprising comparing the peptides eluted from tumor MHCI to a database of all possible novopeptides from the human proteome. It is also understood that antibody responses to a novopeptide can also be desirable in therapeutic methods. Therefore, disclosed herein are embodiments of methods of identifying a novopeptide that induces a protective immune response to cancer, further comprising determining if antibodies raised to the novopeptide react with tumor cells expressing the novopeptide and not with normal cells. Also disclosed are methods of identifying a novopeptide that induces a protective immune response to cancer, comprising identifying a novopeptide by informatics (odds ratios of tumor to normals); sequencing candidate DNA or RNA; performing mass spectrometry on peptides eluted from MHCI of tumor cells and normal cells, and detecting the peptides that are expressed by tumor cells; and determining if antibodies raised to the novopeptide react with tumor cells expressing the novopeptide and not with normal cells.

It is understood and herein contemplated that the disclosed methods of identifying novopeptides that produce an anti-cancer immune response will produce peptides useful in producing an immune response to cancer. Thus, the novopeptides identified by the methods disclosed herein and those specifically elucidated can be used as a therapeutic or prophylactic agent to treat or prevent a cancer either alone or in combination with other peptides or known anti-cancer agents. Thus, for example, the disclosed methods can identify novopeptides that can be used to develop an anti-cancer vaccine. Therefore, disclosed herein are cancer vaccines comprising a novopeptide or nucleic acid encoding a novopeptide that has been identified by any of the methods of identifying novopeptides disclosed herein. It is understood and herein contemplated that such a vaccine can be delivered by any method known in the art including but not limited to gene gun, as gene vaccine, viral vector or as peptide or peptide fusion to another carrier such as a protein, sugar, or oil:water emulsion.

The disclosed prophylactic and therapeutic vaccines are suitable for administration to human and non-human subjects. Thus, disclosed herein are prophylactic vaccines that are administered to a non-human animal selected from the group consisting of dog, cat, guinea pig, mouse, rat, rabbit, pig, horse, cow, monkey, chimpanzee, or other non-human primate to prevent cancer, or to any other animal susceptible to cancer.

Thus, disclosed herein are embodiments of methods of identifying a novopeptide that induces a protective immune response to cancer, comprising identifying a novopeptide by informatics (odds ratios of tumor to normals); sequencing candidate DNA or RNA; performing mass spectrometry on peptides eluted from MHCI of tumor cells and normal cells, and detecting the peptides that are expressed by tumor cells; and determining whether T-cells reactive to the novopeptide react with MHCI matched tumor cells but not normal cells. It is understood that additional steps may be needed to identify novopeptides. Thus, disclosed herein are embodiments of methods, further comprising comparing the peptides eluted from tumor MHCI to a database of all possible novopeptides from the human proteome. It is also understood that antibody responses to a novopeptide can also be desirable in therapeutic methods. Therefore, disclosed herein are embodiments of methods of identifying a novopeptide that induces a protective immune response to cancer, further comprising determining if antibodies raised to the novopeptide react with tumor cells expressing the novopeptide and not with normal cells. Also disclosed are methods of identifying a novopeptide that induces a protective immune response to cancer, comprising identifying a novopeptide by informatics (odds ratios of tumor to normals); sequencing candidate DNA or RNA; performing mass spectrometry on peptides eluted from MHCI of tumor cells and normal cells, and detecting the peptides that are expressed by tumor cells; and determining if antibodies raised to the novopeptide react with tumor cells expressing the novopeptide and not with normal cells.

The disclosed methods can also be used in conjunction with animal models. Thus, disclosed herein are embodiments of methods of identifying a novopeptide that produces an anti-cancer immune response, comprising identifying a novopeptide by informatics, genomics, proteomics, or immunological screens; and determining that the novopeptide induces an immune response that differentiates between tumor cells and normal cells, wherein the anticancer immune response of the novopeptide is further determined by administering a non-human animal homolog of a human novopeptide to the non-human animal in a prophylactic or therapeutic cancer model; and measuring the anti-cancer effect of the novopeptide in the animal model of cancer.

It is understood and herein contemplated that any of the disclosed methods benefit by the distinction and identification of immune responses limited to tumor cells (i.e., not present or present at only low levels in normal cells). Thus, disclosed herein are embodiments of methods, for further identifying the induction of an immune response that differentiates between tumor cells and normal cells, wherein human cells are exposed to the novopeptide, and the reactivity of the exposed cells to human cancer cells and normal cells is determined, wherein a stronger reactivity against human cancer cells compared to normal cells indicates a cancer-specific immune response.

Tumor specific antigens can come from many sources. One advantage of the present disclosure over previous methods is the identification of tumor-specific antigens in genes previously not associated with oncogenesis (i.e., cancer). For example, one source of tumor-specific antigens is frameshifts of genes. The genes can be oncogenic or non-oncogenic. A frameshift originating from an oncogene is an "oncogenic-related frameshift," whereas, a frameshift derived from a non-oncogenic tumor gene is a "bystander frameshift." Thus, for example, specifically contemplated herein are tumor-specific antigens wherein the antigen is the result of a bystander frameshift in the gene source.

In embodiments, a method for identifying novopeptide vaccine antigens comprises two major tasks. The first, hereinafter referred to as a novopeptide identification screen, entails identifying novopeptides and/or novopeptide nucleic acid sequences that are likely to be expressed and/or are experimentally determined to be expressed in one or more cancerous cell types. The second task, hereinafter referred to as a novopeptide immunological screen, entails immunological screening of the novopeptides so identified, or novopeptides encoded by the novopeptide nucleic acid sequences so identified, to evaluate each candidate novopeptide for suitability as a component of a vaccine.

An important and novel insight underlying the disclosure hereof, and verified by the experiments described below, is that the widely held assumption that antigens expressed in cancerous cells and minimally expressed or not expressed in noncancerous cells are derived from oncogenes, particularly or exclusively those containing microsatellite sequences, does not withstand scrutiny, in fact, cancer cells can express many genes that have undergone a novopeptide associated mutation or variation, resulting in the expression of one or more non-MS novopeptides or other non-oncogene associated novopeptides by the cell.

The novopeptide identification screen in one aspect relates to identification of novopeptides that are expressed, or are predicted to be expressed, in cancerous cells. This can be accomplished in a number of ways, for example, the methods described by the examples disclosed herein. The method extends to the approaches described herein, which are offered as examples only and not intended to limit the scope of the disclosure, as well as any of the other methods known to persons having ordinary skill in the art for identifying peptides, peptide sequences, and/or nucleic acid sequences encoding peptides, that are experimentally determined to be expressed or predicted to be expressed in a predetermined cell type and/or that exhibit predetermined characteristics.

One method for performing the novopeptide identification screen comprises generating a library of candidate novopeptide sequences, and/or novopeptide nucleic acid sequences, bioinformatically from a known genome sequence or subsequence, or from cDNA, mRNA, EST, protein or peptide sequence, nucleic acid or peptide microarray data, or any other data from which the sequence encoding any non-cancerous reference sequence can be determined or inferred. At least one non-cancerous reference sequence is extracted from such data. Without limiting the generality of the foregoing, and by way of example only, one way of extracting a non-cancerous reference sequence from such data is to extract the DNA or RNA sequence corresponding to a known gene or open reading frame from available sequence data. Because many novopeptide associated mutations or variations are the result of events occurring at the level of RNA processing and/or translation, RNA sequences are another important source of sequence data for identification of candidate novopeptides. Ideally, a non-cancerous reference sequence so extracted is a sequence that, when mutated and fragmented and/or recombined to form novopeptide nucleic acid sequences, is likely to be expressed in a cancerous cell; however, novopeptide identification is in part a trial and error process, so not all non-cancerous reference sequences so extracted will be ideal. Nevertheless, the selection of non-cancerous reference sequences can, in appropriate circumstances, be optimized by any of the methods known to a person having ordinary skill in the art for estimating the likelihood of expression of a sequence, such as, by way of example only, taking into account the locus of the sequence in question with respect to a known promoter and/or other regulatory elements, and/or taking into account the relationship of the sequence in question to a gene known to be expressed in cancerous cells of a type for which a vaccine is desired. From each non-cancerous reference sequence extracted from the sequence data, one or more novopeptide nucleic acid sequences is generated by applying a novopeptide associated mutation or variation and extracting one or more subsequences affected by the novopeptide associated mutation or variation and having lengths corresponding to novopeptides of the desired length. Many other methods for identifying candidate novopeptide sequences from genomic, proteomic, or other similar data will be apparent to a person having ordinary skill in the art. Once a library of candidate novopeptide sequences has been generated, physical novopeptides can readily be generated therefrom by any of the many methods known to a person having ordinary skill in the art for synthesizing or producing physical polypeptides from specified sequences, including without limitation and by way of example only, FMOC synthesis, in vitro translation, and genetically engineered bacterial, phage, or yeast expression systems.

There exist large public databases that contain the sequences of DNA or cDNA from various tumor samples and from normal tissues. The NCI EST database currently contains more than 41 million entries. The Cancer Genome Atlas Project is another source of tumor cell sequence data. Comparison of sequences in the tumor databases to non-cancerous reference sequence open reading frames reveals putative insertions, deletions, mis-splicings, and other variations that can lead to translation and expression of novopeptides.

The disclosure hereof in one aspect relates to the task of identifying novopeptides likely to be expressed in cancer cells and not at all or at a low level in non-cancerous cells, which may, in embodiments, be accomplished by comparing EST sequences from a tumor database with EST sequences from a non-tumor related EST database or other sequence database to identify sequences arising from frame shift mutations or variations. EST sequences are particularly useful because they represent sequences known to be expressed, and capture variation occurring at the RNA level that may not be apparent in the corresponding DNA sequence. In some embodiments, all possible frame shifted sequences are generated from the non-tumor EST database, and the tumor EST database is then searched for sequences matching the frame shifted sequences so generated. The matching sequences found in the tumor EST database are then ranked for selection taking into account the number of times each frame shifted sequence appears in the tumor EST database as compared to the number of times the unshifted noncancerous reference sequence appears in the non-tumor EST database. Both databases are highly redundant, being repositories for data from many experiments by many researchers, and represent a reasonable sample of expression in tumor and non-tumor cells, respectively. Another factor to be taken into account is the size of the insertion or deletion resulting in a frameshift found in the tumor EST database. Insertions or deletions of three or fewer nucleotides have a significant likelihood of being due to sequencing errors, while longer insertions or deletions, particularly those appearing in multiple EST's deposited from multiple sources, are highly likely to represent true novopeptides that are actually expressed in tumor cells. It will be noted that the bioinformatic approach just described also provides information useful for selecting novopeptides that are expressed in multiple tumor types.

In embodiments, another method for identifying novopeptides expressed in tumor cells may entail extracting RNA from tumor cells and sequencing the RNA so extracted, using any of the methods familiar to a person having ordinary skill in the art for extracting and purifying RNA from cells and determining the sequence of the RNA. An interesting finding upon sequencing genes in human tumor cell lines for frame shift variants that are predicted to occur based on the bioinformatic prediction methods described herein is that many frame shifted sequences terminate at a shorter length than statistically expected. Since three of the 64 possible codons are stop codons, one would expect a stop codon to occur on average approximately once every 21 codons, or about once every 63 amino acids, if codons were randomly distributed, but many immediate terminations were observed and frame shift variants longer than about 20 amino acids were rarely encountered.

Also disclosed herein are embodiments of methods of performing a novopeptide identification screen comprising extracting novopeptides in physical form from a sample containing known or suspected cancerous cells, and identifying the novopeptides so extracted. A variety of methods exist that are capable of extracting any novopeptides that can be present in or on one or more cells (typically but not necessarily together with other substances that can be present in the sample including other cellular proteins and peptides). Several such methods are known to those of skill in the art, and include without limitation and by way of example only, washing with selected solvents or buffers, acid elution, sonication, and elution from MHC by competition with other chemical entities having an affinity for MHC. A method may be chosen that can extract antigens present on the surface of cells in the sample. Methods that preferentially extract antigens displayed in MHC are of particular utility since novopeptides expressed by cancerous cells are likely to be so displayed. Once an extraction containing novopeptides has been obtained, the novopeptides contained therein can be characterized and their sequence determined by any of the methods known to a person having ordinary skill in the art for extracting and sequencing peptides from an inhomogeneous sample. Commonly used methods include without limitation sample separation by chromatographic and/or electrophoretic means, followed by characterization of the fractions thus separated, which can be by sequencing methods such as Edman degradation, or by mass spectroscopy. Other methods exist for identification of specific sequences using antibody or other probes, including without limitation ELISA and microarray analysis. A particularly useful and heretofore unfeasible approach enabled by various embodiments of the methods disclosed herein is separation and identification of novopeptides by liquid chromatography and mass spectroscopy (LC-MS/MS). For a novopeptide to be most effective as a target for a vaccine, it should be presented on the outside of the tumor cells. For T-cell killing of the tumor the peptides should be presented in the context of an MHC molecule. For anti-tumor antibody binding the novopeptides need to be accessible on the surface in some form. Mass spectrometry allows the direct detection of particular sequences of peptides. Identification of novopeptides by MS has heretofore not been possible, in part because mass spectrometers having resolution sufficient to resolve peaks corresponding to novopeptides have only recently become available, and, more importantly, because identification of novopeptides by MS requires a database of novopeptide sequences and corresponding masses, and no such database has existed until created at the inventors' direction for purposes of the methods disclosed herein. In embodiments, such a database can be constructed by assembling a set of candidate novopeptide nucleic acid sequences by any of the methods for doing so disclosed herein or known to a person of ordinary skill in the art, and analyzing each sequence using software (such as, by way of example only, BIMAS and/or SYFPEITHI) for predicting the ability of a sequence to bind to or be displayed in the MHC types present in the tumor cells from which the novopeptides are being eluted and to identify preferred 9-mer sequences or subsequences that are capable of being displayed in those MHC types. Spectra corresponding to each preferred 9-mer sequence so determined may be generated and compared with spectra measured via LC-MS/MS using software (such as, by way of example only, Spectrum Mill) suitable for generating spectra from peptide sequences, comparing the spectra so generated with measured spectra, and from such comparison assessing whether a peptide sequence corresponds to any of the measured spectra. Because novopeptides may be present at low levels and only one sequence presented, until recently the sensitivity of mass spectrometry was not high enough to detect them. It should be noted that the method just described can be used both for identification of candidate novopeptides and as a screen to support or verify the identification by one of the other methods described.

Particularly with regard to human cancers, it is useful to perform bioinformatic screening of candidate novopeptides for likely HLA compatibility, since humans are outbred, while laboratory mice are not. It is understood and herein contemplated that the effectiveness of a particular novopeptide as a vaccine for human use depends in part upon the ability of the novopeptide to be displayed by the HLA types present in the human patient to whom it is administered. Vaccine candidate novopeptides can be assessed for likely ability to be displayed by given HLA types using algorithms known to those having ordinary skill in the art, such as, for example, those described herein. For vaccination of a particular human patient, the vaccine should preferably include one or more novopeptides predicted to have a high probability of binding to at least one of the HLA types expressed in the cells of the patient. For a vaccine intended for non-personalized use in humans, the vaccine should include one or more novopeptides in each of a number and selection of HLA types sufficient that a high percentage of individuals in the target population will have at least one of the HLA types represented in the vaccine, keeping in mind that it is not uncommon for one peptide to be presented by two or more MHC molecules, thereby reducing the number of distinct novopeptides required for a desired level of population coverage. It is also useful to take into account the particular tumor types in which particular novopeptides are expressed or are predicted to be expressed, the frequency with which those tumor types appear in the target population, the urgency of finding effective treatment or prophylaxis for those tumor types (keeping in mind that no effective treatments exist for some cancers and that cancer types differ in terms of life expectancy after diagnosis and severity of effects), and any other criteria deemed important in designing a vaccine. The methods and compositions disclosed herein enable preferential selection for further testing of novopeptides that are expressed in multiple tumors, that are more commonly occurring, that are more urgently in need of an effective vaccine, or that meet other criteria.

Also disclosed are embodiments of methods of performing a novopeptide identification screen comprising comparing the RNA expression level of a particular novopeptide in tumor cells of the type being targeted to the RNA expression level of the same novopeptide in one or more non-cancerous cell types. This can be accomplished by any of the methods known to a person having ordinary skill in the art for assaying for RNA expression levels, such as, without limitation and by way of example only, microarray expression analysis, reverse transcriptase PCR, and SAGE analysis. For inclusion in vaccines, novopeptides that are highly expressed in tumor cells and minimally expressed or not expressed in non-cancerous cells are preferred. For an effective vaccine, the novopeptide or a functionally similar peptide should preferably be expressed in the tumor being targeted, and ideally not in non-cancerous cells, and since some novopeptides are highly differentially expressed in tumor vs. non-cancerous cells and others are not, the RNA expression level screen is useful for optimizing the selection of novopeptides for inclusion in vaccine formulations.

Disclosed herein are embodiments of methods for performing novopeptide immunological screens. For example, disclosed herein are embodiments of methods for immunologically screening for the existence of a B cell response to a particular novopeptide comprising assaying for the presence of antibodies reactive to that novopeptide in serum samples from individuals having a type of cancerous cells predicted to express the novopeptide, and for the absence, or presence below a prespecified titer, of such reactive antibodies in serum obtained from one or more individuals not having such cancer. The presence in sera of antibodies reactive to a given novopeptide may be detected and quantified by an ELISA assay in which the novopeptide is adsorbed onto a solid surface, serum is applied, and antibodies remaining bound to the novopeptides after washing are detected. The initial immune response to variant antigens displayed on naturally occurring tumors is suppression and tolerization due to the absence of the co-regulatory signals required for mounting of an immune response; this has been demonstrated in animal models and is probably the case in humans. However, in at least some individuals, a strong immune response develops late in the tumor progression process. Therefore, serum antibody reactivity to a candidate novopeptide, even if detected in the serum of only one or a few individuals having the cancer type in question, is strong evidence that the novopeptide is expressed in that cancer type.

Disclosed herein are embodiments of methods for immunologically screening for a T cell response to a particular novopeptide comprising first preparing cytotoxic T lymphocytes ("CTL's") having T cell receptors specific for the novopeptide as displayed in MHC or HLA. These CTL's may then be tested for reactivity against each of (1) cancerous cells, and (2) non-cancerous cells, each having an MHC or HLA type matching that of the MHC or HLA for which the CTL's are specific.

In embodiments, another method for screening of novopeptides entails testing in a suitable animal model by immunizing with a novopeptide to be evaluated and observing whether the immunization is effective in producing a prophylactically or therapeutically beneficial immune response upon challenge with tumor cells, or in an animal having or prone to having a tumor. The response can be assessed by, for example, measuring tumor volume over time, or assessing survival rates, in comparison to non-immunized controls. Example 2 is illustrative of these methods.

Any one or more of the screening methods described in the preceding discussion can be used to identify novopeptides that are prevalent in tumors relative to noncancerous cells. By screening a panel of tumor and non-cancerous cells it is possible to establish the frequency of a novopeptide in specific tumor types as well as in tumors generally. Further, by screening a novopeptide against the known frequencies of HLA types it is possible to establish the percentage of a population that are likely to respond to the antigen.

As already noted, a second task to which the disclosure hereof is directed is that of performing a novopeptide immunological screen of the candidate novopeptides identified via the novopeptide identification screen or otherwise. A goal of the novopeptide immunological screen is to determine the suitability of a given candidate novopeptide for inclusion in a therapeutic or prophylactic vaccine. In embodiments, a novopeptide immunological screen can be carried out by employing the methods disclosed in the preceding paragraphs, or by any of the methods known to a person having ordinary skill in the art for determining or estimating the likely efficacy and safety of a biomolecule as a vaccine component, singly or in combination and in any appropriate order. In an embodiment, a novopeptide immunological screen entails determining whether T-cells made reactive to the novopeptide exclusively or disproportionately react with cancerous cells but not normal cells. With regard to B-cell response, an embodiment of a novopeptide immunological screen may entail determining whether antibodies against the novopeptide specifically react against tumor cells and not normal cells. Novopeptides are inherently relatively unlikely to be expressed in non-cancerous cells, since novopeptides are derived from altered nucleic acid sequences. It is preferable that novopeptide vaccine antigens not be expressed in non-cancerous cells, since such expression would imply a likelihood of existing tolerance, and since it is preferable that a vaccine not produce an immune response against non-cancerous cells. However, the preference for non-expression in non-cancerous cells is not a rigid one, since even treatments that produce undesired side effects can be therapeutically useful.

Disclosed herein are embodiments of methods and compositions useful in the formulation of prophylactic and/or therapeutic vaccines to be administered for the purpose of raising an immune response against tumor cells. The disclosure hereof extends to the composition of novopeptide-based vaccines and to methods of administration thereof. A novopeptide-based vaccine can be prepared and administered in any of the ways familiar to persons having ordinary skill in the art, including the very simple approach of preparing a vaccine comprising a novopeptide dissolved or suspended in a suitable carrier, and administering it once or at predetermined intervals to the animal or human patient to be vaccinated. However, in embodiments, better success may be had by other methods, and a particular approach entails genetic immunization using gene gun technology, in which the vaccine is administered in the form of a linear expression element encoding the desired novopeptide, as illustrated in the examples below. The composition of a vaccine can include both novopeptide and other components. The inclusion of multiple distinct novopeptides can improve the level of immunoprotection conferred, and may be employed to confer immunoprotection against additional tumor types. Single novopeptides may be found that confer immunoprotection against more than one tumor type, but the repertoire of target tumor types can be expanded by inclusion of additional novopeptides. The inclusion of multiple novopeptides is of particular utility in vaccines intended for administration in humans, due to the need for including a number and selection of novopeptides sufficient to ensure that at least one novopeptide in the vaccine will be capable of being displayed by at least one HLA type present in each individual in a predetermined percentage of the target population. In embodiments, two or more novopeptides can be fused into a single entity. In embodiments, novopeptide-based vaccines can include other components familiar to a person having ordinary skill in the art for improving the immunoprotection conferred or otherwise improving the efficacy and/or safety of the vaccine formulation, including without limitation and by way of example only, adjuvants and hapten carriers.

Experiments have been performed to assess directly the feasibility of creating general prophylactic cancer vaccines and therapeutic cancer vaccines. In contrast to existing dogma, results from these experiments indicate that it is possible to immunize prophylactically with novopeptide vaccines that cross-protect across different tumor types and in different MHC backgrounds. These results show that cancer vaccines do not have to be personalized; can contain a defined set of tumor specific antigens (novopeptides) that cover the majority of human MHCs; and can be administered prophylactically and so avoid the necessity of delaying treatment until an individual develops a tumor (at which point the battle is harder to win) so that a sufficient personalized sample can be obtained to allow formulation of a drug or vaccine.

In embodiments, the tumor-specific antigens (novopeptides) disclosed herein can come from or relate to any known tumor cell. Thus contemplated herein are methods of screening for tumor specific antigens, wherein the tumor cell is from a cancer selected from the group of cancers consisting of lymphomas (Hodgkin's and non-Hodgkin's), B cell lymphoma, T cell lymphoma, leukemias, myeloid leukemia, carcinomas, carcinomas of solid tissues, squamous cell carcinomas, squamous cell carcinomas of the mouth, throat, larynx, and lung, adenocarcinomas, sarcomas, gliomas, high grade gliomas, blastomas, neuroblastomas, plasmacytomas, histiocytomas, melanomas, adenomas, hypoxic tumours, myelomas, AIDS-related lymphomas or sarcomas, metastatic cancers, mycosis fungoides, bladder cancer, brain cancer, nervous system cancer, lung cancers such as small cell lung cancer and non-small cell lung cancer, ovarian cancer, pancreatic cancer, prostate cancer, hepatic cancer, colon cancer, cervical cancer, cervical carcinoma, breast cancer, and epithelial cancer, renal cancer, genitourinary cancer, esophageal carcinoma, head and neck carcinoma, large bowel cancer, hematopoietic cancers, and testicular cancer. The source of novopeptides can be from sequences relating to any tumor type, and some novopeptides are applicable to a wide variety of tumors; when pooled, an appropriate selection of such novopeptides can give rise to a universal prophylactic vaccine.

An advantage of the disclosed approach is that it provides insights into cancer. For example, one of the 11-mer frameshift peptides that was isolated (peptide FS 6-21) was found to have homology to a region of Huntingtin interacting protein (HIP1), the level of which is positively correlated with disease progression in patients with Huntington's disease (Kerr, 2002). Interestingly, there are a number of studies that have shown that this disorder is associated with a significantly lower incidence of cancer (Sorenson et al., 1999).

In embodiments, novopeptides are provided that are associated with cancer cells. The disclosed components can be used to prepare the disclosed compositions as well as in the compositions themselves to be used within the methods disclosed herein. These and other materials are disclosed herein, and it is understood that when combinations, subsets, interactions, groups, etc. of these materials are disclosed, while specific reference of each various individual and collective combinations and permutations of these compounds may not be explicitly disclosed, each is specifically contemplated and described herein. For example, if a particular novopeptide or novopeptide associated mutation or variation (e.g., peptide FS 1-78, peptide FS 6-21, or peptide FS SMC1A) is disclosed and discussed and a number of modifications that can be made to a number of molecules including the FS 1-78, FS 6-21, and FS SMC1A are discussed, specifically contemplated is each and every combination and permutation of FS1-78, FS 6-21, and FS SMC1A and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods.

The disclosed screening methods can be used to identify novopeptide associated mutations or variations associated with cancers. The disclosed novopeptide associated mutations or variations are differentially expressed in cancerous cells as compared to noncancerous cells. Since novopeptide associated mutations or variations occur in all cancers tested, the novopeptides furnish a basis for therapeutic vaccines. Therefore, disclosed herein are vaccines for a cancer comprising one or more novopeptides, wherein the novopeptide is derived from a novopeptide associated mutation or variation, and wherein the novopeptide(s) is identified via the disclosed screening methods or by any other method. Specifically disclosed herein are novopeptides, wherein the novopeptide is associated with a frameshift of the SMC1A gene. Disclosed herein, are frameshift mutation peptides that have been identified that are present only or predominantly in cancerous tissue. See, for example, the list of peptides in the Sequence Listing. Specifically disclosed herein are tumor-specific antigens, wherein the antigen is a peptide as set forth in SEQ ID NOs: 2, 4, 6, and 8. It is understood that there are numerous nucleotide sequences that can encode for the peptides disclosed herein. For example, one example of a nucleotide that encodes the peptide set forth in SEQ ID NOs: 2, 4, and 6 are the nucleotide sequences of SEQ ID NOs: 1, 3, and 5, respectively. It is understood and herein contemplated are each and every nucleotide sequence that encodes the disclosed peptides.

Because the novopeptides in the Sequence Listing have been shown by the present screening method to be present only or predominantly in non-normal (e.g., cancerous) tissue, each disclosed novopeptide can be used as a reagent for detecting the presence of anti-novopeptide antibodies in a subject. Thus, the novopeptides have utility in a method of detecting the presence of non-normal (e.g., cancerous) tissue in a subject as further described below.

Because the novopeptide associated mutation or variation is present and/or expressed at higher levels in cancerous tissue as compared to normal or noncancerous tissue, the novopeptide associated mutations or variations itself can be used as the basis for a target for drug or antibody treatment as well as methods of identifying subjects at risk for a cancer by virtue of the presence of the novopeptide associated mutation or variation. Therefore, the disclosure hereof extends to antibodies to novopeptides or to FS-novopeptides or to non-MS novopeptides. It is understood that the antibody can be specific to any novopeptide disclosed herein. For example, the antibody can be directed to a frameshift mutant of the SMC1A gene. The disclosure hereof extends, by way of example only, to antibodies directed toward a novopeptide comprising a sequence set forth in SEQ ID NOs: 2, 4, 6, or 8. It is understood that the antibody can be administered by itself or as a component of another composition. Thus, herein disclosed are compositions comprising antibodies specific for the tumor specific antigens disclosed herein. The vaccines disclosed herein can be used to treat or prevent cancer due to the presence of the novopeptides or novopeptide associated mutations or variations in tumor cells. Alternatively, since the mutation does not occur or is not prevalent in normal cells it can also be used as a prophylactic vaccine. Thus disclosed herein are compositions comprising a prophylactic vaccine including components as disclosed herein such that they would be predicted to provide protection to 10% or more of a population against a particular tumor or group of tumors by taking into account the frequency of the peptides in the tumors and the frequency of the MHCI types in the population.

Thus, disclosed herein are embodiments of methods of treating cancer comprising administering to a subject in need thereof the vaccines disclosed herein. Also disclosed herein are embodiments of methods of preventing a cancer comprising administering to a subject at risk thereof the vaccines disclosed herein. The disclosed vaccines can be used to treat cancer due to the presence of disclosed tumor-specific antigens in all cancers. Contemplated and disclosed herein are vaccinations and compositions for treating or preventing cancer wherein the cancer is of any type, including, by way of example only, those selected from the group of cancers consisting of lymphomas (Hodgkin's and non-Hodgkin's), B cell lymphoma, T cell lymphoma, leukemias, myeloid leukemia, carcinomas, carcinomas of solid tissues, squamous cell carcinomas, squamous cell carcinomas of the mouth, throat, larynx, and lung, adenocarcinomas, sarcomas, gliomas, high grade gliomas, blastomas, neuroblastomas, plasmacytomas, histiocytomas, melanomas, adenomas, hypoxic tumours, myelomas, AIDS-related lymphomas or sarcomas, metastatic cancers, mycosis fungoides, bladder cancer, brain cancer, nervous system cancer, lung cancers such as small cell lung cancer and non-small cell lung cancer, ovarian cancer, pancreatic cancer, prostate cancer, hepatic cancer, colon cancer, cervical cancer, cervical carcinoma, breast cancer, and epithelial cancer, renal cancer, genitourinary cancer, esophageal carcinoma, head and neck carcinoma, large bowel cancer, hematopoietic cancers, and testicular cancer.

The antibodies disclosed herein can be combined with other agents, molecules, or compounds to increase binding, elicit additional immune responses, or deliver toxic effects to the proximity of the target antigen, e.g., to cells that express the frameshift mutation. Such combinations can occur through the formation of fusion constructs, immunoconjugates, or other combination platforms as known in the art. Thus, in embodiments, the antibodies disclosed herein can be combined with a toxin such as diphtheria toxin, ricin toxin, tetanus toxoid, botulinum toxin, or any other toxin as a fusion construct to form an antibody-toxin fusion. For example, the antibody-toxin fusion construct can comprise the disclosed antibody fused to a diphtheria toxin. In embodiments, the disclosed toxins such as tetanus and diphtheria can comprise truncation mutants to avoid the antibody response from previous exposure to the toxin. For example, a diphtheria toxin can comprise a truncation mutant diphtheria toxin wherein the toxin comprises a 145-152 amino acid truncation of the c-terminal end of the diphtheria toxin.

Immunogenic fusion protein derivatives, such as those described in the examples, may be made by fusing a polypeptide sufficiently large to improve immunogenicity to the target sequence by cross-linking in vitro or by recombinant cell culture transformed with DNA encoding the fusion. For example, a FS novopeptide can be fused to a carrier such as a protein or sugar. Methods for improving the immunogenic properties of a peptide by fusing, conjugating or otherwise associating it with a hapten or other carrier are well known to persons having ordinary skill in the art of immunology.

The terms homology, similarity, and identity may be used interchangeably herein and have equivalent meaning except where otherwise specifically indicated or where context requires otherwise. Thus, for example, if the use of the word homology is used between two non-natural sequences it is understood that this is not necessarily indicating an evolutionary relationship between these two sequences, but rather refers to the similarity or relatedness between their nucleic acid sequences. Many of the methods for determining homology between two evolutionarily related molecules are routinely applied to any two or more nucleic acids or proteins for the purpose of measuring sequence similarity regardless of whether they are evolutionarily related or not.

In general, it is understood that one way to define any known variants and derivatives or those that might arise, of the disclosed genes and proteins herein, is through defining the variants and derivatives in terms of homology to specific known sequences. In general, variants of genes and proteins herein disclosed typically have at least, about 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99 percent homology or sequence identity to the stated sequence or the native sequence or other sequence with which comparison is made. Those of skill in the art readily understand how to determine the homology of two proteins or nucleic acids, such as genes. For example, the homology can be calculated after aligning the two sequences so that the homology is at its highest level.

In embodiments, homology can be computed using published algorithms. Optimal alignment of sequences for comparison may be conducted by the local homology algorithm of Smith and Waterman Adv. Appl. Math. 2: 482 (1981), by the homology alignment algorithm of Needleman and Wunsch, J. Mol. Biol. 48: 443 (1970), by the search for similarity method of Pearson and Lipman, Proc. Natl. Acad. Sci. U.S.A. 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by inspection.

Homology can be determined for nucleic acids by any of the methods known to a person having ordinary skill in the art, including without limitation, for example, the algorithms disclosed in Zuker, M. Science 244:48-52, 1989, Jaeger et al. Proc. Natl. Acad. Sci. USA 86:7706-7710, 1989, Jaeger et al Methods Enzymol. 183:281-306, 1989 which are herein incorporated by reference for at least the material related to nucleic acid alignment. In embodiments, any of the methods typically can be used and in certain instances the results of these various methods may differ, but the skilled artisan understands that if identity is found with at least one of these methods, the sequences would be said to have the stated identity, and be disclosed herein.

For example, as used herein, a sequence may be recited as having a particular percent homology to another sequence when the sequences have the recited homology as calculated by any one or more of the calculation methods described above. For example, a first sequence has 80 percent homology, as defined herein, to a second sequence if the first sequence is calculated to have 80 percent homology to the second sequence using the Zuker calculation method even if the first sequence does not have 80 percent homology to the second sequence as calculated by any of the other calculation methods. As another example, a first sequence has 80 percent homology, as defined herein, to a second sequence if the first sequence is calculated to have 80 percent homology to the second sequence using both the Zuker calculation method and the Pearson and Lipman calculation method even if the first sequence does not have 80 percent homology to the second sequence as calculated by the Smith and Waterman calculation method, the Needleman and Wunsch calculation method, the Jaeger calculation methods, or any of the other calculation methods. As yet another example, a first sequence has 80 percent homology, as defined herein, to a second sequence if the first sequence is calculated to have 80 percent homology to the second sequence using each of calculation methods (although, in practice, the different calculation methods will often result in different calculated homology percentages).

A variety of molecules disclosed herein that are nucleic acid based, including for example the nucleic acids that encode FS1-78, FS 6-21, FS SMC1A, or fragments thereof, as well as various functional nucleic acids. In embodiments, the disclosed nucleic acids may be made up of, for example, nucleotides, nucleotide analogs, or nucleotide substitutes. Non-limiting examples of these and other molecules are discussed herein. For example, when a vector is expressed in a cell, the expressed mRNA will typically be made up of A, C, G, and U. The disclosure hereof extends to the nucleic acid sequences described herein and to any and all other nucleic acids that are similar or homologous thereto, regardless of whether comprised in whole or in part of nucleotides, nucleotide analogs, or nucleotide substitutes, or any combination thereof and regardless of whether or not linked to conjugates or other molecules or moieties. Likewise, if, for example, an antisense molecule is introduced into a cell or cell environment through exogenous delivery, it is advantageous that the antisense molecule be made up of nucleotide analogs that reduce the degradation of the antisense molecule in the cellular environment.

A nucleotide is a molecule that contains a base moiety, a sugar moiety and a phosphate moiety. Nucleotides can be linked together through their phosphate moieties and sugar moieties creating an internucleoside linkage. The base moiety of a nucleotide can be adenin-9-yl (A), cytosin-1-yl (C), guanin-9-yl (G), uracil-1-yl (U), and thymin-1-yl (T). The sugar moiety of a nucleotide is a ribose or a deoxyribose. The phosphate moiety of a nucleotide is pentavalent phosphate. A non-limiting example of a nucleotide would be 3'-AMP (3'-adenosine monophosphate) or 5'-GMP (5'-guanosine monophosphate). There are many varieties of these types of molecules available in the art and available herein.

A nucleotide analog is a nucleotide which contains some type of modification to either the base, sugar, or phosphate moieties. Modifications to nucleotides are well known in the art and would include for example, 5-methylcytosine (5-me-C), 5-hydroxymethyl cytosine, xanthine, hypoxanthine, and 2-aminoadenine as well as modifications at the sugar or phosphate moieties. There are many varieties of these types of molecules available in the art and available herein.

Nucleotide substitutes are molecules having similar functional properties to nucleotides, but which do not contain a phosphate moiety, such as peptide nucleic acid (PNA). Nucleotide substitutes are molecules that will recognize nucleic acids in a Watson-Crick or Hoogsteen manner, but which are linked together through a moiety other than a phosphate moiety. Nucleotide substitutes are able to conform to a double helix type structure when interacting with the appropriate target nucleic acid. There are many varieties of these types of molecules available in the art and available herein.

It is also possible to link other types of molecules (conjugates) to nucleotides or nucleotide analogs to enhance for example, cellular uptake. Conjugates can be chemically linked to the nucleotide or nucleotide analogs. Such conjugates include but are not limited to lipid moieties such as a cholesterol moiety. (Letsinger et al., Proc. Natl. Acad. Sci. USA, 1989, 86, 6553-6556). There are many varieties of these types of molecules available in the art and available herein.

A Watson-Crick interaction is at least one interaction with the Watson-Crick face of a nucleotide, nucleotide analog, or nucleotide substitute. The Watson-Crick face of a nucleotide, nucleotide analog, or nucleotide substitute includes the C2, N1, and C6 positions of a purine based nucleotide, nucleotide analog, or nucleotide substitute and the C2, N3, C4 positions of a pyrimidine based nucleotide, nucleotide analog, or nucleotide substitute.

A Hoogsteen interaction is the interaction that takes place on the Hoogsteen face of a nucleotide or nucleotide analog, which is exposed in the major groove of duplex DNA. The Hoogsteen face includes the N7 position and reactive groups ($NH_2$ or O) at the C6 position of purine nucleotides.

There are a variety of sequences related to the protein and/or peptide molecules disclosed herein, including without limitation and by way of example only, FS 1-78 (SEQ ID NO: 2), FS 6-21, and FS SMC1A, or any of the nucleic acids disclosed herein, including without limitation and by way of example only, those encoding all or part of FS 1-78, FS 6-21, and FS SMC1A. The disclosure hereof extends to analogs of these genes, as well as other alleles of these genes, and splice variants and other types of variants, in humans and in any other species exhibiting specific immunity including without limitation mammals, fish, and birds. The sequences of various of the foregoing to the extent currently known are available in a variety of protein and gene databases, including Genbank. Such sequences available at the time of filing this application at Genbank are herein incorporated by reference in their entireties as well as for individual subsequences contained therein. Genbank can be accessed via the web site of the National Center for Biotechnology Information. Those of skill in the art understand how to resolve sequence discrepancies and differences and to adjust the compositions and methods relating to a particular sequence and to other related sequences. Primers and/or probes can be designed for any given sequence given the information disclosed herein and known in the art.

As discussed herein there are numerous variants of the FS1-78, FS 6-21 and FS SMC1A protein that are known and herein contemplated. In addition to the known functional FS 1-78, FS 6-21, FS SMC1A, and other novopeptide variants there are derivatives of the FS1-78, FS6-2, and FS SMC1A and other novopeptides which also function in the disclosed methods and compositions. Protein and peptide variants and derivatives are well understood to those of skill in the art and can involve amino acid sequence modifications. For example, amino acid sequence modifications typically fall into one or more of three classes: substitutional, insertional or deletional variants. Insertions include amino and/or carboxyl terminal fusions as well as intrasequence insertions of single or multiple amino acid residues. Insertions ordinarily will be smaller insertions than those of amino or carboxyl terminal fusions, for example, on the order of one to ten residues. Deletions are characterized by the removal of one or more amino acid residues from the protein sequence. These variants may be prepared by site specific mutagenesis of nucleotides in the DNA encoding the protein, thereby producing DNA encoding the variant, and thereafter expressing the DNA in recombinant cell culture, or by any of the other methods known to a person having ordinary skill in the art for making or obtaining proteins or peptides having a specified sequence. Techniques for making substitution mutations at predetermined sites in DNA having a known sequence are well known, for example Ml 3 primer mutagenesis and PCR mutagenesis. Amino acid substitutions are typically of single residues, but can occur at a number of different locations at once; insertions usually will be on the order of about from 1 to 10 amino acid residues; and deletions will range about from 1 to 30 residues. Substitutions, deletions, insertions or any combination thereof may be combined to arrive at a final construct. Mutations to DNA encoding the variant should typically not place the sequence out of reading frame and preferably will not create complementary regions that could produce undesired secondary mRNA structure. Substitutional variants are those in which at least one residue has been removed and a different residue inserted in its place. Substitutions in which a residue is replaced with a different amino acid having chemical, biological, or other properties similar to those of the residue that it is replacing, such as, for example, those shown in the following tabulation, are referred to as conservative substitutions.

| Amino Acid | Abbreviation | | Conservative Substitution |
|---|---|---|---|
| alanine | ala | A | ser |
| allosoleucine | alle | | |
| arginine | arg | R | lys, gln |
| asparagine | asn | N | gln, his |
| aspartic acid | asp | D | glu |
| cysteine | cys | C | ser |
| glutamic acid | glu | E | asn |
| glutamine | gln | Q | asp |
| glycine | gly | G | pro |
| histidine | his | H | asn, gln |

-continued

| Amino Acid | Abbreviation | | Conservative Substitution |
|---|---|---|---|
| isoleucine | ile | I | leu, val |
| leucine | leu | L | ile, val |
| lysine | lys | K | arg, gln |
| phenylalanine | phe | F | leu, ile |
| proline | pro | P | met, leu, tyr |
| pyroglutamic acid | pyr | | |
| serine | ser | S | thr |
| threonine | thr | T | ser |
| tyrosine | tyr | Y | tyr |
| tryptophan | trp | W | trp, phe |
| valine | val | V | ile, leu |

The replacement of one amino acid residue with another that is biologically and/or chemically similar is known to those skilled in the art as a conservative substitution. Without limiting the generality of the foregoing, and by way of example only, the substitutions tabulated above are conservative substitutions. In embodiments, conservative substitutions may also include any substitution that would be regarded by one having ordinary skill in the art as conservative, and may include, without limitation, substitutions having a log odds score of zero or above in the BLOSUM 62 matrix, or having a relatively high log odds score in any other substitution matrix in common usage. For example, a conservative substitution may entail replacing one hydrophobic residue for another, or one polar residue for another. Such substitutions include combinations such as, for example, Gly, Ala; Val, Ile, Leu; Asp, Glu; Asn, Gln; Ser, Thr; Lys, Arg; and Phe, Tyr. Such conservatively substituted variations of each explicitly disclosed sequence are included within the polypeptides disclosed herein.

Substantial changes in function or immunological identity are made by selecting substitutions that are less conservative than those shown above, i.e., selecting residues that differ more significantly in their effect on maintaining (a) the structure of the polypeptide backbone in the area of the substitution, for example as a sheet or helical conformation, (b) the charge or hydrophobicity of the molecule at the target site or (c) the bulk of the side chain. The substitutions which in general are expected to produce the greatest changes in the protein properties will be those in which (a) a hydrophilic residue, e.g. seryl or threonyl, is substituted for (or by) a hydrophobic residue, e.g. leucyl, isoleucyl, phenylalanyl, valyl or alanyl; (b) a cysteine or proline is substituted for (or by) any other residue; (c) a residue having an electropositive side chain, e.g., lysyl, arginyl, or histidyl, is substituted for (or by) an electronegative residue, e.g., glutamyl or aspartyl; or (d) a residue having a bulky side chain, e.g., phenylalanine, is substituted for (or by) one not having a side chain, e.g., glycine; or (e) by increasing the number of sites for sulfation and/or glycosylation.

Substitutional or deletional mutagenesis can be employed to insert sites for N-glycosylation (Asn-X-Thr/Ser) or 0-glycosylation (Ser or Thr). Deletions of cysteine or other labile residues also may be desirable. Deletions or substitutions of potential proteolysis sites, e.g. Arg, is accomplished for example by deleting one of the basic residues or substituting one by glutaminyl or histidyl residues.

Certain post-translational derivatizations are the result of the action of recombinant host cells on the expressed polypeptide. Glutaminyl and asparaginyl residues are frequently post-translationally deamidated to the corresponding glutamyl and asparyl residues. Alternatively, these residues are deamidated under mildly acidic conditions. Other post-translational modifications include hydroxylation of proline and lysine, phosphorylation of hydroxyl groups of seryl or threonyl residues, methylation of the o-amino groups of lysine, arginine, and histidine side chains (T. E. Creighton, Proteins: Structure and Molecular Properties, W. H. Freeman & Co., San Francisco pp 79-86 [1983]), acetylation of the N-terminal amine and, in some instances, amidation of the C-terminal carboxyl.

It is understood that one way to define the variants and derivatives of the disclosed proteins herein is through defining the variants and derivatives in terms of homology/identity to specific known sequences. For example, SEQ ID NO: 2 sets forth a particular sequence of peptide 1-78 and SEQ ID NO:4 sets forth a particular sequence of peptide 6-21. Specifically disclosed are variants of these and other proteins herein disclosed which have at least 70% or 75% or 80% or 85% or 90% or 95% homology to the stated sequence. Those of skill in the art readily understand how to determine the homology of two proteins. For example, the homology can be calculated after aligning the two sequences so that the homology is at its highest level. It is understood that the description of conservative mutations and homology can be combined together in any combination, such as embodiments that have at least 70% homology to a particular sequence wherein the variants are conservative mutations.

As this specification discusses various proteins and protein sequences it is understood that the nucleic acids that can encode those protein sequences are also disclosed. This would include all degenerate sequences related to a specific protein sequence, i.e. all nucleic acids having a sequence that encodes one particular protein sequence as well as all nucleic acids, including degenerate nucleic acids, encoding the disclosed variants and derivatives of the protein sequences. Thus, while each particular nucleic acid sequence may not be written out herein, it is understood that each and every sequence is in fact disclosed and described herein through the disclosed protein sequence. For example, one of the many nucleic acid sequences that can encode the protein sequence set forth in SEQ ID NO:2 is set forth in SEQ ID NO:1. In addition, nucleic acid sequences encoding disclosed conservative derivatives of SEQ ID NO:2 are also disclosed. It is also understood that while no amino acid sequence indicates what particular DNA sequence encodes that protein within an organism, where particular variants of a disclosed protein or peptide are disclosed herein, the known nucleic acid sequence that encodes that protein is also known and herein disclosed and described.

It is understood that there are numerous amino acid and peptide analogs which can be incorporated into the disclosed compositions. For example, there are numerous D amino acids or amino acids which have a different functional substituent than the 20 naturally occurring amino acids tabulated above. The opposite stereoisomers of naturally occurring peptides are disclosed, as well as the stereoisomers of peptide analogs. These analog amino acids can readily be incorporated into polypeptide chains by charging tRNA molecules with the amino acid of choice and engineering genetic constructs that utilize, for example, amber codons, to insert the analog amino acid into a peptide chain in a site specific way (Thorson et al., Methods in Molec. Biol. 11:A2>-12> (1991), Zoller, Current Opinion in Biotechnology, 3:348-354 (1992); Ibba, Biotechnology & Genetic Engineering Reviews 13:197-216 (1995), Cahill et al., TIBS, 14(10):400-403 (1989); Benner, TIB Tech, 12:158-163 (1994); Ibba and Hennecke, Biotechnology, 12:678-682 (1994) all of which are herein incorporated by reference at least for material related to amino acid analogs).

Molecules can be produced that resemble peptides, but which are not connected via a natural peptide linkage. For example, linkages for amino acids or amino acid analogs can include CH2NH—, —CH2S—, —CH2-CH2-, —CH=CH- (cis and trans), —COCH2-, —CH(OH)CH2-, and —CHH2SO—. (These and others can be found in Spatola, A. F. in Chemistry and Biochemistry of Amino Acids, Peptides, and Proteins, B. Weinstein, eds., Marcel Dekker, New York, p. 267 (1983); Spatola, A. F., Vega Data (March 1983), Vol. 1, Issue 3, Peptide Backbone Modifications (general review); Morley, Trends Pharm Sci (1980) pp. 463-468; Hudson, D. et al., Int J Pept Prot Res 14:177-185 (1979) (—CH2NH—, CH2CH2-); Spatola et al. Life Sci 38:1243-1249 (1986) (—CH H2-S); Hann J. Chem. Soc Perkin Trans. 1307-314 (1982) (—CH—CH—, cis and trans); Almquist et al. J. Med. Chem. 23:1392-1398 (1980) (—COCH2-); Jennings-White et al. Tetrahedron Lett 23:2533 (1982) (—COCH2-); Szelke et al. European Appln, EP 45665 CA (1982): 97:39405 (1982) (—CH(OH)CH2-); Holladay et al. Tetrahedron. Lett 24:4401-4404 (1983) (—C (OH)CH2-); and Hruby V., Sci 31:189-199 (1982) (—CH2-S—); each of which is incorporated herein by reference. A particularly preferred non-peptide linkage is —CH2NH—. It is understood that peptide analogs can have more than one atom between the bond atoms, such as b-alanine, g-aminobutyric acid, and the like.

Amino acid analogs and peptide analogs may have enhanced or desirable properties, such as, more economical production, greater chemical stability, enhanced pharmacological properties (half-life, absorption, potency, efficacy, etc.), altered specificity (e.g., a broad-spectrum of biological activities), reduced antigenicity, and others.

D-amino acids can be used to generate more stable peptides, because D-amino acids are not recognized by peptidases. Systematic substitution of one or more amino acids of a consensus sequence with a D-amino acid of the same type (e.g., D-lysine in place of L-lysine) can be used to generate more stable peptides. Cysteine residues can be used to cyclize or attach two or more peptides together. This can be beneficial to constrain peptides into particular conformations. (Rizo and Gierasch Ann. Rev. Biochem. 61:387 (1992), incorporated herein by reference).

The compositions disclosed herein can be used for treatment or prophylaxis against any disease where uncontrolled cellular proliferation occurs, such as cancers. It is understood and herein contemplated that, in embodiments, such compositions may be characterized by any novopeptide associated mutation or variation disclosed herein. Therefore, disclosed herein are embodiments of methods of treating a cancer comprising administering a composition to a subject in need thereof, wherein the composition comprises a novopeptide, a FS-novopeptide, a non-MS novopeptide, a non-MS novopeptide that is also a FS-novopeptide, and/or any combination of the foregoing. Thus, for example, the novopeptide associated mutation or variation can be a frameshift of the SMC1A gene. It is also understood that the frameshift can be a peptide. Thus, by way of example only and without limiting the generality of the foregoing, disclosed herein are embodiments of methods of treating cancer comprising administering to a subject in need thereof a composition comprising a novopeptide, wherein the novopeptide comprises the sequence set forth in SEQ ID NO: 2, 4, 6, or 8.

An aspect of the disclosure hereof relates to the identification of novopeptides, including, for example, novopeptides referred to herein as novopeptide vaccine antigens, suitable for inclusion in a prophylactic or therapeutic cancer vaccine. A novopeptide vaccine antigen is a novopeptide that is capable, when administered in an appropriately constituted prophylactic or therapeutic vaccine, of fostering an appreciable immune response, which may be humoral, cellular, or both, against at least one cancerous cell type in at least one individual.

The utility of the methods, compositions, and articles of manufacture disclosed herein has been convincingly demonstrated in an animal model, as disclosed herein in the examples, and selected aspects of the disclosed technology capable of being demonstrated without a need for human clinical testing have been experimentally confirmed in other experiments disclosed herein. The disclosure hereof is applicable to human and murine cancers, and similarly to cancers of all other organisms having mechanisms for specific immunity, specifically including all mammals, as well as birds and fish. The disclosure hereof is of high potential significance not only in providing prophylactic and therapeutic interventions for human cancer, but also for its veterinary applications, particularly in companion animals such as dogs and cats, for which cancer is a leading cause of death. Embodiments disclosed herein can readily be applied to dog cancer since the dog genome sequence determination has been completed.

While significant progress has been made over the past decade in understanding the basic immunology underlying cancer, thus far no one has produced a cancer vaccine that can, reliably and consistently, induce tumor destruction or improve patient survival (Lewis, 2004; Leaf, 2004). The scientific literature discloses a variety of cancer vaccination strategies that have been investigated by others, each proving less than ideal. The majority of personalized cancer vaccine studies to date have focused on the use of undefined whole tumor-cell extracts prepared from a patient's own tumor. Experiments using autologous vaccines in melanoma have shown that, in principle, immunologic intervention can enhance specific anti-tumor immune responses, and even mediate regression in some cases, but this approach presents difficult challenges, including (1) the potential for causing autoimmunity; (2) dilution of TAAs since the majority of antigens will be "normal"; (3) undermining of specificity (one of the most attractive unique features of immunotherapy); (4) dependence on the patient having a large enough tumor to make the vaccine, precluding early treatment; and (5) the need for custom preparation of a personalized vaccine for each patient.

Another approach to cancer vaccination is to use vaccine formulations composed of known and defined TAAs, since this maximizes specificity and obviates the problem of antigen dilution. To date, several hundred human TAAs have been identified using a variety of strategies, and criteria exist for selecting TAAs suitable for immunotherapy. Functionally, TAAs may be classified as self and non-self. Self-TAAs are derived from non-mutated genes whose expression is limited to certain tissues or to over-expressed proteins. Most TAAs identified and tested to date are self antigens. Potential problems associated with such antigens include autoimmunity and tolerance. For practical purposes, this limits the use of self TAAs to non-vital organs (such as reproductive organs). Pre-existing immune tolerance to self antigens is also problematic, for not only does it suppress a desired anti-tumor immune response, but more recently it has emerged as a possible mechanism of immune escape.

All or most TSAs are non-self antigens and can originate either exogenously (such as those derived from viral proteins in virally-associated tumors, e.g. human papilloma virus) or endogenously. The latter subclass includes unmutated proteins that might never have been presented to the immune system before (some embryonic or immune privileged antigens), as well as mutated proteins that arise as a consequence of mutations in tumors. Mutation-derived TSAs can arise from events such as point mutations, frame shift mutations, translocations, improper splicing, and post transcriptional events. TSAs have a great advantage over self TAAs as cancer vaccines since they avoid the problems of autoimmunity and systemic tolerance. In mouse models TSAs have been shown to generate high-avidity T cell responses more readily than self TAAs.

In principle, vaccination can be used either prophylactically or therapeutically. As a practical matter, therapeutic vaccination strategies face several difficult challenges, and, in general, have failed to fulfill their early promise. Many or most antigens presented by cells in an established tumor are recognized as self by the immune system. To the extent that tumor cells do display mutated antigens that the immune system is capable of recognizing as non-self, by the time tumor development has advanced sufficiently to allow diagnosis, immune tolerance to the mutated antigens will have developed owing to their gradual exposure to the immune system in the absence of the co-regulatory danger signals that would be required for an immune response. Recent studies have shown that in the absence of co-stimulatory signals, tolerance can be induced even to foreign antigens expressed by a tumor. MHC expression is often down-regulated or impaired in established tumor cells, reducing the display of any non-self antigen, and the reduced MHC expression is of course selected for to the extent that any therapeutic immunization strategy is effective in killing cells that do display recognizable non-self antigen in MHC. (The term "MHC" is used herein in a generic sense and is intended to include MHC, HLA, and any other entities at least one of whose functions is to display endogenous or exogenous antigens or fragments thereof on the surface of a cell. Where reference is made to a particular MHC class, the reference includes any corresponding class of HLA or other such entity.) Finally, it has been shown by multiple groups that immunization with irradiated tumor cells, tumor cell lysate, or tumor-derived heat shock proteins (HSPs) protects only against challenge with the same tumor; it does not protect against challenge with a different tumor; vaccines derived from one tumor did not protect against another. These findings have led to an assumption nearly universally held in the field of cancer immunology, but disproved by the experimental evidence disclosed herein, that cancer vaccines must be personalized. Companies exist based on a technology in which they receive a tumor from a patient, isolate HSPs or extracts from that tumor, and return the tumor derived HSPs or extracts as a patient-specific vaccine. Early clinical trials implementing this approach showed promise, but it is expensive and not every cancer patient has enough tumor from which to make a vaccine. A recent Phase III trial by Antigenics, Inc. using this strategy was stopped for lack of efficacy.

A fundamental problem for prophylactic vaccination as a cancer preventative treatment has been the supposition that each tumor in each organism presents a unique immunological profile, and the consequent assumption that no prophylactic vaccine could offer a practicable breadth of protection against multiple tumor types or even against multiple variants of a single tumor type. The problem is exacerbated by the assumed need for any vaccine to be personalized to the organism receiving it. In contrast, a basic contention hereof is that there are novopeptides that are produced in common between two or more types of cancers and that these can be used to formulate a prophylactic vaccine. The challenge was to develop a systematic method to find such novopeptides; such a method is disclosed herein.

The peptides disclosed herein can be administered to a subject as a peptide or encoded by a nucleic acid. Thus, for example, disclosed herein are embodiments of methods of treating a cancer comprising administering a composition to a subject in need thereof, wherein the composition comprises a tumor-specific antigen, and wherein the tumor-specific antigen is a novopeptide, a FS-novopeptide, a non-MS novopeptide, a non-MS novopeptide that is also a FS-novopeptide, and/or any combination of the foregoing, and/or wherein the tumor-specific antigen is a peptide encoded by a nucleic acid set forth in SEQ ID NOs: 1, 3, or 5. The nucleic acids encoding the novopeptides disclosed herein can be provided by any gene delivery system disclosed herein such as gene gun, viral vector, or plasmid.

"Treatment" means a method of reducing the effects of a disease or condition. Treatment can also refer to a method of reducing the disease or condition itself rather than just the symptoms. The treatment can be any reduction from native levels and can be but is not limited to the complete ablation of the disease, condition, or the symptoms of the disease or condition. For example, a disclosed method for reducing the effects of a cancer is considered to be a treatment if there is a 10% reduction in one or more symptoms of the disease (e.g., tumor size) in a subject with the disease when compared to native levels in the same subject or control subjects. Thus, the reduction can be a 10, 20, 30, 40, 50, 60, 70, 80, 90, 100%, or any amount of reduction in between as compared to native or control levels. It is also understood and contemplated herein that treatment can refer to any reduction in the progression of a disease or cancer. Thus, for example, a method of reducing the effects of a cancer is considered to be a treatment if there is a 10% reduction in the tumor growth rate relative to a control subject or tumor growth rates in the same subject prior to the treatment. It is understood that the reduction can be a 10, 20, 30, 40, 50, 60, 70, 80, 90, 100%, or any amount of reduction in between as compared to native or control levels.

"Inhibit," "inhibiting," and "inhibition" mean to decrease an activity, response, condition, disease, or other biological parameter. This can include but is not limited to the complete ablation of the activity, response, condition, or disease. This may also include, for example, a 10% reduction in the activity, response, condition, or disease as compared to the native or control level. Thus, the reduction can be a 10, 20, 30, 40, 50, 60, 70, 80, 90, 100%, or any amount of reduction in between as compared to native or control levels.

The disclosed methods can be used for the treatment or inhibition of any cancer. Thus disclosed herein are embodiments of methods of treating, preventing, or inhibiting cancer, wherein the cancer may be of any type, such as, by way of example only, a cancer selected from the group of cancers consisting of lymphomas (Hodgkin's and non-Hodgkin's), B cell lymphoma, T cell lymphoma, leukemias, myeloid leukemia, carcinomas, carcinomas of solid tissues, squamous cell carcinomas, squamous cell carcinomas of the mouth, throat, larynx, and lung, adenocarcinomas, sarcomas, gliomas, high grade gliomas, blastomas, neuroblastomas, plasmacytomas, histiocytomas, melanomas, adenomas, hypoxic tumours, myelomas, AIDS-related lymphomas or sarcomas, metastatic cancers, mycosis fungoides, bladder cancer, brain cancer, nervous system cancer, lung cancers such as small cell lung cancer and non-small cell lung cancer, ovarian cancer, pancreatic cancer, prostate cancer, hepatic cancer, colon cancer, cervical cancer, cervical carcinoma, breast cancer, and epithelial cancer, renal cancer, genitourinary cancer, esophageal carcinoma, head and neck carcinoma, large bowel cancer, hematopoietic cancers, and testicular cancer.

It is understood that, in addition to the present methods of identifying a subject at risk of developing cancer, the identification of subjects at risk of developing a cancer can be accomplished by any means known in the art. Thus, for example, a subject at risk can be identified by exposure to a known carcinogen, behavioral activities associated with cancer (e.g., smoking with respect to lung cancer), or genetic predisposition to a given cancer. Specifically disclosed herein are embodiments of methods of preventing a cancer in a subject at risk thereof wherein the subject is identified by genetic screening. Because the frameshift peptides disclosed herein are associated with cancer, the presence of the frameshift can be used to identify subjects at risk of developing a cancer. Therefore, disclosed herein are embodiments of methods of identifying a subject at risk for developing a cancer comprising obtaining a tissue sample from the subject and contacting an antibody with the tissue sample, wherein antibody binding indicates the subject is at risk for the cancer.

Compounds disclosed herein may also be used for the treatment of precancer conditions such as cervical and anal dysplasias, other dysplasias, severe dysplasias, hyperplasias, atypical hyperplasias, and neoplasias.

The disclosed methods can be used to treat or protect any subject in need thereof or at risk of acquiring any disease disclosed herein. In embodiments, a subject may include any animal capable of displaying specific immunity such as bird, fish, and mammal. Thus, for example, a subject for use with any of the disclosed methods can be human, chimpanzee (or other non-human primate), monkey, cow, horse, pig, dog, cat, rat, guinea pig, and mouse.

A significant advantage of the methods, compositions, and articles of manufacture disclosed herein is that vaccination with a single novopeptide has been shown capable of conferring immunoprotection against more than one tumor type and in unrelated individuals, as demonstrated by the examples disclosed herein. This is a highly novel result, particularly in the light of the widely held dogma based on the whole-cell vaccine studies previously noted that immunization with one tumor cell line does not cross-protect against another. The results shown here may be reconciled with the whole-cell vaccine studies by observing that tumors do have antigens in common, but immunization with cell lysates or irradiated tumors do not show cross-protection because the concentration of cross protective peptides in MHC is not high enough in whole-cell vaccines to activate T cells; in other words, whole-cell vaccine strategies fail because of antigen dilution. Prevaccination with one or a few novopeptides concentrates the immune system on these antigens and confers protection. This experimental finding leads to the very important result that novopeptides expressed in common by multiple tumor types can support prophylactic vaccination conferring immunoprotection against those tumor types. This is an important conceptual, experimental, and practical breakthrough. It will be noted that the disclosure hereof provides an effective and systematic method for finding and evaluating novopeptides that are commonly expressed among multiple tumor types.

In some cases a novopeptide produced in human tumors will be the same or very similar to that produced in an animal tumor model such as mouse or dog. For example, the FS 1-78 and FS 6-21 novopeptides described below were found in mouse tumors as there described, but have also been identified in certain human tumors. The SMC1A novopeptide, described below, was found originally by searching human databases, but also is expressed in mouse tumors. If a novopeptide is found in both human and mouse tumors, significant evidence of the potential effectiveness of the novopeptide as a tumor vaccine antigen in humans can be obtained by immunizing mice and challenging with the appropriate tumor line. Alternatively, cancer prone mice can be vaccinated with the novopeptide to determine whether tumorigenesis and/or tumor progression is reduced or eliminated.

Disclosed herein are therapeutic antibodies to a tumor-specific antigen, wherein the antigen is a novopeptide identified by the steps comprising identifying a novopeptide by informatics, genomics, proteomics, or immunological screens; and determining that the novopeptide induces an immune response that differentiates between tumor cells and normal cells. It is understood and herein contemplated that the novopeptide can be a tumor-specific antigen. Thus, for example, the novopeptide can comprise the sequence set forth in SEQ ID NO: 2, 3, or 6. Similarly, the novopeptide can comprise a frameshift of the SMC1A gene. Thus for example, the novopeptide can comprise the sequence set forth in SEQ ID NO: 8. It is also understood that the disclosed therapeutic antibodies can be used alone or in combination with another agent as a therapeutic treatment. It is also contemplated herein that the therapeutic treatments disclosed herein can be used to treat cancer. In other words, disclosed herein are embodiments of methods of treating a cancer comprising administering to a subject the therapeutic antibodies disclosed herein or identified by the methods disclosed herein. Thus, for example, disclosed herein are embodiments of methods of therapeutic treatment, wherein the cancer may be of any type, such as, by way of example only, a cancer selected from the group of cancers consisting of lymphomas (Hodgkin's and non-Hodgkin's), B cell lymphoma, T cell lymphoma, leukemias, myeloid leukemia, carcinomas, carcinomas of solid tissues, squamous cell carcinomas, squamous cell carcinomas of the mouth, throat, larynx, and lung, adenocarcinomas, sarcomas, gliomas, high grade gliomas, blastomas, neuroblastomas, plasmacytomas, histiocytomas, melanomas, adenomas, hypoxic tumours, myelomas, AIDS-related lymphomas or sarcomas, metastatic cancers, mycosis fungoides, bladder cancer, brain cancer, nervous system cancer, lung cancers such as small cell lung cancer and non-small cell lung cancer, ovarian cancer, pancreatic cancer, prostate cancer, hepatic cancer, colon cancer, cervical cancer, cervical carcinoma, breast cancer, and epithelial cancer, renal cancer, genitourinary cancer, esophageal carcinoma, head and neck carcinoma, large bowel cancer, hematopoietic cancers, and testicular cancer.

In embodiments, the compositions disclosed herein can be used for example as targets in combinatorial chemistry protocols or other screening protocols to isolate molecules that possess desired functional properties related to inhibiting tumor growth and treating cancer. Thus, disclosed herein are embodiments of methods of screening for a cancer therapeutic or prophylactic comprising contacting the candidate therapeutic or prophylactic with a novopeptide, wherein a candidate therapeutic or prophylactic that binds the novopeptide is selected for further evaluation as a therapeutic or prophylactic.

The disclosed compositions can also be used as diagnostic tools related to diseases such as cancer. For example, the disclosed methods can be used to determine if a cell growth is cancerous. Thus, disclosed herein are embodiments of methods of diagnosing a tumor or other growth as cancerous or precancerous comprising screening for a novopeptide comprising obtaining a tumor cell, extracting RNA from the cell, and assaying for novopeptide associated mutations or variations, wherein the presence of a novopeptide associated mutation or variation indicates the tumor is cancerous or potentially cancerous. Also disclosed are methods of diagnosing an individual with cancer comprising obtaining a tissue sample, and screening for the presence of a novopeptide associated mutation or variation. It is understood that the tissue can be any tissue present in the subject. For example, the tissue can be blood, saliva, skin, or cells from a tissue biopsy. It is also understood that the disclosed tissues can be obtained by any method known in the art such as, for example, lung lavage, venous bleeding, tissue biopsy, or mucosal tissue swab. Thus, for example, disclosed herein are embodiments of methods of diagnosing wherein the sample is blood. The method can involve determining the presence of a novopeptide associated mutation or variation identified to be associated with cancer. Alternatively, the method can involve screening for the presence of an immune response to a novopeptide. It is understood that the immune response can be an antibody or cell-mediated response. Thus, for example, the immune response can be a T cell response such as a CD8 T cell response (e.g., cytolytic killing or cytokine secretion) or CD4 T cell response (cytokine secretion). It is specifically contemplated herein that any known immunological measure may be used to determine the presence of the immune response. For example, antibody responses can be measured by ELISA, ELISPOT, or agglutination assays. T cell responses can be detected by, for example, ELISA, ELISPOT, tetramer staining, intracellular cytokine staining, or chromium release assays.

It is possible that novopeptide associated mutations or variations identified by the methods disclosed herein may result in an otherwise non-oncogenic gene becoming oncogenic. For example, the SMC1A gene is not oncogenic; however, a frameshift of the SMC1A gene as disclosed herein may be oncogenic. The methods of detecting novopeptide associated mutations or variations in tumor cells disclosed herein showed a frameshift in the SMC1A gene which as a frameshift mutant is oncogenic. Thus, disclosed herein are embodiments of methods of identifying oncogenes, comprising detecting a novopeptide associated mutation or variation in a gene not previously associated with cancer.

The compositions disclosed herein and the compositions necessary to perform the disclosed methods can be made using any method known to those of skill in the art for that particular reagent or compound unless otherwise specifically noted.

For example, nucleic acids, such as, for example, oligonucleotides to be used as primers or nucleic acids encoding novopeptides, can be made using standard chemical synthesis methods or can be produced using enzymatic methods or any other known method. Such methods can range from standard enzymatic digestion followed by nucleotide fragment isolation (see for example, Sambrook et al., Molecular Cloning: A Laboratory Manual, 2nd Edition (Cold Spring Harbor Laboratory Press, Cold Spring Harbor, N.Y., 1989) Chapters 5, 6) to purely synthetic methods, for example, by the cyanoethyl phosphoramidite method using a Milligen or Beckman System 1Plus DNA synthesizer (for example, Model 8700 automated synthesizer of Milligen-Biosearch, Burlington, Mass. or ABI Model 380B). Synthetic methods useful for making oligonucleotides are also described by Ikuta et al., Ann. Rev. Biochem. 53:323-356 (1984), (phosphotriester and phosphite-triester methods), and Narang et al., Methods EnzymoL, 65:610-620 (1980), (phosphotriester method). Protein nucleic acid molecules can be made using known methods such as those described by Nielsen et al., Bioconjug. Chem. 5:3-7 (1994).

An example of a method of producing the disclosed proteins and peptides is to link two or more peptides or polypeptides together by protein chemistry techniques. For example, peptides or polypeptides can be chemically synthesized using currently available laboratory equipment using either Fmoc (9-fluorenylmethyloxycarbonyl) or Boc (Xert-butyloxycarbonoyl) chemistry. (Applied Biosystems, Inc., Foster City, Calif.). One skilled in the art can readily appreciate that a peptide or polypeptide corresponding to the disclosed proteins, for example, can be synthesized by standard chemical reactions. For example, a peptide or polypeptide can be synthesized and not cleaved from its synthesis resin whereas the other fragment of a peptide or protein can be synthesized and subsequently cleaved from the resin, thereby exposing a terminal group which is functionally blocked on the other fragment. By peptide condensation reactions, these two fragments can be covalently joined via a peptide bond at their carboxyl and amino termini, respectively, to form an antibody, or fragment thereof, or other polypeptide of interest. (Grant G A (1992) Synthetic Peptides: A User Guide. W.H. Freeman and Co., N.Y. (1992); Bodansky M and Trost B., Ed. (1993) Principles of Peptide Synthesis. Springer-Verlag Inc., NY (which is herein incorporated by reference at least for material related to peptide synthesis). Alternatively, a peptide or polypeptide may be independently synthesized in vivo as described herein. Once isolated, these independent peptides or polypeptides may be linked to form a peptide or fragment thereof via similar peptide condensation reactions.

For example, enzymatic ligation of cloned or synthetic peptide segments allow relatively short peptide fragments to be joined to produce larger peptide fragments, polypeptides or whole protein domains (Abrahmsen L et al., Biochemistry, 30:4151 (1991)). Alternatively, native chemical ligation of synthetic peptides can be utilized to synthetically construct large peptides or polypeptides from shorter peptide fragments. This method consists of a two step chemical reaction (Dawson et al. Synthesis of Proteins by Native Chemical Ligation. Science, 266:776-779 (1994)). The first step is the chemoselective reaction of an unprotected synthetic peptide-thioester with another unprotected peptide segment containing an amino-terminal Cys residue to give a thioester-linked intermediate as the initial covalent product. Without a change in the reaction conditions, this intermediate undergoes spontaneous, rapid intramolecular reaction to form a native peptide bond at the ligation site (Baggiolini M et al. (1992) FEBS Lett. 307:97-101; Clark-Lewis I et al., J. Biol. Chem., 269:16075 (1994); Clark-Lewis I et al., Biochemistry, 30:3128 (1991); Rajarathnam K et al., Biochemistry 33:6623-30 (1994)).

Alternatively, unprotected peptide segments may be chemically linked where the bond formed between the peptide segments as a result of the chemical ligation is an unnatural (nonpeptide) bond (Schnolzer, M et al. Science, 256:221 (1992)). This technique has been used to synthesize analogs of protein domains as well as large amounts of relatively pure proteins with full biological activity (deLisle Milton R C et al., Techniques in Protein Chemistry IV. Academic Press, New York, pp. 257-267 (1992)).

The term "antibodies" is used herein in a broad sense and includes both polyclonal and monoclonal antibodies. In addition to intact immunoglobulin molecules, also included in the term "antibodies" are fragments or polymers of immunoglobulin molecules, and human or humanized versions of immunoglobulin molecules or fragments thereof. These may be chosen for their ability to interact with FS 1-78, FS 6-21, FS SMC1A, or other novopeptides or targets of interest, and in embodiments may be used such that tumor growth is inhibited. The antibodies can be tested for their desired activity using the in vitro assays described herein, or by analogous methods, after which their in vivo therapeutic and/or prophylactic activities may be tested according to known clinical testing methods.

As used herein, the term "antibody" encompasses, but is not limited to, whole immunoglobulin (i.e., an intact antibody) of any class. Native antibodies are usually heterotetrameric glycoproteins, composed of two identical light (L) chains and two identical heavy (H) chains. Typically, each light chain is linked to a heavy chain by one covalent disulfide bond, while the number of disulfide linkages varies between the heavy chains of different immunoglobulin isotypes. Each heavy and light chain also has regularly spaced intrachain disulfide bridges. Each heavy chain has at one end a variable domain (V(H)) followed by a number of constant domains. Each light chain has a variable domain at one end (V(L)) and a constant domain at its other end; the constant domain of the light chain is aligned with the first constant domain of the heavy chain, and the light chain variable domain is aligned with the variable domain of the heavy chain. Particular amino acid residues are believed to form an interface between the light and heavy chain variable domains. The light chains of antibodies from any vertebrate species can be assigned to one of two clearly distinct types, called kappa (k) and lambda (1), based on the amino acid sequences of their constant domains. Depending on the amino acid sequence of the constant domain of their heavy chains, immunoglobulins can be assigned to different classes. There are five major classes of human immunoglobulins: IgA, IgD, IgE, IgG and IgM, and several of these may be further divided into subclasses (isotypes), e.g., IgG-I, IgG-2, IgG-3, and IgG-4; IgA-I and IgA-2. One skilled in the art would recognize the comparable classes for mouse. The heavy chain constant domains that correspond to the different classes of immunoglobulins are called alpha, delta, epsilon, gamma, and mu, respectively.

The term "variable" is used herein to describe certain portions of the variable domains that differ in sequence among antibodies and are used in the binding and specificity of each particular antibody for its particular antigen. However, the variability is not usually evenly distributed through the variable domains of antibodies. It is typically concentrated in three segments called complementarity determining regions (CDRs) or hypervariable regions both in the light chain and the heavy chain variable domains. The more highly conserved portions of the variable domains are called the framework (FR). The variable domains of native heavy and light chains each comprise four FR regions, largely adopting a beta sheet configuration, connected by three CDRs, which form loops connecting, and in some cases forming part of, the beta sheet structure. The CDRs in each chain are held together in close proximity by the FR regions and, with the CDRs from the other chain, contribute to the formation of the antigen binding site of antibodies (see Kabat E. A. et al., "Sequences of Proteins of Immunological Interest," National Institutes of Health, Bethesda, Md.). The constant domains are not involved directly in binding an antibody to an antigen, but exhibit various effector functions, such as participation of the antibody in antibody-dependent cellular toxicity.

As used herein, the term "antibody or fragments thereof" encompasses chimeric antibodies and hybrid antibodies, with dual or multiple antigen or epitope specificities, and fragments, such as F(ab')2, Fab', Fab, sFv, scFv, and the like, including hybrid fragments. Thus, fragments of the antibodies that retain the ability to bind their specific antigens are provided. For example, fragments of antibodies which maintain FS 1-78, FS 6-21, FS SMC1A binding activity are included within the meaning of the term "antibody or fragment thereof" Such antibodies and fragments can be made by techniques known in the art and can be screened for specificity and activity according to the methods set forth in the Examples and in general methods for producing antibodies and screening antibodies for specificity and activity (See Harlow and Lane. Antibodies, A Laboratory Manual. Cold Spring Harbor Publications, New York, (1988)).

Also included within the meaning of "antibody or fragments thereof" are conjugates of antibody fragments and antigen binding proteins (single chain antibodies) as described, for example, in U.S. Pat. No. 4,704,692, the contents of which are hereby incorporated by reference.

The fragments, whether attached to other sequences or not, can also include insertions, deletions, substitutions, or other selected modifications of particular regions or specific amino acids residues, provided the activity of the antibody or antibody fragment is not significantly altered or impaired compared to the non-modified antibody or antibody fragment. These modifications can provide for some additional property, such as to remove/add amino acids capable of disulfide bonding, to increase its bio-longevity, to alter its secretory characteristics, etc. In any case, the antibody or antibody fragment must possess a bioactive property, such as specific binding to its cognate antigen. Functional or active regions of the antibody or antibody fragment may be identified by mutagenesis of a specific region of the protein, followed by expression and testing of the expressed polypeptide. Such methods are readily apparent to a skilled practitioner in the art and can include site-specific mutagenesis of the nucleic acid encoding the antibody or antibody fragment. (Zoller, M J. Curr. Opin. Biotechnol. 3:348-354, 1992).

The term "monoclonal antibody" as used herein refers to an antibody obtained from a substantially homogeneous population of antibodies, i.e., the individual antibodies within the population are identical except for possible naturally occurring mutations that may be present in a small subset of the antibody molecules. The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, as long as they exhibit the desired antagonistic activity (See, U.S. Pat. No. 4,816,567 and Morrison et al., Proc. Natl. Acad. Sd. USA, 81:6851-6855 (1984)).

The disclosed monoclonal antibodies can be made using any procedure which produces monoclonal antibodies. For example, disclosed monoclonal antibodies can be prepared using hybridoma methods, such as those described by Kohler and Milstein, Nature, 256:495 (1975). In a hybridoma method, a mouse or other appropriate host animal is typically immunized with an immunizing agent to elicit lymphocytes that produce or are capable of producing antibodies that will specifically bind to the immunizing agent. Alternatively, the lymphocytes may be immunized in vitro, e.g., using the HIV Env-CD4-co-receptor complexes described herein.

The monoclonal antibodies may also be made by recombinant DNA methods, such as those described in U.S. Pat. No. 4,816,567 (Cabilly et al.). DNA encoding the disclosed monoclonal antibodies can be readily isolated and sequenced using conventional procedures (e.g., by using oligonucleotide probes that are capable of binding specifically to genes encoding the heavy and light chains of murine antibodies). Libraries of antibodies or active antibody fragments can also be generated and screened using phage display techniques, e.g., as described in U.S. Pat. No. 5,804,440 to Burton et al. and U.S. Pat. No. 6,096,441 to Barbas et al.

In vitro methods are also suitable for preparing monovalent antibodies. Digestion of antibodies to produce fragments thereof, particularly, Fab fragments, can be accomplished using routine techniques known in the art. For instance, digestion can be performed using papain. Examples of papain digestion are described in WO 94/29348 published Dec. 22, 1994 and U.S. Pat. No. 4,342,566. Papain digestion of antibodies typically produces two identical antigen binding fragments, called Fab fragments, each with a single antigen binding site, and a residual Fc fragment. Pepsin treatment yields a fragment that has two antigen combining sites and is still capable of cross-linking antigen.

As used herein, the term "antibody" or "antibodies" can also refer to a human antibody and/or a humanized antibody, where context so indicates. Many non-human antibodies (e.g., those derived from mice, rats, or rabbits) are naturally antigenic in humans, and thus can give rise to undesirable immune responses when administered to humans. Therefore, the use of human or humanized antibodies in the methods serves to lessen the chance that an antibody administered to a human will evoke an undesirable immune response.

In embodiments, human antibodies can be prepared using any operable technique. Examples of techniques for human monoclonal antibody production include those described by Cole et al. (Monoclonal Antibodies and Cancer Therapy, Alan R. Liss, p. 77, 1985) and by Boemer et al. (J. Immunol., 147(1):86-95, 1991). Human antibodies (and fragments thereof) can also be produced using phage display libraries (Hoogenboom et al., J. Mol. Biol, 227:381, 1991; Marks et al., J Mol. Biol, 222:581, 1991).

Human antibodies can also be obtained from transgenic animals. For example, transgenic, mutant mice that are capable of producing a full repertoire of human antibodies, in response to immunization, have been described (see, e.g., Jakobovits et al., Proc. Natl Acad. ScL USA, 90:2551-255 (1993); Jakobovits et al., Nature, 362:255-258 (1993); Bruggermann et al., Year in Immunol., 7:33 (1993)). Specifically, the homozygous deletion of the antibody heavy chain joining region (J(H)) gene in these chimeric and germ-line mutant mice results in complete inhibition of endogenous antibody production, and the successful transfer of the human germ-line antibody gene array into such germ-line mutant mice results in the production of human antibodies upon antigen challenge. Antibodies having the desired activity are selected using Env-CD4-co-receptor complexes as described herein.

Antibody humanization techniques generally involve the use of recombinant DNA technology to manipulate the DNA sequence encoding one or more polypeptide chains of an antibody molecule. Accordingly, a humanized form of a non-human antibody (or a fragment thereof) is a chimeric antibody or antibody chain (or a fragment thereof, such as an Fv, Fab, Fab', or other antigen-binding portion of an antibody) which contains a portion of an antigen binding site from a non-human (donor) antibody integrated into the framework of a human (recipient) antibody.

To generate a humanized antibody, residues from one or more complementarity determining regions (CDRs) of a recipient (human) antibody molecule are replaced by residues from one or more CDRs of a donor (non-human) antibody molecule that is known to have desired antigen binding characteristics (e.g., a certain level of specificity and affinity for the target antigen), in some instances, Fv framework (FR) residues of the human antibody are replaced by corresponding non-human residues. Humanized antibodies may also contain residues which are found neither in the recipient antibody nor in the imported CDR or framework sequences. Generally, a humanized antibody has one or more amino acid residues introduced into it from a source which is non-human, in practice, humanized antibodies are typically human antibodies in which some CDR residues and possibly some FR residues are substituted by residues from analogous sites in rodent antibodies. Humanized antibodies generally contain at least a portion of an antibody constant region (Fc), typically that of a human antibody (Jones et al., Nature, 321:522-525 (1986), Reichmann et al., Nature, 332:323-327 (1988), and Presta, Curr. Opin. Struct. Biol, 2:593-596 (1992)).

Methods for humanizing non-human antibodies are well known in the art. For example, humanized antibodies can be generated according to the methods of Winter and co-workers (Jones et al., Nature, 321:522-525 (1986), Riechmann et al., Nature, 332:323-327 (1988), Verhoeyen et al., Science, 239:1534-1536 (1988)), by substituting rodent CDRs or CDR sequences for the corresponding sequences of a human antibody. Methods that can be used to produce humanized antibodies are also described in U.S. Pat. No. 4,816,567 (Cabilly et al.), U.S. Pat. No. 5,565,332 (Hoogenboom et al.), U.S. Pat. No. 5,721,367 (Kay et al.), U.S. Pat. No. 5,837,243 (Deo et al.), U.S. Pat. No. 5,939,598 (Kucherlapati et al.), U.S. Pat. No. 6,130,364 (Jakobovits et al.), and U.S. Pat. No. 6,180,377 (Morgan et al.).

Administration of the antibodies can be carried out as disclosed herein. Nucleic acid approaches for antibody delivery also exist. Broadly neutralizing antibodies and antibody fragments can also be administered to patients or subjects as a nucleic acid preparation (e.g., DNA or RNA) that encodes the antibody or antibody fragment, such that the patient's or subject's own cells take up the nucleic acid and produce and secrete the encoded antibody or antibody fragment. The delivery of the nucleic acid can be by any operable means, such as, for example, those disclosed herein.

In embodiments, compositions disclosed herein can be used as targets for any combinatorial technique to identify molecules or macromolecular molecules that interact with the disclosed compositions in a desired way. Also disclosed are the compositions that are identified through combinatorial techniques or screening techniques in which the compositions disclosed in SEQ ID NOS: 2, 4, 6, and 8 or portions thereof, or other novopeptides disclosed herein or portions thereof, are used as the target in a combinatorial or screening protocol.

It is understood that when using the disclosed compositions in combinatorial techniques or screening methods, molecules, such as macromolecules, may be identified that have particular desired properties such as inhibition or stimulation of the target molecule's function. The molecules identified and isolated when using the disclosed compositions are also disclosed.

Combinatorial chemistry includes but is not limited to all art-accepted methods for isolating small molecules or macromolecules that are capable of binding either a small molecule or another macromolecule, typically in an iterative process. Proteins, oligonucleotides, and sugars are examples of macromolecules. For example, oligonucleotide molecules with a given function, such as, for example, catalysis or ligand-binding, can be isolated from a complex mixture of random oligonucleotides in what has been referred to as "in vitro genetics" (Szostak, TIBS 19:89, 1992). One synthesizes a large pool of molecules bearing random and defined sequences and subjects that complex mixture, for example, approximately $10^{15}$ individual sequences in 100 μg of a 100 nucleotide RNA, to some selection and enrichment process. Through repeated cycles of affinity chromatography and PCR amplification of the molecules bound to the ligand on the column, Ellington and Szostak (1990) estimated that 1 in $10^{10}$ RNA molecules folded in such a way as to bind a small molecule dye. DNA molecules with such ligand-binding behavior have been isolated as well (Ellington and Szostak, 1992; Bock et al, 1992). Techniques aimed at similar goals exist for small organic molecules, proteins, antibodies and other macromolecules known to those of skill in the art. Screening sets of molecules for a desired activity whether based on small organic libraries, oligonucleotides, or antibodies is broadly referred to as combinatorial chemistry. Combinatorial techniques are particularly suited for defining binding interactions between molecules and for isolating molecules that have a specific binding activity, often called aptamers when the macromolecules are nucleic acids.

There are a number of methods for isolating proteins which either have de novo activity or a modified activity. For example, phage display libraries have been used to isolate numerous peptides that interact with a specific target. (See for example, U.S. Pat. Nos. 6,031,071; 5,824,520; 5,596,079; and 5,565,332 which are herein incorporated by reference at least for their material related to phage display and methods relate to combinatorial chemistry)

A method for isolating proteins that have a given function is described by Roberts and Szostak (Roberts R. W. and Szostak J. W. Proc. Natl. Acad. Sci. USA, 94(23)12997-302 (1997). This combinatorial chemistry method couples the functional power of proteins and the genetic power of nucleic acids. An RNA molecule is generated in which a puromycin molecule is covalently attached to the 3' end of the RNA molecule. An in vitro translation of this modified RNA molecule causes the correct protein, encoded by the RNA to be translated. In addition, because of the attachment of the puromycin, a peptidyl acceptor which cannot be extended, the growing peptide chain is attached to the puromycin which is attached to the RNA. Thus, the protein molecule is attached to the genetic material that encodes it. Normal in vitro selection procedures can now be employed to isolate functional peptides. Once the selection procedure for peptide function is complete traditional nucleic acid manipulation procedures are performed to amplify the nucleic acid that codes for the selected functional peptides. After amplification of the genetic material, new RNA is transcribed with puromycin at the 3' end, new peptide is translated and another functional round of selection is performed. Thus, protein selection can be performed in an iterative manner similar to nucleic acid selection techniques. The peptide which is translated is controlled by the sequence of the RNA attached to the puromycin. This sequence can be anything from a random sequence engineered for optimum translation (i.e. no stop codons etc.) or it can be a degenerate sequence of a known RNA molecule to look for improved or altered function of a known peptide. The conditions for nucleic acid amplification and in vitro translation are well known to those of ordinary skill in the art and may be performed as in Roberts and Szostak (Roberts R. W. and Szostak J. W. Proc. Natl. Acad. Sci. USA, 94(23)12997-302 (1997)).

Another combinatorial method designed to isolate peptides is described in Cohen et al. (Cohen B. A., et al., Proc. Natl. Acad. Sci. USA 95(24): 14272-7 (1998)). This method utilizes and modifies two-hybrid technology. Yeast two-hybrid systems are useful for the detection and analysis of protein-protein interactions. The two-hybrid system, initially described in the yeast Saccharomyces cerevisiae, is a powerful molecular genetic technique for identifying new regulatory molecules, specific to the protein of interest (Fields and Song, Nature 340:245-6 (1989)). Cohen et al., modified this technology so that novel interactions between synthetic or engineered peptide sequences could be identified which bind a molecule of choice. The benefit of this type of technology is that the selection is done in an intracellular environment. The method utilizes a library of peptide molecules that attach to an acidic activation domain. For example, a peptide such as FS 1-78 may be attached to a DNA binding domain of a transcriptional activation protein, such as Gal 4. By performing the two-hybrid technique on this type of system, molecules that bind peptide FS 1-78, can be identified.

Using methodology well known to those of skill in the art, in combination with various combinatorial libraries, one can isolate and characterize those small molecules or macromolecules, which bind to or interact with the desired target. The relative binding affinity of these compounds can be compared and optimum compounds identified using competitive binding studies, which are well known to those of skill in the art.

Techniques for making combinatorial libraries and screening combinatorial libraries to isolate molecules which bind a desired target are well known to those of skill in the art. Representative techniques and methods can be found in but are not limited to U.S. Pat. Nos. 5,084,824, 5,288,514, 5,449,754, 5,506,337, 5,539,083, 5,545,568, 5,556,762, 5,565,324, 5,565,332, 5,573,905, 5,618,825, 5,619,680, 5,627,210, 5,646,285, 5,663,046, 5,670,326, 5,677,195, 5,683,899, 5,688,696, 5,688,997, 5,698,685, 5,712,146, 5,721,099, 5,723,598, 5,741,713, 5,792,431, 5,807,683, 5,807,754, 5,821,130, 5,831,014, 5,834,195, 5,834,318, 5,834,588, 5,840,500, 5,847,150, 5,856,107, 5,856,496, 5,859,190, 5,864,010, 5,874,443, 5,877,214, 5,880,972, 5,886,126, 5,886,127, 5,891,737, 5,916,899, 5,919,955, 5,925,527, 5,939,268, 5,942,387, 5,945,070, 5,948,696, 5,958,702, 5,958,792, 5,962,337, 5,965,719, 5,972,719, 5,976,894, 5,980,704, 5,985,356, 5,999,086, 6,001,579, 6,004,617, 6,008,321, 6,017,768, 6,025,371, 6,030,917, 6,040,193, 6,045,671, 6,045,755, 6,060,596, and 6,061,636.

Combinatorial libraries can be made from a wide array of molecules using a number of different synthetic techniques. For example, libraries containing fused 2,4-pyrimidinediones (U.S. Pat. No. 6,025,371) dihydrobenzopyrans (U.S. Pat. Nos. 6,017,768 and 5,821,130), amide alcohols (U.S. Pat. No. 5,976,894), hydroxy-amino acid amides (U.S. Pat. No. 5,972,719) carbohydrates (U.S. Pat. No. 5,965,719), 1,4-benzodiazepin-2,5-diones (U.S. Pat. No. 5,962,337), cyclics (U.S. Pat. No. 5,958,792), biaryl amino acid amides (U.S. Pat. No. 5,948,696), thiophenes (U.S. Pat. No. 5,942,387), tricyclic tetrahydroquinolines (U.S. Pat. No. 5,925,527), benzofurans (U.S. Pat. No. 5,919,955), isoquinolines (U.S. Pat. No. 5,916,899), hydantoin and thiohydantoin (U.S. Pat. No. 5,859,190), indoles (U.S. Pat. No. 5,856,496), imidazol-pyrido-indole and imidazol-pyrido-benzothiophenes (U.S. Pat. No. 5,856,107) substituted 2-methylene-2, 3-dihydrothiazoles (U.S. Pat. No. 5,847,150), quinolines (U.S. Pat. No. 5,840,500), PNA (U.S. Pat. No. 5,831,014), containing tags (U.S. Pat. No. 5,721,099), polyketides (U.S. Pat. No. 5,712,146), morpholino-subunits (U.S. Pat. Nos. 5,698,685 and 5,506,337), sulfamides (U.S. Pat. No. 5,618, 825), and benzodiazepines (U.S. Pat. No. 5,288,514).

The disclosure hereof provides methods, compositions, and articles of manufacture useful in the formulation of prophylactic and/or therapeutic vaccines to be administered for the purpose of raising an immune response against tumor cells. The disclosure hereof extends to the composition of novopeptide-based vaccines and to methods of administration thereof. A novopeptide-based vaccine may be prepared and administered in any of the ways familiar to persons having ordinary skill in the art, including the very simple approach of preparing a vaccine comprising a novopeptide dissolved or suspended in a suitable carrier, and administering it once or at predetermined intervals to the animal or human patient to be vaccinated. However, success may also be had by other methods, and a particular approach entails genetic immunization using gene gun technology, in which a vaccine is administered in the form of a linear expression element encoding the desired novopeptide, as illustrated in the examples below. The composition of a vaccine may include both novopeptide and other components. The inclusion of multiple distinct novopeptides may prove useful in improving the level of immunoprotection conferred, and/or by conferring immunoprotection against additional tumor types, as illustrated by the examples below. In some embodiments, single novopeptides may be found to confer immunoprotection against more than one tumor type, but the repertoire of target tumor types may also be expanded by inclusion of additional novopeptides. The inclusion of multiple novopeptides is of particular utility in vaccines intended for administration in humans, due to the desirability of including a number and selection of novopeptides sufficient to ensure that at least one novopeptide in the vaccine will be capable of being displayed by at least one HLA type present in each individual in a predetermined percentage of the target population. In embodiments, two or more novopeptides may be fused into a single entity; this is a standard practice in the field of vaccine design. Novopeptide-based vaccines may include other components familiar to a person having ordinary skill in the art for improving the immunoprotection conferred or otherwise improving the efficacy and/or safety of the vaccine formulation, including without limitation and by way of example only, adjuvants and hapten carriers.

There are a number of compositions and methods which can be used to deliver nucleic acids to cells, either in vitro or in vivo. These methods and compositions can largely be broken down into two classes: viral based delivery systems and non-viral based delivery systems. For example, the nucleic acids can be delivered through a number of direct delivery systems such as electroporation, lipofection, calcium phosphate precipitation, plasmids, viral vectors, viral nucleic acids, phage nucleic acids, phages, cosmids, or via transfer of genetic material in cells or carriers such as cationic liposomes. Appropriate means for transfection, including viral vectors, chemical transfectants, or physicomechanical methods such as electroporation and direct diffusion of DNA, are described by, for example, in Wolff, J. A., et al., Science, 247, 1465-1468, (1990); and Wolff, J. A. Nature, 352, 815-818, (1991). Such methods are well known in the art and readily adaptable for use with the compositions and methods described herein. In certain cases, the methods will be modified to specifically function with large DNA molecules. Further, these methods can be used to target certain diseases and cell populations by using the targeting characteristics of the carrier.

Transfer vectors can be any nucleotide construction used to deliver genes into cells (e.g., a plasmid), or as part of a general strategy to deliver genes, e.g., as part of recombinant retrovirus or adenovirus (Ram et al. Cancer Res. 53:83-88, (1993)).

As used herein, plasmid or viral vectors are agents that transport the disclosed nucleic acids, such as peptide FS 1-78 into the cell without degradation and include a promoter yielding expression of the gene in the cells into which it is delivered. Viral vectors may include, for example, Adenovirus, Adeno-associated virus, Herpes virus, Vaccinia virus, Polio virus, AIDS virus, neuronal trophic virus, Sindbis and other RNA viruses, including these viruses with the HIV backbone. Also preferred are any viral families which share the properties of these viruses which make them suitable for use as vectors. Retroviruses include Murine Maloney Leukemia virus, MMLV, and retroviruses that express the desirable properties of MMLV as a vector. Retroviral vectors are able to carry a larger genetic payload, i.e., a transgene or marker gene, than other viral vectors, and for this reason are a commonly used vector. However, they are not as useful in non-proliferating cells. Adenovirus vectors are relatively stable and easy to work with, have high titers, and can be delivered in aerosol formulation, and can transfect non-dividing cells. Pox viral vectors are large and have several sites for inserting genes, they are thermostable and can be stored at room temperature. A preferred embodiment is a viral vector which has been engineered so as to suppress the immune response of the host organism, elicited by the viral antigens. Preferred vectors of this type will carry coding regions for Interleukin 8 or 10.

Viral vectors can have higher transaction (ability to introduce genes) abilities than chemical or physical methods to introduce genes into cells. Typically, viral vectors contain, nonstructural early genes, structural late genes, an RNA polymerase II transcript, inverted terminal repeats necessary for replication and encapsidation, and promoters to control the transcription and replication of the viral genome. When engineered as vectors, viruses typically have one or more of the early genes removed and a gene or gene/promoter cassette is inserted into the viral genome in place of the removed viral DNA. Constructs of this type can carry up to about 8 kb of foreign genetic material. The necessary functions of the removed early genes are typically supplied by cell lines which have been engineered to express the gene products of the early genes in trans.

A retrovirus is an animal virus belonging to the virus family of Retroviridae, including any types, subfamilies, genus, or tropisms. Retroviral vectors, in general, are described by Verma, L M., Retroviral vectors for gene transfer, in Microbiology-1985, American Society for Microbiology, pp. 229-232, Washington, (1985), which is incorporated by reference herein. Examples of methods for using retroviral vectors for gene therapy are described in U.S. Pat. Nos. 4,868,116 and 4,980,286; PCT applications WO 90/02806 and WO 89/07136; and Mulligan, (Science 260:926-932 (1993)); the teachings of which are incorporated herein by reference.

A retrovirus is essentially a package which has packed into it nucleic acid cargo. The nucleic acid cargo carries with it a packaging signal, which ensures that the replicated daughter molecules will be efficiently packaged within the package coat. In addition to the package signal, there are a number of molecules which are needed in cis, for the replication, and packaging of the replicated virus. Typically a retroviral genome, contains the gag, pol, and env genes which are involved in the making of the protein coat. It is the gag, pol, and env genes which are typically replaced by the foreign DNA that it is to be transferred to the target cell. Retrovirus vectors typically contain a packaging signal for incorporation into the package coat, a sequence which signals the start of the gag transcription unit, elements necessary for reverse transcription, including a primer binding site to bind the tRNA primer of reverse transcription, terminal repeat sequences that guide the switch of RNA strands during DNA synthesis, a purine rich sequence 5' to the 3' LTR that serve as the priming site for the synthesis of the second strand of DNA synthesis, and specific sequences near the ends of the LTRs that enable the insertion of the DNA state of the retrovirus to insert into the host genome. The removal of the gag, pol, and env genes allows for about 8 kb of foreign sequence to be inserted into the viral genome, become reverse transcribed, and upon replication be packaged into a new retroviral particle. This amount of nucleic acid is sufficient for the delivery of a one to many genes depending on the size of each transcript. It is preferable to include either positive or negative selectable markers along with other genes in the insert.

Since the replication machinery and packaging proteins in most retroviral vectors have been removed (gag, pol, and env), the vectors are typically generated by placing them into a packaging cell line. A packaging cell line is a cell line which has been transfected or transformed with a retrovirus that contains the replication and packaging machinery, but lacks any packaging signal. When the vector carrying the DNA of choice is transfected into these cell lines, the vector containing the gene of interest is replicated and packaged into new retroviral particles, by the machinery provided in cis by the helper cell. The genomes for the machinery are not packaged because they lack the necessary signals.

The construction of replication-defective adenoviruses has been described (Berkner et al., J. Virology 61:1213-1220 (1987); Massie et al., Mol. Cell. Biol. 6:2872-2883 (1986); Haj-Ahmad et al., J. Virology 51:261-21 A (1986); Davidson et al., J. Virology 61:1226-1239 (1987); Zhang "Generation and identification of recombinant adenovirus by liposome-mediated transfection and PCR analysis" BioTechniques 15:868-872 (1993)). The benefit of the use of these viruses as vectors is that they are limited in the extent to which they can spread to other cell types, since they can replicate within an initial infected cell, but are unable to form new infectious viral particles. Recombinant adenoviruses have been shown to achieve high efficiency gene transfer after direct, in vivo delivery to airway epithelium, hepatocytes, vascular endothelium, CNS parenchyma and a number of other tissue sites (Morsy, J. Clin. Invest. 92:1580-1586 (1993); Kirshenbaum, J. Clin. Invest. 92:381-387 (1993); Roessler, J Clin. Invest. 92:1085-1092 (1993); Moullier, Nature Genetics 4:154-159 (1993); La Salle, Science 259:988-990 (1993); Gomez-Foix, J Biol. Chem. 267:25129-25134 (1992); Rich, Human Gene Therapy 4:461-476 (1993); Zabner, Nature Genetics 6:75-83 (1994); Guzman, Circulation Research 73:1201-1207 (1993); Bout, Human Gene Therapy 5:3-10 (1994); Zabner, Cell 75:207-216 (1993); Caillaud, Eur. J. Neuroscience 5:1287-1291 (1993); and Ragot, J. Gen. Virology 74:501-507 (1993)). Recombinant adenoviruses achieve gene transduction by binding to specific cell surface receptors, after which the virus is internalized by receptor-mediated endocytosis, in the same manner as wild type or replication-defective adenovirus (Chardonnet and Dales, Virology 40:462-477 (1970); Brown and Burlingham, J. Virology 12:386-396 (1973); Svensson and Persson, J. Virology 55:442-449 (1985); Seth, et al., J. Virol. 51:650-655 (1984); Seth, et al., Mol. Cell. Biol. 4:1528-1533 (1984); Varga et al., J. Virology 65:6061-6070 (1991); Wickham et al., Cell 73:309-319 (1993)).

A viral vector can be one based on an adenovirus which has had the E1 gene removed and these virions are generated in a cell line such as the human 293 cell line. In another embodiment both the E1 and E3 genes are removed from the adenovirus genome.

Another type of viral vector is based on an adeno-associated virus (AAV). This defective parvovirus is a preferred vector because it can infect many cell types and is nonpathogenic to humans. AAV type vectors can transport about 4 to 5 kb and wild type AAV is known to stably insert into chromosome 19. Vectors which contain this site specific integration property are preferred. An especially preferred embodiment of this type of vector is the P4.1 C vector produced by Avigen, San Francisco, Calif., which can contain the herpes simplex virus thymidine kinase gene, HSV-tk, and/or a marker gene, such as the gene encoding the green fluorescent protein, GFP.

In another type of AAV virus, the AAV contains a pair of inverted terminal repeats (ITRs) which flank at least one cassette containing a promoter which directs cell-specific expression operably linked to a heterologous gene. Heterologous in this context refers to any nucleotide sequence or gene which is not native to the AAV or B19 parvovirus.

Typically the AAV and B 19 coding regions have been deleted, resulting in a safe, non-cytotoxic vector. The AAV ITRs, or modifications thereof, confer infectivity and site-specific integration, but not cytotoxicity, and the promoter directs cell-specific expression. U.S. Pat. No. 6,261,834 is herein incorporated by reference for material related to the AAV vector.

The disclosed vectors thus provide DNA molecules which are capable of integration into a mammalian chromosome without substantial toxicity.

The inserted genes in viral and retroviral vectors usually contain promoters, and/or enhancers to help control the expression of the desired gene product. A promoter is generally a sequence or sequences of DNA that function when in a relatively fixed location in regard to the transcription start site. A promoter contains core elements required for basic interaction of RNA polymerase and transcription factors, and may contain upstream elements and response elements.

Molecular genetic experiments with large human herpes viruses have provided a means whereby large heterologous DNA fragments can be cloned, propagated and established in cells permissive for infection with herpes viruses (Sun et al., Nature Genetics 8: 33-41, 1994; Cotter and Robertson, Curr Opin Mol Ther 5: 633-644, 1999). These large DNA viruses (herpes simplex virus (HSV) and Epstein-Barr virus (EBV), have the potential to deliver fragments of human heterologous DNA>150 kb to specific cells. EBV recombinants can maintain large pieces of DNA in the infected B-cells as episomal DNA. Individual clones carried human genomic inserts up to 330 kb appeared genetically stable the maintenance of these episomes requires a specific EBV nuclear protein, EBNA1, constitutively expressed during infection with EBV. Additionally, these vectors can be used for transfection, where large amounts of protein can be generated transiently in vitro. Herpes virus amplicon systems are also being used to package pieces of DNA>220 kb and to infect cells that can stably maintain DNA as episomes.

Other useful systems include, for example, replicating and host-restricted non-replicating Vaccinia virus vectors.

In embodiments, compositions disclosed herein can be delivered to target cells in a variety of ways. For example, the compositions can be delivered through electroporation, or through lipofection, or through calcium phosphate precipitation. The delivery mechanism chosen will depend in part on the type of cell targeted and whether the delivery is occurring for example in vivo or in vitro.

Thus, the compositions can comprise, in addition to the disclosed FS 1-78, FS 6-21, FS SMC1A, and other disclosed novopeptides, vectors, such as, for example, lipids such as liposomes, which may include cationic liposomes (e.g., DOTMA, DOPE, DC-cholesterol) and/or anionic liposomes. Liposomes can further comprise proteins to facilitate targeting a particular cell, if desired. Administration of a composition comprising a compound and a cationic liposome can be administered to the blood afferent to a target organ or inhaled into the respiratory tract to target cells of the respiratory tract. Regarding liposomes, see, e.g., Brigham et al. Am. J. Resp. Cell. Mol. Biol. 1:95-100 (1989); Feigner et al. Proc. Natl. Acad. Sci USA 84:7413-7417 (1987); U.S. Pat. No. 4,897,355. Furthermore, the compound can be administered as a component of a microcapsule that can be targeted to specific cell types, such as macrophages, or where the diffusion of the compound or delivery of the compound from the microcapsule is designed for a specific rate or dosage.

In the methods described above which include the administration and uptake of exogenous DNA into the cells of a subject (i.e., gene transduction or transfection), delivery of the compositions to cells can be via a variety of mechanisms. As one example, delivery can be via a liposome, using commercially available liposome preparations such as LIPOFECTIN, LIPOFECTAMINE (GIBCO-BRL, Inc., Gaithersburg, Md.), SUPERFECT (Qiagen, Inc. Hilden, Germany) and TRANSFECTAM (Promega Biotec, Inc., Madison, Wis.), as well as other liposomes developed according to procedures standard in the art. In addition, the disclosed nucleic acid or vector can be delivered in vivo by electroporation, the technology for which is available from Genetronics, Lie. (San Diego, Calif.) as well as by means of a SONOPORATION machine (hnaRx Pharmaceutical Corp., Tucson, Ariz.).

In embodiments, the materials may be in solution or suspension (for example, incorporated into microparticles, liposomes, or cells). These may be targeted to a particular cell type via antibodies, receptors, or receptor ligands. The following references are examples of the use of this technology to target specific proteins to tumor tissue (Senter, et al., Bioconjugate Chem., 2:447-451, (1991); Bagshawe, K. D., Br. J. Cancer, 60:275-281, (1989); Bagshawe, et al., Br. J. Cancer, 58:700-703, (1988); Senter, et al., Bioconjugate Chem., 4:3-9, (1993); Battelli, et al., Cancer Immunol. Immunother., 35:421-425, (1992); Pietersz and McKenzie, Immunolog. Reviews, 129:57-80, (1992); and Roffler, et al., Biochem. Pharmacol, 42:2062-2065, (1991)). These techniques can be used for a variety of other specific cell types. Vehicles such as "stealth" and other antibody conjugated liposomes (including lipid mediated drug targeting to colonic carcinoma), receptor mediated targeting of DNA through cell specific ligands, lymphocyte directed tumor targeting, and highly specific therapeutic retroviral targeting of murine glioma cells in vivo. The following references are examples of the use of this technology to target specific proteins to tumor tissue (Hughes et al., Cancer Research, 49:6214-6220, (1989); and Litzinger and Huang, Biochimica et Biophysica Acta, 1104:179-187, (1992)). In general, receptors are involved in pathways of endocytosis, either constitutive or ligand induced. These receptors cluster in clathrin-coated pits, enter the cell via clathrin-coated vesicles, pass through an acidified endosome in which the receptors are sorted, and then either recycle to the cell surface, become stored intracellularly, or are degraded in lysosomes. The internalization pathways serve a variety of functions, such as nutrient uptake, removal of activated proteins, clearance of macromolecules, opportunistic entry of viruses and toxins, dissociation and degradation of ligand, and receptor-level regulation. Many receptors follow more than one intracellular pathway, depending on the cell type, receptor concentration, type of ligand, ligand valency, and ligand concentration. Molecular and cellular mechanisms of receptor-mediated endocytosis have been reviewed (Brown and Greene, DNA and Cell Biology 10:6, 399-409 (1991)).

Nucleic acids that are delivered to cells which are to be integrated into the host cell genome typically contain integration sequences. These sequences are often viral related sequences, particularly when viral based systems are used. These viral integration systems can also be incorporated into nucleic acids which are to be delivered using a non-nucleic acid based system of delivery, such as a liposome, so that the nucleic acid contained in the delivery system can become integrated into the host genome.

Other general techniques for integration into the host genome include, for example, systems designed to promote homologous recombination with the host genome. These systems typically rely on sequence flanking the nucleic acid to be expressed that has enough homology with a target sequence within the host cell genome that recombination between the vector nucleic acid and the target nucleic acid takes place, causing the delivered nucleic acid to be integrated into the host genome. These systems and the methods necessary to promote homologous recombination are known to those of skill in the art.

In embodiments, compositions disclosed herein can be administered in a pharmaceutically acceptable carrier and can be delivered to the subject's cells in vivo and/or ex vivo by a variety of mechanisms well known in the art (e.g., uptake of naked DNA, liposome fusion, intramuscular injection of DNA via a gene gun, endocytosis and the like).

If ex vivo methods are employed, cells or tissues can be removed and maintained outside the body according to standard protocols well known in the art. The compositions can be introduced into the cells via any gene transfer mechanism, such as, for example, calcium phosphate mediated gene delivery, electroporation, microinjection or proteoliposomes. The transduced cells can then be infused (e.g., in a pharmaceutically acceptable carrier) or homotopically transplanted back into the subject per standard methods for the cell or tissue type. Standard methods are known for transplantation or infusion of various cells into a subject.

The nucleic acids that are delivered to cells typically contain expression controlling systems. For example, the inserted genes in viral and retroviral systems usually contain promoters, and/or enhancers to help control the expression of the desired gene product. A promoter is generally a sequence or sequences of DNA that function when in a relatively fixed location in regard to the transcription start site. A promoter contains core elements required for basic interaction of RNA polymerase and transcription factors, and may contain upstream elements and response elements.

Promoters controlling transcription from vectors in mammalian host cells may be obtained from various sources, for example, the genomes of viruses such as: polyoma, Simian Virus 40 (SV40), adenovirus, retroviruses, hepatitis-B virus and most preferably cytomegalovirus, or from heterologous mammalian promoters, e.g. beta actin promoter. The early and late promoters of the SV40 virus are conveniently obtained as an SV40 restriction fragment which also contains the SV40 viral origin of replication (Fiers et al., Nature, 273: 113 (1978)). The immediate early promoter of the human cytomegalovirus is conveniently obtained as a HmdlH E restriction fragment (Greenway, P J. et al., Gene 18: 355-360 (1982)). Of course, promoters from the host cell or related species also are useful herein.

Enhancer generally refers to a sequence of DNA that functions at no fixed distance from the transcription start site and can be either 5' (Laimins, L. et al., Proc. Natl. Acad. ScL 78:993 (1981)) or 3' (Lusky, M. L., et al., Mol. Cell Bio. 3: 1108 (1983)) to the transcription unit. Furthermore, enhancers can be within an intron (Banerji, J. L. et al., Cell 33: 729 (1983)) as well as within the coding sequence itself (Osborne, T. F., et al., Mol. Cell Bio. 4: 1293 (1984)). They are usually between 10 and 300 bp in length, and they function in cis. Enhancers function to increase transcription from nearby promoters. Enhancers also often contain response elements that mediate the regulation of transcription. Promoters can also contain response elements that mediate the regulation of transcription. Enhancers often determine the regulation of expression of a gene. While many enhancer sequences are now known from mammalian genes (globin, elastase, albumin, -fetoprotein and insulin), typically one will use an enhancer from a eukaryotic cell virus for general expression. Preferred examples are the SV40 enhancer on the late side of the replication origin (bp 100-270), the cytomegalovirus early promoter enhancer, the polyoma enhancer on the late side of the replication origin, and adenovirus enhancers.

The promoter and/or enhancer may be specifically activated either by light or specific chemical events which trigger their function. Systems can be regulated by reagents such as tetracycline and dexamethasone. There are also ways to enhance viral vector gene expression by exposure to irradiation, such as gamma irradiation, or alkylating chemotherapy drugs.

In certain embodiments the promoter and/or enhancer region can act as a constitutive promoter and/or enhancer to maximize expression of the region of the transcription unit to be transcribed, in certain constructs the promoter and/or enhancer region be active in all eukaryotic cell types, even if it is only expressed in a particular type of cell at a particular time. A preferred promoter of this type is the CMV promoter (650 bases). Other preferred promoters are SV40 promoters, cytomegalovirus (full length promoter), and retroviral vector LTF.

It has been shown that regulatory elements can be cloned and used to construct expression vectors that are selectively expressed in specific cell types such as melanoma cells. The glial fibrillary acetic protein (GFAP) promoter has been used to selectively express genes in cells of glial origin.

Expression vectors used in eukaryotic host cells (yeast, fungi, insect, plant, animal, human or nucleated cells) may also contain sequences necessary for the termination of transcription which may affect mRNA expression. These regions are transcribed as polyadenylated segments in the untranslated portion of the mRNA encoding tissue factor protein. The 3' untranslated regions also include transcription termination sites. It is preferred that the transcription unit also contains a polyadenylation region. One benefit of this region is that it increases the likelihood that the transcribed unit will be processed and transported like mRNA. The identification and use of polyadenylation signals in expression constructs is well established. It is preferred that homologous polyadenylation signals be used in the transgene constructs, in certain transcription units, the polyadenylation region is derived from the SV40 early polyadenylation signal and consists of about 400 bases. It is also preferred that the transcribed units contain other standard sequences alone or in combination with the above sequences improve expression from, or stability of, the construct.

In embodiments, viral vectors may include nucleic acid sequence encoding a marker product. This marker product is used to determine if the gene has been delivered to the cell and once delivered is being expressed. Example marker genes are the E. coli lacZ gene, which encodes P-galactosidase, and green fluorescent protein.

In some embodiments a marker may be a selectable marker. Examples of suitable selectable markers for mammalian cells are dihydrofolate reductase (DHFR), thymidine kinase, neomycin, neomycin analog G418, hydromycin, and puromycin. When such selectable markers are successfully transferred into a mammalian host cell, the transformed mammalian host cell can survive if placed under selective pressure. There are two widely used distinct categories of selective regimes. The first category is based on a cell's metabolism and the use of a mutant cell line which lacks the ability to grow independent of a supplemented media. Two examples are: CHO DHFR-cells and mouse LTK-cells. These cells lack the ability to grow without the addition of such nutrients as thymidine or hypoxanthine. Because these cells lack certain genes necessary for a complete nucleotide synthesis pathway, they cannot survive unless the missing nucleotides are provided in a supplemented media. An alternative to supplementing the media is to introduce an intact DHFR or TK gene into cells lacking the respective genes, thus altering their growth requirements. Individual cells which were not transformed with the DHFR or TK gene will not be capable of survival in non-supplemented media.

A second category is dominant selection, which refers to a selection scheme that may be used in any cell type and does not require the use of a mutant cell line. These schemes typically use a drug to arrest growth of a host cell. Those cells which have a novel gene would express a protein conveying drug resistance and would survive the selection. Examples of such dominant selection use the drugs neomycin, (Southern P. and Berg, P., J. Molec. Appl. Genet. 1: 327 (1982)), mycophenolic acid, (Mulligan, R. C. and Berg, P. Science 209: 1422 (1980)) or hygromycin, (Sugden, B. et al., Mol. Cell. Biol. 5: 410-413 (1985)). These three examples employ bacterial genes under eukaryotic control to convey resistance to the appropriate drug G418 or neomycin (geneticin), xgpt (mycophenolic acid) or hygromycin, respectively. Others include the neomycin analog G418 and puramycin.

In embodiments, compositions disclosed herein may be administered in vivo in a pharmaceutically acceptable carrier. By "pharmaceutically acceptable" is meant a material that is not biologically or otherwise undesirable, i.e., the material may be administered to a subject, along with the nucleic acid or vector, without causing unacceptable biological effects or interacting in a deleterious manner with other components of the pharmaceutical composition in which it is contained. The carrier may be selected to minimize any degradation of the active ingredient and to minimize any adverse side effects in the subject, as would be well known to one of skill in the art.

In embodiments, compositions disclosed herein may be administered orally, parenterally (e.g., intravenously), by intramuscular injection, by intraperitoneal injection, transdermally, extracorporeally, topically or the like, including topical intranasal administration or administration by inhalant. As used herein, "topical intranasal administration" means delivery of the compositions into the nose and nasal passages through one or both of the nares and can comprise delivery by a spraying mechanism or droplet mechanism, or through aerosolization of the nucleic acid or vector. Administration of the compositions by inhalant can be through the nose or mouth via delivery by a spraying or droplet mechanism. Delivery can also be directly to any area of the respiratory system (e.g., lungs) via intubation. The exact amount of the compositions required will vary from subject to subject, depending on the species, age, weight and general condition of the subject, the severity of the allergic disorder being treated, the particular nucleic acid or vector used, its mode of administration and the like. Thus, it is not possible to specify an exact amount for every composition. However, an appropriate amount can be determined by one of ordinary skill in the art using only routine experimentation given the teachings herein.

Parenteral administration of the composition, if used, is generally characterized by injection. Injectables can be prepared in conventional forms, either as liquid solutions or suspensions, solid forms suitable for solution of suspension in liquid prior to injection, or as emulsions. A more recently revised approach for parenteral administration involves use of a slow release or sustained release system such that a constant dosage is maintained. See, e.g., U.S. Pat. No. 3,610,795, which is incorporated by reference herein.

In embodiments, materials to be administered may be in solution or suspension (for example, incorporated into microparticles, liposomes, or cells). These may be targeted to a particular cell type via antibodies, receptors, or receptor ligands. The following references are examples of the use of this technology to target specific proteins to tumor tissue (Senter, et al., Bioconjugate Chem., 2:447-451, (1991); Bagshawe, K. D., Br. J. Cancer, 60:275-281, (1989); Bagshawe, et al., Br. J. Cancer, 58:700-703, (1988); Senter, et al., Bioconjugate Chem., 4:3-9, (1993); Battelli, et al., Cancer Immunol. Immunother., 35:421-425, (1992); Pietersz and McKenzie, Immunolog. Reviews, 129:57-80, (1992); and Roffler, et al., Biochem. Pharmacol, 42:2062-2065, (1991)). Vehicles such as "stealth" and other antibody conjugated liposomes (including lipid mediated drug targeting to colonic carcinoma), receptor mediated targeting of DNA through cell specific ligands, lymphocyte directed tumor targeting, and highly specific therapeutic retroviral targeting of murine glioma cells in vivo. The following references are examples of the use of this technology to target specific proteins to tumor tissue (Hughes et al., Cancer Research, 49:6214-6220, (1989); and Litzinger and Huang, Biochimica et Biophysica Acta, 1104:179-187, (1992)). In general, receptors are involved in pathways of endocytosis, either constitutive or ligand induced. These receptors cluster in clathrin-coated pits, enter the cell via clathrin-coated vesicles, pass through an acidified endosome in which the receptors are sorted, and then either recycle to the cell surface, become stored intracellularly, or are degraded in lysosomes. The internalization pathways serve a variety of functions, such as nutrient uptake, removal of activated proteins, clearance of macromolecules, opportunistic entry of viruses and toxins, dissociation and degradation of ligand, and receptor-level regulation. Many receptors follow more than one intracellular pathway, depending on the cell type, receptor concentration, type of ligand, ligand valency, and ligand concentration. Molecular and cellular mechanisms of receptor-mediated endocytosis have been reviewed (Brown and Greene, DNA and Cell Biology 10:6, 399-409 (1991)).

In embodiments, compositions disclosed herein, including antibodies, can be used therapeutically in combination with a pharmaceutically acceptable carrier. Suitable carriers and their formulations are described in Remington: The Science and Practice of Pharmacy (19th ed.) ed. A. R. Gennaro, Mack Publishing Company, Easton, Pa. 1995. Typically, an appropriate amount of a pharmaceutically-acceptable salt is used in the formulation to render the formulation isotonic. Examples of the pharmaceutically-acceptable carrier include, but are not limited to, saline, Ringer's solution and dextrose solution. The pH of the solution is preferably from about 5 to about 8, and more preferably from about 7 to about 7.5. Further carriers include sustained release preparations such as semipermeable matrices of solid hydrophobic polymers containing the antibody, which matrices are in the form of shaped articles, e.g., films, liposomes or microparticles. It will be apparent to those persons skilled in the art that certain carriers may be more preferable depending upon, for instance, the route of administration and concentration of composition being administered.

Pharmaceutical carriers are known to those skilled in the art. These most typically would be standard carriers for administration of drugs to humans, including solutions such as sterile water, saline, and buffered solutions at physiological pH. The compositions can be administered intramuscularly or subcutaneously. Other compounds will be administered according to standard procedures used by those skilled in the art.

In embodiments, compositions disclosed herein may be administered in or with pharmaceutical compositions, which may include carriers, thickeners, diluents, buffers, preservatives, surface active agents and the like in addition to the molecule of choice. Pharmaceutical compositions may also include one or more active ingredients such as antimicrobial agents, anti-inflammatory agents, anesthetics, and the like.

In embodiments, pharmaceutical compositions may be administered in a number of ways depending on whether local or systemic treatment is desired, and on the area to be treated. Administration may be topically (including ophthalmically, vaginally, rectally, intranasally), orally, by inhalation, or parenterally, for example by intravenous drip, subcutaneous, intraperitoneal or intramuscular injection. The disclosed antibodies can be administered intravenously, intraperitoneally, intramuscularly, subcutaneously, intracavity, or transdermally.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

Formulations for topical administration may include ointments, lotions, creams, gels, drops, suppositories, sprays, liquids and powders. Conventional pharmaceutical carriers, aqueous, powder or oily bases, thickeners and the like may be necessary or desirable.

Compositions for oral administration include powders or granules, suspensions or solutions in water or non-aqueous media, capsules, sachets, or tablets. Thickeners, flavorings, diluents, emulsifiers, dispersing aids or binders may be desirable.

In embodiments, compositions may be administered as or with a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

In embodiments, effective dosages and schedules for administering compositions disclosed herein may be determined empirically, and making such determinations is within the skill in the art. In embodiments, a dosage range for the administration of the compositions may include a dosage large enough to produce a desired effect in which the symptoms/disorder are/is affected. In embodiments, a dosage should preferably not be so large as to cause adverse side effects, such as unwanted cross-reactions, anaphylactic reactions, and the like, although adverse effects cannot always be avoided and may be outweighed by the benefits sought. In embodiments, dosage may vary with the age, condition, sex and extent of the disease in the patient, route of administration, or whether other drugs are included in the regimen, and can be determined by one of skill in the art. The dosage can be adjusted by the individual physician in the event of any counterindications. Dosage can vary, and can be administered in one or more dose administrations daily, or according to any dosing schedule found beneficial. Guidance can be found in the literature for appropriate dosages for given classes of pharmaceutical products. For example, guidance in selecting appropriate doses for antibodies can be found in the literature on therapeutic uses of antibodies, e.g., Handbook of Monoclonal Antibodies, Ferrone et al., eds., Noges Publications, Park Ridge, N.J., (1985) ch. 22 and pp. 303-357; Smith et al., Antibodies in Human Diagnosis and Therapy, Haber et al., eds., Raven Press, New York (1977) pp. 365-389. A typical daily dosage of an antibody used alone might range from about 1 mg/kg to up to 100 mg/kg of body weight or more per day, depending on the factors mentioned above.

Following administration of a disclosed composition, such as a vaccine or an antibody, for treating, inhibiting, or preventing a cancer, the efficacy of the therapy or prophylaxis can be assessed in various ways well known to the skilled practitioner. For instance, one of ordinary skill in the art will understand that a composition, such as a vaccine or an antibody, disclosed herein is efficacious in treating, inhibiting, or preventing a cancer in a subject by observing that the composition reduces tumor growth or prevents a further increase in tumor size.

Also disclosed herein are embodiments of kits that are drawn to reagents that can be used in practicing the methods disclosed herein. The kits can include any reagent or combination of reagent discussed herein or that would be understood to be required or beneficial in the practice of the disclosed methods. For example, the kits could include primers to perform the amplification reactions discussed in certain embodiments of the methods, as well as the buffers and enzymes required to use the primers as intended. For example, disclosed is a kit for assessing a subject's risk for acquiring prostate cancer, comprising the peptides set forth in SEQ ID Nos: 2, 4, and 8.

In embodiments, there is provided an anti-cancer vaccine, to be administered prophylactically or therapeutically or both to a population comprising a plurality of mammalian subjects in accordance with the disclosure hereof, useful for reducing the susceptibility of the population to at least one cancer. (The use of the word 'vaccine' is not intended to limit the disclosure hereof to a particular mechanism of action; although there is sound theoretical and experimental support for an immunological basis for their effectiveness, the disclosure hereof extends to the disclosed compositions and methods regardless of their mechanism of action.) Reducing the susceptibility of the population to at least one cancer may include any improvement in the health status of at least one subject relative to at least one cancer, such as, by way of example only, a temporary or permanent reduction in the likelihood of at least one member of the population contracting a cancer; a temporary or permanent reduction in the incidence rate of a cancer in the population; a temporary or permanent improvement in the average severity, amenability to treatment, and/or average prognosis of the cancer in the population; a temporary or permanent reduction in a rate of tumor progression in at least one member of the population; an improvement in the efficacy of a cancer treatment in at least one member of the population; and/or an improvement in a survival rate in the population relative to at least one cancer; and/or an improvement in the survival time of at least one member of the population after contracting a cancer.

In some embodiments, an anti-cancer vaccine may include at least one peptide component. In embodiments, a peptide component of an anti-cancer vaccine may include a continuous synthetic or recombinant amino acid chain, from about 8 to about 40 amino acids in length, having at least 75%, or 80%, or 85%, or 90%, or 95%, or 99% sequence identity over its length with a continuous amino acid sequence (or continuous portion thereof) according to the formula D1-D2, wherein D1 and D2 are amino acid sequences each encoded by a different nucleic acid sequence or portion thereof of a genome of a mammalian species for which the vaccine is intended, wherein D1 is read in its wild-type reading frame, and D2 is read in a non-wild-type reading frame. In some embodiments, the nucleic acid sequence encoding D2 is not contiguous, in the genome of the mammalian species, with the nucleic acid sequence encoding D1; for example, the nucleic acid sequence encoding D2 may comprise all or part of a different gene, a different exon, a non-coding region, a different nucleic acid strand, and/or a different chromosome, relative to the nucleic acid sequence encoding D1. A synthetic or recombinant amino acid chain may include and extend to any non-naturally occurring amino acid chain, such as, for example, an amino acid chain produced by chemical synthesis, by an expression system, by in vitro translation, by chemical, physical, or other isolation, by inducing expression in a host cell such as by genetic immunization, or by any other method resulting in an amino chain having a sequence and/or other characteristics not obtainable from nature.

It will be apparent to persons of skill in the art that the functional characteristics of a peptide may typically be retained in whole or part by other peptides having similar or related sequences, such as where insertions, deletions, and/or substitutions are made that are not so significant in character or degree to disrupt the interactions giving rise to the function of interest. The disclosure hereof extends to anti-cancer vaccine peptide components comprising peptide sequences within the range of similarity to the disclosed sequences that would be regarded by persons of skill in the art as of probable full or partial functional similarity to any of the disclosed sequences. In some embodiments, an anti-cancer vaccine may include in lieu of a peptide component as disclosed herein, a biochemically acceptable substitute. A biochemically acceptable substitute may include any molecular entity that a person of skill in the art would regard as functionally similar or equivalent to a peptide component disclosed herein, such as, for example, a peptide having, relative to a peptide component disclosed herein, an alignment score, obtained according to an art-recognized sequence alignment method, that a person of skill in the art would regard as implying likely full or partial functional similarity, or a peptide differing from a peptide component disclosed herein by reason of fewer than 10, or fewer than 7, or fewer than 5, or fewer than 4, or fewer than 3, or fewer than 2, or fewer than 1 conservative substitutions, or any of the other molecular entities disclosed elsewhere herein or recognized in the art as fully or partially functionally equivalent in their biochemical characteristics to a peptide component disclosed herein.

In embodiments, there is provided a method of reducing the susceptibility of a population including a plurality of mammalian subjects to at least one cancer, the method including administering to at least one member of the population an effective dose of an anti-cancer vaccine.

In some embodiments an anti-cancer vaccine may be administered by any method of administration operable to expose the organism to be vaccinated to an effective dose of the vaccine, such as, for example, by subcutaneous, intramuscular, or other direct administration of an embodiment of the anti-cancer vaccine including one or more peptide components in a pharmaceutically acceptable carrier, and optionally accompanied by a suitable adjuvant, according to an effective administration protocol. In some embodiments, an anti-cancer composition may be administered as a genetic vaccine, and/or may include, for example, a nucleic acid sequence encoding one or more peptide components. In some embodiments, the nucleic acid sequence may form part of a vector, plasmid, LEE, or other entity whereby a cell of the mammalian subject may be induced to express the peptide component. The disclosure hereof extends to nucleic acid sequences adapted for administration by genetic immunization and/or for inclusion in a vector, plasmid, LEE, or other entity or carrier adapted for genetic immunization or for expression in an expression system, encoding any of the peptide components disclosed herein, and to vectors, plasmids, LEE's, or other entities comprising the nucleic acid sequences. By way of example, the nucleic acid sequences of SEQ ID NO:1, SEQ ID NO:3, SEQ ID NO:5, SEQ ID NO:231, SEQ ID NO:233, SEQ ID NO:235, SEQ ID NO:237, SEQ ID NO:239, and SEQ ID NO:241 are disclosed as nucleic acid sequences that in whole or part encode the peptide component sequences SEQ ID NO:294, SEQ ID NO:4, SEQ ID NO:6, SEQ ID NO:232, SEQ ID NO:234, SEQ ID NO:236, SEQ ID NO:238, SEQ ID NO:240, and SEQ ID NO:242, respectively.

An effective dose of an anti-cancer vaccine may be any quantity operable to reduce the susceptibility of a mammalian subject to which an anti-cancer vaccine is administered, or a population to which the subject belongs, to at least one cancer. In some embodiments, an effective dose of an anti-cancer vaccine may include any quantity operable to expose the immune system of a subject to a peptide component thereof. By way of example only, an effective dose of an anti-cancer vaccine administered in the form of synthetic or recombinant peptides in a carrier may be a quantity operable to produce in the subject an antibody response, which may be detected, for example, by an ELISA or other assay confirming the presence in serum of the subject antibodies specific for one or more of the peptide components. In some embodiments, for example, an effective dose of an anti-cancer vaccine for administration in the form of peptides in or on a carrier may be at least 50 µg KLH-conjugated peptide, or at least 100 µg KLH-conjugated peptide, or at least 200 µg KLH-conjugated peptide. By way of example only, an effective dose of an anti-cancer vaccine administered in the form of a genetic vaccine including nucleic acid(s) encoding the peptide components may be a quantity operable to cause expression of at least one peptide component in a cell, such as, for example, an antigen presenting cell, of the subject, and display of the peptide component or a fragment thereof in MHC. In embodiments, for example, an effective dose for genetic immunization by gene gun may be at least 20 ng per bullet, or at least 50 ng per bullet, or at least 100 ng per bullet, in at least one shot, or at least two shots, or at least four shots, or at least six shots.

In some embodiments of an anti-cancer vaccine, it may be found useful to select peptide components having a cancer association ratio of at least 2:1, or at least 3:1, or at least 4:1, or at least 5:1. A cancer association ratio of a peptide component may be employed as a measure of the presence of the peptide component (or its homolog or equivalent) in cancer tissue relative to its presence in comparable non-cancerous tissue. Thus a peptide that presents an epitope abundantly present in identical or recognizable form in cancerous tissue and rarely or never present in comparable non-cancerous tissue would have a relatively high cancer association ratio, making it a desirable candidate as a peptide component of a vaccine. In embodiments, the cancer association ratio of a peptide component may be measured or estimated in any way operable to yield an informative indication, of the degree of presence of an epitope equivalent or immunologically similar to an epitope of the peptide component in a cancerous tissue of interest, relative to a comparable non-cancerous tissue. In some embodiments, a cancer association ratio may preferably be determined and/or computed in a manner that would be regarded by a person of skill in the art as providing acceptable statistical and experimental validity. In some embodiments, for example, a cancer association ratio may be estimated by measuring or estimating a level of expression of the sequence (or relevant portion or homolog thereof) in mRNA transcripts in cells of a tissue sample of the cancer type of interest, making a similar measurement or estimate in cells of a sample of non-cancerous tissue of similar or comparable type, and taking the ratio of the two. In some embodiments, a cancer association ratio may be measured or estimated as an odds ratio, computed as disclosed in Example 5 herein. In some embodiments, a cancer association ratio may be measured or estimated by determining the prevalence of the sequence (or relevant portion or homolog thereof) in a cancer EST library or database, as compared to a non-cancer EST library or database. In some embodiments wherein it would be apparent from art-accepted principles of molecular biology that the sequence of interest would not be expressed by normal cells, a cancer association ratio may be assumed to be >>1 if significant presence of the sequence is confirmed in the cancerous tissue of interest, or in mRNA or cDNA thereof.

In some embodiments, of an anti-cancer vaccine, it may be found useful to select peptide components having a cancer serum recognition percentage of at least 40%, or at least 60%, or at least 80%. A cancer serum recognition percentage may be determined or estimated in any way operable to provide an informative and reasonably repeatable measure, in a mammalian population cohort consisting of subjects having a cancer, of the percentage of subjects whose serum shows specific antibody reactivity to the peptide component or a portion or homolog thereof. In embodiments, such reactivity may be measured or estimated in any operable way, such as, for example, by ELISA or by microarray assay. In embodiments, the population cohort should preferably include a representative selection and quantity of subjects, such as, for example, at least 10, or at least 20, or at least 30 independent samples from distinct cancerous individuals. In embodiments, a cancer serum recognition percentage should preferably be determined and/or computed in a manner that would be regarded by a person of skill in the art as providing acceptable statistical and experimental validity.

In some embodiments, there is provided a peptide component of an anti-cancer vaccine to be administered to a mammalian subject belonging to a first mammalian species, having a sequence determined by homology to a peptide component whose utility has been assessed relative to a second mammalian species recognized in the art as an appropriate model with respect to the first mammalian species. Thus, by way of example only, a peptide component for use in a human vaccine may have a sequence determined in whole or part by reference to a peptide component that has been assessed in a mouse model, by combining the non-frame-shifted human sequence corresponding to the homologous gene or gene fragment comprising the non-frame-shifted portion of the mouse peptide component with the frame-shifted human sequence corresponding to the nucleic acid sequence homologous to the gene or gene fragment from which the frame-shifted portion of the mouse peptide component is transcribed. Accordingly, where peptide components are disclosed herein corresponding to novo-peptides relating to human, mouse, or dog sequences, the disclosure hereof extends to the homologous counterparts of these peptide components in the others of these species. Thus, for example, in addition to the mouse-targeted sequences FS 1-78 (SEQ ID NO: 294), FS 6-21 (SEQ ID NO: 291), FS SMC1A (SEQ ID NO: 297), FS RBM (SEQ ID NO: 232), and FS THAP2 (SEQ ID NO: 238) as disclosed, also disclosed herein are the corresponding sequences for human (SEQ ID NO: 293, SEQ ID NO: 290, SEQ ID NO: 296, SEQ ID NO: 234, and SEQ ID NO: 240, respectively) and dog (SEQ ID NO: 295, SEQ ID NO: 292, SEQ ID NO: 298, SEQ ID NO: 236, and SEQ ID NO: 242, respectively).

In some embodiments there is provided an anti-cancer vaccine including a peptide component or a plurality of distinct peptide components, and a pharmaceutically acceptable carrier. Peptide components may include peptide chains as disclosed herein which may be in any form operable for administration as disclosed herein, such as, for example, free and/or unbound peptide chains in a carrier solution or suspension, peptide chains bound or associated to other entities, or peptide chains conjugated to other entities, such as KLH-conjugated peptides. Carriers may be any pharmaceutically acceptable entities or compositions operable to contain, suspend, bind to, or otherwise associate with peptide components for administration to a mammalian subject. In some embodiments there is provided an anti-cancer vaccine for administration by genetic immunization, including a nucleic acid or a plurality of nucleic acids, encoding a peptide component or a plurality of peptide components, and a carrier adapted for administration of the anti-cancer vaccine by genetic immunization, which may include any pharmaceutically acceptable entity or composition operable to facilitate the administration of the nucleic acid(s) to a mammalian subject whereby the peptide components encoded by the nucleic acids may be expressed by cells of the subject. Examples include vectors, plasmids, LEE's, or other entities incorporating sequences or functionality for facilitating such expression, which may in some embodiments be applied, adsorbed, conjugated to, or otherwise associated with a physical delivery entity such as a gold nanoparticle or other genetic immunization 'bullet'.

In some embodiments an anti-cancer vaccine includes a plurality of peptide components, or a nucleic acid portion encoding peptide components, wherein each peptide component is targeted to a different cancer type, so that the susceptibility of a receiving subject or population may be reduced with respect to more than one cancer type. In some embodiments an anti-cancer vaccine includes a plurality of peptide components, or a plurality of nucleic acids encoding peptide components, wherein the peptide components are displayable in different MHC or HLA types, so that the coverage of the anti-cancer vaccine extends to subjects of more than one MHC or HLA type. In some embodiments, it may be found useful to confirm by art-recognized computational methods that a peptide component is displayable in MHC of a type expressed by a mammalian subject, which may be a member of a population for which a vaccine composition is intended. In embodiments, a population for which a vaccine composition is intended may be the population of all mammals of a species or subspecies of interest, or may be a sub-population defined by one or more characteristics of interest such as, for example, a sub-population having a particular genetic trait, or a particular susceptibility. In some embodiments, a peptide component may be displayable by MHC of a type expressed by a minimum percentage of a population of a mammalian species or sub-population for which an anti-cancer vaccine is intended, such as, for example, at least 2%, or at least 4%, or at least 6%, or at least 10%, or at least 20% of the population or sub-population. In some embodiments, an anti-cancer vaccine may include two or more peptide components (or nucleic acid(s) encoding them, in the case of a genetic vaccine), wherein a first peptide components is displayable by a first MHC type expressed in one cohort of the target population or sub-population, and a second peptide component is displayable by a second MHC type expressed in a different cohort of the target population or sub-population, so that the potential coverage of the vaccine extends to both cohorts. It will be apparent that by appropriate selection of peptide components displayable by different MHC types, it is possible for a cocktail vaccine to extend the benefit of the vaccine to an arbitrary proportion of the target population.

In some embodiments, disclosed herein is a synthetic or recombinant peptide component for an anti-cancer vaccine for administration in a population of a mammalian species, including a continuous amino acid chain, or a continuous portion thereof from 8 to 40 amino acids in length, according to the formula D1-D2, wherein D1 and D2 each have at least threshold identity to a polypeptide sequence encoded by a different exon or continuous portion thereof of the genome of the mammalian species, wherein D1 is encoded in a wild type reading frame and D2 is encoded in a non-wild type reading frame. In embodiments, a threshold identity may be any level of sequence identity or similarity, determined according to metric thereof, that would be regarded by a person of skill in the art as providing a reasonable measure of functional similarity, such as, by way of example only, 75% sequence identity, or 80% sequence identity, or 85% sequence identity, or 90% sequence identity, or 95% sequence identity.

In some embodiments of a peptide component, the portion of D1 immediately adjacent to D2 is not a microsatellite or portion thereof. In some embodiments neither D1 nor D2 has above a threshold identity to a peptide sequence encoded by an oncogene. In some embodiments of a peptide component, the RefSeq of the mammalian species does not contain a nucleic acid sequence encoding the sequence of the peptide component. In some embodiments of a peptide component, the normal transcriptome of the mammalian species does not contain a nucleic acid sequence encoding the sequence of the peptide component. In some embodiments of a peptide component, the peptide component aligns with at least threshold identity to all or a portion of an mRNA transcript expressed in at least one cancer type of the mammalian species. In some embodiments of a peptide component, the peptide component has a cancer association ratio of at least 2:1 with respect to at least one cancer type of the mammalian species. In some embodiments of a peptide component, the peptide component has a cancer serum recognition percentage of at least 40% with respect to at least one cancer type of the mammalian species. In some embodiments of a peptide component, the peptide component is capable of being displayed in a Class I major histocompatibility complex (MHC-I) of a type expressed by at least 4 percent of the population.

In some embodiments of a peptide component, the mammalian species is mouse and the continuous amino acid chain has at least threshold sequence identity to a sequence selected from: peptide FS 1-78 (SEQ ID NO: 294), peptide FS 6-21 (SEQ ID NO:291), peptide FS SMC1A (SEQ ID NO: 297), peptide FS RBM (SEQ ID NO: 232), or peptide FS THAP2 (SEQ ID NO: 238). In some embodiments of a peptide component, the mammalian species is human and the continuous amino acid chain has at least threshold sequence identity to a sequence selected from: peptide FS 1-78 (SEQ ID NO: 293), peptide FS 6-21 (SEQ ID NO: 290), peptide FS SMC1A (SEQ ID NO: 296), peptide FS RBM (SEQ ID NO: 234), or peptide FS THAP2 (SEQ ID NO: 240). In some embodiments of a peptide component, the mammalian species is dog and the continuous amino acid chain has at least threshold sequence identity to a sequence selected from: peptide FS 1-78 (SEQ ID NO: 295), peptide FS 6-21 (SEQ ID NO: 292), peptide FS SMC1A (SEQ ID NO: 298), peptide FS RBM (SEQ ID NO: 236), or peptide FS THAP2 (SEQ ID NO: 242).

Also disclosed herein are embodiments of an anti-cancer vaccine for administration in a population of a mammalian species, including a plurality of any of the peptide components disclosed herein, in a pharmaceutically acceptable carrier; also disclosed herein are embodiments of a method including administering to a mammal an effective dose of the anti-cancer vaccine. Also disclosed herein are embodiments of an anti-cancer vaccine for administration in a population of a mammalian species, including a synthetic or recombinant nucleic acid or plurality thereof encoding a plurality of any of the peptide components disclosed herein, and a carrier adapted for administration of the anti-cancer vaccine by genetic immunization; also disclosed herein are embodiments of a method including administering to a mammal an effective dose of the anti-cancer vaccine, which may employ genetic immunization methods. In some embodiments of an anti-cancer vaccine, there is provided a plurality of peptide components including a first peptide component displayable in a first MHC type expressed in a first cohort of the population and a second peptide component displayable in a second MHC type expressed in a second cohort of the population, wherein the first and second cohort together are more numerous by at least 2 percent of the population than either cohort.

In some embodiments, there is disclosed a method including: administering to a mammal by genetic immunization an effective dose of an anti-cancer vaccine including a synthetic or recombinant nucleic acid or plurality thereof, encoding a plurality of any of the peptide components as disclosed herein, and a carrier adapted for administration of the anti-cancer vaccine by genetic immunization; and at least two weeks thereafter, administering to the mammal an effective dose of an anti-cancer vaccine including at least one of the plurality of peptide components in a pharmaceutically acceptable carrier.

In embodiments, disclosed herein is a composition including synthetic or recombinant peptides each including a continuous amino acid chain, or continuous portion thereof from 8 to 40 amino acids in length, having at least threshold identity to a sequence or continuous portion thereof of SEQ ID NO: 310, SEQ ID NO: 311, and SEQ ID NO: 312. Also disclosed are embodiments of a synthetic or recombinant nucleic acid or plurality thereof encoding peptides each including a continuous amino acid chain, or continuous portion thereof from 8 to 40 amino acids in length, having at least threshold identity to a sequence or continuous portion thereof of SEQ ID NO: 310, SEQ ID NO: 311, and SEQ ID NO: 312.

Also disclosed are embodiments of a synthetic or recombinant peptide including a continuous amino acid chain, or a continuous portion thereof from 8 to 40 amino acids in length, having at least threshold identity to a sequence or continuous portion thereof selected from the group consisting of SEQ ID NO: 240 and SEQ ID NO: 243 through SEQ ID NO: 289. Also disclosed are embodiments of a synthetic or recombinant nucleic acid encoding a continuous amino acid chain, or a continuous portion thereof from 8 to 40 amino acids in length, having at least threshold identity to a sequence or continuous portion thereof selected from the group consisting of SEQ ID NO: 240 and SEQ ID NO: 243 through SEQ ID NO: 289. Also disclosed are embodiments of a synthetic or recombinant peptide including a continuous amino acid chain, or a continuous portion thereof from 8 to 40 amino acids in length, having at least threshold identity to a sequence or continuous portion thereof selected from the group consisting of SEQ ID NO: 242, SEQ ID NO: 236, and SEQ ID NO: 306 through SEQ ID NO: 309. Also disclosed are embodiments of a synthetic or recombinant nucleic acid encoding a continuous amino acid chain, or a continuous portion thereof from 8 to 40 amino acids in length, having at least threshold identity to a sequence or continuous portion thereof selected from the group consisting of SEQ ID NO: 242, SEQ ID NO: 236, and SEQ ID NO: 306 through SEQ ID NO: 309. Also disclosed are embodiments of a synthetic or recombinant peptide including a continuous amino acid chain, or a continuous portion thereof from 8 to 40 amino acids in length, having at least threshold identity to a sequence or continuous portion thereof selected from the group consisting of SEQ ID NO: 238, SEQ ID NO: 242, and SEQ ID NO: 299 through SEQ ID NO: 305. Also disclosed are embodiments of a synthetic or recombinant nucleic acid encoding a continuous amino acid chain, or a continuous portion thereof from 8 to 40 amino acids in length, having at least threshold identity to a sequence or continuous portion thereof selected from the group consisting of SEQ ID NO: 238, SEQ ID NO: 242, and SEQ ID NO: 299 through SEQ ID NO: 305. Also disclosed are embodiments of a composition including synthetic or recombinant peptides each including a continuous amino acid chain, or continuous portion thereof from 8 to 40 amino acids in length, having at least threshold identity to a sequence or continuous portion thereof of SEQ ID NO: 310, SEQ ID NO: 311, and SEQ ID NO: 312. Also disclosed are embodiments of a synthetic or recombinant nucleic acid or plurality thereof encoding peptides each including a continuous amino acid chain, or continuous portion thereof from 8 to 40 amino acids in length, having at least threshold identity to a sequence or continuous portion thereof of SEQ ID NO: 310, SEQ ID NO: 311, and SEQ ID NO: 312. Also disclosed are embodiments of a synthetic or recombinant peptide including a continuous amino acid chain, or a continuous portion thereof from 8 to 40 amino acids in length, having at least threshold identity to a sequence or continuous portion thereof selected from the group consisting of SEQ ID NO: 310 through SEQ ID NO: 332. Also disclosed are embodiments of a synthetic or recombinant nucleic acid encoding a continuous amino acid chain, or a continuous portion thereof from 8 to 40 amino acids in length, having at least threshold identity to a sequence or continuous portion thereof selected from the group consisting of SEQ ID NO: 310 through SEQ ID NO: 332. Also disclosed are embodiments of a synthetic or recombinant peptide including a continuous amino acid chain, or a continuous portion thereof from 8 to 40 amino acids in length, having at least threshold identity to a sequence or continuous portion thereof selected from the group consisting of SEQ ID NO: 333 through SEQ ID NO: 341. Also disclosed are embodiments of a synthetic or recombinant nucleic acid encoding a continuous amino acid chain, or a continuous portion thereof from 8 to 40 amino acids in length, having at least threshold identity to a sequence or continuous portion thereof selected from the group consisting of SEQ ID NO: 333 through SEQ ID NO: 341. Also disclosed are embodiments of a synthetic or recombinant peptide including a continuous amino acid chain, or a continuous portion thereof from 8 to 40 amino acids in length, having at least threshold identity to a sequence or continuous portion thereof selected from the group consisting of and SEQ ID NO: 342 through SEQ ID NO: 348. Also disclosed are embodiments of a synthetic or recombinant nucleic acid encoding a continuous amino acid chain, or a continuous portion thereof from 8 to 40 amino acids in length, having at least threshold identity to a sequence or continuous portion thereof selected from the group consisting of SEQ ID NO: 342 through SEQ ID NO: 348.

EXAMPLES

The following examples are put forth so as to provide those of ordinary skill in the art with a complete disclosure and description of how the compounds, compositions, articles, devices and/or methods claimed herein are made and evaluated, and are intended to be purely exemplary and are not intended to limit the disclosure. Efforts have been made to ensure accuracy with respect to numbers (e.g., amounts, temperature, etc.), but some errors and deviations should be accounted for. Unless indicated otherwise, parts are parts by weight, temperature is in degrees Celsius or is at ambient temperature, and pressure is at or near atmospheric.

Example 1

To determine the amount of coding sequence that must be sequenced to identify a sufficient number of novopeptides that are expressed in tumor cells and not in non-cancerous cells to produce a practicable cancer vaccine, it is first instructive to determine the frequency of novopeptide associated mutation or variation in a tumor. To assess this frequency, the C-terminal 600 bp of 550 genes that are expressed in the mouse melanoma cell line, B16-F10 were sequenced. To confirm that the in vitro-derived FS were expressed in vivo, RNA was extracted from B16 lung metastases after injection of cells systemically, cDNA was generated, and the FS confirmed by RT-PCR sequencing. As illustrated in FIG. 2a, cDNA was generated from RNA isolated from cultured cells. It was sequenced directly by RT-PCR sequencing. FIG. 2b illustrates in vivo confirmation of in vitro-derived FS mutations. To confirm that the FS was expressed in vivo, RNA was extracted from B16 lung metastases after injection of cells systemically. cDNA was generated and the FS confirmed by RT-PCR sequencing.

Figure 1B:
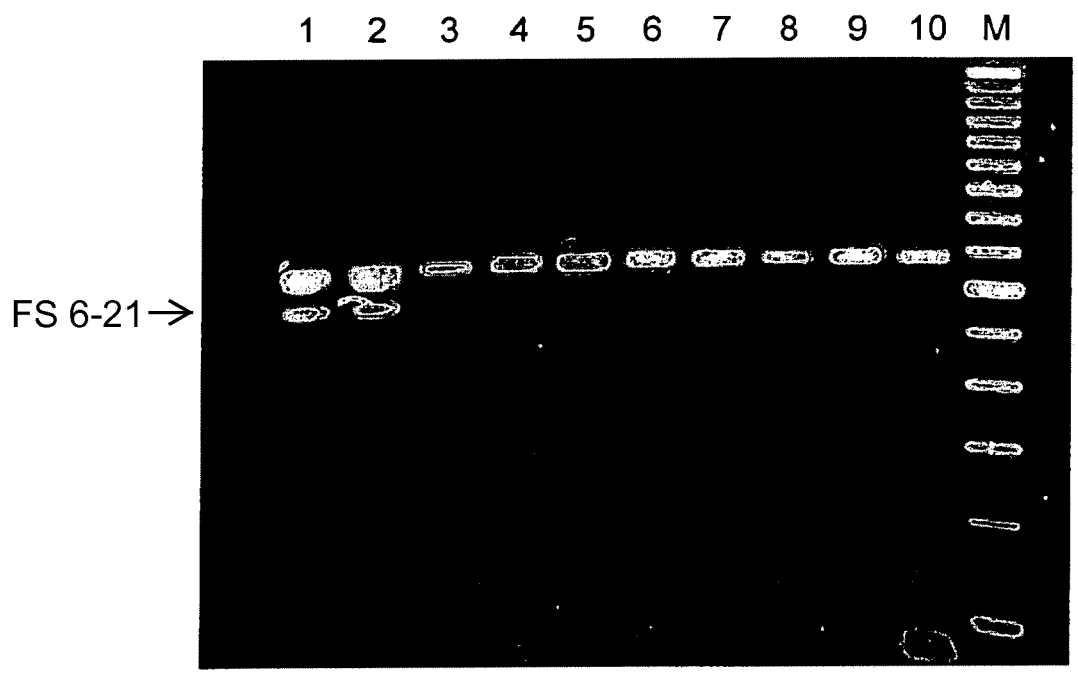
Figure 2:
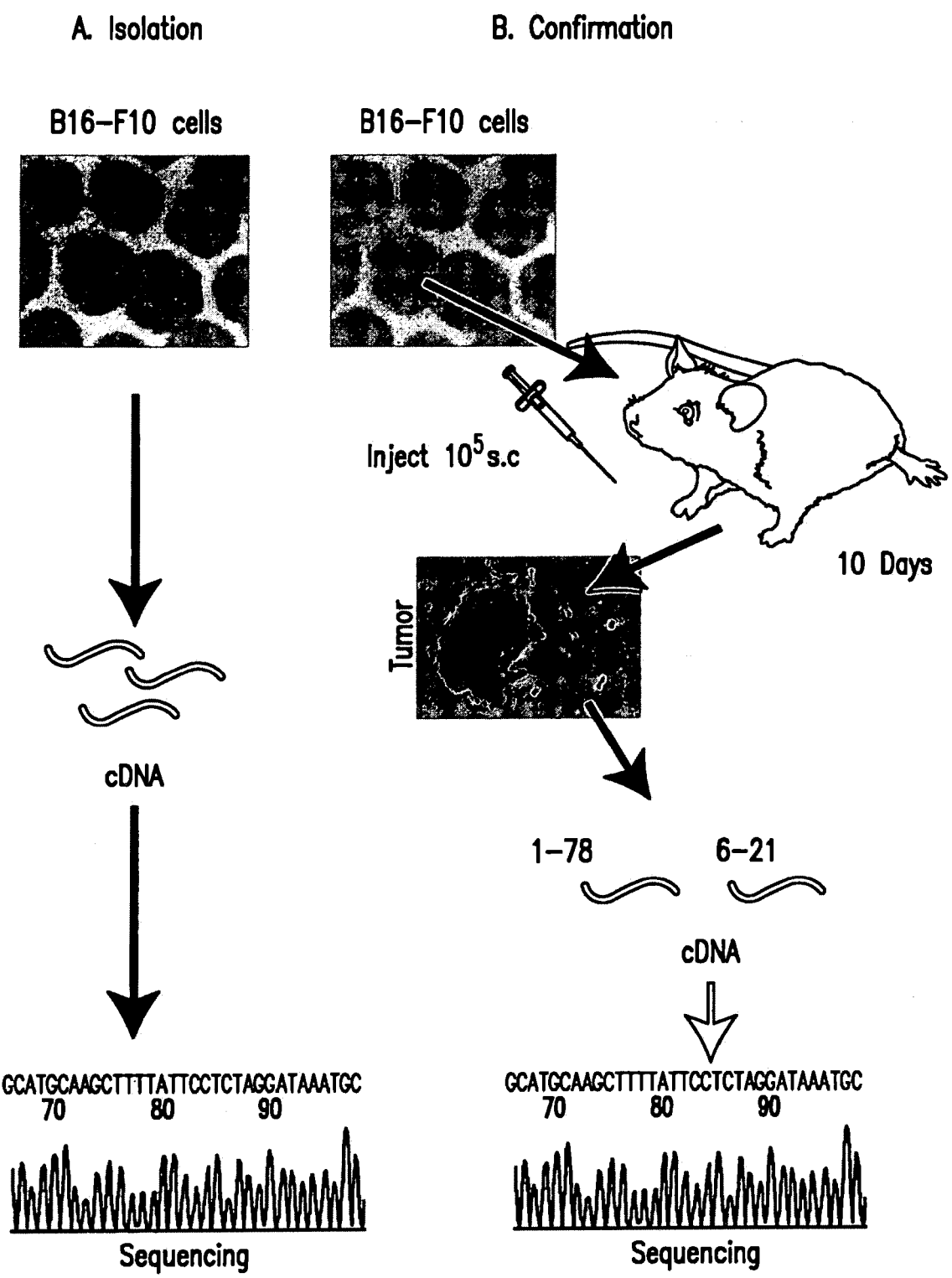

Three novopeptides were isolated, indicating that FS occur at a frequency of roughly one per 183 segments of 600 bp of genes (FIG. 2). FS 1-78 (SEQ ID NO: 2) was identified as a frameshift relative to the normal reference sequence. One other frameshift peptide, FS 6-21 (SEQ ID NO: 4) was also identified, as was a 3 amino acid insertion. The parent protein of FS 1-78 is a zinc finger protein, but a deletion of 396 bp results in expression of an 11 amino acid novopeptide in an alternate frame before termination. Table 1 shows the sequences identified. Underlined amino acids comprise the peptide predicted to be presented by H-2 Db (C57BL6 mice) and H-2 Kd (Balb/c mice). Upper case amino acids indicate primary frame and lower case amino acids indicate the frame shift residues. Fusions of primary and alternate frames often form antigenic peptides. FIG. 1a shows PCR amplification of FS 1-78. Arrow indicates FS 1-78 band; other bands are wild type alleles. Lane 1: B16/F10 tumor cells; Lane 2: B16/F10 tumor cells; Lane 3: normal heart; Lane 4: normal intestine; Lane 5: normal kidney; Lane 6: normal liver; Lane 7: normal lung; Lane 8: normal skeletal muscle; Lane 9: normal skin; Lane 10: normal spleen; Lane M: Molecular weight marker. FIG. 1b shows the analysis of the occurrence of the FS 6-21 frameshift in the mouse tumor versus RNA from normal tissue. Arrow indicates FS 6-21 FS band. Lanes are as in FIG. 1a. It is noted that FS 1-78 expression is detected in the tumor cells and not in any of the noncancerous cells tested.

TABLE 1

| Gene Name | FS mutation | Novopeptide Sequence | SEQ ID NO |
|---|---|---|---|
| 1-78 | 396 bp deletion | IPRMQPQASAnhcqllkvmva* | SEQ ID NO: 2 |

TABLE 1-continued

| Gene Name | FS mutation | Novopeptide Sequence | SEQ ID NO |
|---|---|---|---|
| 6-21 | 95 bp deletion | AVLLMCQLYQpwmckeyyrll* | SEQ ID NO: 4 |
| 3-83 | 3 aa insertion | . . . GTEDsrdSDDALL . . . | SEQ ID NO: 6 |

Example 2

Figure 3:
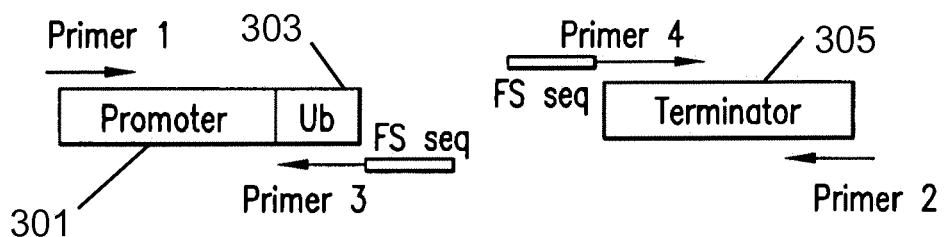
FIG. 3 shows an embodiment of a linear expression element construction (LEE).
Figure 3:
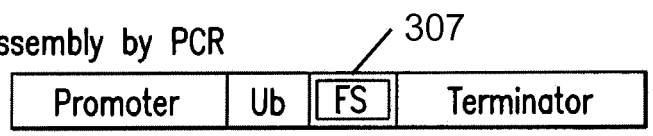
Figure 3:
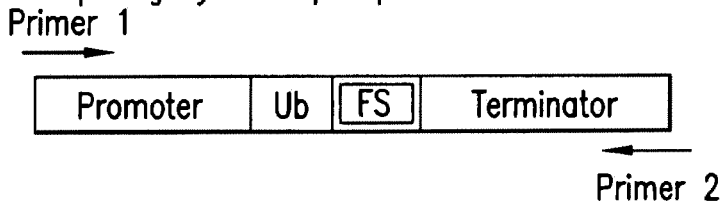
Figure 4:
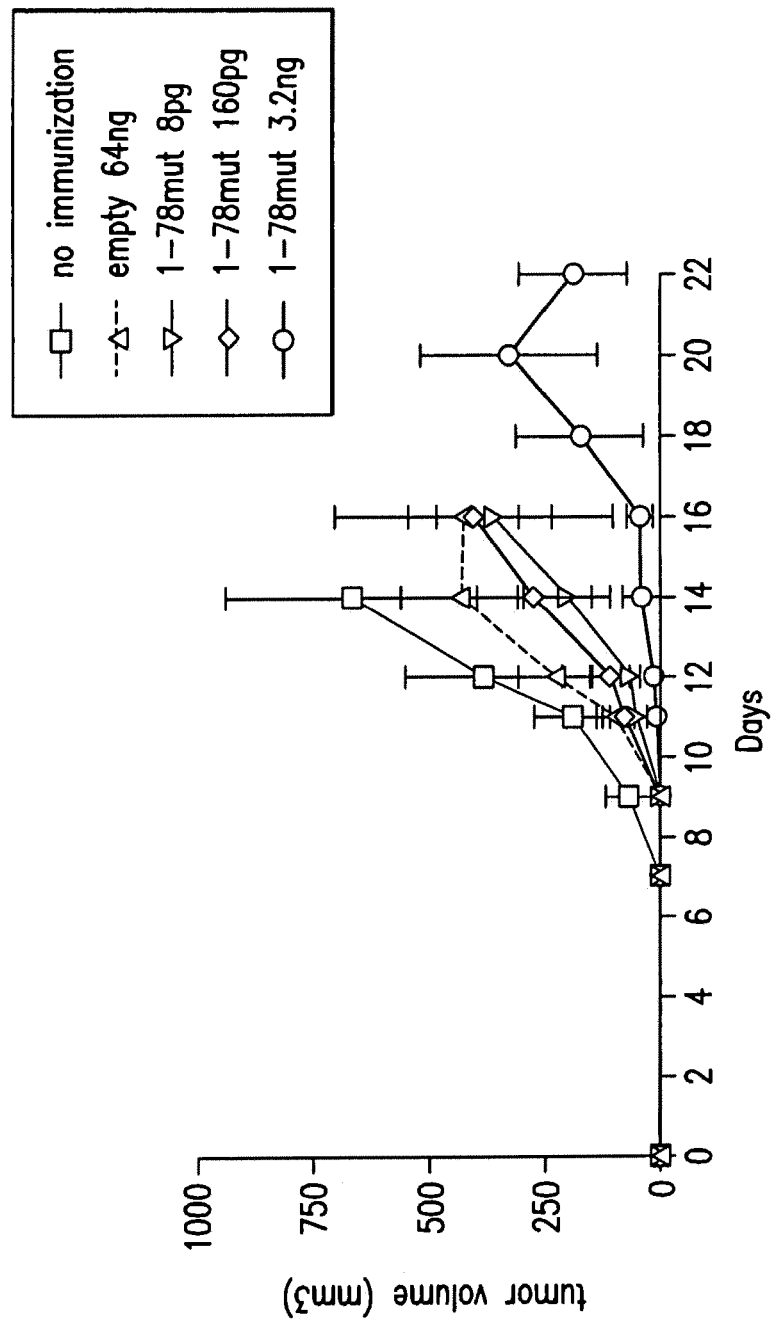
FIG. 4 shows results of prophylactic immunization of C57B6 mice with FS 1-78 on tumor challenge.

The FS 1-78 novopeptide identified above was chemically synthesized as a genetic linear expression element (LEE) as diagrammed in FIG. 3 according to the methods described in (Sykes, K. F., and S. A. Johnston (1999) Nat. Biotechnol. 17:355). Each LEE comprises a fragment that may contain a mammalian promoter 301, a ubiquitin gene (Ub) 303 for stronger intracellular processing, and a fragment 305 that contains transcriptional and translational terminators. The two fragments are linked via the frameshift sequence 307, here FS 1-78. Using gene gun technology, C57BL6 mice were then genetically immunized with the FS 1-78 LEE construct in doses as shown in FIG. 4 and a plasmid expressing GM-CSF (1 μg of pGM-CSF). Mice were boosted 2 weeks later with the same FS 1-78 LEE and pGM-CSF and then challenged one week after boost (day 0) with $1 \times 10^5$ B16 F10 melanoma tumor cells. As shown in FIG. 4, tumor growth was markedly delayed compared to mice administered control empty LEE and compared to those receiving no immunization, and at the highest dose (3.2 ng), tumor volume decreased after the already delayed rise.

Example 3

Figure 5:
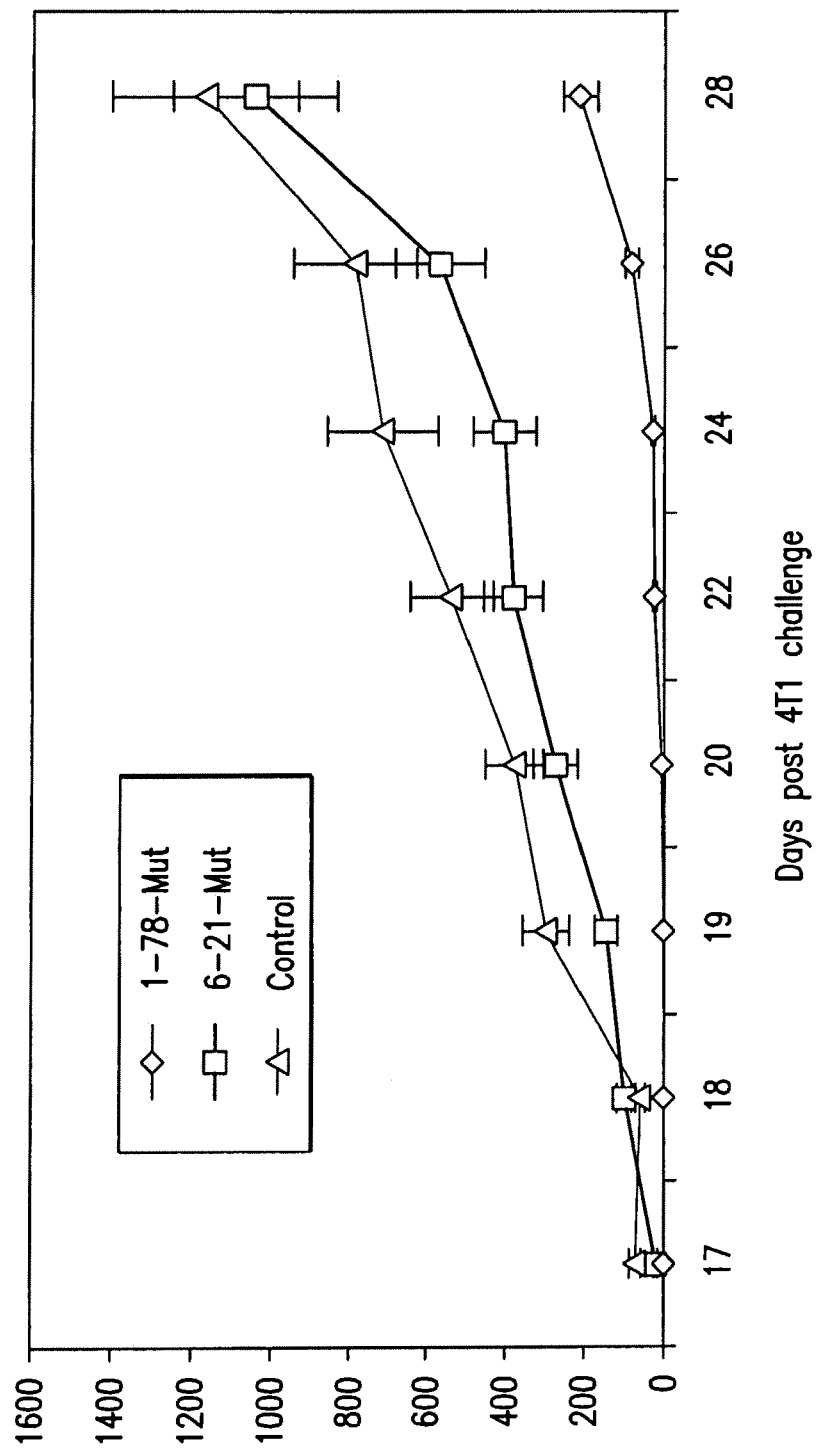
FIG. 5 shows results of prophylactic immunization of Balb/c mice with FS 1-78 and FS 6-21 on tumor challenge.

Immunization with a single FS-novopeptide identified based on one tumor type may be immunoprotective against a different tumor type in a different mouse strain. Disclosed herein is a procedure for such immunization. Immunization with novopeptides common to multiple types of tumors can result in cross-protection, obviating the requirement that a patient must develop a tumor before a personalized vaccine can be formulated, prepared and administered. Balb/c mice were immunized in the same manner as the C57BL6 mice in Example 2 above, with 3.2 ng of FS 1-78 LEE+1 μg of pGM-CSF, and boosted with the same gene vaccine after 2 weeks. One week after the boost, mice were challenged with $1 \times 10^4$ 4T1 breast tumor cells. Seventeen days after 4T1 challenge, tumors started to grow. As shown in FIG. 5, prophylactic immunization of Balb/c mice with FS 1-78 novopeptide significantly delayed and reduced 4T1 tumor growth in comparison to both controls immunized with pGM-CSF plasmid alone and controls immunized with another novopeptide (FS 6-21) that is not found in 4T1 tumors.

Example 4

Figure 6:
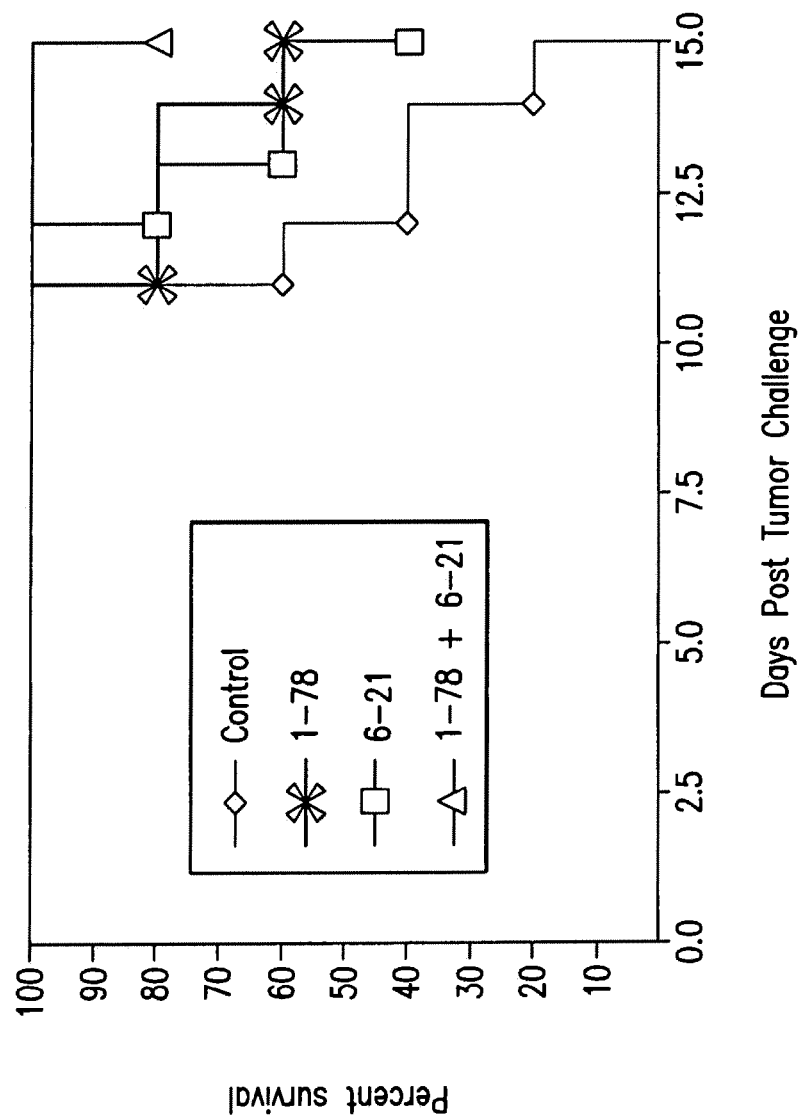
FIG. 6 shows the survival curve in response to prophylactic vaccination by genetic immunization with a pooled vaccine.

Vaccines combining more than one novopeptide can be highly effective in conferring immunoprotection against cancer. Mice were vaccinated using a vaccine comprising a combination of FS 1-78 and FS 6-21 novopeptides. On challenge with B16 tumor cells, most vaccinated mice were completely protected from tumor growth. FIG. 6 compares the relative protection of the FS 1-78 and FS 6-21 peptides by themselves and when pooled as a single vaccine. On Day −8, mice were immunized with the FS 6-21 peptide (squares), the FS 1-78 peptide (crosses), a combination of both (triangles), or an irrelevant peptide sequence (diamonds). Tumor cells were implanted on Day 0. The 80 percent of mice in the group receiving the combined vaccine that were alive on day 15 remained alive and apparently healthy thereafter and until the experiment was terminated. This experiment demonstrates that pooling of novopeptides can give increased protection over single peptide immunization.

Example 5

Candidate novopeptide nucleic acid sequences, expressed by cancerous cells and not by non-cancerous cells, can be identified and predicted by bioinformatics analysis comparing tumor database data with genomic data. This example illustrates an embodiment of the methods by which this was done. FS-novopeptide candidates were identified by bioinformatic analysis of frame shifts by comparing sequences obtained from tumor and normal EST library databases. Exact FS peptide sequences were then confirmed by DNA sequencing across the frame shift region and comparison to the non-cancerous reference sequence. It is noteworthy that several of the tumor-specific variants are not encoded at the DNA level but involve RNA splicing variants that are predominant in the tumors. Table 2a shows frame shift sequences predicted by the bioinformatic comparison and verified by DNA sequence analysis, and shows that these sequences are present in the indicated number of tumor EST's and not in non-cancerous EST's.

TABLE 2a

| Gene Name | FS mutation | EST analysis | Novopeptide Sequence | |
|---|---|---|---|---|
| RIPK2 | 154 bp deletion | Tumor: 6 of 16 Normal: 0 of 8 | . . . HIHTPLLDrklnil mllgh* | SEQ ID NO: 9 |
| DTYMK | 91 bp deletion | Tumor: 3 of 86 Normal: 0 of 30 | . . . SANRWEQVifp* | SEQ ID NO: 10 |
| 6-21 | 95 bp deletion | Tumor: NA Normal: NA | . . . LLMCQCQLY Qpwmckeyyrll* | SEQ ID NO: 11 |
| DYRK4 | 61 bp deletion | Tumor: 4 of 10 Normal: 0 of 11 | . . . EQLACIMEipkvfl ki* | SEQ ID NO: 12 |
| MTCH2 | 68 bp deletion | Tumor: 5 of 88 Normal: 0 of 63 | . . . SYSQAVTGscwwmp sllpniyvldrllvhatkrg eyeprk* | SEQ ID NO: 13 |
| FTH1 | 62 bp insertion | Tumor: 17 of 2157 Normal: 0 of 243 | . . . ASYVYLSMivtatc lwgslv* | SEQ ID NO: 14 |

Bioinformatic identification of possible novopeptides was performed as follows: the NCBI EST database was screened using information obtained from the NCI EST database to classify each NCBI EST into one of three sets: tumor EST's, normal EST's and EST's for which there was insufficient information to classify as tumor or normal. The latter were discarded. Each human reference sequence in the NCBI database was then aligned with both the normal EST set and the tumor EST set using BLAST, and the number of frame-shifted and unframeshifted hits of at least 100 base pairs and 85% sequence identity were counted. To identify candidates for further screening, an odds ratio was computed for each FS variant sequence arising from an indel of at least 10 base pairs. The odds ratio provides an indication of the relative expression of the FS variant in tumor and normal cells, as compared to the expression of the nonvariant wild type sequence in tumor and normal cells. The ratio of FS variants to wild type in tumor cells (the "tumor cell variant ratio") was computed as the ratio of the number of sequence matches obtained upon search of the tumor EST databases for the FS variant sequence to the number of sequence matches obtained upon search of the tumor EST databases for the wild type sequence. The ratio of FS variants to wild type in normal cells (the "normal cell variant ratio") was computed as the ratio of the number of sequence matches obtained upon search of the normal EST databases for the FS variant sequence to the number of sequence matches obtained upon search of the normal EST databases for the wild type sequence. In computing this ratio, the former number was arbitrarily set to 1 if the number of matches were zero so as to avoid division by zero in computing the odds ratio; this approximation was deemed reasonable since the difference between zero and 1 is likely within the range of uncertainty associated with sequence alignment and the setting of alignment parameters. An odds ratio was computed as the ratio of the tumor cell variant ratio to the normal cell variant ratio, with FS variant sequences having a ratio above 2.0 being selected for further study. Table 2b shows six FS variant sequences for which RNA expression ratios of the FS variant in tumor vs. normal cells were determined, confirming the differential expression.

TABLE 2b

| Accession | Gene Name | FS Peptides | RNA |
|---|---|---|---|
| NM 006306 | SMC1L1 | GCCGIYCHEEPQREDSSI (SEQ ID NO: 15) | 98X |
| NM 015336 | HIP 14 | PWMCKKYYRLL (SEQ ID NO: 16) | 4X |
| XM 044434 | KIAA1458 | NPCQLLKPMVA (SEQ ID NO: 17) | 6.3X |
| NM_014342 | MTCH2 | SCWWMPSLLPNIYVLDRLL VHA TKRGEYEPRK (SEQ ID NO: 18) | 2.2X |
| NM 006833 | COPS6 | RGPL (SEQ ID NO: 19) | 9.75X |
| NM 000314 | PTEN | | 41X |

Table 2c shows FS variants having high odds ratios, computed as described above; for CIAPIN1 and STYXL1, RNA expression ratios were measured to be 2.6× and 2.0×, respectively; RNA expression in tumor cells exceeding that in normal cells was confirmed by PCR and inspection of electrophoresis gel band intensities in BCL2L12 and DNPEP; and expression in tumor cells was verified by RNA extraction and sequencing for BCL2L12, DNPEP, and STYXL1.

TABLE 2c

| Accession ID | Gene name | FS peptide | Odds Ratio |
|---|---|---|---|
| NM_001745 | CAMLG | VHICSISYFTTCVHGIIQIFSQE (SEQ ID NO: 20) | 2.50 |
| NM_001014438 | CARS | GSVHTSRWEKGDVVLLWANRL (SEQ ID NO: 21) | 2.86 |
| NM_020313 | CIAPIN1 | SAHKESSFDIICQV (SEQ ID NO: 22) | 2.22 |
| NM 006716 | DBF4 | SS | 4.09 |
| NM 017996 | DET1 | TRHLLKSMSTRAARQQRTYCRDT KEKSCPMAMTSGQ (SEQ ID NO: 23) | 2.67 |
| NM 012100 | DNPEP | GWLQ (SEQ ID NO: 24) | 2.36 |
| NM 006705 | GADD45G | LRGQGG (SEQ ID NO: 25) | 2.38 |
| NM_000849 | GSTM3 | LLTMIEANGWM (SEQ ID NO: 26) | 3.82 |
| NM 201612 | IKIP | CGRNLKLSWNN (SEQ ID NO: 27) | 15.43 |
| NM_001012634 | IL32 | HQAIERFYDKMLQNQDVDR (SEQ ID NO: 28) | 4.63 |
| NM_015416 | LETMD1 | ESLEPGHASHILPASSLVETSFE DSYNCDSPTGQGFGKAGDWPADC SGSKIGLLSPWPEFYAYW (SEQ ID NO: 29) | 3.08 |
| NM_002405 | MFNG | GPTLWSPTAPRNTATQLCPARWL LSSTPSWPVGLGGSAMWTMTTM (SEQ ID NO: 30) | 2.47 |
| NM 198883 | MTX1 | KYNADYDLSARQGADTLAFMSLL EEKLLPVL (SEQ ID NO: 31) | 3.08 |
| NM_152298, NM_002482 | NASP | SNH | 3.65 |
| NM 006985 | NPIP | SRSQLGMAVIFLFTPR (SEQ ID NO: 32) | 2.11 |
| NM 153681 | PIGP | KNLKGSRVC (SEQ ID NO: 33) | 3.69 |
| NM 018845 | RAG1API | KLR | 2.29 |
| NM 015014 | RBM34 | GKRSSEC (SEQ ID NO: 34) | 11.08 |
| NM 183400 | RNF14 | AICSMQALRQPMGRTPWQRGPVC LDAIS (SEQ ID NO: 35) | 11.73 |
| NM_016211 | SEC31A | PSEWLE (SEQ ID NO: 36) | 2.33 |
| NM_001009939 | SEPT5- | VENQAHCDFVKLRNMLIRTHMHD LKDVTCDVHYENYRAHCIQQMTS KLTQDSRMESPIPILPLPTPDAE T (SEQ ID NO: 37) | 2.63 |
| NM_005827 | SLC35B1 | WWIVPGAGSMLPVLSPIWVPWSP AIQHYSLSTTQLRSLVNPASQSQ SCSLG (SEQ ID NO: 38) | 9.45 |
| NM_003473 | STAM | GVILKYVKN (SEQ ID NO: 39) | 2.14 |
| NM 003763 | STX16 | A | 2.70 |
| NM_016086 | STYXL1 | GTGCISAIPH (SEQ ID NO: 40) | 7.27 |
| NM_032026 | TATDN1 | VYDYRWKSTRQ (SEQ ID NO: 41) | 3.63 |
| NM_001001563 | TIMM50 | DHRAHQPLPSPRPSAGTVLPATL HARFGAHRRPLAS (SEQ ID NO: 42) | 2.92 |
| NM_100486 | WAC | MEDKHSSDASSLLPQNILSQTSR HNDRDYRLPRAETHSSSTPVQHP IKPVVHPTATPSTVPSSPFTLQS DHQPKKSFDANGASTLSKLPTP TSSVPAQKTERK (SEQ ID NO: 43) | 2.70 |
| NM 024061 | ZNF655 | GHTSPPSHHPDS (SEQ ID NO: 44) | 2.09 |

Table 2d shows FS variant sequences for which sequence matches were found in the tumor EST databases but for which, in the normal EST databases, no sequence matches were found for either the FS variant or the parent wild type sequence; this prevented computation of an odds ratio, but obviously nonexpression in normal cells is a desirable characteristic. Note that very short FS variant sequences are nevertheless significant since, when expressed, they result in peptides representing fusions of the FS variant with the adjacent unshifted sequence.

TABLE 2d

| Accession ID | Gene Name | FS Peptides |
|---|---|---|
| NM_212533 NM_001606 | ABCA2 | E |
| NM_172027 | ABTB1 | VLCLLVWARGAGTLPSGQWSPLRGQHLRW (SEQ ID NO: 45) |
| NM_001033055 | AIPL1 | VIFHFRTMKCDEERTVIDDSRQVGQPMHIIIGNMFKLEVWEILL TSM RVH EVAEFWCDTI (SEQ ID NO: 46) |
| NM_001707 | BCL7B | GQSLAMLSRLVVNSWPQAVPRP (SEQ ID NO: 47) |

TABLE 2d-continued

| Accession ID | Gene Name | FS Peptides |
|---|---|---|
| NM_004328 | BCS1L | LES |
| XM_043653 | BEXL1 | PLTEASYVNLPTIALCNTDSPLRYVDIAIPCNNKGAHS (SEQ ID NO: 48) |
| NM_139343 | BIN1 | LRKGPPVPPPPKHTPSKEVKQEQILSLFEDTFVPEISVTTPSQPAEAS EVAGGTQPAAGAQEPGETAASEAAS (SEQ ID NO: 49) |
| NM_015412 | C3orf17 | G |
| NM_001009186 | CCT6A | QIQHPTASLIAKVATAQDDITGDGTTSNVLIIGELLKQADLYISE (SEQ ID NO: 50) |
| NM_134445 | CD99L2 | QPWDHTNNHHNK (SEQ ID NO: 51) |
| NM_033488 | CDC2L1 | SVCTSPNDERGLQRQSESQPLESQPASAAAGAVRVGRRPEASKRR E NGRKGPAVRLTGHQRQREEDQLGRVLVSRIRLRF (SEQ ID NO: 52) |
| NM_001005271 NM_001005273 | CHD3 | EMGEEGGGRTGNH (SEQ ID NO: 53) |
| NM_017828 | COMMD4 | VRPSTVSMANPCPVNCSSWGCPKSTRPACAAVMRRSKAPCRSTC GSAAYA (SEQ ID NO: 54) |
| NM_032179 | CPSF3L | SCLD (SEQ ID NO: 55) |
| NM_004715 | CTDP1 | KWTTSLEKAATTATARRGGLRSRRRSPSPGSQGPAGSGRSGHLRP ARGARQGAGGPEAT RGS (SEQ ID NO: 56) |
| NM_001930 | DHPS | AERGRLRCLHQHSPGV (SEQ ID NO: 57) |
| NM_182908 | DHRS2 | FHGNESLWKNFKEHHQLQRIGESEDCAGIVSFLCSPDASYVNGENI AVAGYSTRL (SEQ ID NO: 58) |
| NM_021931 | DHX35 | HDLSSQRLQGE (SEQ ID NO: 59) |
| NM_001009894 | DKFZp434 N2030 | ISHTFGLD (SEQ ID NO: 60) |
| NM_032378 | EEF1D | AQAPGPPAAPAETTVSSSSGLPVWKWRTRVCVAWYRSCSRPSPS WRPG (SEQ ID NO: 61) |
| NM_024311 | ET | RRVTEEQCLLP (SEQ ID NO: 62) |
| NM_023109 | FGFR1 | CIHRDLAARNVLVTEDNVMKIADFGLARDIHHIDYY (SEQ ID NO: 63) |
| NM_001001662 | FLJ16636 | KDVGEPSLFPLA (SEQ ID NO: 64) |
| NM_024578 | FLJ22709 | VSLTGRGSPGRASRQKI (SEQ ID NO: 65) |
| NM_005087 NM_001013439 | FXR1 | GKRCD (SEQ ID NO: 66) |
| NM_002106 | H2AFZ | VGI |
| NM_014056 | HIGD1A | VFGDSPALSPRLECSGRISAHCSLCLLGSSDSPTSAS (SEQ ID NO: 67) |
| NM_003529 | HIST1 H3A | R |
| NM_153490 | KRT13 | GPGPSR (SEQ ID NO: 68) |

TABLE 2d-continued

| Accession ID | Gene Name | FS Peptides |
|---|---|---|
| NM_019016 | KRT24 | ATPTWK (SEQ ID NO: 69) |
| NM_015848 | KRT2B | TLLQEQGTKTVRQNLEPLFEQYINNLRRQLDNIVGERGRLDS (SEQ ID NO: 70) |
| NM_002272 | KRT4 | ESWYQTKYEELQITAGRHGDDLRNTKQEIAEINRMIQRLRSEIDHV KKQCANLQAAIADAEQRGEMALKDAKNKLE (SEQ ID NO: 71) |
| NM_153486 | LDHD | GRRLR (SEQ ID NO: 72) |
| XM_060417 | LOCI 27295 | LARMCVPTLLLTNLRARLVRKREELSNVLAAMKKA TAKKD (SEQ ID NO: 73) |
| XM_497978 | LOC132391 | RVRHGVRGPGHRDSRGSGRNGRHPEREGDHAKPERPPGLLPGQ Q (SEQ ID NO: 74) |
| XM_211339 | LOC284120 | LLSFCCPGWSSVA (SEQ ID NO: 75) |
| XM_208312 | LOC284120 | LDDSIVVKLVSPGSALPRIFGLSPESLSADH (SEQ ID NO: 76) |
| XM_293903 | LOC284120 | IVEERKMHWSPRTWSLGNQFMERRESRFRKEMTKLSTE (SEQ ID NO: 77) |
| XM_370672 | LOC284120 | TVKHPVCV (SEQ ID NO: 78) |
| XM_495875 | LOC284120 | FHVNHVKRSRVPLSVGDHTNSS (SEQ ID NO: 79) |
| XM_372840 | LOC391209 | LARMCVPTLLLTNLRARLVRKREELSNVLAAMKKATAKKD (SEQ ID NO: 80) |
| XM_497922 | LOC391538 | RCVLKIGEHTPSALAIMENAKCSGPLCQYLPAEWHCAHRGA (SEQ ID NO: 81) |
| XM_496658 | LOC440976 | GGGGRAERPAGLAGVQGQTGWVSVLKPPALLPQLRSKVKRLIRF (SEQ ID NO: 82) |
| XM_497335 | LOC441632 | AKQVLLGRKVVVVRCEGINISGNFYTKQVEVPRFPPQADEHQLLPR LL PLPGPQPHLLADRARY AAPQDQARPGRSGPPQGV (SEQ ID NO: 83) |
| XM_497347 | LOC441641 | GNFYRNKLKYLAFLRKRMNTNPSRGPYHFRAPSRIFWRTVRGML PHKTKRGQAALDRLKVFDGIPPPTT (SEQ ID NO: 84) |
| XM_497605 | LOC441836 | VGDEAQSKRGILTLKYPIEHGIVTTPSTTSCAWPRRSTRCC (SEQ ID NO: 85) |
| XM_029323 | LOC90133 | QAPRL (SEQ ID NO: 86) |
| NM_138779 | LOC93081 | GTCWRKWHRKCKLPIKSTGLRRQIIPWQ (SEQ ID NO: 87) |
| NM_002383 | MAZ | GFTTAAYLRIHAVKDHGLQAPRADRILCKLCSVHCKTPAQLAGHM QTHLGGAAPPVPGDAPQPQPTC (SEQ ID NO: 88) |
| NM_174923 | MGC31967 | REEMSTQWLPTYVPIPPSCHKFPKNSQNHCSPHL (SEQ ID NO: 89) |
| NM_182523 | MGC61571 | YFLSSIRFISTF (SEQ ID NO: 90) |
| NM_025259 | MSH5 | RNPQQMPL (SEQ ID NO: 91) |
| NM_002485 | NBN | V |

TABLE 2d-continued

| Accession ID | Gene Name | FS Peptides |
|---|---|---|
| NM_001001716 | NFKBIB | RHCTWL (SEQ ID NO: 92) |
| NM_020729 | ODF2L | WRIFLH (SEQ ID NO: 93) |
| NM_001007157 | PHF14 | GLADS (SEQ ID NO: 94) |
| NM_015937 | PIGT | EFSSQLWTLKEGAEVAPGQ (SEQ ID NO: 95) |
| NM_007221 | PMF1 | SPLLHWDGSAWSPPALWWTVCETGLQLGGVQVTT GEEGGNL (SEQ ID NO: 96) |
| NM_001017431 | RBM3 | VVVVKDRETQRSRGFGFITFTNPDLWMVVRSVWIMQASLLGEPE EVALGPMGVVAATL (SEQ ID NO: 97) |
| NM_015725 | RDH8 | LFLWLSSQALTLRPCTTSGTSISQPPGSCFAPWDRTHRTWFRPLST SSARLDHPCADRPTSATRR (SEQ ID NO: 98) |
| NM_194452 | RNF121 | IW |
| NM_001005 | RPS3 | KLVGNSQKECGVS (SEQ ID NO: 99) |
| NM_058192 | RPUSD1 | GVSGVGGVLVVTEGKLRHRATKLMLGHPEHQGRAGNKHSCVLNS TPCSLSASHLTQGPCWLLTDSLGVWLAAILQDRAPPWPCPHQW (SEQ ID NO: 100) |
| NM_207521 | RTN4 | MDLKEQPGNTISAGQEDFPSVLLETAASL (SEQ ID NO: 101) |
| NM_173073 | SLC35C2 | RAALVLVVLLIAGGLFMFTYK (SEQ ID NO: 102) |
| NM_130849 | SLC39A4 | VRMARGGAALGRELSRGAEQGR (SEQ ID NO: 103) |
| NM_003096 | SNRPG | KKLNGGRHVQGILRGFDPFMNLVIDECVEMATSGQQNNIGMVVI R GNSIIMLEALERV (SEQ ID NO: 104) |
| NM_014748 | SNX17 | VGLAPLP (SEQ ID NO: 105) |
| NM_013403 | STRN4 | MLLRRRGTPSSPCARTTTAFVPWPSTTASRLCSPPPRTARSSSGTC RRRSRPRRMRR (SEQ ID NO: 106) |
| NM_006521 | TFE3 | RGLQDPCHVVIFFIEGLAAAAANAGPGAGAGEA (SEQ ID NO: 107) |
| NM_003299 | TRA1 | AWTRFAMRA (SEQ ID NO: 108) |
| NM_176880 | TRA 16 | VHRALRLSTRL (SEQ ID NO: 109) |
| NM_173500 | TTBK2 | GTKTCEAEPGAVVRAVHQQPQEAAGQHRGGTGSSGLGAEKHAG P GGGPQEQTMRMKSTSAQQQRMNL (SEQ ID NO: 110) |
| NM_018299 | UBE2W | SCLLVKIFLFILMFIAMVISVYPF (SEQ ID NO: 111) |
| NM_018206 | VPS 3 5 | SLIIIKRYGHF (SEQ ID NO: 112) |
| NM_001006612 NM_001006614 | WBP5 | A |
| NM_017528 | WBSCR22 | K |

TABLE 2d-continued

| Accession ID | Gene Name | FS Peptides |
|---|---|---|
| NM_001033518 NM_001033519 | WIPI-2 | TRYGRCVHCREIVLQQPSGHRQP (SEQ ID NO: 113) |
| XM_374912 | XRRA 1 | EDRKRGCCPTSSSLPISLRVRLS (SEQ ID NO: 114) |

Table 2e shows FS variant sequences for which the number of sequence matches for the FS variant sequence against the normal EST databases was zero; this number was arbitrarily set at 1 for purposes of computing the odds ratio. RNA expression ratios measured for sequences C7orf24 and ZWILCH were 3.6× and 10.4×, respectively; RNA expression in tumor cells exceeding that in normal cells was confirmed by PCR and inspection of electrophoresis gel band intensities in DYRK4, HNRPUL1, MAP3K10, PPP4C, and RIPK2; and expression of the FS variant in tumor cells was confirmed by RNA extraction and sequencing for DYRK4, HNRPUL1, RIPK2, and ZWILCH.

TABLE 2e

| Accession ID | Gene name | FS peptide | Odds Ratio |
|---|---|---|---|
| NM_001033054 | AIPL1 | HTGVYPILSRSLRQMAQGKDPTEWHVHTCGLANMFAY HTLGYEDLDELQKEPQPLVFVIELLQ (SEQ ID NO: 115) | 3.00 |
| NM_005787 | ALG3 | TQRLTGRPTWPR (SEQ ID NO: 116) | 2.79 |
| NM_001002857 | ANXA2 | VWMRSPLSTF (SEQ ID NO: 117) | 4.12 |
| NM_175073 | APTX | SLRKRQRTLAWKHTGRERDQATVIL (SEQ ID NO: 118) | 4.92 |
| NM_005174 | ATP5C1 | CHQETKVHQKHPENYQVYENGSGSKICPS (SEQ ID NO: 119) | 2.62 |
| NM_001003785 | ATP5H | IFFFFGIHLGSIFILWHGNLQRIK (SEQ ID NO: 120) | 2.57 |
| NM_004047 | ATP6V0B | GS | 2.13 |
| NM_080598 | BAT1 | GCCFFWWSVYQEG (SEQ ID NO: 121) | 2.12 |
| NM_013980 | BNIP1 | SNQASWRKANLTCKIAIDNLEKAELLQGGDLLRQRPPK RAWPRHPVPSLRASWGSAG (SEQ ID NO: 122) | 5.33 |
| NM_018045 | BSDC1 | G | 2.38 |
| NM_001032363 | C1orfI51 | ESW | 4.47 |
| NM_014145 | C20orf30 | APSCCQATSAKGGQTGPFQC (SEQ ID NO: 123) | 6.25 |
| NM_004649 | C21orf33 | DPGAPEPWRG (SEQ ID NO: 124) | 2.31 |
| NM_005768 | C3F | AERE (SEQ ID NO: 125) | 3.00 |
| NM_024051 | C7orf24 | ARRG (SEQ ID NO: 126) | 5.00 |
| NM_018491 | CBWD1 | VIQRLLC (SEQ ID NO: 127) | 3.04 |
| NM_018246 | CCDC25 | GKNCDSGEESK (SEQ ID NO: 128) | 3.00 |
| NM_001782 | CD72 | RPRG (SEQ ID NO: 129) | 5.83 |
| NM_006319 | CDIPT | AACWTLSMDTLLALLIKEPGLGPCWTC (SEQ ID NO: 130) | 2.11 |

TABLE 2e-continued

| Accession ID | Gene name | FS peptide | Odds Ratio |
|---|---|---|---|
| NM_024300 | CHCHD7 | CRSCSTF (SEQ ID NO: 131) | 6.55 |
| NM_001009566 | CLSTN1 | GERRE (SEQ ID NO: 132) | 3.79 |
| NM_199442 | COPE | RDSIVAELDREMSRSVDVTNTTFLLMAASIYLHDQNPD AALRALHQGDSLE (SEQ ID NO: 133) | 3.30 |
| NM_032589 | DSCR8 | LQTLEIKKVLE (SEQ ID NO: 134) | 7.00 |
| NM_020185 | DUSP22 | DKTFQRKY (SEQ ID NO: 135) | 5.00 |
| NM_003845 | DYRK4 | IPKVFLKI (SEQ ID NO: 136) | 7.33 |
| NM_001967 | EIF4A2 | DPKGNSGTWRLYGSHLSCLHWWNKCSK (SEQ ID NO: 137) | 5.62 |
| NM_019002 | ETAA16 | KFKFECNFRSYEYRNYYL (SEQ ID NO: 138) | 3.00 |
| NM_032231 | FAM96A | VGNLHF (SEQ ID NO: 139) | 4.26 |
| NM_005687 | FARSLB | NI | 5.28 |
| NM_001031704 | FLJ20211 | GCQPDHGAGAWAACVP (SEQ ID NO: 140) | 2.00 |
| NM_013393 | FTSJ2 | IPALLLASCLG (SEQ ID NO: 141) | 2.22 |
| NM_203504 | G3BP2 | EL | 2.82 |
| NM_004127 | GPS1 | SCRTHPTPSLRAAWSPQPWTRPGWRPRGRRRC (SEQ ID NO: 142) | 6.31 |
| NM_012203 | GRHPR | AVRWSSGTRMSPSLPRS (SEQ ID NO: 143) | 17.27 |
| NM_147149 | GSTM4 | LPYLIDGAHKITQSNAILCYIARKHNLCGETEEEKIRVDI LENQAMDVSNQLARVCYSPDFEKL (SEQ ID NO: 144) | 2.41 |
| NM_000853 | GSTT1 | VWPSCST (SEQ ID NO: 145) | 6.32 |
| NM_145871 | GSTZ1 | LAIIEYLEEMRPTPRLLPQDPKKRASVRMISDLIAGGIQP LQ (SEQ ID NO: 146) | 7.31 |
| NM_000858 | GUK1 | GR | 2.68 |
| NM_000187 | HGD | GTA | 3.33 |
| NM_003537 | HIST1H3B | RW | 2.15 |
| NM_001002032 | HN1 | GEGDIHENVDTDLPGSLGQSEEKPVPAAPVPSPVAPAPV PSRRNPPGGKSSLVLG (SEQ ID NO: 147) | 45.29 |
| NM_144733 | HNRPUL1 | MPWTILPGRTNSTIPKSSNKKTSQATRGDHWKWSSSRPI VQK (SEQ ID NO: 148) | 2.40 |
| NM_016371 | HSD17B7 | MIKKWLYVICVEDHVSEIRLYISKCWDHA (SEQ ID NO: 149) | 2.77 |
| NM_144981 | IMMP1L | CQWVMFG (SEQ ID NO: 150) | 2.00 |
| NM_024710 | ISOC2 | EHDPGPPRPGAAGPCGGGRLLLTQPGGPAGGSGPHETE W CLPLHQRR AHS A ACGRCRPPP V | 8.85 |

TABLE 2e-continued

| Accession ID | Gene name | FS peptide | Odds Ratio |
|---|---|---|---|
| | | QGDPETHQGARPRQ RTAGPLPRPELPPPL (SEQ ID NO: 151) | |
| NM_005886 | KATNB1 | A | 3.50 |
| XM_371877 | K1AA0960 | RKAQRYTGQ (SEQ ID NO: 152) | 5.00 |
| NM_138787 | LOC119710 | DLLLLPGEVEQDV STSIPSCIPFV AQPPTCEVKPKPS VKR MDKQTEEILGDEVQLFSLDEEFDYDNVMLTSKFSPAEIE NIKELCKQQKRKDTSPDLEKSCD (SEQ ID NO: 153) | 5.25 |
| XM_059341 | LOC129293 | GSSLL (SEQ ID NO: 154) | 2.50 |
| NM_001031744 | LOC158160 | MIKKWLYVICVEDHVSEIRPYISKCWDHA (SEQ ID NO: 155) | 3.64 |
| NM_174928 | LOC221143 | VPSWKNRQQNSLE (SEQ ID NO: 156) | 4.44 |
| XM_290671 | LOC339047 | CKTWHSAWV (SEQ ID NO: 157) | 4.36 |
| NM_001005920 | LOC339123 | VSACPSVPGHSRPCWARPLSPLPAPAEVPGPVLPRQVAGF VWGQSGPAEHRQHLLLPQSGLALPGVCGAAAAPPGPHLP GQ (SEQ ID NO: 158) | 6.67 |
| XM_292085 | LOC341457 | MPSTASPW AASPLSCLQTSFQRQQETFML (SEQ ID NO: 159) | 7.66 |
| XM_495885 | LOC440055 | YVYQSQYCGFLQPEQNCHPREEGMEFMVLAQKF (SEQ ID NO: 160) | 6.32 |
| XM_352159 | LOC440341 | CKTWHSAWV (SEQ ID NO: 161) | 2.55 |
| NM_002446 | MAP3K10 | RMLGPRPPRAARFR (SEQ ID NO: 162) | 4.80 |
| NM_181514 | MRPL21 | G | 2.86 |
| NM_145330 | MRPL33 | KNILVRMVSEAGTGFCFNTKRNRLREKLTLLHYDPVVK QRVLFVEKKKIRSL (SEQ ID NO: 163) | 17.50 |
| NM_012333 | MYCBP | SVGSLI (SEQ ID NO: 164) | 3.78 |
| NM_012225 | NUBP2 | R | 7.14 |
| NM_000430 | PAFAH1B1 | MKN | 2.17 |
| NM_001003 891 | PCQAP | RGCHEESWCGTQ (SEQ ID NO: 165) | 5.60 |
| NM_020992 | PDL1M1 | I | 2.77 |
| NM_002677 | PMP2 | EVGVGLPPGKWLAWPNLT (SEQ ID NO: 166) | 4.50 |
| NM_174930 | PMS2L5 | LFQL (SEQ ID NO: 167) | 2.12 |
| NM_006243 | PPP2R5A | KLYCSF (SEQ ID NO: 168) | 2.00 |
| NM_180977 | PPP2R5D | LFLIH (SEQ ID NO: 169) | 3.11 |

TABLE 2e-continued

| Accession ID | Gene name | FS peptide | Odds Ratio |
|---|---|---|---|
| NM_002720 | PPP4C | RCAATSMDNSMTSKSCSE (SEQ ID NO: 170) | 3.81 |
| NM_032864 | PRPF38A | RNAMY (SEQ ID NO: 171) | 4.44 |
| NM_002767 | PRPSAP2 | ENKSTNSRVCEGKRCFHHPNCFEGREHHHHGAPDHGV CM (SEQ ID NO: 172) | 7.38 |
| NM_021222 | PRUNE | K | 2.77 |
| NM_003579 | RAD54L | DA | 2.43 |
| NM_005493 | RANBP9 | AKFVSYCGASNTRRSGRCQFWATSFRV (SEQ ID NO: 173) | 3.00 |
| NM_006743 | RBM3 | VSGWSSDPCGSCRQV CSGNQRRWLWGPWAWSQLL (SEQ ID NO: 174) | 3.81 |
| NM_181471 | RFC2 | GH | 3.28 |
| NM_003821 | RIPK2 | RKLNILMLLGH (SEQ ID NO: 175) | 4.80 |
| NM_001016 | RPS12 | YVYQSQYCGFLQPEQNCHPREEGMEFMVLAQKF (SEQ ID NO: 176) | 6.21 |
| NM_007008 | RTN4 | GFVFAPR (SEQ ID NO: 177) | 6.68 |
| NM_005888 | SLC25A3 | YSCEFGSAKYYALCGFGGVLSCGLTHTAVVPLDLV (SEQ ID NO: 178) | 2.38 |
| NM_003136 | SRP54 | VCY | 3.38 |
| NM_139276 | STAT3 | FIDAVWK (SEQ ID NO: 179) | 2.31 |
| NM_003195 | TCEA2 | RLSPSVSHSICRRQQFGV (SEQ ID NO: 180) | 4.00 |
| NM_144582 | TEX261 | D | 2.14 |
| NM_005727 | TSPAN1 | VCETQLHRLMTKSPLAFDTRPWDSQTLLWTPLGSGFCL TFPGGGLGQGGHEGLSLPKTQTPVPHSVLLHPPPHLHC (SEQ ID NO: 181) | 4.91 |
| NM_018943 | TUBA8 | MRECISVHVGQAGV (SEQ ID NO: 182) | 2.85 |
| NM_145345 | UBXD5 | EDEVDMLSDGCGSEERRSQSLPAMAA (SEQ ID NO: 183) | 3.67 |
| NM_005153 | USP10 | DKNIRELSLVSMKSLNPVTLCREPPATVFQAH (SEQ ID NO: 184) | 2.07 |
| NM_022170 | WBSCR1 | GFRDDFLGGRGGSRPGDRRTGPPMGSRFRDGPPLRGSN MDFREPTEEERAQRPRLQLKPRTVATPLNQVANPNSAIFG GARPREEVVQKEQE (SEQ ID NO: 185) | 2.55 |
| NM_024699 | ZFAND1 | IFFHLCVMIVQEYF (SEQ ID NO: 186) | 2.81 |
| NM_017975 | ZWILCH | CPAEIK (SEQ ID NO: 187) | 4.42 |

Table 2f shows FS variant sequences for which computed odds ratios were less than 2.0, but which are likely to be involved in tumorigenesis; RNA expression of BCL2L13 and DTYMK in tumor cells exceeding that in normal cells was confirmed by PCR and inspection of electrophoresis gel band intensities, and expression of DTYMK in tumor cells was confirmed by RNA extraction and sequencing.

TABLE 2f

| Accession ID | Gene Name | Function | FS Peptides |
|---|---|---|---|
| NM_015367 | BCL2L13 | Apoptosis | QFWCLWFCYDKCFWN (SEQ ID NO: 188) |
| NM_012145 | DTYMK | Kinase | IFP |
| NM_152255 | PSMA7 | ETC | RYTQSNGRRPFGISALIVGFDFDGTPR LYQTDPSGTYHAWKANAIGRGAKSVRE FLEKNYTDEAIETDDLTIKLVIKALLE VVQSGGKNIELAVMRRDQSLKILNPEE IEKYVAEIEKEKEENEKKKQKKAS (SEQ ID NO: 189) |
| NM_024572 | GALNT14 | ETC | KYGPSHTPSRSSRRSCACQSSPCSLAP QWFLSFARMEMTDSNGPKLVPTSST (SEQ ID NO: 190) |
| NM_003089 | SNRP70 | ETC | RPGPGP (SEQ ID NO: 191) |

Table 2g shows genes for which FS variants were predicted and odds ratios computed as shown, but whose variants arise from indels of less than 10 bp, increasing the likelihood that the difference are due to a sequencing error.

TABLE 2g

| Accession ID | Definition | Odds Ratio | FS Peptides |
|---|---|---|---|
| XP_060328.1-11 | PREDICTED: similar to 60S acidic | 53.19 | VSELACIYSASFCTTMR (SEQ ID NO: 192) |
| NP_001772.1-67 | CD69 antigen (p60, early T-cell) | 48 | VQANTHSQCHQTAMFLH ALRTGLATRGNATLFLL (SEQ ID NO: 193) |
| NP_001022.1-13 | ribosomal protein S28 [Homo sapiens] | 41.66 | SPRSWAGPVLRDSARRC AWNSWTTRADPSSAM (SEQ ID NO: 194) |
| XP_060328.1-51 | PREDICTED: similar to 60S acidic ribosomal protein P2 | 33.65 | ATSTLGASSAM (SEQ ID NO: 195) |
| NP_000995.1-62 | [Homo sapiens] | 22.47 | VLASLPVYLLVGL (SEQ ID NO: 196) |
| NP_001025172.1-16 | ribosomal protein S29 isoform 2 | 20.69 | VLALVVSVQTGTV (SEQ ID NO: 197) |
| XP_497649.1-13 | PREDICTED: similar to Cofilin, | 18.67 | VSDGVIKGVQRHEGA (SEQ ID NO: 198) |
| NP_000080.2-10 | alpha 2 type I collagen (Homo | 16 | VHQGPCWPPWSPWPSWT SRCKRWWL (SEQ ID NO: 199) |
| XP_170597.1-16 | PREDICTED: similar to A TP synthase, H+ | 14.36 | WAASPLSCLQTRSQRQQ KIFVL (SEQ ID NO: 200) |
| NP_005167.1-74 | transporting, murine mammary | 14.14 | LGASSLVMPGTLL (SEQ ID NO: 201) |
| NP_001559.1-45 | tumor integration | 13.52 | WTFLVIPTW (SEQ ID NO: 202) |
| NP_01002032.1-20 | hematological and neurological | 12.8 | CGLQVVDPIFH (SEQ ID NO: 203) |
| NP_722550.1-286 | reticulon 4 isoform B [Homo | 12.5 | LQVDVGIYLCWCLV (SEQ ID NO: 204) |
| NP_01017430.1-47 | RNA binding motif-protein 3 calnexin precursor | 12.48 | VLVSSPSPTQSMLQLP (SEQ ID NO: 205) |
| NP_001737.1-18 | [Homo sapiens] | 11.66 | MLRLMMDMMMM (SEQ ID NO: 206) |
| NP_008939.1-112 | reticulon 4 isoform C [Homo | 10.71 | LQVDVGIYLCWCLV (SEQ ID NO: 207) |
| NP_001017430.1-48 | RNA binding motif protein 3 | 10.70 | LVSSPSPTQSMLQLP (SEQ ID NO: 208) |
| NP_954654.1-144 | Nucleophos-min 1 isoform 2 [Homo | 10.28 | LEVVARFHRKK (SEQ ID NO: 209) |
| NP_97001.1-48 | general transcription factor IIH, | 10.2 | WLMSSRSEWVN (SEQ ID NO: 210) |
| NP_002801.1-36 | proteasome 26S non-ATPase subunit 4 | 10.11 | VIQRPAATLRTTWALSH WLMTVKC (SEQ ID NO: 211) |
| NP_004252.2-93 | 15 kDa selenoprotein isoform 1 | 10.09 | VDENWEGSLKSKLC (SEQ ID NO: 212) |

TABLE 2g-continued

| Accession ID | Definition | Odds Ratio | FS Peptides |
|---|---|---|---|
| XP_371019.1-12 | PREDICTED: similar to ribosomal | 10 | CEYSTPTSMGGGK (SEQ ID NO: 213) |

Example 6

Figure 7A:
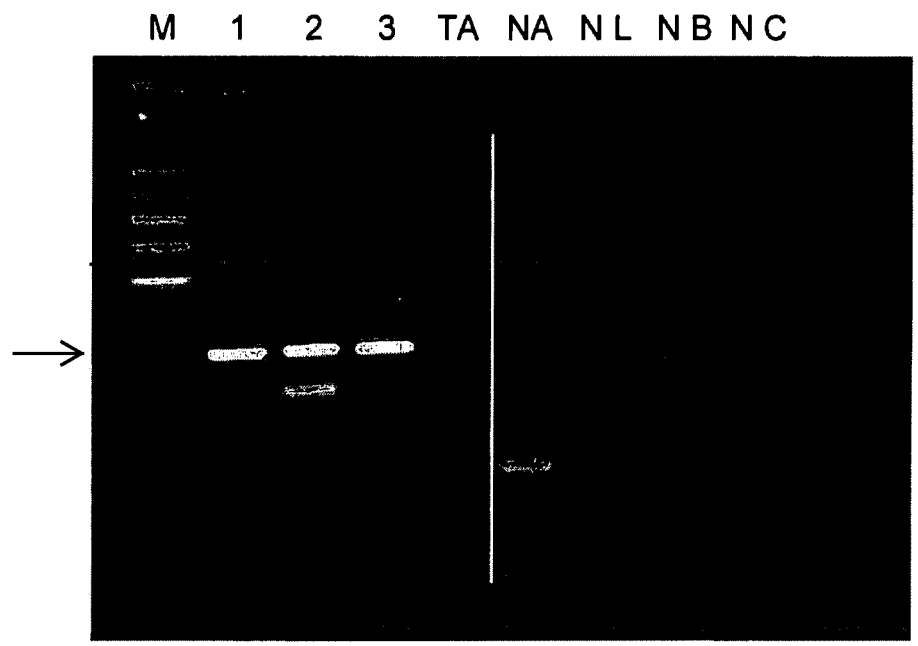
FIGS. 7a, 7b and 7c show an example of a comparison of RNA expression levels of novopeptides in tumor cells with that in non-cancerous cells.
Figure 7B:
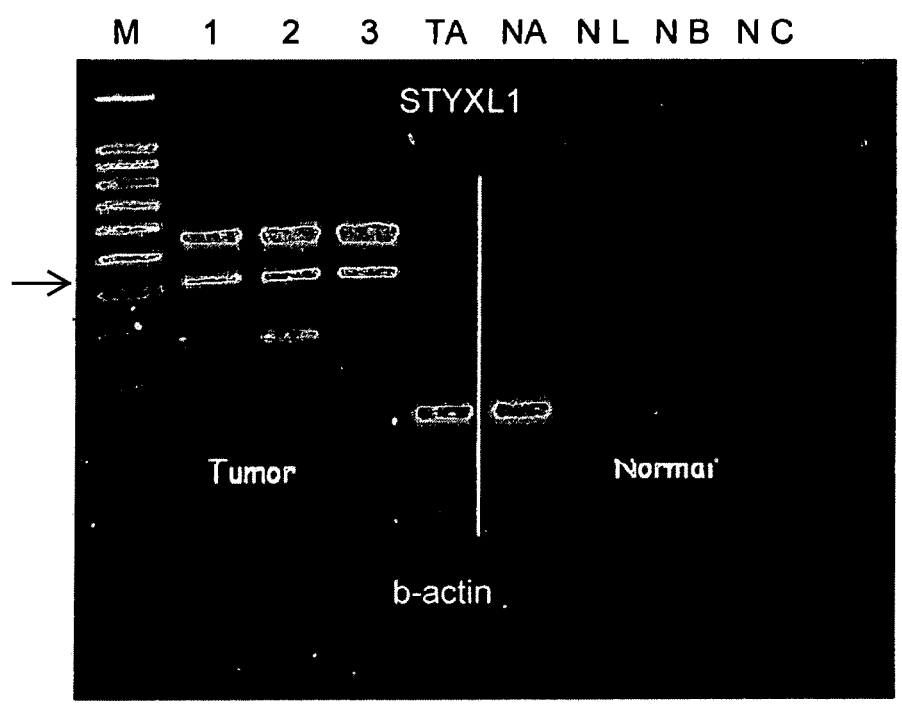
Figure 7C:
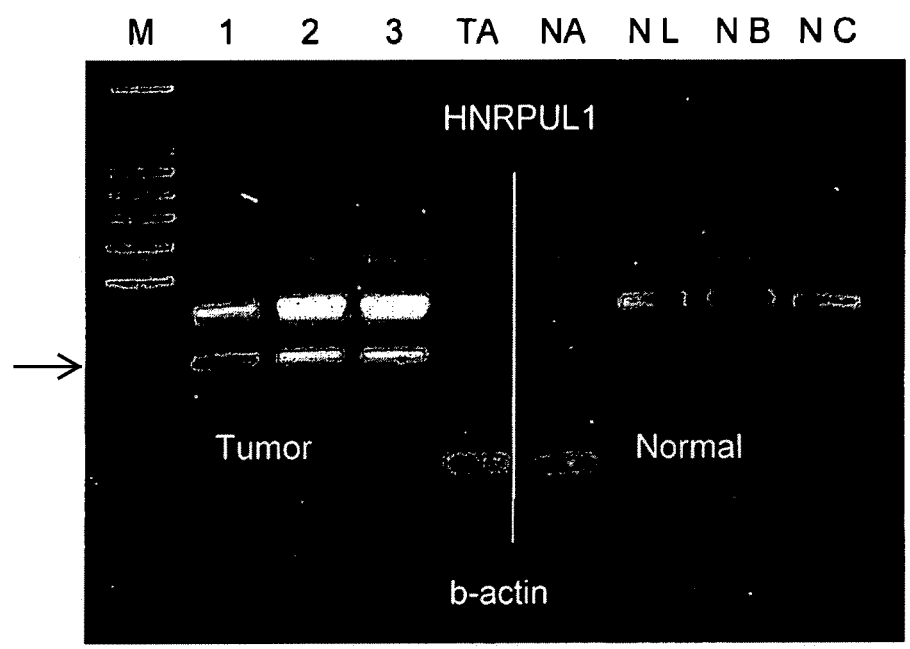

FIGS. 7a, 7b, and 7c illustrate examples of a method for assessing the likely utility of a predicted candidate novopeptide as a cancer vaccine component by comparing the RNA expression level of transcripts containing the sequence of the novopeptide in tumor cells with that in non-cancerous cells. FIG. 7a demonstrates amplification of a FS variant in BCL2L13 cDNA from three different human tumor cell lines, but not cDNA obtained from normal tissue. PCR primers were designed such that they flanked the BCL2L13 FS region and amplify a FS of 253 bp if present. The left half of the figure shows amplification of three different human tumor cDNA preparations. Lane labels in FIG. 7 are as follows. Lane M, 100 bp molecular weight marker; Lane 1, MCF-7 human breast cancer cell line; Lane 2, SW480 human colon cancer cell line; Lane 3, DU-145, human prostate cancer cell line; Lane TA beta actin from SW480 cell line. Right side of gel: Lane NA, beta actin from normal colon; Lane NL, normal lung; NB, normal breast; NC normal colon.

FIGS. 7b and 7c show two additional examples of amplification of cDNA from transcripts containing sequence corresponding to frameshifted novopeptides relating to genes designated STYXL1 and HNRPUL1. The agarose gel shows a frameshift encoding a novopeptide present in tumor cells, but not present in cDNA from normal lung, breast and colon. PCR was performed as in 7a, but with primers that flank the predicted frameshifts. Lanes are the same as FIG. 7a. Arrows mark the FS bands in each figure.

Example 7

Quantitative PCR measurement showed over-expression in tumor samples of transcripts containing sequence corresponding to another frameshift variant, SMC-1A cDNA from four fresh human pancreas tumor samples were tested for relative expression message containing sequence corresponding to SMC-1A FS using PCR primers specific for the FS sequence. Levels of FS SMC-1A cDNA were compared to SMC-1A cDNA amplified from normal pancreas from the same patient. Table 3 shows that three of four pancreas tumors overexpressed FS SMC-1A, compared to the normal wild type sequence.

TABLE 3

| Sample | Relative Expression Level | |
|---|---|---|
|  | FS | WT |
| Panc-C | 2.69 | 0.094 |
| Panc-E | 30.7 | 0.852 |
| Panc-F | 1.15 | 0.26 |
| Panc-G | 0.512 | 0.696 |

Example 8

This example shows that novopeptides actually expressed by tumor cells can be identified via mass spectrometry, and discloses a method for doing so, and also illustrates and discloses a method for identifying subsequences likely to be displayed in MHC. Peptides were eluted from the surface of tumor cells by exposure to 100 mM citric acid for 30 seconds, or phosphate buffered saline for 4 hours, or peptides were competed from cell surface HLA molecules with a biotinylated peptide having high affinity for the HLA molecule of interest. A database of frame shifted peptide sequences was constructed from the sequences predicted bioinformatically as described above, to enable the use of LC-MS/MS to identify novopeptides actually present in the eluted sample. The peptide sequence database was used to search spectra obtained from LC-MS/MS, using Spectrum Mill, for peptides eluted from MCF-7 breast tumor cells HLA-A*0201, -B* 18/44 and -Cw*05. The HLA types were determined for the tumor cells of interest as described above. Unexpectedly, peptides longer than 8-10 amino acids were identified from LC-MS/MS analysis of the elutions that matched some sequences in the FS database. These longer peptides have been analyzed using MHC class I binding algorithms, BIMAS and SYFPEITHI, to identify preferred 9-mer sequences that are capable of binding multiple HLA class I molecules as shown below in Table 4a-4e. The algorithms use different methods of scoring peptides for binding. Sometimes the algorithms are complementary, but often they are not. BIMAS values over 150 and SYFPEITHI values over 20 have the best chance for peptides binding to MHC intracellularly and being transported to the cell surface.

TABLE 4a

Parent sequence #1 eluted from MCF-7 tumor cells: VIKSLQSWYLRLVI (SEQ ID NO: 225)

| HLA | SEQ | BIMASS | SYFPEITHI |
|---|---|---|---|
| A*0201 | SLQSWYLRL (SEQ ID NO: 214) | 32 | 23 |
| A*1101 | KSLQSWYLR (SEQ ID NO: 215) | .036 | 21 |

TABLE 4b

Parent sequence #2 eluted from MCF-7 tumor cells: FLSPMSGLLSTTQQSACTGIHRTS (SEQ ID NO: 226)

| HLA | SEQ | BIMASS | SYFPEITHI |
|---|---|---|---|
| A*0201 | FLSPMSGLL (SEQ ID NO: 216) | 12.7 | 23 |
| A*1101 | QSACTGIHR (SEQ ID NO: 217) | 0.008 | 23 |
| A*6801 | QSACTGIHR (SEQ ID NO 217) | 45 | 20 |

TABLE 4c

Parent sequence #3 eluted from MCF-7 tumor cells: PSPQETEFPGPGVVRPILDVGKIS (SEQ ID NO: 227)

| HLA | SEQ | BIMASS | SYFPEITHI |
|---|---|---|---|
| A*0201 | GVVRPILDV (SEQ ID NO: 218) | 13 | 21 |
| A*1301 | VVRPILDVG (SEQ ID NO: 219) | 0.405 | 20 |

TABLE 4c-continued

Parent sequence #3 eluted from MCF-7 tumor cells:
PSPQETEFPGPGVVRPILDVGKIS (SEQ ID NO: 227)

| HLA | SEQ | BIMASS | SYFPEITHI |
|---|---|---|---|
| B*0702 | GPGVVRPIL (SEQ ID NO: 220) | 120 | 23 |
| B*2705 | VRPILDVGK (SEQ ID NO: 221) | 2000 | 23 |
| B*5101 | RPILDVGKI (SEQ ID NO: 222) | 200 | 24 |
| B*5102 | RPILDVGKI (SEQ ID NO: 222) | 2640 | NA |

TABLE 4d

Parent sequence #4 eluted from MCF-7 tumor cells:
GQDCYRVPVTED (SEQ ID NO: 228)

NO HLA matches

TABLE 4e

Parent sequence #5 eluted from MCF-7 tumor cells:
AGLGTKLAAEGLAPN (SEQ ID NO: 229)

| HLA | SEQ | BIMASS | SYFPEITHI |
|---|---|---|---|
| A*0301 | KLAAEGLAP (SEQ ID NO: 223) | 0.120 | 23 |
| A*0801 | GTKLAAEGL (SEQ ID NO: 224) | 4.0 | 22 |

In related LC-MS/MS experiments, a 9-mer peptide bioinformatically predicted to be a FS of the BCL2L13 gene was identified in LC-MS/MS spectra from MCF-7 breast tumor cell elution experiments using the methods described above. The sequence of this peptide is CLWFCYDKC (SEQ ID NO: 230) and fits the HLA-A*0201 binding motif.

Example 9

Figure 8:
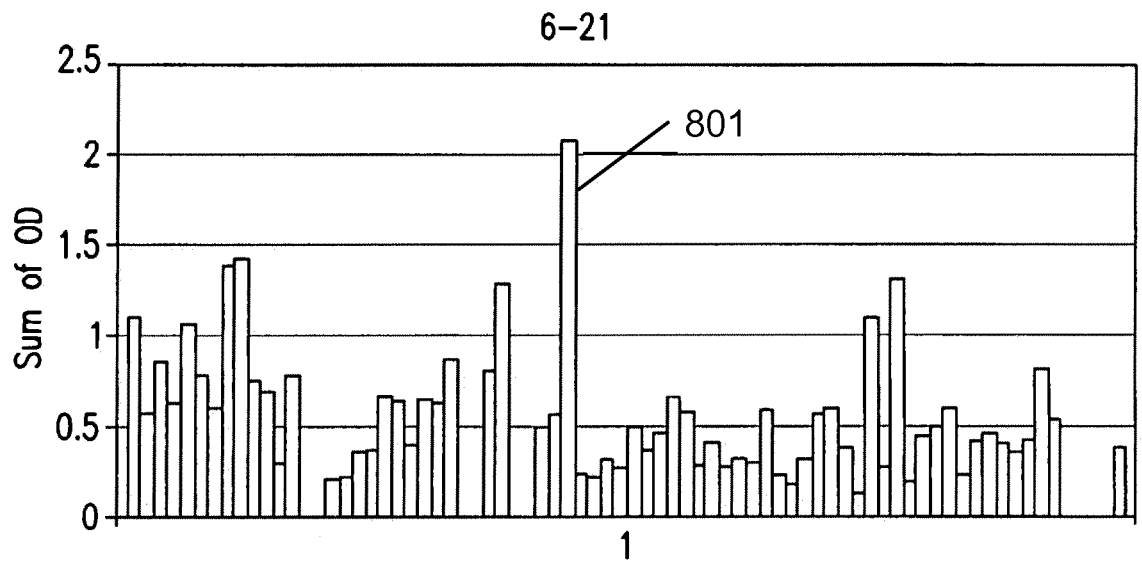
FIG. 8 shows ELISA results indicating reactivity of serum from 23 cancer patients to FS 6-21 (SEQ ID NO: 4).

Novopeptides in the FS database in association with particular tumor cell types were identified. As described in Example 8, it was observed that peptides longer than 8-10 amino acids (the expected size for MHC elutions) were obtained that matched FS sequences in the FS database. Typically peptides longer than 8-10 amino acids form epitopes for antibodies. Pursuant to the current teaching that protective or therapeutic antibodies may be generated to FS after vaccination, serum taken from patients with different tumor types was assayed for reactivity with predicted novopeptides by standard ELISA techniques. FIG. 8 shows one cancer patient in 23 with antibody reactivity in sera to peptide FS 6-21 sequence. This finding reveals novopeptides that elicit an anti-tumor antibody response upon vaccination with said novopeptides. Reactive sera 801 is indicated.

Example 10

Figure 9:
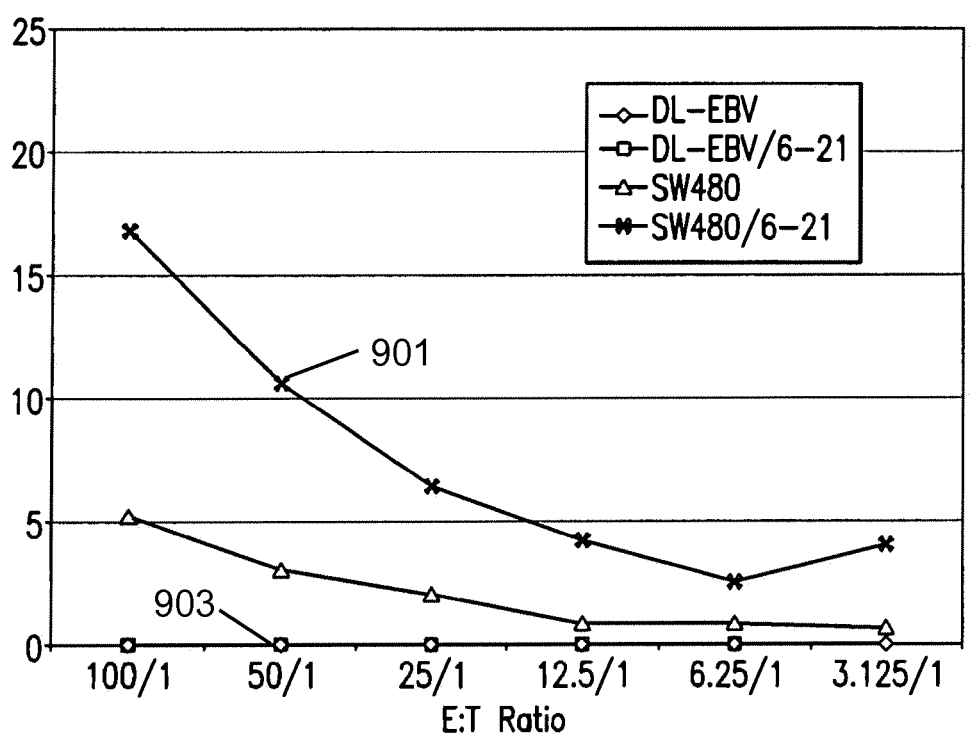
FIG. 9 shows results of an immunological screen via a CTL assay.

FIG. 9 shows that the probable immunoprotectiveness of a predicted novopeptide can be assayed by immunological screening via a CTL assay, and discloses one method for doing so. CTLs activated against novopeptide FS 6-21, described above were able to kill MHC-matched tumor cells pulsed with FS 6-21 peptide 901, but not unpulsed SW480 tumor cells 903 as shown by the square symbol. Since SW480 tumor cells do not express FS 6-21 novopeptide endogenously, the cells required peptide pulsing. This is a standard Cr release assay that anyone skilled in the art would be able to do.

Example 11

Figure 10:
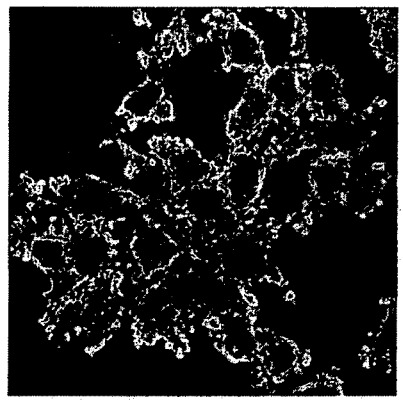
FIG. 10 shows immunofluorescence images of anti-FS 6-21 serum applied to B16 and 4T1 tumor cells and preimmune serum applied to B16 tumor cells.
Figure 10:
Figure 10:
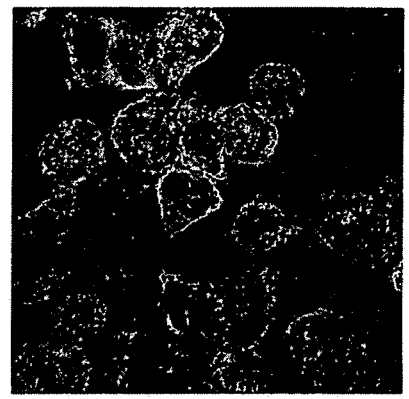

A predicted novopeptide elicits a strong antibody response by genetic vaccination. A method for assay of this response is shown. Mice were immunized as described above with a gene vaccine encoding FS 6-21 novopeptide. Serum was obtained from the mice and incubated with B16 tumor cells. Antibodies specific to novopeptide FS 6-21 were shown to specifically bind B16 murine tumor cells, while pre-immune sera did not bind. FIG. 10 shows immunofluorescence images demonstrating that the anti-FS 6-21 serum binds specifically to B16 tumor cells and 4T1 breast tumor line cells and the pre-immune serum does not.

Example 12

Figure 11:
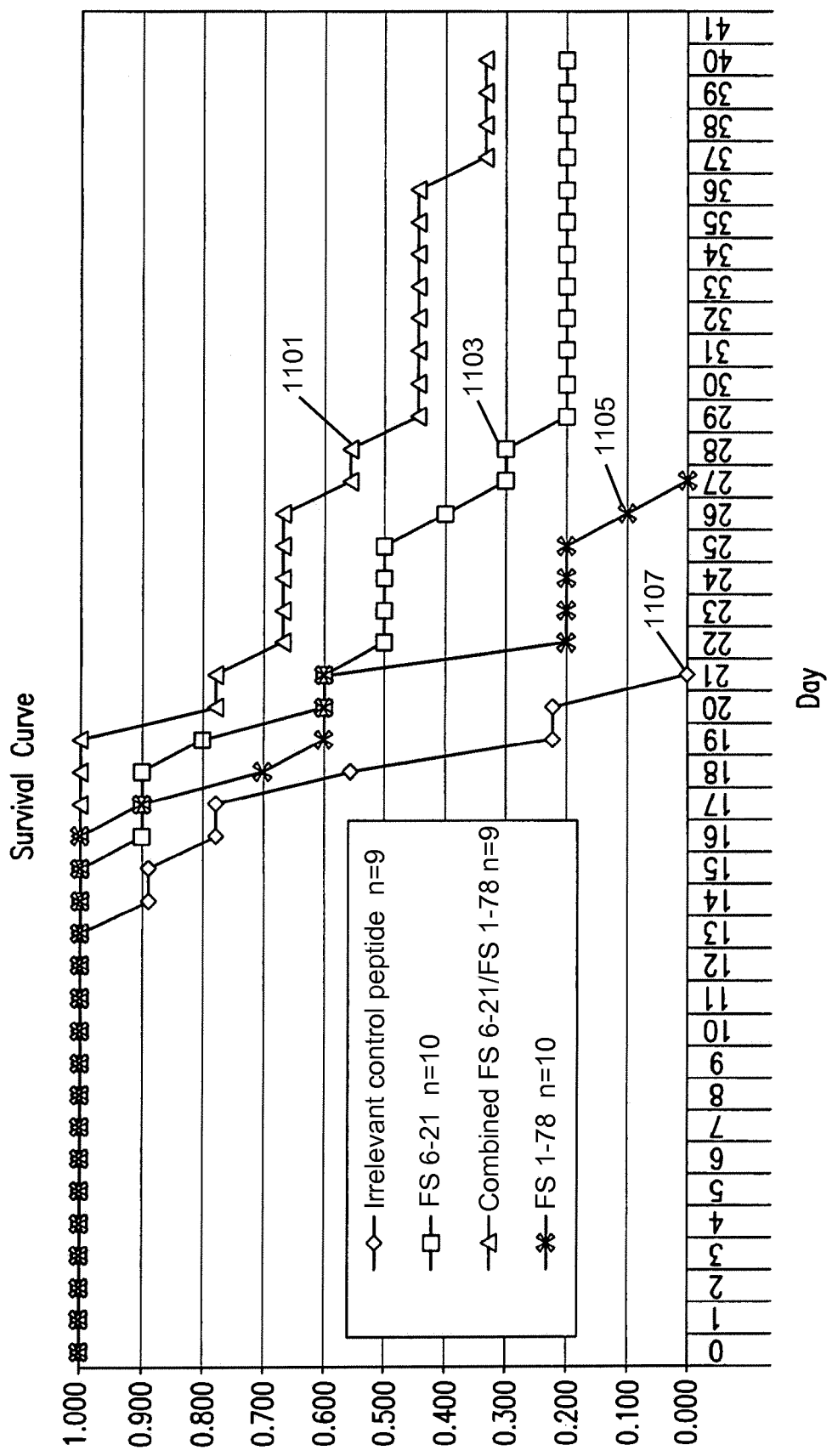
FIG. 11 shows an animal survival curve in response to therapeutic vaccination with frameshift peptide-encoding sequences.

Novopeptides can also confer therapeutic as well as prophylactic protection. Mice were injected with the B16 tumor cells and then one day later immunized with the FS 1-78 and FS 6-21 novopeptides as gene vaccines. As shown in FIG. 11, the animals receiving both peptides were protected relative to the control animals, but this protection is not as strong as a prophylactic vaccination, as indicated by the lower survival rate (one-third of the mice survived, triangle symbol, compared to 80 percent survival shown in FIG. 6 for prophylactic immunization). On Day 0, mice were injected with $10^5$ tumor cells. One day later, mice were vaccinated with the FS 6-21 peptide sequence 1103, the FS1-78 peptide sequences 1105, a combination of both 1101, or an irrelevant peptide sequence 1107.

Example 13

Candidate novopeptides that are capable of being displayed only in one or a few HLA types that are poorly represented in the target population are less desirable than those capable of being displayed in multiple HLA types that are shared by larger segments of the target population. Here, tumor targets of interest were HLA typed, with the results as shown in Table 5, so that bioinformatically identified candidate novopeptides can then be screened using MHC class I binding algorithms, such as, for example, BIMAS and SYFPEITHI, to determine the novopeptide sequences most likely to be capable of being displayed on the MHC types present in the tumors of interest. This information was used to determine the HLA types for purposes of LC-MS/MS identification and sequencing as described above.

TABLE 5

| Tumor cell line | Histological type | HLA type |
|---|---|---|
| MCF-7 | Breast (epithelial adenocarinoma) | A*02/02, B* 18/44, Cw*05/05 |
| SW480 | Colon (adenocarinoma) | A*02/24, B*07/15, Cw*07/07 |
| A549 | Lung (carcinoma) | A*25/30, B* 18/44, Cw* 12/16 |
| Panc-1 | Pancreas (epithelioid carcinoma) | A*02/I 1, B*38/38, Cw*12/12 |
| DU-145 | Prostate (carcinoma) | A*03/33, B*50/57, Cw*06/06 |

Example 14

A novopeptide associated mutation was identified that occurs in all tumors of humans and mouse identified in the public databases. This comprised a frameshift and the frameshifted gene encodes the SMC1A gene and has the sequence NGSGCSGVYCHEEPQGEDSSV (SEQ ID NO: 8) as compared to the normal wild type sequence of: NGSGKSNVMDALSFVMGEKIAN (SEQ ID NO: 7). The frameshift was found through informatic analysis of human cancer cDNA sequences compared to normal tissue. Public databases were used. The presence of the same FS was determined in mouse breast and melanoma tumor lines by sequencing cDNA from these tumor lines in the homolog of the SMC1A gene. Thirty-one (31) human tumor libraries were examined for the presence of the FS. In all 30 that were sequenced, the FS in SMC1A was identified as appearing in all lung, breast and melanoma samples but not normal samples. This correlation indicates that this mutation is oncogenic. This frameshift mutation can be used alone or in combination as a component or entirety of a vaccine, either therapeutic or prophylactic, against cancer. It can also be used diagnostically to detect early cancers. This mutation creates an oncogene that is a new anti-cancer drug target.

Figure 12A:
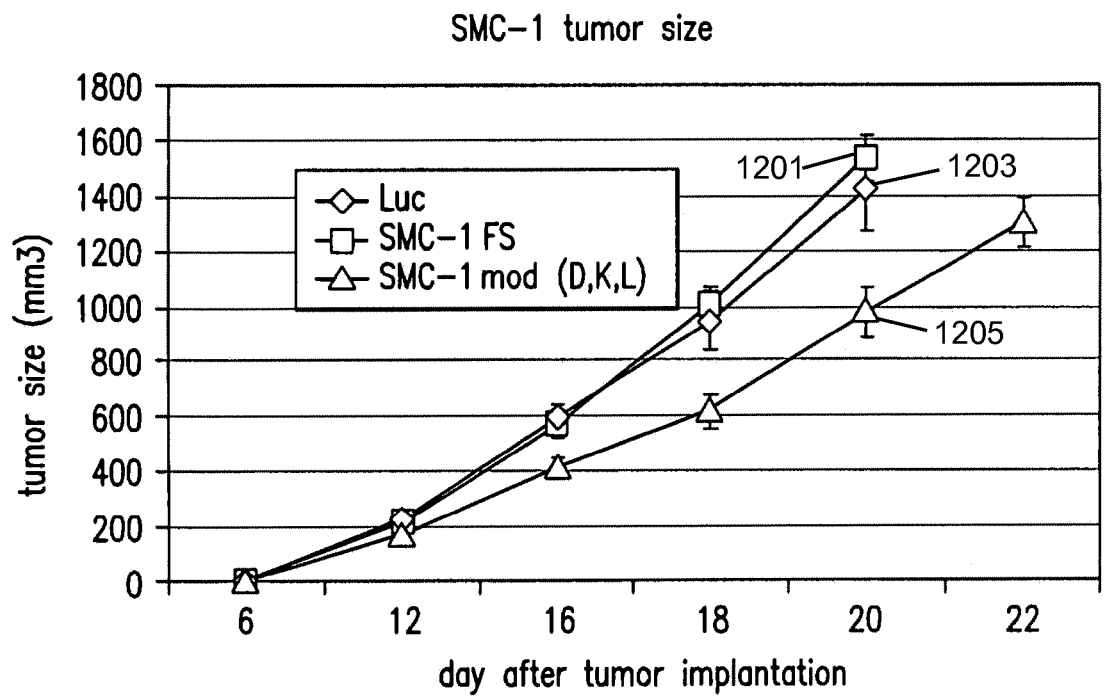
FIGS. 12a and 12b show tumor progression and survival following tumor challenge in mice receiving therapeutic vaccination with an embodiment of a novopeptide associated with a frame shift mutation or variation in FS SMC-1A (SEQ ID NO:8).
Figure 12B:
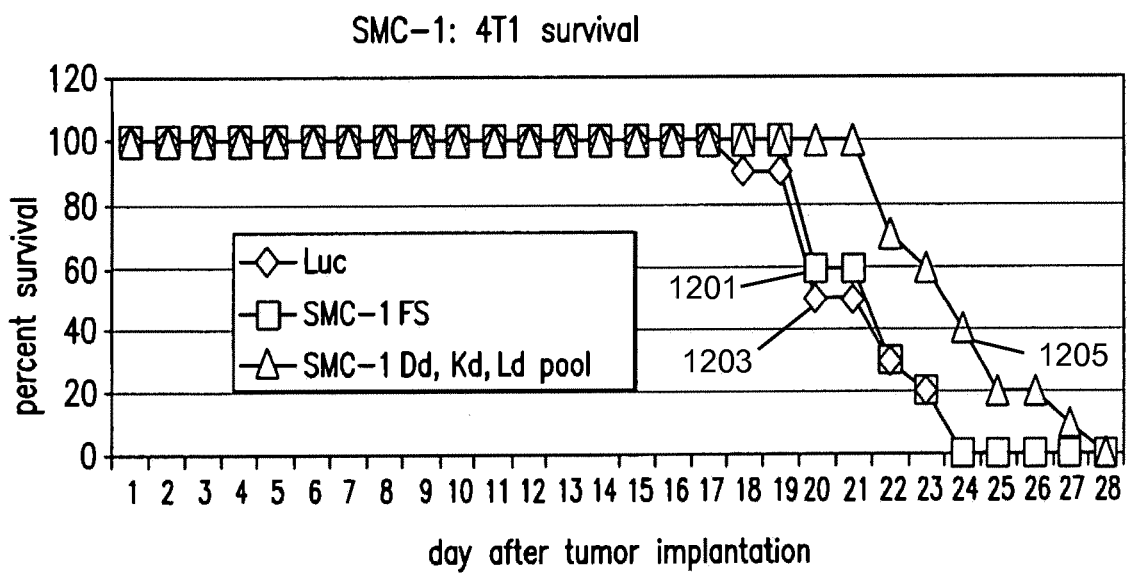

The FS was tested for therapeutic value as a vaccine in the mouse tumor model. The B16 melanoma line was inoculated into mice. One day later the mice were vaccinated with a gene vaccine encoding the FS. As shown in FIG. 12a, no therapeutic effect on tumor size progression was noted for the SMC-1 FS 1201 relative to the control 1203. However, the 17aa novopeptide is predicted to bind the mouse B16 MHC class I molecules (MHCI) poorly. Therefore epitope-enhanced variants were made based on public programs for improving MHCI binding. When these mice were therapeutically vaccinated using the epitope enhanced novopeptide 1205 there was a positive effect. Similarly, as shown in FIG. 12b, the non-epitope enhanced novopeptide 1201 did not show significant improvement in survival time relative to the control 1203, but the epitope enhanced variant 1205 did show an improvement. Therefore the FS is present specifically in human and mouse tumors and is therapeutic when epitope enhanced for mouse. Epitope enhancement is not necessary for human tumors.

Example 15

An example embodiment of a method for producing vaccine components as disclosed herein is as follows:

(a) The NCI database and/or data from the Cancer Genome Atlas is searched and analyzed to find either a variant in the cDNA (RNA) of tumors or in the genomic DNA of tumors that is rare or absent in normal sequences of cDNA (RNA) or DNA.

(b) The presence of the variant in cDNA or mutation in DNA is confirmed by sequencing the cDNA or DNA of tumor cells and normal cells and comparing the two. A panel of tumor and normal cell cDNA and DNA are used to obtain an initial estimate of the frequency of the mutation or variation in tumors versus normal cells.

(c) RNA is extracted from tumor and normal cells and the relative expression of normal messenger RNA versus the RNA encoding the novopeptide is estimated by PCR. In the case of a mutation noted in the DNA, if the mRNA of that mutation is not present in the tumors, the corresponding novopeptide is not pursued. In the case of a variant in RNA, if the variant RNA is present at nearly the same level in tumors as normal cells, the corresponding novopeptide is not pursued.

(d) Candidates remaining at this point may be screened by mass spectrometry for being present as novopeptides on the surface of tumor cells but not normal cells. The preference is to elute peptides by acid elution or incubation in buffer to collect the medium. While peptides binding the MHCI can be eluted by more specific protocols, these would miss non MHCI peptides that may be targets of anti-tumor antibodies generated by the vaccine. Chromatographs from the mass spectrometry are compared to the unique database of possible frameshift novopeptides described herein. Candidate novopeptides may be confirmed by mass spectrometry sequencing. If a novopeptide is discovered which is longer than 9 amino acids, the MHCI eluted peptides may be specifically analyzed for the presence of a nested peptide sequence that would be predicted to bind the HLA of the particular tumor cell.

(e) The candidate novopeptide sequences or nested subsequences thereof may be screened for predicted binding to human MHCI molecules. Those that are predicted to bind tightly to common MHCIs receive relatively higher scores than those predicted to bind weakly, or to bind strongly to rare MHCIs.

(f) For those peptides that receive relatively high scores, mouse tumor cells may be assayed by PCR or sequencing for the presence of the RNA encoding the novopeptide. If present in mouse tumors, mice may be vaccinated with the novopeptide and then challenged with tumor cells to determine if the peptide is protective.

(g) In parallel the high scoring candidates may be screened for their presence in human tumors. A number of tumors of the same type as well as a number of different tumors are screened by PCR or sequencing of RNA to determine the overall frequency in patients. In parallel a large number of cell types and cell types from a large number of normal subjects may be screened in the same fashion for the presence of the novopeptide encoding RNA. Novopeptide variants that are very infrequent or at very low levels in normal RNA and are present at higher levels in at least 10% of tumors of one type or in 10% in all tumor types proceed to the final screen.

(h) A final defining screen may be employed to determine if the candidate is useful in a prophylactic vaccine. This step may be required before testing of a vaccine in human subjects would be permitted or appropriate. The first screen is for T-cell reactivity. T-cells from humans with the relevant MHCIs will be activated with the test novopeptide. Once a population of such T-cells are created they will be reacted with human tumor cells with the corresponding MHCI type. If these tumor cells are killed or inhibited in growth, such would confirm that these tumor cells are presenting the novopeptide and are susceptible to the vaccine. This same T-cell preparation will also be reacted against a panel of normal cells of the same MHCI. If these cells are not killed or growth inhibited by the novopeptide activated T-cells, such would confirm that this novopeptide is a validated candidate for a cancer vaccine.

(i) For antibody screening the process is simpler. Antibody will be generated to the test novopeptide. This antibody will be reacted against tumor cells to determine if it binds to the surface. If it does this indicates that the tumor is susceptible to the antibody. As above, the same antibody will be reacted to a panel of human normal cells. Novopeptides that induce antibody specific binding are validated as components of a prophylactic cancer vaccine.

Example 16

Novopeptides useful (in their entirety, or operable portions or equivalents thereof) as peptide components of an anti-cancer vaccine are disclosed in Tables 6, 7, and 8 and were identified as follows: Bioinformatic screening was performed to identify chimeric transcripts in the NCBI EST sequence database by screening for transcripts containing a continuous sequence that aligns to two distinct RefSeq sequences simultaneously, and that, on translation, would produce a frameshift relative to wild type in the portion corresponding to the downstream RefSeq. Approximately 8 million sequences were screened, resulting in approximately 5,000 candidates. From this candidate set, candidates were excluded if a functional transcriptional coding sequence was not present in the upstream portion; if the chimeric EST sequence was not present in at least two independent cDNA libraries, or in three or more copies in one library, or had a junction point at an exon boundary of both portions; if the upstream portion corresponded to a reverse strand; or if the candidate was too short (less than 6 residues, or otherwise too short to accommodate primers for PCR verification). The remaining 233 candidates were screened against 50 breast cancer lines by RTPCR using primer pairs designed to amplify the predicted chimeric sequences. Of the candidates screened, 48 were verified as present in cDNA of the cancer lines. Table 6 shows these validated sequences, in which the first 10 residues are the 10 residues of the upstream sequence immediately adjacent to the junction point, read in their wild type reading frame, and the remaining residues are the downstream sequence from the junction point to the first stop codon, read in the non-wild-type reading frame arising from the out of frame junction. Also shown are the two reference exons to which the two conjoined domains align.

TABLE 6

| SEQ ID | REFERENCE EXONS | NOVOPEPTIDE SEQUENCE |
|---|---|---|
| SEQ ID NO: 240 | THAP2_Exon2_TME M19_Exon3 | FDFCTHIKSMVTYDLFLRGVGCFLLLFLF |
| SEQ ID NO: 243 | BOLA2_Exon2_SMG 1_Exon12 | EGKPLLQRHRLLNR |
| SEQ ID NO: 244 | GFOD1_Exon1_C6or f114_Exon2 | LTRQIAVKTLEPGHQRKKISRQKNTGEKKMPRGSVQLSFCSLQHPH MGHLFTPHDAALGESQGTGFKPLGMQPV |
| SEQ ID NO: 245 | MDS1_Exon2_EVI1_ Exon4 | NLKDPSYGWEILDEFYNVKFCIDASQPDVGSWLKYIRFAGCYDQHN LVACQINDQIFYRVVADIAPGEELLLFMKSEDYPHETMAPDIHEERQ YRCEDCDQLFESKAELADHQKFPCSTPHSAFSMVEEDFQQKLESEN DLQEIHTIQECKECDQVFPDLQSLEKHMLSHTEEREYKCDQCPKAFN WKSNLIRHQMSHDSGKHYECENCAKVFTDPSNLQRHIRSQHVGAR AHACPECGKTFATSSGLKQHKHIHSSVKPFICEV |
| SEQ ID NO: 246 | C11orf79_Exon3_C1 1orf66_Exon5 | NDWDIYYWATGPEGPFRHPGARASGHHGAGAQGSASAPPAAGP GPAGAGELPTWPTLHDVGVQFQVSQGPSRPARFLAEEIDRRKGGE WLHQTVPPEPHCLPTALTGPPWGPCPPPRPECHQVRLPPQDSPT WR |
| SEQ ID NO: 247 | ABHD14A_Exon3_A CY1_Exon2 | GYRAVALDLPAHHAQRHDQQGSRGGAPIGDALPPVPAYPHCPAQ A |
| SEQ ID NO: 248 | RBM14_NA_RBM4_ Exon2 | GRVIECDVVKGSCQDGEAVHRKPAPGGYRAGDSLTLRAVWEGAG M |
| SEQ ID NO: 249 | C20orf29_Exon2_VI SA_Exon2 | LRKEQILAVASLVSSQSIHPSWGQSPLSRI |
| SEQ ID NO: 250 | RRM2_Exon9_C2orf 48_Exon2 | LMLELGFSKVLGDREVQSRWSPGPRGDSTPVREMETNHPPSVRG |
| SEQ ID NO: 251 | ELAC1_Exon2_SMA D4_Exon2 | QLMKSQLKAGYPEYMSNNFPCNVSCCFSLFPKDQNCFRNWRHI |
| SEQ ID NO: 252 | BCAS4_Exon1_BCAS 3_Exon24 | LFLTPEPGAEVPLTGA |
| SEQ ID NO: 253 | C22orf39_Exon2_HI RA_Exon2 | WEERRNAEAQASRFFQLIFTLTGPSSQLEDKGRILGRL |
| SEQ ID NO: 254 | PMF1_Exon4_BGLA P_Exon4 | QVQAQQQAWQVRSPAVQSPAKVQPLCPSRRAAR |
| SEQ ID NO: 255 | SDHD_Exon3_TEX12 _Exon3 | LAAALTLHGHCLQCQIVHSCPLLENQIHLSLKFPDYFIKMKPWRKI |
| SEQ ID NO: 256 | PRR13_Exon3b_PCB P2_Exon2 | KHHKYHKHGKFLAFTPNQ |
| SEQ ID NO: 257 | RMND5A_Exon2_AN APC1_Exon25 | VSRVGKAIDKDSL |
| SEQ ID NO: 258 | TYMP_Exon9_SCO2 _Exon2 | VDVGQRLRRGASDPCCC |

TABLE 6-continued

| SEQ ID | REFERENCE EXONS | NOVOPEPTIDE SEQUENCE |
|---|---|---|
| SEQ ID NO: 259 | NAIP_Exon13_OCLN_Exon5 | ISAEYDPSKLG |
| SEQ ID NO: 260 | C1orf151_Exon1_NBL1_Exon3 | CLADAVVKIGLWRPRA |
| SEQ ID NO: 261 | DDIT3_^Exon3_MARS_^Exon21 | ENGGTYVSPPLPLGASGGFPSATANCFFRSKSFATSAATSFLSAFCAFSSRTMFPCFVTSSISACICCGLAVVTVSTTAGFGDVFAWPPPKRCLKLSIWSFSNFWNKGLTVPIWCPAGKVHRKFVSRILQAGGGSCSWAWIVALTVGM |
| SEQ ID NO: 262 | RIPK3_Exon9_ADCY4_Exon2 | RTPEPNPVTGADLRPELPDHCAVRAGRLLAAAGPRFPGAATAALDASPVRLGMGRAASARPRLPVHRGRGERLGPGVLFSLRHLHGVCHAALGHAGRRRRGPRLLTLASAGPRAVSWATAGLTACTAAAVGSKRSAVPVRERGRSVPQGADGARPAGHVPGGTQLPALTPAAGHREEAPGTPSLVHPSCLPGPRDEGRDHGTAAGRTGVTAREH |
| SEQ ID NO: 263 | COMMD3_Exon1_BMI1_Exon2 | LDAQADEAVLGFFIKQKCIEQRESRSLS |
| SEQ ID NO: 264 | MED8_Exon7c_ELOVL1_Exon2 | KSASMHPYQRVLSQDGGCCELVPRGDEARRSPDPGLPSDGVPLANDLHSPDLRVLRSLTWASHHG |
| SEQ ID NO: 265 | POLR2J3_Exon2_LOC100134053_NA | DHTLGNIIKSRACFPPFAFCRDCQFPEASPATLSVQPAEL |
| SEQ ID NO: 266 | BGLAP_^Exon2_PMF1_^Exon5 | QVQAQQQAWQVRSPAVQSPAKVQPLCPSRRAAR |
| SEQ ID NO: 267 | TMEM199_Exon5_SARM1_Exon2 | QYIFTEMASRPRGAHWAGRDPEPGEGTRTRRAGAERGRHLGAHVQAFGGDMPEAGGGRRPGRGAVLVPPHGPRAAAPLRAGAGQLRAARGPGGAATHGREARSRVALPARLLQGGRAASAARLPRSSGVGD |
| SEQ ID NO: 268 | C1QTNF6_Exon2_IL2RB_Exon2 | PYINITILKGLPSSAPPCGCNGGPCSVLASAPPHPPPAPGYLLGICSGEWHFPVHMLLQLESQHLLCLEPRWGSAGHFLPSPCLAGQTAVEPNL |
| SEQ ID NO: 269 | LOC100131434_NA_FLJ44451_NA | KLEEAGMLEMRPSTPCLHGAALHLHSGHGSGSRLTNSSCFPGTRRLLALQFTQQTGTVGHPTWQPVIR |
| SEQ ID NO: 270 | COX19_Exon2_CENTA1_Exon2 | KEYLECRMERSRLGLLHSGRLHLPELLGNPPEYPPGQQGEVRPPGRLGGGPSGVHGLPRERRRESQV |
| SEQ ID NO: 271 | ACSF2_Exon10_CHAD_^Exon4 | INKINMKDLVRNLRKKLQHGKMDSKAPMSC |
| SEQ ID NO: 272 | TIMM23B_NA_LOC100132418_NA | TMTGMLYKCTVSEMALDSPFCVLLSGS |
| SEQ ID NO: 273 | NDUFA13_Exon4_YJEFN3_Exon2 | IIMKDVPDWKGLGAAAPTCRHGKSGA |
| SEQ ID NO: 274 | ADHFE1_Exon13_C8orf46_NA | PALVKGTLPQYPVQPEEEPKALSTS |
| SEQ ID NO: 275 | HPS4_Exon13_ASPHD2_^Exon4 | QLPALYEMTVSNSCTS |
| SEQ ID NO: 276 | KIAA1267_Exon2_ARL17P1_Exon3 | DIYKQIRANKVSVWRQ |
| SEQ ID NO: 277 | LOC100129406_NA_CTTNBP2NL_NA | RTSALAERTHSIGHISTMLMAF |
| SEQ ID NO: 278 | RNF216_Exon7_RBAK_Exon2 | LKGHYAITRKVYQPQSLHVSKSSRK |
| SEQ ID NO: 279 | DEDD_Exon4_NIT1_Exon6 | PYVTLKRRRAAPSGLGL |
| SEQ ID NO: 280 | RAD54B_Exon3_LOC100128414_NA | LATLDPPHTVQTWMRRHRLVPVHYR |
| SEQ ID NO: 281 | TOPORS_Exon2_DDX58_Exon2 | PARPAPASSEKRCSIFRLRKTTRAQWRLPHFFSSSCWSSRRKAGSVAFWMP |
| SEQ ID NO: 282 | NDUFC2_Exon2_KCTD14_Exon2 | LHPEDFPEEDVYCCGAERRG |

TABLE 6-continued

| SEQ ID | REFERENCE EXONS | NOVOPEPTIDE SEQUENCE |
|---|---|---|
| SEQ ID NO: 283 | LRRC57_^Exon5_SNAP23_Exon8 | CCPRLKILRLSALSVIRFICGF |
| SEQ ID NO: 284 | IPO11_NA_SLRN_NA | LLSLLPSDNSLASKGP |
| SEQ ID NO: 285 | SNRPF_Exon2_CCDC38_^Exon12 | VSVDGYMNMQQDFHLHLGNIETK |
| SEQ ID NO: 286 | NDUFB8_Exon4_SEC31B_Exon2 | GDVYPVYQPVDRP |
| SEQ ID NO: 287 | MIA_Exon3_RAB4B_Exon2 | KPGKVDVKTDTSSSNSW |
| SEQ ID NO: 288 | NIT1_Exon6_DEDD_Exon4 | GSITGPAHWEQPVSS |
| SEQ ID NO: 289 | Rnf139_Exon1_Ndufb9_Exon2 | IVLQIFLRLFETNTDTLLV |

As already noted, it is accepted by persons of skill in the art that homologous sequences in closely related organisms that are accepted in the art as suitable models one for another are expected to function similarly. Thus, for example, the novopeptides disclosed in Table 6 may be species-adapted for use in other closely related species such as, for example, dog and mouse. A novopeptide identified with respect to a first species may be species-adapted for use as a peptide component of an anti-cancer vaccine for administration in a second species in any manner operable to better adapt the novopeptide to function in the second species. By way of example, a novopeptide identified as having a first domain that aligns with all or part of a first gene of the first species, and a second domain that aligns with all or part of a second gene of the first species, may be adapted by modifying the first domain to improve its alignment with all or part of a gene of the second species that is homologous to the first gene, and modifying the second domain to improve its alignment with all or part of a gene of the second species that is homologous to the second gene. Accordingly, also disclosed herein are several of the novopeptides disclosed in Table 6, that have been species-adapted for dog (Table 7) and mouse (Table 8).

TABLE 7

| SEQ ID | RELATED SEQ. | NOVOPEPTIDE SEQUENCE |
|---|---|---|
| SEQ ID NO: 242 | THAP2_Exon2_TMEM19_Exon3 | FDFCTHLKSMAIYSLFLLGVGCSLSSFLF |
| SEQ ID NO: 236 | Rbm14_Exon1_Rbm4b_Exon2 | GRVIECDVVKGAYQDGEAVHRKPAPGGHRAGDPLTLRAVWEGAGV |
| SEQ ID NO: 306 | IPO11-SLRN | LLSLLPSDNSRLTSKGP |
| SEQ ID NO: 307 | MIA-RAB4B | KPGKIDVKTDSNRTPTTQSAWSLDLG |
| SEQ ID NO: 308 | MED8-ELOVL1 | KSASMHPYQRVP |

TABLE 7-continued

| SEQ ID | RELATED SEQ. | NOVOPEPTIDE SEQUENCE |
|---|---|---|
| SEQ ID NO: 309 | ABHD14A-ACY1 | YTQEQFWAVKLTKRGA |

TABLE 8

| SEQ ID | RELATED SEQ. | NOVOPEPTIDE SEQUENCE |
|---|---|---|
| SEQ ID NO: 238 | THAP2_Exon2_TMEM19_Exon3 | FDFCTHIKSLVTFGLFLRGAGCSPSSFLL |
| SEQ ID NO: 232 | Rbm14_Exon1_Rbm4b_Exon2 | GRVIECDVVKGSCQDGEAVHWKSAPGGHRAGDPLTLRAVREGAGM |
| SEQ ID NO: 299 | Thap2 + Tmem 19(2) | FDFCTHIKSLGWWSDSS |
| SEQ ID NO: 300 | Rnf 139 + Ndufb 9 | GLQIFLRLLGTSTGTLLA |
| SEQ ID NO: 301 | Lats2 + Xpo4 | IAPEVLLRKGTTFHGQ |
| SEQ ID NO: 302 | Slc35a3 + Hiat 1 | QSVWIRNIQLASRNRLP |
| SEQ ID NO: 303 | Rbm14 + Rbm4b | GRVIECDVVKGGMCVG |
| SEQ ID NO: 304 | Mia 1 + Rab4b(1) | KPGKIDMKTDSNRTPTTLSAWSLDPGWSTLGGRL |
| SEQ ID NO: 305 | Lats2 + Xpo4 | KPGKIDMKTDTSSSNSW |

Example 17

From the candidate FS peptide sequences disclosed in Table 8 two candidates were selected for in vivo confirmation. The candidates chosen will be referred to herein as FS RBM (SEQ ID NO:232) and FS THAP2 (SEQ ID NO:238), these novopeptides having upstream in-frame portions that align with the mouse Rbm14 and Thap2 genes, respectively. These candidates were chosen as the longest candidates the presence of whose sequence was confirmed by RT-PCR in cDNA of Tubo tumor, a mouse breast cancer cell line derived from the BALB-neuT mouse model intended to be used. The BALB-neuT mouse model is a transgenic mouse breast cancer model, in which all ten mammary glands of a female mouse will develop breast tumor around 20 weeks of age, driven by overexpression of a mutant rat Her2 gene.

FS RBM and FS THAP2 peptides were tested in vivo as candidate peptide components of a prophylactic anti-cancer vaccine. BALB-neuT mice were immunized at 4 to 6 weeks old (primary genetic immunization); 8 to 10 weeks old (boost genetic immunization) and 12 to 14 weeks old (boost peptide immunization). All genetic immunization had the same genetic adjuvant for each bullet for gene gun immunization: 250 ng mixed LTA-LTB/pCMVi and 2.5 µgCpG 2216. All mice received two shots at each ear by gene gun for each genetic immunization. At primary immunization, the vaccine group got two shots of bullets containing 100 ng (high dosage) or 20 ng (low dosage) mixed FS antigen plasmids per bullet; while negative group got two shots of 100 ng mixed empty plasmids for each shot. At boost genetic immunization, all mice received genetic immunizations twice, three days apart, with dosage of 1 µg of mixed FS antigen plasmids or empty plasmids for each bullet. At boost peptide immunization, each mouse received subcutaneously injected total 100 µl vaccine formulated with 50 µl Alum and 50 µgCpG 2216 as adjuvant; and 50 µg total single FS peptide conjugated KLH or equally combined different FS peptide conjugated KLH (vaccine group) or 50 µg KLH protein (negative group). There were 14 mice in the no treatment group; 30 mice in the negative control group; 22 mice in the FS RBM group and 24 mice in the FS THAP2 group.

Figure 13A:
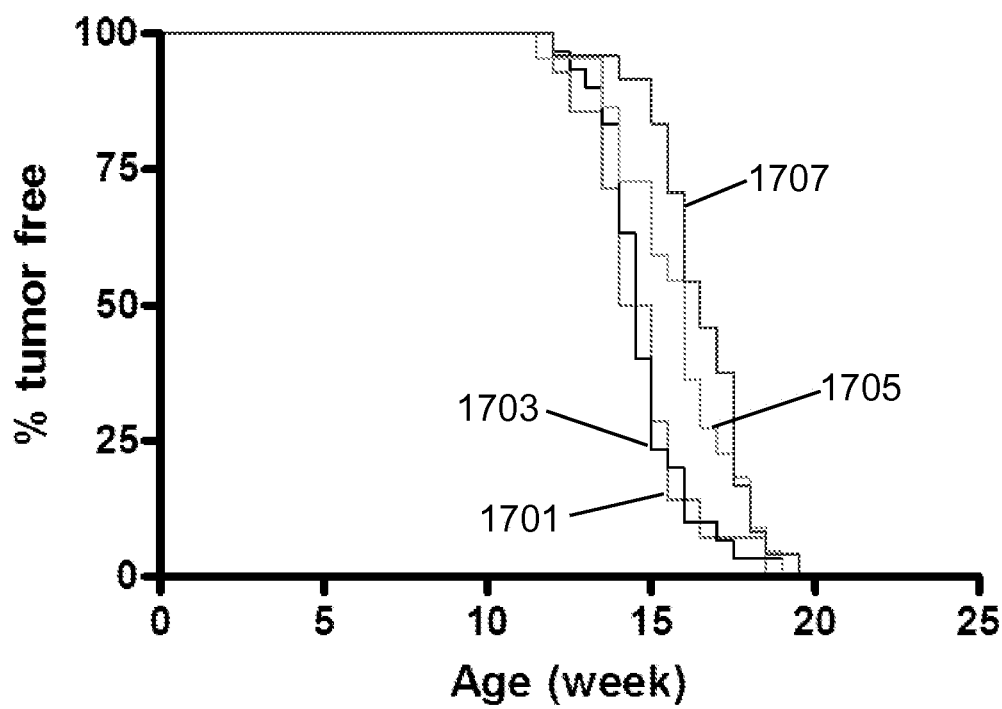
FIGS. 13a and 13b show tumor progression and tumor count in an example embodiment wherein BALB-neuT mice received prophylactic immunization with FS RBM peptide (SEQ ID NO:232) or FS THAP2 peptide (SEQ ID NO:238).
Figure 13B:
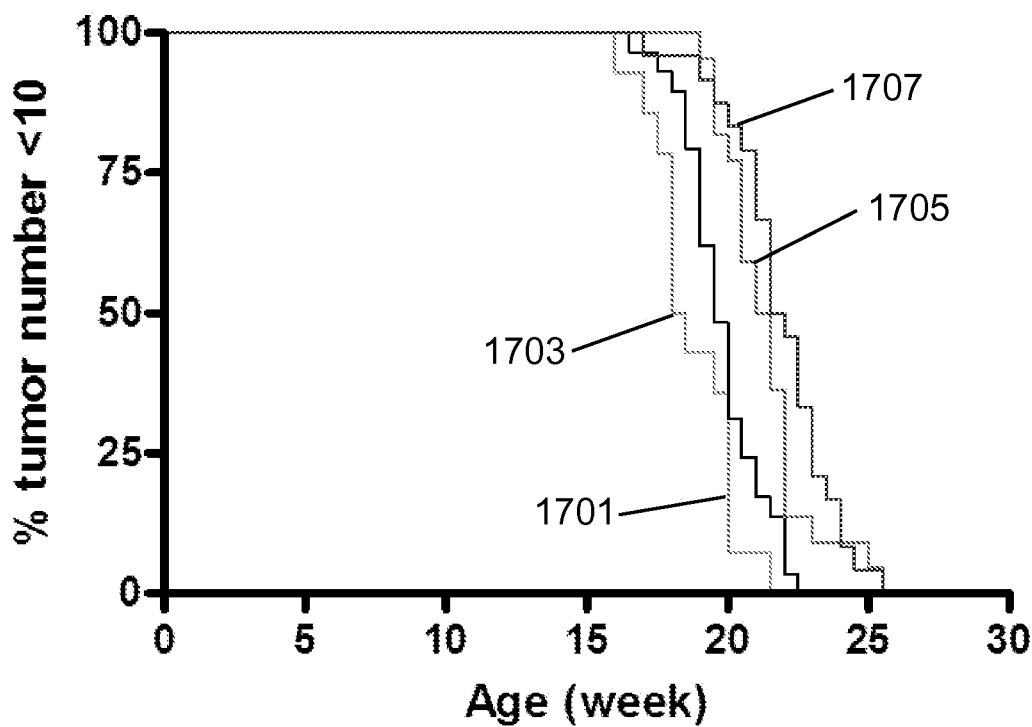

Both FS RBM and FS THAP2 showed significant prophylactic protection in inhibiting first tumor onset and tumor progression in BALB-neuT mice as compared to the non-treated group and negative control group, as shown in FIGS. 13a and 13b. The data shown combines two experiments with different dosages at the primary genetic immunization (20 ng and 100 ng of the vector); no significant difference in results was noted as between the two dosages. FIG. 13a shows the percent tumor-free status over the course of the experiment for the no-treatment group 1301, the negative control 1303, the FS RBM group 1305, and the FS THAP2 group 1307. FIG. 13b shows percent tumor-free status of the 10 mammary glands over the course of the experiment for the no-treatment group 1301, the negative control 1303, the FS RBM group 1305, and the FS THAP2 group 1307. By both measures it can be seen that tumor progression is significantly delayed for the immunized groups as compared to the controls.

Example 18

Figure 14A:
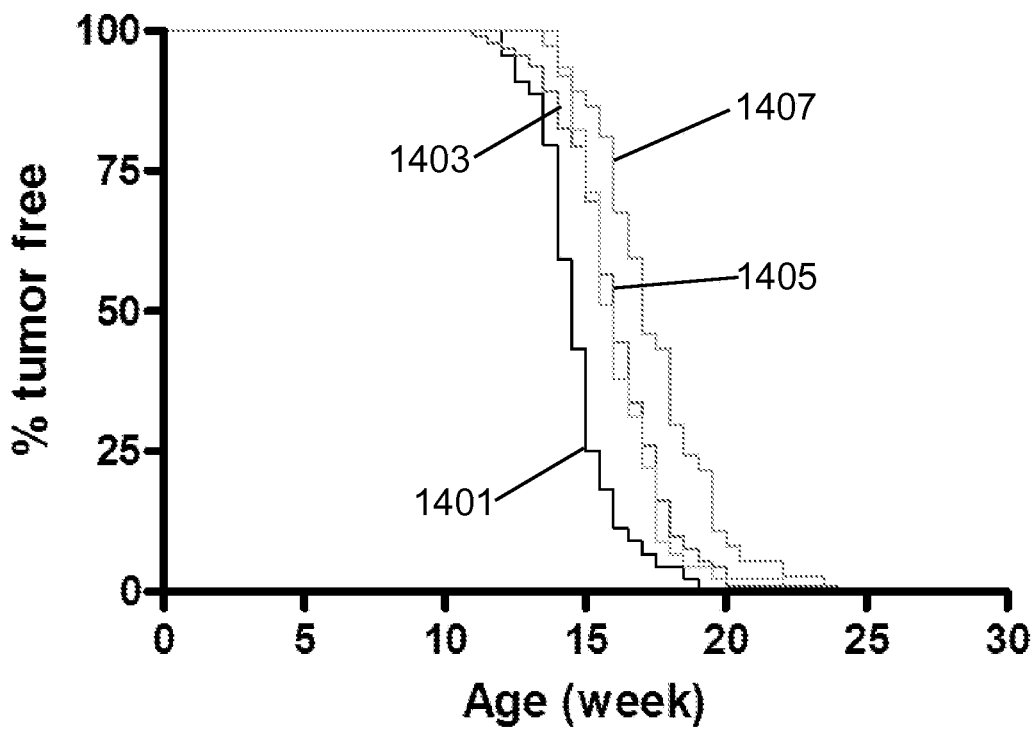
FIGS. 14a and 14b show tumor progression and tumor count in an example embodiment wherein BALB-neuT mice received prophylactic immunization with pooled antigen compositions.
Figure 14B:
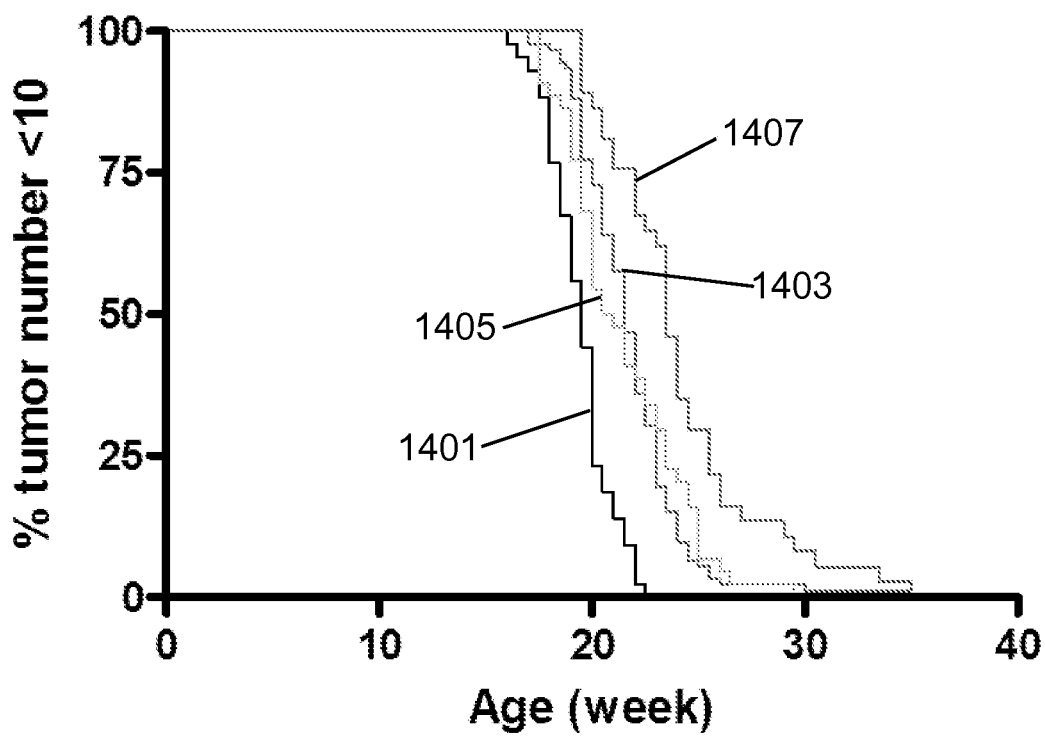

In vivo evaluation of prophylactic immunization using anti-cancer vaccine compositions including several pooled FS antigens was performed with results as shown in FIGS. 14a and 14b for four groups: control group (44 mice, including no-treatment group and negative control group); individual FS group (102 mice) including groups each immunized with one of FS SMC1A (SEQ ID NO:8), FS 1-78 (SEQ ID NO:2), FS RBM (SEQ ID NO: 232) or FS THAP2 (SEQ ID NO: 238); three antigen group, immunized with a vaccine composition wherein FS SMC1A, FS 1-78, and FS RBM were pooled; and four antigen group, immunized with a vaccine composition wherein FS SMC1A, FS 1-78, FS THAP2, and FS RBM were pooled. Mice were immunized substantially in accordance with the protocol disclosed in Example 17 above.

FIG. 14a shows the percent tumor-free status over the course of the experiment for the control group 1401, the individual FS group 1403, the three antigen group 1407, and four antigen group 1405. FIG. 14b shows percent tumor-free status of the 10 mammary glands over the course of the experiment for the no-treatment group 1401, the individual FS group 1403, the three antigen group 1407, and four antigen group 1405. It can be seen that all the immunized groups showed significant protection relative to the control group, and the pooled three antigen group showed superior protection relative to the individual FS group.

Example 19

Sequences, 23 in number, for use as peptide components of an anti-cancer vaccine were determined based on frameshifts as bioinformatically predicted to arise from microsatellite loci in mouse. These are enumerated in Table 9.

TABLE 9

| SEQ ID NO | Mouse Gene ID | Sequence |
|---|---|---|
| SEQ ID NO: 310 | NM_153511.3 | TLCMEVMLRWNTRELGYLYLQLCFLNTHFL HTSQEEKLLTLGRFLTWTSRCGSFVIRPL |
| SEQ ID NO: 311 | NM_053009.3 | ICMSPPLLWATLQAPETTSAACKASYRPEG LYL |
| SEQ ID NO: 312 | NM_010086.4 | YFSCDKRCIKHYAGNKSLLTFSGY |
| SEQ ID NO: 313 | NM_001114663.1 | KKSCPRYDPTLISLLYQCVS |
| SEQ ID NO: 314 | NM_146792.2 | FLFPAFSCMPDLFITFLVTNTLLYFIQFSL PC |
| SEQ ID NO: 315 | NM_001081355.3 | SAGTESDPSEEQICEAEGRPEGHFRGVLTY LPLL |
| SEQ ID NO: 316 | NM_029998.3 | LSKTPSKKCSLRMNTKFYRSFTSLKSLIVT FLRMVWWMLLRLEPISWKI |
| SEQ ID NO: 317 | NM_001163189.1 | HIQGQAEAGAVPGRALACWDLSAPVLPFTW DEGVEIYRGPNTVVLL |
| SEQ ID NO: 318 | NM_147003.1 | FPPPGRCGLSSLDSHGL |
| SEQ ID NO: 319 | NM_009499.3 | HPQVCPPQGYLGQVMEQGQPHPLHPHSLQH RAPIVGVPGPQAWLLPLLEPNSGK |
| SEQ ID NO: 320 | NM_130448.3 | KKRASPLLGRTPLATRIRETLAHHLCYQK |
| SEQ ID NO: 321 | NM_033618.3 | IPSWGRSFYCGNVLPSYHSEWWQL |
| SEQ ID NO: 322 | NM_001081302.1 | GLFHARISVQEQYQGELPLLGGKCGERSL |
| SEQ ID NO: 323 | NM_028664.1 | GVNGARRNSRIGEFRKVTIFLTARV |
| SEQ ID NO: 324 | NM_001034881.3 | VTAGYQEEEMEASACGAKGPGLAPWPPSW LALQDSLLCVVVALADLRRKSCCS |

TABLE 9-continued

| SEQ ID NO | Mouse Gene ID | Sequence |
|---|---|---|
| SEQ ID NO: 325 | NM_001033226.4 | LSLSFLHRWMDKTVGTI |
| SEQ ID NO: 326 | NM_153511.3 | TLCMEVMLRWNTRELGYLYLQLCFLNTHFL HTSQEEKLLTLGRFLTWTSRCGSFVIRPL |
| SEQ ID NO: 327 | NM_001160399.1 | RVYSKLENQKAAKEGGNTQVKRKGGHRASA FSKQSRR |
| SEQ ID NO: 328 | NM_025441.3 | AKEQAAAEAAEEQAAACRCGSQPVSLCQCQ KIL |
| SEQ ID NO: 329 | NM_001109759.1 | RQKKIRPPKKKRSIQGQRQKPPRDHRCECD QLFCFFWWGGNP |
| SEQ ID NO: 330 | NM_028787.4 | LLCVVFGKFVIPRSTFRHTGCHSEYFVFNF WTFYFNPCSCISE |
| SEQ ID NO: 331 | NM_027009.2 | LKSAPLQATTTLKLIPVMRGTATEL |
| SEQ ID NO: 332 | NM_001081345.2 | VLPNLPSQSSTF |

Figure 15:
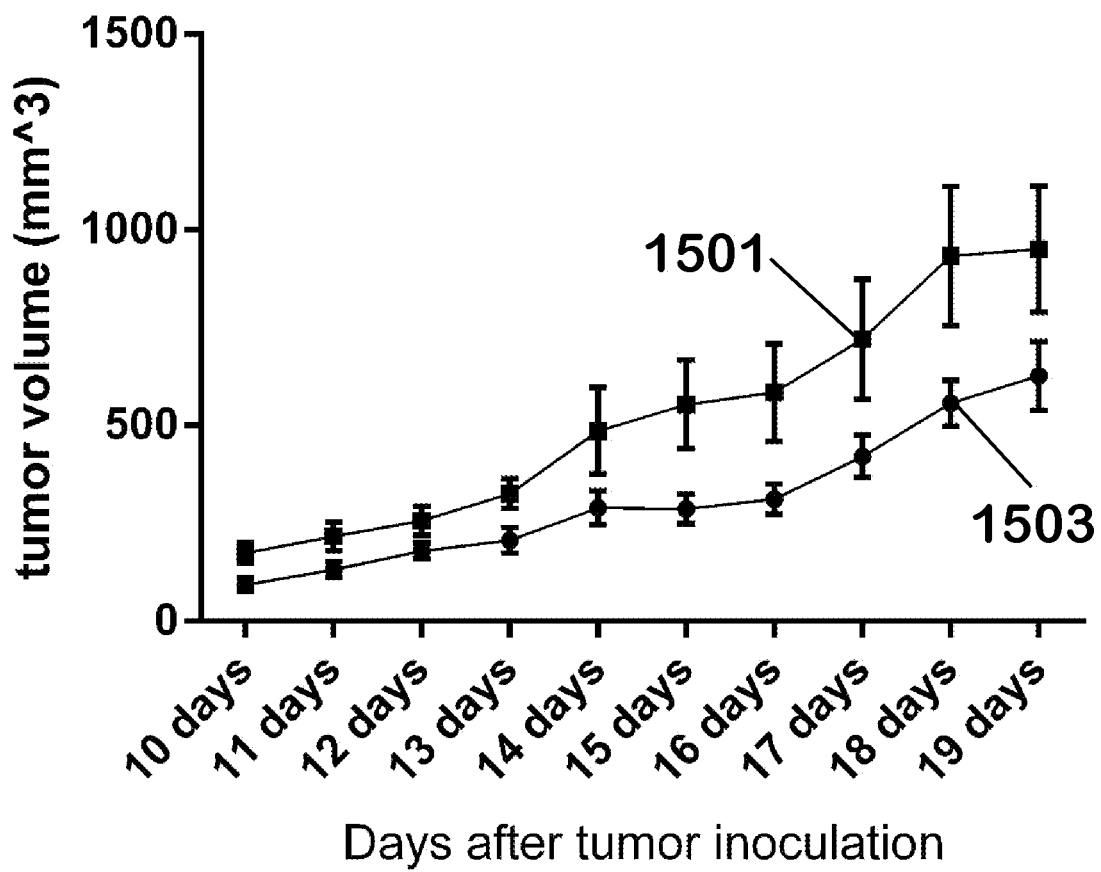
FIG. 15 shows prophylactic inhibition of tumor progression in BALB/C-4T1 mice vaccinated with an embodiment of an anti-cancer vaccine.

The first three peptides (SEQ ID NO: 310, SEQ ID NO: 311, and SEQ ID NO: 312) were tested in vivo and shown effective in prophylactically inhibiting tumor progression in BALB/C-4T1 mouse transplant breast tumor model. Primary genetic immunization was administered with the three peptide components (10 mice) or with empty vector (negative controls, 4 mice) at 7 weeks old and 13 weeks old. Three weeks after the last immunization, all mice were challenged with 5,000 4T1 tumor cells. Tumor size was measured each day after palpable tumors appeared. FIG. 15 shows average tumor size for the negative control group 1501 and the immunized group 1503. Error bars show standard error.

Human and dog peptide candidate sequences homologous to those of Table 9 are shown in Tables 10 and 11, respectively (not all of the mouse sequences of Table 9 have homologs in human and dog).

TABLE 10

| SEQ ID NO | Human Gene ID | Sequence |
|---|---|---|
| SEQ ID NO: 333 | NM_015866.4 | SASTESNSSEKQICKAEGRLEKCL |
| SEQ ID NO: 334 | NM_152512.3 | QSRIPSKKCSLRKSTKSYKSCTNLRNLAPT |
| SEQ ID NO: 335 | NM_003370.3 | PPHPQVCPLRGSQLQRTEQGEDHPLHPLSR QHRALVVGELGPQAWPQLLLEPNSGKSASR RRPQGGPQPPKLRVVEAEVGDSWKR |

TABLE 10-continued

| SEQ ID NO | Human Gene ID | Sequence |
|---|---|---|
| SEQ ID NO: 336 | NM_007192.3 | IPCWGRPFYCGNVLPSYHSEWWQL |
| SEQ ID NO: 337 | NM_007118.2 | KEGLLHAGIPV |
| SEQ ID NO: 338 | NM_152549.2 | RVNSDLEN |
| SEQ ID NO: 339 | NM_025181.3 | LLCVVFGKFVISRSTFRHTSCYS |
| SEQ ID NO: 340 | NM_002915.3 | LKLAPLQVTTTLKLILVMLEIVTE |
| SEQ ID NO: 341 | NM_001271.3 | KLLNLSCQSCT |

TABLE 11

| SEQ ID NO | Dog Gene ID | Sequence |
|---|---|---|
| SEQ ID NO: 342 | XM_850372.3 | QSRIPSKKCSLRKSTKSYKSCTSLKSLVPT |
| SEQ ID NO: 343 | NM_001003256.1 | HPLVCPSQGALRQGTEQGEAHPLRPLSPQH KAPVVGEQGPPVLQQPLPEPNSGKSASKRR PQGGPQSLKQRALEARAGG |
| SEQ ID NO: 344 | XM_846473.3 | VPGRGRPFYCGNVLPSYHSEWWQL |
| SEQ ID NO: 345 | XM_005639663.1 | KKGLLDARIPV |
| SEQ ID NO: 346 | XM_005626355.1 | RVYSELENQKAAKEGGNFQVKGKSREPIST LS |
| SEQ ID NO: 347 | XM_533330.4 | LLCVVSGKFVVSRSTFRHTGCYS |
| SEQ ID NO: 348 | XM_005618324.1 | ILLNLSSESCTF |

Example 20

Sequences, 142 in number, for use as peptide components of an anti-cancer vaccine were determined by comparing NCBI EST database sequences with human RefSeq generally according to the criteria described in Example 16 above and identifying sequences wherein the upstream non-frameshifted domain and the conjoined frameshifted domain corresponded to different genes. These are tabulated in Table 12. Sequences shown are the 10 residues of the upstream non-frameshifted domain immediately adjacent to the junction point, together with the full sequence of the frameshifted domain up to the first stop codon.

TABLE 12

| SEQ ID NO | Upstream ID | Downstream ID | Sequence |
|---|---|---|---|
| SEQ ID NO: 349 | NM001080414.2 | NM198530.2 | MDVTVSELLEN |
| SEQ ID NO: 350 | NM001127716.1 | NM004589.2 | MFRAAAPGQLS |
| SEQ ID NO: 351 | NM001005409.1 | NM001127398.1 | MPAGPVQAVPS |
| SEQ ID NO: 352 | NM182568.3 | NM002767.2 | MASWGGEKRGL |

TABLE 12-continued

| SEQ ID NO | Upstream ID | Downstream ID | Sequence |
|---|---|---|---|
| SEQ ID NO: 353 | NM000094.3 | NM033199.3 | MTLRLLVAALA |
| SEQ ID NO: 354 | NM004536.2 | NM002538.2 | MATQQKASDEG |
| SEQ ID NO: 355 | XM001725801.1 | XM377073.4 | MTPVRMQHSLR |
| SEQ ID NO: 356 | XM001725801.1 | NM182905.3 | MTPVRMQHSLR |
| SEQ ID NO: 357 | XM001717526.1 | NM018081.1 | MGSKIYSYEFV |
| SEQ ID NO: 358 | NM001131028.1 | XM001715307.1 | MEEDEFIGEKV |
| SEQ ID NO: 359 | NM080664.2 | NM016106.2 | MAEGSRIPQAGF |
| SEQ ID NO: 360 | NM016616.3 | NM017549.3 | MASKKREVQLII |
| SEQ ID NO: 361 | NM004136.2 | NM181354.4 | MDAPKAGYAFEI |
| SEQ ID NO: 362 | NM015004.3 | NM003278.2 | MASVTLSEAESA |
| SEQ ID NO: 363 | NM013293.3 | NM024322.1 | MSDVEENNFEVF |
| SEQ ID NO: 364 | NM005085.2 | NM175878.3 | MGDEMDAMIPAP |
| SEQ ID NO: 365 | XM001129743.1 | NM001031716.1 | MAFGEVEHTDDA |
| SEQ ID NO: 366 | XM001721832.1 | NM053052.2 | MRARLRFLPSDC |
| SEQ ID NO: 367 | NM001145.3 | NM002937.3 | MVMGLGVLLLHL |
| SEQ ID NO: 368 | NM033542.2 | NM001048225.1 | MAGQFRSYVWWS |
| SEQ ID NO: 369 | NM018281.2 | NM004462.3 | MLRVLCLLRPDLP |
| SEQ ID NO: 370 | NM002300.5 | NM016078.4 | MATLKEKLIAGSF |
| SEQ ID NO: 371 | NM022780.2 | NM022662.2 | MDQCVTVEREDSL |
| SEQ ID NO: 372 | XM001717653.1 | NM152705.1 | MYFLNDALCAGKQ |
| SEQ ID NO: 373 | XM001719888.1 | NM004906.3 | MAERGGWREADSR |
| SEQ ID NO: 374 | XM001717673.1 | NM201554.1 | MGGGPAREKGPTL |
| SEQ ID NO: 375 | NM005004.2 | NM015490.3 | MAVARAGVLGDRP |
| SEQ ID NO: 376 | NM020984.3 | NM001042427.1 | MAAKTPSSEELCWP |
| SEQ ID NO: 377 | NM016406.3 | NM005614.3 | MADEATRRVVGNPH |
| SEQ ID NO: 378 | NM032775.2 | NM182895.1 | MAEEQEFTQLRDQV |
| SEQ ID NO: 379 | NM030940.3 | NM016548.2 | MSASLVRATVDSQR |
| SEQ ID NO: 380 | NM001002001.1 | XM001715885.1 | MPHIDNDVKLGADK |
| SEQ ID NO: 381 | NM001031827.1 | NM015092.3 | MASAKSLDRWFCTE |
| SEQ ID NO: 382 | XM001718309.1 | NM015681.3 | MRTGSRAPSEVSRV |
| SEQ ID NO: 383 | XM943571.2 | NM022483.3 | MRRPRLPAQAVLEM |
| SEQ ID NO: 384 | XM001716831.1 | NM017897.1 | MYPHKKPPALGMCF |
| SEQ ID NO: 385 | NM001013845.1 | XM001720996.1 | MKFGCLSFRQLQNP |
| SEQ ID NO: 386 | NM178124.3 | XM001720996.1 | MKFGCLSFRQLQNP |
| SEQ ID NO: 387 | NM014251.2 | NM006304.1 | MAAAKVALTKLGWLR |
| SEQ ID NO: 388 | NM001928.2 | NM005481.2 | MHSWERLAVTLTRS |
| SEQ ID NO: 389 | NM016374.5 | NM001037277.1 | MKISFEV |
| SEQ ID NO: 390 | NM005600.1 | NM032998.2 | MLGFITRPPHQPVSS |
| SEQ ID NO: 391 | NM001487.2 | NM002905.3 | MLSRLLKEHQGFLVW |

TABLE 12-continued

| SEQ ID NO | Upstream ID | Downstream ID | Sequence |
|---|---|---|---|
| SEQ ID NO: 392 | NM001032363.1 | NM182744.2 | MSESELGRKWLWRPRA |
| SEQ ID NO: 393 | NM001010974.1 | NM001099432.1 | MQRTGGGAPRVPLTGA |
| SEQ ID NO: 394 | NM006868.3 | NM001402.5 | MMAIRELKVCCRENYP |
| SEQ ID NO: 395 | NM015215.1 | NM018948.2 | MWRAEGKWLPGMKATG |
| SEQ ID NO: 396 | NM001002840.1 | NM001013739.2 | MQHREVRVKCNTEKSA |
| SEQ ID NO: 397 | XM001130925.2 | XM001126402.2 | MASASCSPGRWNNPKF |
| SEQ ID NO: 398 | NM001134779.1 | NM181506.4 | MVQPIIHLGYLASKGP |
| SEQ ID NO: 399 | NM006328.3 | NM002896.2 | MKIFVGNVDGGGMCVG |
| SEQ ID NO: 400 | NM152350.2 | NM014288.3 | MFPGSLSRGRHDVAIKS |
| SEQ ID NO: 401 | NM015004.3 | NM003278.2 | MASVTLSEAECCEHKDV |
| SEQ ID NO: 402 | NM014662.2 | NM004147.3 | MRTTKVYKLVLWSGVSL |
| SEQ ID NO: 403 | NM006837.2 | NM012207.2 | MAASGSGMAQVTMGKAA |
| SEQ ID NO: 404 | NM001113756.1 | NM005138.2 | MAALMTPGTGASDPCCC |
| SEQ ID NO: 405 | NM032998.2 | NM005600.1 | MAGLKRRASQAPSGLGL |
| SEQ ID NO: 406 | NM001113756.1 | NM005138.2 | MAALMTPGTGASDPCCC |
| SEQ ID NO: 407 | XM001714553.1 | NM001114620.1 | MWNAALPGPTHGCLLIP |
| SEQ ID NO: 408 | NM133638.3 | NM014031.3 | MRLTHICCCCERRKCRNH |
| SEQ ID NO: 409 | NM001005354.2 | NM001128914.1 | MWNPNAGGPPFLAFTPNQ |
| SEQ ID NO: 410 | XM001715546.1 | NM020987.2 | MANETLFSSPSLMPMQVT |
| SEQ ID NO: 411 | NM004388.2 | NM005274.2 | MSRPQLRRWRKFPRQLQT |
| SEQ ID NO: 412 | NM016622.3 | NM022912.2 | MAASAFAGAVSRGFGGRG |
| SEQ ID NO: 413 | NM000296.2 | XM001725512.1 | MPPAAPARLAVDGRMATWM |
| SEQ ID NO: 414 | NM001098504.1 | NM005839.3 | LPTGFVAPILKSLGLKMML |
| SEQ ID NO: 415 | NM012112.4 | NM001031711.2 | MSQVKSSYSYMEMCGMHMS |
| SEQ ID NO: 416 | NM018233.3 | NM031885.2 | MNGKRPAEPGPRKKLSPLA |
| SEQ ID NO: 417 | NM022739.3 | XM001719702.1 | MSNPGGRRNGVLSRVMTTP |
| SEQ ID NO: 418 | NM182471.1 | NM001005.3 | MSKPHSEAGTGSANIQEEEVCR |
| SEQ ID NO: 419 | XM001722372.1 | NM018704.2 | MAGRPGSQEQSIGHISTMLMAF |
| SEQ ID NO: 420 | NM153260.2 | NM003825.2 | MGNSALRAHVSALSVIRFICGF |
| SEQ ID NO: 421 | NM014774.2 | NM022745.3 | MKKRKELNALRCLGETVCEQRIH |
| SEQ ID NO: 422 | NM016040.3 | NM015361.2 | MGDKIWLPFPIKLYPTSSKTTKE |
| SEQ ID NO: 423 | XM001714221.1 | XM001714962.1 | MRTLPLRFAGYFNSRPHLCPAGS |
| SEQ ID NO: 424 | NM182533.2 | XM001714962.1 | MEAARRPRLGYFNSRPHLCPAGS |
| SEQ ID NO: 425 | NM003095.2 | NM182496.1 | MSLPLNPKPFQDFHLHLGNIETK |
| SEQ ID NO: 426 | NM001127184.1 | NM015147.2 | MSAEVIHQVEDILLSAGRADLLAV |
| SEQ ID NO: 427 | NM030980.1 | NM052998.2 | MSTLLLNLDFGSAAKAADGCRTGG |
| SEQ ID NO: 428 | NM001630.2 | XM001715226.1 | MAWWKAWDSGILPLRNALLLG |
| SEQ ID NO: 429 | NM207116.1 | NM021163.3 | MEEGNNNEEVVYQPQSLHVSKSSRK |
| SEQ ID NO: 430 | NM012415.2 | XM001722896.1 | MRRSAAPSQLQTWMRRHRLVPVHYR |

TABLE 12-continued

| SEQ ID NO | Upstream ID | Downstream ID | Sequence |
|---|---|---|---|
| SEQ ID NO: 431 | NM182641.3 | NM002266.2 | MRGRRGRPPKSFLPLSHNHVHQREC |
| SEQ ID NO: 432 | NM015965.5 | NM198537.2 | MQEPRRVTPCGLGAAAPTCRHGKSGA |
| SEQ ID NO: 433 | NM005833.2 | XM001715611.1 | MKQLPVLEPGTGFHRVSQDGLDLLTS |
| SEQ ID NO: 434 | NM001128208.1 | NM001100916.1 | MAGIKALISLRVQMSASGTYPSSPGL |
| SEQ ID NO: 435 | NM014637.2 | XM001720291.1 | MLGWIKRLIRSLPAGFIQPHVSKHCLG |
| SEQ ID NO: 436 | XM928114.3 | XM001719607.1 | MEGGGGSGNKVSEMALDSPFCVLLSGS |
| SEQ ID NO: 437 | NM016026.3 | NM006370.1 | MVELMFPLLLWQRWRRSYVMHPCLSETP |
| SEQ ID NO: 438 | NM022730.1 | NM002867.2 | MAGEQKPSSNVETGFHLVSQDGLDLLTS |
| SEQ ID NO: 439 | NM006454.2 | NM006503.2 | MELNSLLILLSRQGGSEDPAGAAESDGWI |
| SEQ ID NO: 440 | NM025149.4 | NM001267.2 | MAVYVGMLRLRNLRKKLQHGKMDSKAPMSC |
| SEQ ID NO: 441 | NM000031.5 | NM024939.2 | MQPQSVLHSGSIVFEARGDKAEIRDGALQQG |
| SEQ ID NO: 442 | NM006116.2 | NM018133.2 | MAAQRRSLLQTFATRSYCTHQLHLPTLCLQNL |
| SEQ ID NO: 443 | NM007221.2 | NM199173.3 | MAEASSANLGVRSPAVQSPAKVQPLCPSRRAAR |
| SEQ ID NO: 444 | NM007221.2 | NM199173.3 | MAEASSANLGVRSPAVQSPAKVQPLCPSRRAAR |
| SEQ ID NO: 445 | NM007221.2 | NM199173.3 | MAEASSANLGVRSPAVQSPAKVQPLCPSRRAAR |
| SEQ ID NO: 446 | NM005358.4 | NM000358.2 | MKKIRICHIFKCWTPWSAMSTLSCSMPSATIWW AGES |
| SEQ ID NO: 447 | NM016075.2 | NM018676.2 | MDRFVWTSGLCFWGKKSQSGREKGHEETKDLGF CQSE |
| SEQ ID NO: 448 | NM001012754.2 | NM170719.2 | MARFWVCVAGFQGGLQSSSCYDIFLWNNPRKSI SQRKT |
| SEQ ID NO: 449 | NM014637.2 | XM001720291.1 | MLGWIKRLIRVPSSWLYSAPRVQALSGIALYWKT WPIL |
| SEQ ID NO: 450 | NM018049.1 | NM032482.2 | MRYNEKELQATETPRDPRQACPASQGMLRAMD SREIQK |
| SEQ ID NO: 451 | NM145301.1 | NM173622.3 | MLQQDSNDDTEPSEMSCTRNFKREFSAGRRGRQ DIRTRI |
| SEQ ID NO: 452 | NM024061.3 | XM001716989.1 | MEEIPAQEAADFQFPSLMGSPSWNRIYRSLIWKL RLEKS |
| SEQ ID NO: 453 | XM001715735.1 | NM014393.1 | MVARPLHSTERLPTTRTLAYFLKIEEKKEDRKRRTQ RYTK |
| SEQ ID NO: 454 | XM001719043.1 | NM138401.2 | MSVSVLAPAGSPAPSRGHPPALARASRRNLATSC ALVLWAA |
| SEQ ID NO: 455 | NM006098.4 | NM015458.3 | MTEQMTLRGTVRPGWSAVVRSRLTASSASRVHTI LLPQPPE |
| SEQ ID NO: 456 | NM001013839.1 | XM001725398.1 | MIPPQEASARISPGHEHDFRVKHLSEALNDKHGPL AGEYRSPA |
| SEQ ID NO: 457 | NM018696.2 | NM005359.5 | MSMDVTFLGTYPEYMSNNFPCNVSCCFSLFPKD QNCFRNWRHI |
| SEQ ID NO: 458 | NM001034.1 | NM182626.1 | MLSLRVPLAPLGDREVQSRWSPGPRGDSTPVRE METNHPPSVRG |
| SEQ ID NO: 459 | XM001714450.1 | XM001714789.1 | MGSSAVQSQLWHFSTPLEPMPRRNKGCAASPW LTQWPRPRKSQR |
| SEQ ID NO: 460 | XM001721832.1 | NM023007.1 | MRARLRFLPSTGLRCSLLCLDRPGRARPHLHHTQC EEGLGTHHS |
| SEQ ID NO: 461 | NM006328.3 | NM002896.2 | MKIFVGNVDGGSCQDGEAVHRKPAPGGYRAGD SLTLRAVWEGAGM |

TABLE 12-continued

| SEQ ID NO | Upstream ID | Downstream ID | Sequence |
|---|---|---|---|
| SEQ ID NO: 462 | NM001006947.1 | NM017771.3 | MAGIIKKQILNILFECKEEFLWKTAGRLLEDTVTLIC LTTAYRLQA |
| SEQ ID NO: 463 | NM001031665.1 | NM001105552.1 | MLREEATKKSGSIDIQGCGHRILSGGVEMPGPCSE DSIQRCDVGEL |
| SEQ ID NO: 464 | NM003002.1 | NM031275.4 | MAVLWRLSAVCLQCQIVHSCPLLENQIHLSLKFPD YFIKMKPWRKI |
| SEQ ID NO: 465 | NM006743.3 | XM001127723.2 | MSSEEGKLFVLGGGGQRQTEPGRLGGDDWSCM RPRSHLWMVDLPWA |
| SEQ ID NO: 466 | NM207116.1 | NM018053.2 | MEEGNNNEEVGLASAHPSWASRGHCSTTTGPCA PASPPSRSWAWAPP |
| SEQ ID NO: 467 | NM001079673.1 | NM001984.1 | MAEHPPLLDTNRLPFGASKKQSAIGQEKNGIEAD FQQQVLWGIAESF |
| SEQ ID NO: 468 | NM005802.2 | NM014314.3 | MGSQPPLGSPKRCSIFRLRKTTRAQWRLPHFFSSS CWSSRRKAGSVAFWMP |
| SEQ ID NO: 469 | NM007273.3 | NM181642.2 | MAQNLKDLAGALRGPARHRTLQGEHPALVLQPL QRTLRPLYLWWLLRQQEQL |
| SEQ ID NO: 470 | NM001320.5 | NM021221.2 | MSSSEEVSWISSCSRHPDVPLLPRRRPFCRMHFRL REVYHQQLIPVHGDHHLL |
| SEQ ID NO: 471 | XM001132260.1 | NM018427.3 | MAKRRRPKKRDSQRHFWNISGKNCRTQVILPSSG RLLEIILEAFWQELNLFLLLL |
| SEQ ID NO: 472 | NM000972.2 | NM000787.3 | MPKGKKAKGKLSHPPGPGGVPGALMECQLHPG GHPFPAPGAEAQGWRPVWDVRPWRA |
| SEQ ID NO: 473 | XM001723697.1 | XM001716892.1 | MRGQTEEVVASASWAVPSTCCFRSCKPLLAMAS GYLWSRQEQLERRWILPRVAMPSASSGF |
| SEQ ID NO: 474 | NM007221.2 | NM199173.3 | MAEASSANLGCEAQRCRVQQRCSLCVQAGGQR GSEETQALPVSMAGSPSPLPGSPGAQEGGV |
| SEQ ID NO: 475 | XM001721832.1 | NM053052.2 | MRARLRFLPSEAEEAWTLAHTDPGTDEQGCLHP HLAVHLLPGAQEAMGYWTAVLNIAVAQVHD |
| SEQ ID NO: 476 | NM006396.1 | NM001098785.1 | MALNGAEVDDGGAAAVGHVLVVPAVGPVRVNP GLQTPVPRPELLPGPVILPPFGQLLPTGCGPV |
| SEQ ID NO: 477 | NM153260.2 | NM130798.1 | MGNSALRAHVMLLHGQTQRPQHLLSSVKVFSVS LMSLFIWSKPSSMRFSCSFCSSSIVMVLIPAS |
| SEQ ID NO: 478 | XM001713865.1 | XM001714058.1 | MDPASRGCLGRPSTPCLHGAALHLSGHGSGSRL TNSSCFPGTRRLLALQFTQQTGTVGHPTWQPVIR |
| SEQ ID NO: 479 | NM000985.3 | NM001035005.2 | MVRYSLDPENLRSSSLGKWCAFLVSSFQFCSGSTK NSWSHIYTLWFPPSLVVYGLRKQYKNPMIQTKAK |
| SEQ ID NO: 480 | NM017882.1 | NM033429.2 | MEATRRRQHLRKWRAGFLHFSDHYAHANKTRRP KERNSSSHVDGGQGEERLRHGVRPAVKTHESGG EAHPQGSG |
| SEQ ID NO: 481 | NM012447.2 | NM005395.2 | MSSPLQRAVGLDYVDMEIHLPLSTAPLPAPLPSPP LHDDVWLGDNHTPQKLDGCSSPTSHPRMLSSHQ GPVAATPPG |
| SEQ ID NO: 482 | NM015001.2 | NM001042704.1 | MVRETRHLWVFWNPGAEDHVGGCDLGGLPGY QELWGQGGGPLLHPGHRQHPVPGQSGPFRAPV CNDRCLPGPCAHHDHRGA |
| SEQ ID NO: 483 | NM003755.3 | NM207346.2 | MPTGDFDSKPPWSFSISLCCRQHTFLMEVPGCW RSLGAWKSSLMFTRPTLWPHSERITLANPMPGCA LVDLMSLSQTSAASSGCLTRVGMSL |
| SEQ ID NO: 484 | NM182486.1 | NM000878.2 | MQWLRVRESPLPSSAPPCGCNGGPCSVLASAPP HPPPAPGYLLGICSGEWHFPVHMLLQLESQHLLCL EPRWGSAGHFLPSPCLAGQTAVEPNL |
| SEQ ID NO: 485 | NM020987.2 | NM005888.2 | MAHAASQLKKSGCVIAILGKRCSRPWRTWRGRT PSTRHICSWCTMVSGTSAAAPQGPRASPAALAT WQPPPWKSSIAVTMDLADSLSFVDLEELLAVAQH |

TABLE 12-continued

| SEQ ID NO | Upstream ID | Downstream ID | Sequence |
|---|---|---|---|
| | | | IQHWFL |
| SEQ ID NO: 486 | NM000921.3 | NM001128220.1 | MAVPGDAARVEQDCQWRLPQRPPGAEPQPHR ARCGPHHEPARQPPVHLPPQPWPGAAPRTDQE QPGRQQASRPLAHTDPGGAAAEPALRDHLCLGW RPQLQPLALPHRAQRLCRARACQLPEATERCHHL |
| SEQ ID NO: 487 | NM178276.4 | XM001722866.1 | MSAQCCAGQLATKVPTSRASSAGAGPSSGSRWP PAGYACCCTCVRWSLPSAAPPGSSLCDDIGGPLGF VGLQPGKCHLLNSVPGAGTGALCLSGSEKALRLHS GTSSLLFPPSYFGKFSSRSSHVFSIQLSCHSFS |
| SEQ ID NO: 488 | NM004083.4 | NM004990.2 | MAAESLPFSFLPLGASGGFPSATANCFFRSKSFATS AATSFLSAFCAFSSRTMFPCFVTSSISACICCGLAVV TVSTTAGFGDVFAWPPPKRCLKLSIWSFSNFWNK GLTVPIWCPAGKVHRKFVSRILQAGGGSCSWAWI VALTVGM |
| SEQ ID NO: 489 | XM001716912.1 | NM199511.1 | MREVQKDQRSPFSTSHSCVFPQPGKHINPSAFTP GNKETKPDYGGKGDKKDPGTLKRERVRFRNRQD WTLRDVLCQHKGLAHTDTRDRGETADKWRYKDL EGQLLSPHPTCPEGKKTQPERKGIGSALRSGQAVD LWRYSESWSCSTPLLYCSPSVKRERAGRKSSSSRKL SWEPNF |
| SEQ ID NO: 490 | NM006871.3 | NM139247.2 | MSCVKLWPSGADLRPELPDHCAVRAGRLLAAAG PRFPGAATAALDASPVRLGMGRAASARPRLPVHR GRGERLGPGVLFSLRHLHGVCHAALGHAGRRRR GPRLLTLASAGPRAVSWATAGLTACTAAAVGSKR SAVPVRERGRSVPQGADGARPAGHVPGGTQLPA LTPAAGHREEAPGTPSLVHPSCLPGPRDEGRDHG TAAGRTGVTAREH |

Example 21

Sequences tabulated in Table 13 for use as peptide components of an anti-cancer vaccine were determined by identifying tumor-associated frameshift alternative splicing variant peptides. The NCBI EST sequence database was screened against the human RefSeq database to identify single EST sequences that align with two RefSeqs, in which an exon is skipped, and in which the sequence downstream of the splice is frameshifted relative to the normal wild type when the EST sequence is translated. From these, sequences were identified wherein either the sequence corresponded to at least 3 tumor EST sequences and no non-cancerous EST sequences, or in which the sequence corresponded to at least three times as many tumor EST sequences as non-cancerous EST sequences.

TABLE 13

| SEQ ID NO | Name | ID | Sequence |
|---|---|---|---|
| SEQ ID NO: 491 | C11orf2 | NM0132652 | PCTGLSLHPMAPRIWSRWSFPAGRCQDRPNKHVWPPQ KKKKKKKKKK |
| SEQ ID NO: 492 | C20orf96 | NM080571.1 | CFTSSPLRW |
| SEQ ID NO: 493 | CYBASC3 | NM001161452.1 | LLLQLRPGSRPFPVTYVSVTGRQPYKSW |
| SEQ ID NO: 494 | KRT8 | NM0022733 | LLRSHSTRILPTAAGLRLRACTRSSMRSCRAWLGSTGM TCGAQRLRSLR |
| SEQ ID NO: 495 | MVK | NM001114185.1 | GGPRRIWS |
| SEQ ID NO: 496 | NAA10 | NM003491.2 | RSVKWSPNTMQMGRTPMP |
| SEQ ID NO: 497 | PDCD2 | NM001199462.1 | GLWLFRPQNVLQMPQSILLQQGASDPRLEIGT |
| SEQ ID NO: 498 | RPS3A | NM001006.3 | FGKAHGASW |
| SEQ ID NO: 499 | TFE3 | NM006521.4 | CSAQARNRSEDETQPLPLGTLLAF |
| SEQ ID NO: 500 | HNRNPA2B | NM031243.2 | KEGVLLQVTNEEVVNHRVFKK |
| SEQ ID NO: 501 | NOLI2 | NM0243112 | VPTACCRCCFCWDV |
| SEQ ID NO: 502 | RPLP0 | NM001002.3 | GVRQWQHLQP |
| SEQ ID NO: 503 | DPH2 | NM001384.4 | LPCSSLTSYWEMLWLWLHDWRRRQGQRCSFWVTQPT AAAAWMCWVLSKLELRLSYILALPA |

TABLE 13-continued

| SEQ ID NO | Name | ID | Sequence |
|---|---|---|---|
| SEQ ID NO: 504 | GNB2L1 | NM006098.4 | GWPGHVMGSQRRQTPLHARWWGHHQRPVLQP |
| SEQ ID NO: 505 | RPL8 | NM000973.3 | IRELCHRYLPQP |
| SEQ ID NO: 506 | IGFLR1 | NM024660.2 | NCPVWRHNPCLASWMSWRCWKS |
| SEQ ID NO: 507 | KARS | NM001130089.1 | VGSMPKELLGESSSSMIFEERG |
| SEQ ID NO: 508 | MRPS28 | NM014018.2 | EIPERNQGPVAAIRS |
| SEQ ID NO: 509 | HNRNPA2B | NM031243.2 | EGVLLQVTNEEVVNHRVFKK |
| SEQ ID NO: 510 | SMC1A | NM006306.2 | CCGIYCHEEPQREDSSI |
| SEQ ID NO: 511 | NRM | NM007243.1 | AGDAVLGAHTQRPCVVGGSG |
| SEQ ID NO: 512 | PRSS27 | NM031948.3 | PLRRPCTRSCWGQGS |
| SEQ ID NO: 513 | TXN2 | NM012473.3 | CQRCPLCWP |
| SEQ ID NO: 514 | RDH11 | NM016026.3 | SLPPNPSAARETKGISPIKDSKCVFPRTSPGKDPLP |
| SEQ ID NO: 515 | BORA | NM024808.2 | FSLKMSSYPLLGLIMKGNSFHNVIPVNALT |
| SEQ ID NO: 516 | RPS3 | NM001005.3 | GLLWCAAVHHGEWGQRLRGCGVWETPRTEG |
| SEQ ID NO: 517 | SAAL1 | NM138421.2 | GDGGSGSKGRPVEQTEVFLCISKPSSFL |
| SEQ ID NO: 518 | SEMA3B | NM0010059141 | LPQQDLWHLQFHQGLPRRCHPVCAEPPPHVQLCPAHW GAPSFPTSWSQLHLHSNCRGPGCSR |
| SEQ ID NO: 519 | FPGS | NM0010180781 | AGPSPGTWTVRTPPAARRPACAGSARRCRAARGRAVA PRFESCSSMLPGTGTRRPC |
| SEQ ID NO: 520 | SLC13A3 | NM001193342.1 | GIGAVCMDWWAAAPPGECAPRPGCAAHHCGHRLLH |
| SEQ ID NO: 521 | ARHGEFI | NM199002.1 | GVGGGILPPETPPVSAWGELCPPAWLHL |
| SEQ ID NO: 522 | FANCI | NM001113378.1 | VSPGVSELRRNSKKYGKAGEAVWFSSDPPVLFFHFLRTE |
| SEQ ID NO: 523 | SARS2 | NM017827.3 | LHARAPGPRGPPLLCPCCLRVSH |
| SEQ ID NO: 524 | CAPN3 | NM000070.2 | CLQKHLPVALSTSLC |
| SEQ ID NO: 525 | SPAG5 | NM006461.3 | ISVSIMWTQRRKL |
| SEQ ID NO: 526 | ZNF263 | NM005741.4 | SHSQSGGPRHPGGTRRKAMGSQCPELQGGPEPQRPSS RRREI |
| SEQ ID NO: 527 | DFFA | NM213566.1 | SPKLPLVRRWMQ |
| SEQ ID NO: 528 | NSL1 | NM001042549.1 | GAKPGGLALGAV |
| SEQ ID NO: 529 | C17orf85 | NM018553.3 | CYQHPFPKKSQFPGAYWTSFEGEEEGSGQLTLPGP |
| SEQ ID NO: 530 | CIRH1A | NM032830.2 | LLSSHHPLKRRNLEP |
| SEQ ID NO: 531 | APEH | NM001640.3 | SPSQAMWATRM |
| SEQ ID NO: 532 | DPP3 | NM130443.2 | HFPACQLLPLCDLISSALPYVE |
| SEQ ID NO: 533 | EEF1A1 | NM0014025 | CLQNWWYWYCSCWPSGDWCSQTRYGGHLCSSQRYN GSKICRNAP |
| SEQ ID NO: 534 | ARMC8 | NM014154.2 | RHEKCCNWKQQAESQSHCFRSCSKIVVLASARNLKHRA EN |
| SEQ ID NO: 535 | TMEM179 | NM207379.1 | QFRTPGWPLKALAGRGWPEDASPGQEPSKGAGRGWA |
| SEQ ID NO: 536 | VASP | NM003370.3 | WPQLLLEPNSGKSASRRRPQGGPQPPKLRVVEAEVGDS WKR |
| SEQ ID NO: 537 | MRPL43 | NM032112.2 | PASGGSDLVNHSFLCKWHP |
| SEQ ID NO: 538 | MRPL43 | NM032112.2 | CLLLGAVTL |
| SEQ ID NO: 539 | DEDD | NM001039712.1 | AAAAAHHHSPRPAALRHPQEETGCVP |

TABLE 13-continued

| SEQ ID NO | Name | ID | Sequence |
|---|---|---|---|
| SEQ ID NO: 540 | AURKB | NM004217.2 | DHGGVGRCSNVLPWEEGDSQRHKARKSALRAQGRAEDC |
| SEQ ID NO: 541 | CRCP | NM001040648.1 | TSASQIQAILVP |
| SEQ ID NO: 542 | WTAP | NM152858.1 | GLMASDYSEEVATSEKFPF |
| SEQ ID NO: 543 | NUP43 | NM198887.1 | QENCSNPGGRGCSDPRSCHFTPAWAKEQNAISKNIHI |
| SEQ ID NO: 544 | SRSF5 | NM006925.3 | VKGVLHSLTAAGQTH |
| SEQ ID NO: 545 | HSPHI | NM006644.2 | DSCGIVNSY |
| SEQ ID NO: 546 | IGFLRI | NM024660.2 | NCPVWRHNPCLASWMSWRCWKSDEVFALPLAHLLQTQNQGYTHFCRGGHFRYTLPVFLHGPHRVWG |
| SEQ ID NO: 547 | NUDT8 | NM1818431 | LTAVITEFALQLLAPGTYQPRLAGLTCSGAEGLARPKQPLASPCQASSTPGLNKGL |
| SEQ ID NO: 548 | STK25 | NM006374.3 | KHQAMDHHGVPGRRLSTGLA |
| SEQ ID NO: 549 | TNFAIP2 | NM0062912 | PRAAVSGIQQWWNGRQNWKRKKEKMSSRLAGAFRVLWRAVSTASIRRHIQVAPRPLQAGPAMGP |
| SEQ ID NO: 550 | TTLLI2 | NM015140.3 | LIVGGGAPDRKGFQ |
| SEQ ID NO: 551 | UQCC | NM001184977.1 | GVRCLIHSIHGFL |
| SEQ ID NO: 552 | WDR34 | NM0528443 | VAARAWAQPPLPGAECGHRREGATLAGHRGRPAAAHRGLRPGHAAAATEHQAQEASPRGDRGGRHGSGLLQLHRDSRGSGRNGRHPEREGDHAKPERPPGLLPGQSEEPGDREPEAG |
| SEQ ID NO: 553 | KRT18 | NM1991871 | EQNPGALGEEGTPGQRLEPLLQDHRGPEGSDLRKYCGQCPHRSAD |
| SEQ ID NO: 554 | NOP16 | NM016391.4 | SGKTSSILCRRGRWRWS |
| SEQ ID NO: 555 | SNX27 | NM030918.5 | HFPDGEVTAERCGHLAFPYPLPFPSPPSSYSFHVPFQTE |
| SEQ ID NO: 556 | RAB25 | NM020387.2 | GTIVVQWGPSWCLT |
| SEQ ID NO: 557 | ATP5B | NM001686.3 | TTNPSRISLPSWVWMNFLRKTS |
| SEQ ID NO: 558 | BFAR | NM0165612 | WSCSSITGAAGNLNTTSWSTRLWPNGRRKKLSSGWSSWALGHLFTGKGFYLNE |
| SEQ ID NO: 559 | C16orf62 | NM020314.5 | GSADRDDGKV |
| SEQ ID NO: 560 | C19orf40 | NM152266.3 | DAAFFMSPKLrWWQEMATERGLFGLEIPIILKELRVQGTLVHCPTRHLSQRRGPGRQRGNSLPEPSSMLTCPQQPHRAT |
| SEQ ID NO: 561 | C9orfi40 | NM1784483 | FPAAPGLQGCPRTGPSQPSMQLPSYPEDGSGLSRGHKDVRPGPPGQERVQVLRACAPQPQHQVDCSAVGGPVAAREKPPVSRLGSAHQGLPTSAFEGACHALGDPGIFTGLEAGDRTVSVPG |
| SEQ ID NO: 562 | DERA | NM015954.2 | LLQPPFVFIPPGCVML |
| SEQ ID NO: 563 | EXOSC2 | NM014285.5 | GFWSRFPPPW |
| SEQ ID NO: 564 | GTPBP5 | NM015666.3 | GPRGHAGEGGRQSCGRPVLRGR |
| SEQ ID NO: 565 | HSPH1 | NM006644.2 | DSCGIVNSY |
| SEQ ID NO: 566 | IST1 | NM0147612 | IVGPGPKPEASAKLPSRPADNYDNFVLPELPSVPDTLPTASAGASTSASEDIDFDDLSRRFEEL |
| SEQ ID NO: 567 | MAGED2 | NM1774331 | RCQPDRHSHIWALRWPWWSWCQHQWQLWCLWFLLQV |
| SEQ ID NO: 568 | MED19 | NM153450.1 | ETPSDSDHKKKKKKKEEDPERKRKKKEKKKKKVE |
| SEQ ID NO: 569 | MRPL2 | NM015950.3 | AGNVRSNSRPSIQR |
| SEQ ID NO: 570 | MTFR1 | NM001145839.1 | LHWGSTKVHLLLI |

TABLE 13-continued

| SEQ ID NO | Name | ID | Sequence |
|---|---|---|---|
| SEQ ID NO: 571 | MVK | NM0004312 | GGPRRIWS |
| SEQ ID NO: 572 | NUPL2 | NM007342.2 | AKFCPTFNKSMEEQGK |
| SEQ ID NO: 573 | PEX13 | NM002618.3 | DYRRLPPGPANFFCIFSRDGVSPCYPGWSPSPDLVMSPL RSPKVLGLQA |
| SEQ ID NO: 574 | PSPH | NM004577.3 | CDLNSLCIFVAIFHTKCFKCGESIKHLYSGLWMVVRSVWI MQASLLGEPEEVALGPMGVVAATLEVVGTRAM |
| SEQ ID NO: 575 | RBM3 | NM006743.4 | GVAGIMTVDLEGMDMDMDVPETIMAETRVVMTATQE EITETIMTT |
| SEQ ID NO: 576 | RNF217 | NM1525532 | GLFVFPIYCLC |
| SEQ ID NO: 577 | RPL7L1 | NM198486.2 | EVWRHLLGRPHS |
| SEQ ID NO: 578 | SENP2 | NM021627.2 | GIFELFIL |
| SEQ ID NO: 579 | SLC29A2 | NM001532.2 | SPCPSSPPSQPW |
| SEQ ID NO: 580 | SLC35B2 | NM178148.2 | VLSDLGCAAGKSDDPQLWGHSHITG |
| SEQ ID NO: 581 | TH | NM199293.2 | HQALGAVPSCEGV |
| SEQ ID NO: 582 | WIPI2 | NM001033519.1 | RYGRCVHCREIVLQQPSGHRQP |
| SEQ ID NO: 583 | XRRAI | NM182969.1 | DRKRGCCPTSSSLPISLRVRLS |
| SEQ ID NO: 584 | CIRHIA | NM032830.2 | MTSLLSSHHPLKRRNLEP |
| SEQ ID NO: 585 | TATDN2 | NM014760.3 | GDQQPDRTQAGLKSVSQVEDVFRELIGTQKTRTGCFPPS GS |
| SEQ ID NO: 586 | GTSEI | NM016426.6 | VQMKMMKSSSDPLDIKKDVLLPAWN |
| SEQ ID NO: 587 | C19orf2 | NM1344471 | GFAASWLFKKPRPSECHTVIFKEESYMN |

CONCLUDING MATTER

For clarity and to ensure completeness, certain of the aspects and/or embodiments disclosed herein may be overlapping in scope, described repetitively, or represent recitals of the same or equivalent elements or combinations expressed in alternative language. It will be apparent that the choice of particular phraseology and/or of particular aspects or elements to assert as claims involves many complex technical and legal considerations, and no inference should be drawn that alternative descriptions of a particular element or combination in this written description necessarily do or do not encompass different subject matter; except where context otherwise requires, each described aspect or element should be interpreted according to its own description.

It is intended that this specification be interpreted in accordance with the normal principles of English grammar and that words and phrases be given their ordinary English meaning as understood by persons of skill in the pertinent arts except as otherwise explicitly stated. If a word, term, or phrase is intended to be further characterized, specified, or narrowed in some way, then additional adjectives, modifiers, or descriptive text have been included in accordance with the normal principles of English grammar. It is intended that the meanings of words, terms, or phrases should not be modified or characterized in a manner differing from their ordinary English meaning as understood by persons of skill in the relevant arts except on the basis of adjectives, modifiers, or descriptive text that is explicitly present.

Except as otherwise explicitly stated, terms used in this specification, including terms used in the claims and drawings, are intended as "open" terms. That is, for example, the words "including" and "comprising" should be interpreted to mean "including but not limited to," the word "having" should be interpreted to mean "having at least," the word "includes" should be interpreted to mean "includes but is not limited to," the phrases "for example" or "including by way of example" should be interpreted as signifying that the example(s) given are non-exhaustive and other examples could be given, and other similar words and phrases should be given similar non-exclusive meanings. Except as explicitly stated, ordinals used as adjectives (e.g. "first object", "second object", etc.) in this specification, including claims and drawing figures, are intended merely to differentiate and do not imply that any particular ordering is required. Thus, for example, unless otherwise explicitly stated, "first measurement" and "second measurement" do not imply that the first measurement necessarily takes place before the second measurement, but merely that they are distinct measurements.

In the written description and appended claims, the indefinite articles "a" and/or "an" are intended to mean "at least one" or "one or more" except where expressly stated otherwise or where the enabling disclosure requires otherwise. The word "or" as used herein is intended to mean "and/or", except where it is expressly accompanied by the word "either", as in "either A or B". Applicants are aware of the provisions of 35 U.S.C. § 112, ¶6. The use of the words "function," "means" or "step" in the written description, drawings, or claims herein is not intended to invoke the provisions of 35 U.S.C. § 112, ¶6, to define the invention. To the contrary, if the provisions of 35 U.S.C. § 112, ¶6 are sought to be invoked, the claims will expressly include one of the exact phrases "means for performing the function of" or "step for performing the function of". Moreover, even if the provisions of 35 U.S.C. § 112, ¶6 are explicitly invoked to define a claimed invention, it is intended that the claims not be limited only to the specific structure, material or acts that are described in the preferred embodiments, but in addition, extend to any and all structures, materials or acts that perform the claimed function as described in alternative embodiments or forms of the invention, or that are well known present or later-developed equivalent structures, material or acts for performing the claimed function.

Any of the methods of the present disclosure may be implemented in whole or part in hardware, software, or both, or by a computer program, and may be carried out using any of the disclosed devices or apparatus according to any aspect or embodiment of the present invention, or in any other operable manner.

In the foregoing description, various details, specific aspects, embodiments, and examples have been described in order to illustrate and explain the subject matter, to provide a thorough understanding of the various aspects, to enable persons skilled in the pertinent arts to practice the described subject matter, and to disclose the best mode of doing so known to applicants. These details, specific aspects, embodiments, and examples are not intended to be limiting; rather, it will be apparent to persons of skill in the relevant arts that, based upon the teachings herein, various changes, substitutions, modifications, rearrangements, may be made and various aspects, components, or steps may be omitted or added, without departing from the subject matter described herein and its broader aspects. Except as otherwise expressly stated or where aspects or features are inherently mutually exclusive, aspects and features of any embodiment described herein may be combined with aspects and features of any one or more other embodiments. Descriptions of theoretical principles and/or properties, where given, are intended as explanatory and not limiting. Titles, headings, and subheadings herein and the accompanying abstract are intended merely as a convenience for locating content, and do not limit or otherwise affect the interpretation of the content of the disclosure. The appended claims are intended to encompass within their scope any and all changes, substitutions, modifications, rearrangements, combinations of aspects or features, additions, and omissions that are within the spirit and scope of the subject matter as described herein and/or within the knowledge of a person of skill in the art. The scope of the invention is defined by the claims, and is not limited by or to the particular embodiments or aspects chosen for detailed exposition in the foregoing description, but rather extends to all embodiments or aspects as defined by the claims, as well as any equivalents of such embodiments or aspects, whether currently known or developed in the future.

So as to reduce the complexity and length of the detailed description, and to provide background in certain areas of technology, each of the materials identified in the "REFERENCES" section below is expressly incorporated by reference. Applicants believe that the subject matter incorporated is "non-essential" in accordance with 37 CFR 1.57, because it is referred to for purposes of indicating the background of the invention or illustrating the state of the art. However, if the Examiner concludes that any of the incorporated material constitutes "essential material" within the meaning of 37 CFR 1.57(c)(1)-(3), applicants will amend the specification to expressly recite the essential material that is incorporated by reference as allowed by the applicable rules.

REFERENCES

Berzofsky, J., Terabe, M., Oh, S., Belyakov, L, Ahlers, J., Janik, J. & Morris, J. (2004) Progress on new vaccine strategies for the immunotherapy and prevention of cancer. J. Clin. Invest. 2004 June; 113(11): 1515-1525.

Gite, S., Lim, M., Carlson, R., Olejnik, J., Zehnbauer, B. & Rothschild, K. (2003) A high-throughput nonisotopic protein truncation test. Nature Biotechnology: 21(2): 194-197.

Kerr, C. (2002) Huntington's disease provides cancer clues. The Lancet. Oncology: 3(9): 518.

Leaf, C. (2004) Why we're losing the war on cancer. Fortune: 149(6): 76-82:

Lewis, J. (2004) Therapeutic cancer vaccines: using unique antigens. PNAS: 101 Suppl 2:14653-6.

Linnebacher, M., Gebert, J., Rudy, W., Woerner, S., Yuan, Y., Bork, P. & von Knebel Doeberitz, M. (2001) Frameshift peptide-derived T-cell epitopes: a source of novel tumor-specific antigens. Int. J. Cancer. 93(1): 6-11.

Saeterdal, I., Bjorheim, J., Lislerud, K., Gjertsen, M., Bukholm, L, Olsen, O., Nesland, J., Eriksen, J., Moller, M., Lindblom, A., & Gaudernack, G. (2001) Frameshift-mutation-derived peptides as tumor-specific antigens in inherited and spontaneous colorectal cancer. PNAS: 98(23):13255-60.

Sorensen, S. A., Fenger, K. & Olsen, J. (1999) Significantly lower incidence of cancer among patients with Huntington disease. Cancer: 86(7):1342-6.

Sykes, K. F., and S. A. Johnston. (1999) Linear expression elements: a rapid, in vivo, method to screen for gene functions. Nat Biotechnol 17(4):355-9.

Wang, R., Parkhurst, M., Kawakami, Y., Robbins, P. & Rosenberg, S. A. (1996) Utilization of an alternative open reading frame of a normal gene in generating a novel human cancer antigen. The Journal of Experimental Medicine: 183, 1131-1140.

I claim:

1. A method for designing a cancer vaccine, the method comprising:
    (a) identifying one or more novopeptides or one or more nucleic acids encoding novopeptides in a cancerous tissue sample from an individual, wherein the one or more novopeptides comprise a polypeptide between 8 and 40 amino acids in length, wherein the polypeptide comprises a frameshift mutation and induces a protective immune response to cancer, and wherein the polypeptide comprises a sequence selected from peptide 1-78 (SEQ ID NO: 295), peptide 6-21 (SEQ ID NO: 291), peptide RBM (SEQ ID NO: 232), peptide THAP2 (SEQ ID NO: 238), and combinations thereof; and
    (b) preparing a vaccine comprising one or more polypeptides comprising the one or more novopeptides or one or more nucleic acids encoding the novopeptides.

2. The method of claim 1, wherein identifying the one or more novopeptides comprises:
    (a) obtaining a first nucleic acid sequence from the cancerous tissue sample; and
    (b) comparing the first nucleic acid sequence to a second nucleic acid sequence from an individual without cancer or a noncancerous tissue sample from the individual with cancer.

3. The method of claim 2, wherein the first nucleic acid or the second nucleic acid is a DNA.

4. The method of claim 2, wherein the first nucleic acid or the second nucleic acid is an RNA.

5. The method of claim 2, further comprising measuring expression of the one or more novopeptides in the cancerous tissue.

6. The method of claim 2, wherein the first nucleic acid is obtained from a tumor cell in blood.

7. The method of claim 2, wherein the second nucleic acid is obtained from blood.

8. The method of claim 2, wherein the second nucleic acid sequence is obtained from a database of normal sequences.

9. The method of claim 2, wherein comparing the first nucleic acid sequence to the second nucleic acid sequence detects a mutation comprising an insertion or deletion, a translocation, a single amino acid change, insertion of one or more amino acids, or a frame shift.

10. The method of claim 1, wherein identifying the one or more novopeptides comprises identifying one or more peptides released from a MEW on a cancerous tissue.

11. The method of claim 1, further comprising predicting HLA binding for the one or more novopeptides.

12. The method of claim 1, further comprising predicting an MEW binding strength for the one or more novopeptides.

13. The method of claim 1, wherein identifying the one or more novopeptides comprises:
    (a) obtaining a tumor sample from an individual with cancer;
    (b) isolating polypeptides from the tumor sample;
    (c) obtaining a sequence of the polypeptides; and
    (d) comparing the sequence of the polypeptide to a wild type sequence.

14. The method of claim 1, wherein the method further comprises screening the one or more novopeptides for eliciting an immune response in a tissue sample obtained from an individual with cancer.

15. The method of claim 14, wherein screening the one or more novopeptides for eliciting an immune response comprises contacting a tissue sample to the one or more novopeptides and measuring an immune output.

16. The method of claim 15, wherein the immune output is an antibody response, a T-cell response, or a combination thereof.

17. The method of claim 16, wherein the antibody response is detected using an ELISA assay, an ELISPOT assay, or an agglutination assay.

18. The method of claim 16, wherein the T cell response is detected using an cytolytic assay, a 51Cr release assay, a cytokine assay, an ELISPOT assay, an ELISA assay, an intracellular cytokine staining assay, or a MHC tetramer assay.

19. The method of claim 1, wherein the vaccine comprises a vector.

20. The method of claim 1, wherein the vaccine comprises an adjuvant.

21. The method of claim 20, wherein the adjuvant comprises an oil:water emulsion, a GM-CSF, or an interleukin.

22. A method of identifying a tumor specific antigen for use in a cancer vaccine, the method comprising:
    isolating a nucleic acid from a tumor cell;
    sequencing the nucleic acid from the tumor cell;
    identifying an insertion or deletion in the nucleic acid from the tumor cell, thereby identifying a tumor specific antigen; and
    preparing a cancer vaccine comprising the identified tumor specific antigen,
    wherein the tumor specific antigen comprises a sequence selected from peptide 1-78 (SEQ ID NO: 295), peptide 6-21 (SEQ ID NO: 291), peptide RBM (SEQ ID NO: 232), peptide THAP2 (SEQ ID NO: 238), and combinations thereof.

23. The method of claim 22, wherein the nucleic acid is RNA or DNA.

24. The method of claim 22, wherein the insertion or deletion results in a frameshift in a gene of the tumor cell.

25. The method of claim 24, wherein the frameshift in the gene results in a truncated transcript.

26. The method of claim 22, wherein the tumor specific antigen is a non-oncogene product.

* * * * *

SEQUENCE LISTING

```
<160> NUMBER OF SEQ ID NOS: 587

<210> SEQ ID NO 1
<211> LENGTH: 66
<212> TYPE: DNA
<213> ORGANISM: Artificial Sequence
<220> FEATURE:
<223> OTHER INFORMATION: Synthetic or recombinant sequence

<400> SEQUENCE: 1
```

```
atacctcgaa tgcagcctca ggcttcagcc aatcattgcc agctcctaaa agttatggta    60
gcatga                                                               66
```

```
<210> SEQ ID NO 2
<211> LENGTH: 21
<212> TYPE: PRT
<213> ORGANISM: Artificial Sequence
<220> FEATURE:
<223> OTHER INFORMATION: Synthetic or recombinant peptide

<400> SEQUENCE: 2

Leu Leu Met Cys Gln Cys Gln Leu Tyr Gln Pro Trp Met Cys Lys Glu
1               5                   10                  15

Tyr Tyr Arg Leu Leu
            20
```

```
<210> SEQ ID NO 3
<211> LENGTH: 66
<212> TYPE: DNA
<213> ORGANISM: Artificial Sequence
<220> FEATURE:
<223> OTHER INFORMATION: Synthetic or recombinant sequence

<400> SEQUENCE: 3
gccgtgctgc tcatgtgtca gctgtaccag ccatggatgt gtaaggaata ttatagactt    60
ctttga                                                               66
```

```
<210> SEQ ID NO 4
<211> LENGTH: 21
<212> TYPE: PRT
<213> ORGANISM: Artificial Sequence
<220> FEATURE:
<223> OTHER INFORMATION: Synthetic or recombinant sequence

<400> SEQUENCE: 4

Ala Val Leu Leu Met Cys Gln Leu Tyr Gln Pro Trp Met Cys Lys Glu
1               5                   10                  15

Tyr Tyr Arg Leu Leu
            20
```

```
<210> SEQ ID NO 5
<211> LENGTH: 66
<212> TYPE: DNA
<213> ORGANISM: Artificial Sequence
<220> FEATURE:
<223> OTHER INFORMATION: Synthetic or recombinant sequence

<400> SEQUENCE: 5
gctggaattg ctacacctgg gactgaagac tcaagagact cggatgacgc cctactgaag    60
atgacc                                                               66
```

```
<210> SEQ ID NO 6
<211> LENGTH: 22
<212> TYPE: PRT
<213> ORGANISM: Artificial Sequence
<220> FEATURE:
<223> OTHER INFORMATION: Synthetic or recombinant sequence

<400> SEQUENCE: 6

Ala Gly Ile Ala Thr Pro Gly Thr Glu Asp Ser Arg Asp Ser Asp Asp
1               5                   10                  15

Ala Leu Leu Lys Met Thr
            20
```

-continued

<210> SEQ ID NO 7
<211> LENGTH: 22
<212> TYPE: PRT
<213> ORGANISM: Artificial Sequence
<220> FEATURE:
<223> OTHER INFORMATION: Synthetic or recombinant sequence

<400> SEQUENCE: 7

Asn Gly Ser Gly Lys Ser Asn Val Met Asp Ala Leu Ser Phe Val Met
1               5                   10                  15

Gly Glu Lys Ile Ala Asn
            20

<210> SEQ ID NO 8
<211> LENGTH: 21
<212> TYPE: PRT
<213> ORGANISM: Artificial Sequence
<220> FEATURE:
<223> OTHER INFORMATION: Artificial sequence

<400> SEQUENCE: 8

Asn Gly Ser Gly Cys Ser Gly Val Tyr Cys His Glu Glu Pro Gln Gly
1               5                   10                  15

Glu Asp Ser Ser Val
            20

<210> SEQ ID NO 9
<211> LENGTH: 19
<212> TYPE: PRT
<213> ORGANISM: Artificial Sequence
<220> FEATURE:
<223> OTHER INFORMATION: Synthetic or recombinant sequence

<400> SEQUENCE: 9

His Ile His Thr Pro Leu Leu Asp Arg Lys Leu Asn Ile Leu Met Leu
1               5                   10                  15

Leu Gly His

<210> SEQ ID NO 10
<211> LENGTH: 11
<212> TYPE: PRT
<213> ORGANISM: Artificial Sequence
<220> FEATURE:
<223> OTHER INFORMATION: Synthetic or recombinant sequence

<400> SEQUENCE: 10

Ser Ala Asn Arg Trp Glu Gln Val Ile Phe Pro
1               5                   10

<210> SEQ ID NO 11
<211> LENGTH: 21
<212> TYPE: PRT
<213> ORGANISM: Artificial Sequence
<220> FEATURE:
<223> OTHER INFORMATION: Synthetic or recombinant sequence

<400> SEQUENCE: 11

Leu Leu Met Cys Gln Cys Gln Leu Tyr Gln Pro Trp Met Cys Lys Glu
1               5                   10                  15

Tyr Tyr Arg Leu Leu
            20

<210> SEQ ID NO 12

```
<211> LENGTH: 16
<212> TYPE: PRT
<213> ORGANISM: Artificial Sequence
<220> FEATURE:
<223> OTHER INFORMATION: Synthetic or recombinant sequence

<400> SEQUENCE: 12

Glu Gln Leu Ala Cys Ile Met Glu Ile Pro Lys Val Phe Leu Lys Ile
1               5                   10                  15

<210> SEQ ID NO 13
<211> LENGTH: 40
<212> TYPE: PRT
<213> ORGANISM: Artificial Sequence
<220> FEATURE:
<223> OTHER INFORMATION: Synthetic or recombinant sequence

<400> SEQUENCE: 13

Ser Tyr Ser Gln Ala Val Thr Gly Ser Cys Trp Trp Met Pro Ser Leu
1               5                   10                  15

Leu Pro Asn Ile Tyr Val Leu Asp Arg Leu Leu Val His Ala Thr Lys
            20                  25                  30

Arg Gly Glu Tyr Glu Pro Arg Lys
        35                  40

<210> SEQ ID NO 14
<211> LENGTH: 20
<212> TYPE: PRT
<213> ORGANISM: Artificial Sequence
<220> FEATURE:
<223> OTHER INFORMATION: Synthetic or recombinant sequence

<400> SEQUENCE: 14

Ala Ser Tyr Val Tyr Leu Ser Met Ile Val Thr Ala Thr Cys Leu Trp
1               5                   10                  15

Gly Ser Leu Val
            20

<210> SEQ ID NO 15
<211> LENGTH: 18
<212> TYPE: PRT
<213> ORGANISM: Artificial Sequence
<220> FEATURE:
<223> OTHER INFORMATION: Synthetic or recombinant sequence

<400> SEQUENCE: 15

Gly Cys Cys Gly Ile Tyr Cys His Glu Glu Pro Gln Arg Glu Asp Ser
1               5                   10                  15

Ser Ile

<210> SEQ ID NO 16
<211> LENGTH: 11
<212> TYPE: PRT
<213> ORGANISM: Artificial Sequence
<220> FEATURE:
<223> OTHER INFORMATION: Synthetic or recombinant sequence

<400> SEQUENCE: 16

Pro Trp Met Cys Lys Lys Tyr Tyr Arg Leu Leu
1               5                   10

<210> SEQ ID NO 17
<211> LENGTH: 11
<212> TYPE: PRT
<213> ORGANISM: Artificial Sequence
```

```
<220> FEATURE:
<223> OTHER INFORMATION: Synthetic or recombinant sequence

<400> SEQUENCE: 17

Asn Pro Cys Gln Leu Leu Lys Pro Met Val Ala
1               5                   10

<210> SEQ ID NO 18
<211> LENGTH: 32
<212> TYPE: PRT
<213> ORGANISM: Artificial Sequence
<220> FEATURE:
<223> OTHER INFORMATION: Synthetic or recombinant sequence

<400> SEQUENCE: 18

Ser Cys Trp Trp Met Pro Ser Leu Leu Pro Asn Ile Tyr Val Leu Asp
1               5                   10                  15

Arg Leu Leu Val His Ala Thr Lys Arg Gly Glu Tyr Glu Pro Arg Lys
            20                  25                  30

<210> SEQ ID NO 19
<211> LENGTH: 4
<212> TYPE: PRT
<213> ORGANISM: Artificial Sequence
<220> FEATURE:
<223> OTHER INFORMATION: Synthetic or recombinant sequence

<400> SEQUENCE: 19

Arg Gly Pro Leu
1

<210> SEQ ID NO 20
<211> LENGTH: 23
<212> TYPE: PRT
<213> ORGANISM: Artificial Sequence
<220> FEATURE:
<223> OTHER INFORMATION: Synthetic or recombinant sequence

<400> SEQUENCE: 20

Val His Ile Cys Ser Ile Ser Tyr Phe Thr Thr Cys Val His Gly Ile
1               5                   10                  15

Ile Gln Ile Phe Ser Gln Glu
            20

<210> SEQ ID NO 21
<211> LENGTH: 21
<212> TYPE: PRT
<213> ORGANISM: Artificial Sequence
<220> FEATURE:
<223> OTHER INFORMATION: Synthetic or recombinant sequence

<400> SEQUENCE: 21

Gly Ser Val His Thr Ser Arg Trp Glu Lys Gly Asp Val Val Leu Leu
1               5                   10                  15

Trp Ala Asn Arg Leu
            20

<210> SEQ ID NO 22
<211> LENGTH: 14
<212> TYPE: PRT
<213> ORGANISM: Artificial Sequence
<220> FEATURE:
<223> OTHER INFORMATION: Synthetic or recombinant sequence

<400> SEQUENCE: 22
```

Ser Ala His Lys Glu Ser Ser Phe Asp Ile Ile Cys Gln Val
1               5                   10

<210> SEQ ID NO 23
<211> LENGTH: 36
<212> TYPE: PRT
<213> ORGANISM: Artificial Sequence
<220> FEATURE:
<223> OTHER INFORMATION: Synthetic or recombinant sequence

<400> SEQUENCE: 23

Thr Arg His Leu Leu Lys Ser Met Ser Thr Arg Ala Ala Arg Gln Gln
1               5                   10                  15

Arg Thr Tyr Cys Arg Asp Thr Lys Glu Lys Ser Cys Pro Met Ala Met
            20                  25                  30

Thr Ser Gly Gln
        35

<210> SEQ ID NO 24
<211> LENGTH: 4
<212> TYPE: PRT
<213> ORGANISM: Artificial Sequence
<220> FEATURE:
<223> OTHER INFORMATION: Synthetic or recombinant sequence

<400> SEQUENCE: 24

Gly Trp Leu Gln
1

<210> SEQ ID NO 25
<211> LENGTH: 6
<212> TYPE: PRT
<213> ORGANISM: Artificial Sequence
<220> FEATURE:
<223> OTHER INFORMATION: Synthetic or recombinant sequence

<400> SEQUENCE: 25

Leu Arg Gly Gln Gly Gly
1               5

<210> SEQ ID NO 26
<211> LENGTH: 11
<212> TYPE: PRT
<213> ORGANISM: Artificial Sequence
<220> FEATURE:
<223> OTHER INFORMATION: Synthetic or recombinant sequence

<400> SEQUENCE: 26

Leu Leu Thr Met Ile Glu Ala Asn Gly Trp Met
1               5                   10

<210> SEQ ID NO 27
<211> LENGTH: 11
<212> TYPE: PRT
<213> ORGANISM: Artificial Sequence
<220> FEATURE:
<223> OTHER INFORMATION: Synthetic or recombinant sequence

<400> SEQUENCE: 27

Cys Gly Arg Asn Leu Lys Leu Ser Trp Asn Asn
1               5                   10

<210> SEQ ID NO 28
<211> LENGTH: 19
<212> TYPE: PRT
<213> ORGANISM: Artificial Sequence

```
<220> FEATURE:
<223> OTHER INFORMATION: Synthetic or recombinant sequence

<400> SEQUENCE: 28

His Gln Ala Ile Glu Arg Phe Tyr Asp Lys Met Leu Gln Asn Gln Asp
1               5                   10                  15

Val Asp Arg

<210> SEQ ID NO 29
<211> LENGTH: 64
<212> TYPE: PRT
<213> ORGANISM: Artificial Sequence
<220> FEATURE:
<223> OTHER INFORMATION: Synthetic or recombinant sequence

<400> SEQUENCE: 29

Glu Ser Leu Glu Pro Gly His Ala Ser His Ile Leu Pro Ala Ser Ser
1               5                   10                  15

Leu Val Glu Thr Ser Phe Glu Asp Ser Tyr Asn Cys Asp Ser Pro Thr
                20                  25                  30

Gly Gln Gly Phe Gly Lys Ala Gly Asp Trp Pro Ala Asp Cys Ser Gly
            35                  40                  45

Ser Lys Ile Gly Leu Leu Ser Pro Trp Pro Glu Phe Tyr Ala Tyr Trp
    50                  55                  60

<210> SEQ ID NO 30
<211> LENGTH: 45
<212> TYPE: PRT
<213> ORGANISM: Artificial Sequence
<220> FEATURE:
<223> OTHER INFORMATION: Synthetic or recombinant sequence

<400> SEQUENCE: 30

Gly Pro Thr Leu Trp Ser Pro Thr Ala Pro Arg Asn Thr Ala Thr Gln
1               5                   10                  15

Leu Cys Pro Ala Arg Trp Leu Leu Ser Ser Thr Pro Ser Trp Pro Val
                20                  25                  30

Gly Leu Gly Gly Ser Ala Met Trp Thr Met Thr Thr Met
            35                  40                  45

<210> SEQ ID NO 31
<211> LENGTH: 31
<212> TYPE: PRT
<213> ORGANISM: Artificial Sequence
<220> FEATURE:
<223> OTHER INFORMATION: Synthetic or recombinant sequence

<400> SEQUENCE: 31

Lys Tyr Asn Ala Asp Tyr Asp Leu Ser Ala Arg Gln Gly Ala Asp Thr
1               5                   10                  15

Leu Ala Phe Met Ser Leu Leu Glu Glu Lys Leu Leu Pro Val Leu
                20                  25                  30

<210> SEQ ID NO 32
<211> LENGTH: 16
<212> TYPE: PRT
<213> ORGANISM: Artificial Sequence
<220> FEATURE:
<223> OTHER INFORMATION: Synthetic or recombinant sequence

<400> SEQUENCE: 32

Ser Arg Ser Gln Leu Gly Met Ala Val Ile Phe Leu Phe Thr Pro Arg
1               5                   10                  15
```

```
<210> SEQ ID NO 33
<211> LENGTH: 9
<212> TYPE: PRT
<213> ORGANISM: Artificial Sequence
<220> FEATURE:
<223> OTHER INFORMATION: Synthetic or recombinant sequence

<400> SEQUENCE: 33

Lys Asn Leu Lys Gly Ser Arg Val Cys
1               5

<210> SEQ ID NO 34
<211> LENGTH: 7
<212> TYPE: PRT
<213> ORGANISM: Artificial Sequence
<220> FEATURE:
<223> OTHER INFORMATION: Synthetic or recombinant sequence

<400> SEQUENCE: 34

Gly Lys Arg Ser Ser Glu Cys
1               5

<210> SEQ ID NO 35
<211> LENGTH: 28
<212> TYPE: PRT
<213> ORGANISM: Artificial Sequence
<220> FEATURE:
<223> OTHER INFORMATION: Synthetic or recombinant sequence

<400> SEQUENCE: 35

Ala Ile Cys Ser Met Gln Ala Leu Arg Gln Pro Met Gly Arg Thr Pro
1               5                   10                  15

Trp Gln Arg Gly Pro Val Cys Leu Asp Ala Ile Ser
            20                  25

<210> SEQ ID NO 36
<211> LENGTH: 6
<212> TYPE: PRT
<213> ORGANISM: Artificial Sequence
<220> FEATURE:
<223> OTHER INFORMATION: Synthetic or recombinant sequence

<400> SEQUENCE: 36

Pro Ser Glu Trp Leu Glu
1               5

<210> SEQ ID NO 37
<211> LENGTH: 70
<212> TYPE: PRT
<213> ORGANISM: Artificial Sequence
<220> FEATURE:
<223> OTHER INFORMATION: Synthetic or recombinant sequence

<400> SEQUENCE: 37

Val Glu Asn Gln Ala His Cys Asp Phe Val Lys Leu Arg Asn Met Leu
1               5                   10                  15

Ile Arg Thr His Met His Asp Leu Lys Asp Val Thr Cys Asp Val His
            20                  25                  30

Tyr Glu Asn Tyr Arg Ala His Cys Ile Gln Gln Met Thr Ser Lys Leu
        35                  40                  45

Thr Gln Asp Ser Arg Met Glu Ser Pro Ile Pro Ile Leu Pro Leu Pro
    50                  55                  60

Thr Pro Asp Ala Glu Thr
```

<210> SEQ ID NO 38
<211> LENGTH: 51
<212> TYPE: PRT
<213> ORGANISM: Artificial Sequence
<220> FEATURE:
<223> OTHER INFORMATION: Synthetic or recombinant sequence

<400> SEQUENCE: 38

Trp Trp Ile Val Pro Gly Ala Gly Ser Met Leu Pro Val Leu Ser Pro
1               5                   10                  15

Ile Trp Val Pro Trp Ser Pro Ala Ile Gln His Tyr Ser Leu Ser Thr
            20                  25                  30

Thr Gln Leu Arg Ser Leu Val Asn Pro Ala Ser Gln Ser Gln Ser Cys
        35                  40                  45

Ser Leu Gly
    50

<210> SEQ ID NO 39
<211> LENGTH: 9
<212> TYPE: PRT
<213> ORGANISM: Artificial Sequence
<220> FEATURE:
<223> OTHER INFORMATION: Synthetic or recombinant sequence

<400> SEQUENCE: 39

Gly Val Ile Leu Lys Tyr Val Lys Asn
1               5

<210> SEQ ID NO 40
<211> LENGTH: 10
<212> TYPE: PRT
<213> ORGANISM: Artificial Sequence
<220> FEATURE:
<223> OTHER INFORMATION: Synthetic or recombinant sequence

<400> SEQUENCE: 40

Gly Thr Gly Cys Ile Ser Ala Ile Pro His
1               5                   10

<210> SEQ ID NO 41
<211> LENGTH: 11
<212> TYPE: PRT
<213> ORGANISM: Artificial Sequence
<220> FEATURE:
<223> OTHER INFORMATION: Synthetic or recombinant sequence

<400> SEQUENCE: 41

Val Tyr Asp Tyr Arg Trp Lys Ser Thr Arg Gln
1               5                   10

<210> SEQ ID NO 42
<211> LENGTH: 36
<212> TYPE: PRT
<213> ORGANISM: Artificial Sequence
<220> FEATURE:
<223> OTHER INFORMATION: Synthetic or recombinant sequence

<400> SEQUENCE: 42

Asp His Arg Ala His Gln Pro Leu Pro Ser Pro Arg Pro Ser Ala Gly
1               5                   10                  15

Thr Val Leu Pro Ala Thr Leu His Ala Arg Phe Gly Ala His Arg Arg
            20                  25                  30

```
Pro Leu Ala Ser
        35
```

<210> SEQ ID NO 43
<211> LENGTH: 103
<212> TYPE: PRT
<213> ORGANISM: Artificial Sequence
<220> FEATURE:
<223> OTHER INFORMATION: Synthetic or recombinant sequence

<400> SEQUENCE: 43

```
Met Glu Asp Lys His Ser Ser Asp Ala Ser Ser Leu Leu Pro Gln Asn
1               5                   10                  15

Ile Leu Ser Gln Thr Ser Arg His Asn Asp Arg Asp Tyr Arg Leu Pro
            20                  25                  30

Arg Ala Glu Thr His Ser Ser Ser Thr Pro Val Gln His Pro Ile Lys
        35                  40                  45

Pro Val Val His Pro Thr Ala Thr Pro Ser Thr Val Pro Ser Ser Pro
    50                  55                  60

Phe Thr Leu Gln Ser Asp His Gln Pro Lys Lys Ser Phe Asp Ala Asn
65                  70                  75                  80

Gly Ala Ser Thr Leu Ser Lys Leu Pro Thr Pro Thr Ser Ser Val Pro
                85                  90                  95

Ala Gln Lys Thr Glu Arg Lys
            100
```

<210> SEQ ID NO 44
<211> LENGTH: 12
<212> TYPE: PRT
<213> ORGANISM: Artificial Sequence
<220> FEATURE:
<223> OTHER INFORMATION: Synthetic or recombinant sequence

<400> SEQUENCE: 44

```
Gly His Thr Ser Pro Ser His His Pro Asp Ser
1               5                   10
```

<210> SEQ ID NO 45
<211> LENGTH: 29
<212> TYPE: PRT
<213> ORGANISM: Artificial Sequence
<220> FEATURE:
<223> OTHER INFORMATION: Synthetic or recombinant sequence

<400> SEQUENCE: 45

```
Val Leu Cys Leu Leu Val Trp Ala Arg Gly Ala Gly Thr Leu Pro Ser
1               5                   10                  15

Gly Gln Trp Ser Pro Leu Arg Gly Gln His Leu Arg Trp
            20                  25
```

<210> SEQ ID NO 46
<211> LENGTH: 60
<212> TYPE: PRT
<213> ORGANISM: Artificial Sequence
<220> FEATURE:
<223> OTHER INFORMATION: Synthetic or recombinant sequence

<400> SEQUENCE: 46

```
Val Ile Phe His Phe Arg Thr Met Lys Cys Asp Glu Glu Arg Thr Val
1               5                   10                  15

Ile Asp Asp Ser Arg Gln Val Gly Gln Pro Met His Ile Ile Gly
            20                  25                  30
```

```
Asn Met Phe Lys Leu Glu Val Trp Glu Ile Leu Leu Thr Ser Met Arg
                35                  40                  45

Val His Glu Val Ala Glu Phe Trp Cys Asp Thr Ile
 50                  55                  60

<210> SEQ ID NO 47
<211> LENGTH: 22
<212> TYPE: PRT
<213> ORGANISM: Artificial Sequence
<220> FEATURE:
<223> OTHER INFORMATION: Synthetic or recombinant sequence

<400> SEQUENCE: 47

Gly Gln Ser Leu Ala Met Leu Ser Arg Leu Val Val Asn Ser Trp Pro
1               5                   10                  15

Gln Ala Val Pro Arg Pro
            20

<210> SEQ ID NO 48
<211> LENGTH: 38
<212> TYPE: PRT
<213> ORGANISM: Artificial Sequence
<220> FEATURE:
<223> OTHER INFORMATION: Synthetic or recombinant sequence

<400> SEQUENCE: 48

Pro Leu Thr Glu Ala Ser Tyr Val Asn Leu Pro Thr Ile Ala Leu Cys
1               5                   10                  15

Asn Thr Asp Ser Pro Leu Arg Tyr Val Asp Ile Ala Ile Pro Cys Asn
                20                  25                  30

Asn Lys Gly Ala His Ser
        35

<210> SEQ ID NO 49
<211> LENGTH: 73
<212> TYPE: PRT
<213> ORGANISM: Artificial Sequence
<220> FEATURE:
<223> OTHER INFORMATION: Synthetic or recombinant sequence

<400> SEQUENCE: 49

Leu Arg Lys Gly Pro Pro Val Pro Pro Pro Lys His Thr Pro Ser
1               5                   10                  15

Lys Glu Val Lys Gln Glu Gln Ile Leu Ser Leu Phe Glu Asp Thr Phe
                20                  25                  30

Val Pro Glu Ile Ser Val Thr Thr Pro Ser Gln Pro Ala Glu Ala Ser
            35                  40                  45

Glu Val Ala Gly Gly Thr Gln Pro Ala Ala Gly Ala Gln Glu Pro Gly
     50                  55                  60

Glu Thr Ala Ala Ser Glu Ala Ala Ser
65                  70

<210> SEQ ID NO 50
<211> LENGTH: 45
<212> TYPE: PRT
<213> ORGANISM: Artificial Sequence
<220> FEATURE:
<223> OTHER INFORMATION: Synthetic or recombinant sequence

<400> SEQUENCE: 50

Gln Ile Gln His Pro Thr Ala Ser Leu Ile Ala Lys Val Ala Thr Ala
1               5                   10                  15
```

Gln Asp Asp Ile Thr Gly Asp Gly Thr Thr Ser Asn Val Leu Ile Ile
                20                  25                  30

Gly Glu Leu Leu Lys Gln Ala Asp Leu Tyr Ile Ser Glu
            35                  40                  45

<210> SEQ ID NO 51
<211> LENGTH: 12
<212> TYPE: PRT
<213> ORGANISM: Artificial Sequence
<220> FEATURE:
<223> OTHER INFORMATION: Synthetic or recombinant sequence

<400> SEQUENCE: 51

Gln Pro Trp Asp His Thr Asn Asn His His Asn Lys
1               5                   10

<210> SEQ ID NO 52
<211> LENGTH: 80
<212> TYPE: PRT
<213> ORGANISM: Artificial Sequence
<220> FEATURE:
<223> OTHER INFORMATION: Synthetic or recombinant sequence

<400> SEQUENCE: 52

Ser Val Cys Thr Ser Pro Asn Asp Glu Arg Gly Leu Gln Arg Gln Ser
1               5                   10                  15

Glu Ser Gln Pro Leu Glu Ser Gln Pro Ala Ser Ala Ala Ala Gly Ala
            20                  25                  30

Val Arg Val Gly Arg Arg Pro Glu Ala Ser Lys Arg Arg Glu Asn Gly
        35                  40                  45

Arg Lys Gly Pro Ala Val Arg Leu Thr Gly His Gln Arg Gln Arg Glu
    50                  55                  60

Glu Asp Gln Leu Gly Arg Val Leu Val Ser Arg Ile Arg Leu Arg Phe
65                  70                  75                  80

<210> SEQ ID NO 53
<211> LENGTH: 13
<212> TYPE: PRT
<213> ORGANISM: Artificial Sequence
<220> FEATURE:
<223> OTHER INFORMATION: Synthetic or recombinant sequence

<400> SEQUENCE: 53

Glu Met Gly Glu Glu Gly Gly Gly Arg Thr Gly Asn His
1               5                   10

<210> SEQ ID NO 54
<211> LENGTH: 50
<212> TYPE: PRT
<213> ORGANISM: Artificial Sequence
<220> FEATURE:
<223> OTHER INFORMATION: Synthetic or recombinant sequence

<400> SEQUENCE: 54

Val Arg Pro Ser Thr Val Ser Met Ala Asn Pro Cys Pro Val Asn Cys
1               5                   10                  15

Ser Ser Trp Gly Cys Pro Lys Ser Thr Arg Pro Ala Cys Ala Ala Val
            20                  25                  30

Met Arg Arg Ser Lys Ala Pro Cys Arg Ser Thr Cys Gly Ser Ala Ala
        35                  40                  45

Tyr Ala
    50

<210> SEQ ID NO 55
<211> LENGTH: 4
<212> TYPE: PRT
<213> ORGANISM: Artificial Sequence
<220> FEATURE:
<223> OTHER INFORMATION: Synthetic or recombinant sequence

<400> SEQUENCE: 55

Ser Cys Leu Asp
1

<210> SEQ ID NO 56
<211> LENGTH: 62
<212> TYPE: PRT
<213> ORGANISM: Artificial Sequence
<220> FEATURE:
<223> OTHER INFORMATION: Synthetic or recombinant sequence

<400> SEQUENCE: 56

Lys Trp Thr Thr Ser Leu Glu Lys Ala Ala Thr Thr Ala Thr Ala Arg
1               5                   10                  15

Arg Gly Gly Leu Arg Ser Arg Arg Ser Pro Ser Pro Gly Ser Gln
            20                  25                  30

Gly Pro Ala Gly Ser Gly Arg Ser Gly His Leu Arg Pro Ala Arg Gly
        35                  40                  45

Ala Arg Gln Gly Ala Gly Pro Glu Ala Thr Arg Gly Ser
    50                  55                  60

<210> SEQ ID NO 57
<211> LENGTH: 16
<212> TYPE: PRT
<213> ORGANISM: Artificial Sequence
<220> FEATURE:
<223> OTHER INFORMATION: Synthetic or recombinant sequence

<400> SEQUENCE: 57

Ala Glu Arg Gly Arg Leu Arg Cys Leu His Gln His Ser Pro Gly Val
1               5                   10                  15

<210> SEQ ID NO 58
<211> LENGTH: 55
<212> TYPE: PRT
<213> ORGANISM: Artificial Sequence
<220> FEATURE:
<223> OTHER INFORMATION: Synthetic or recombinant sequence

<400> SEQUENCE: 58

Phe His Gly Asn Glu Ser Leu Trp Lys Asn Phe Lys Glu His His Gln
1               5                   10                  15

Leu Gln Arg Ile Gly Glu Ser Glu Asp Cys Ala Gly Ile Val Ser Phe
            20                  25                  30

Leu Cys Ser Pro Asp Ala Ser Tyr Val Asn Gly Glu Asn Ile Ala Val
        35                  40                  45

Ala Gly Tyr Ser Thr Arg Leu
    50                  55

<210> SEQ ID NO 59
<211> LENGTH: 11
<212> TYPE: PRT
<213> ORGANISM: Artificial Sequence
<220> FEATURE:
<223> OTHER INFORMATION: Synthetic or recombinant sequence

<400> SEQUENCE: 59

```
His Asp Leu Ser Ser Gln Arg Leu Gln Gly Glu
1               5                   10

<210> SEQ ID NO 60
<211> LENGTH: 8
<212> TYPE: PRT
<213> ORGANISM: Artificial Sequence
<220> FEATURE:
<223> OTHER INFORMATION: Synthetic or recombinant sequence

<400> SEQUENCE: 60

Ile Ser His Thr Phe Gly Leu Asp
1               5

<210> SEQ ID NO 61
<211> LENGTH: 48
<212> TYPE: PRT
<213> ORGANISM: Artificial Sequence
<220> FEATURE:
<223> OTHER INFORMATION: Synthetic or recombinant sequence

<400> SEQUENCE: 61

Ala Gln Ala Pro Gly Pro Pro Ala Ala Pro Ala Glu Thr Thr Val Ser
1               5                   10                  15

Ser Ser Ser Gly Leu Pro Val Trp Lys Trp Arg Thr Arg Val Cys Val
            20                  25                  30

Ala Trp Tyr Arg Ser Cys Ser Arg Pro Ser Pro Ser Trp Arg Pro Gly
        35                  40                  45

<210> SEQ ID NO 62
<211> LENGTH: 11
<212> TYPE: PRT
<213> ORGANISM: Artificial Sequence
<220> FEATURE:
<223> OTHER INFORMATION: Synthetic or recombinant sequence

<400> SEQUENCE: 62

Arg Arg Val Thr Glu Glu Gln Cys Leu Leu Pro
1               5                   10

<210> SEQ ID NO 63
<211> LENGTH: 36
<212> TYPE: PRT
<213> ORGANISM: Artificial Sequence
<220> FEATURE:
<223> OTHER INFORMATION: Synthetic or recombinant sequence

<400> SEQUENCE: 63

Cys Ile His Arg Asp Leu Ala Ala Arg Asn Val Leu Val Thr Glu Asp
1               5                   10                  15

Asn Val Met Lys Ile Ala Asp Phe Gly Leu Ala Arg Asp Ile His His
            20                  25                  30

Ile Asp Tyr Tyr
        35

<210> SEQ ID NO 64
<211> LENGTH: 12
<212> TYPE: PRT
<213> ORGANISM: Artificial Sequence
<220> FEATURE:
<223> OTHER INFORMATION: Synthetic or recombinant sequence

<400> SEQUENCE: 64

Lys Asp Val Gly Glu Pro Ser Leu Phe Pro Leu Ala
```

```
1               5                   10
```

<210> SEQ ID NO 65
<211> LENGTH: 17
<212> TYPE: PRT
<213> ORGANISM: Artificial Sequence
<220> FEATURE:
<223> OTHER INFORMATION: Synthetic or recombinant sequence

<400> SEQUENCE: 65

```
Val Ser Leu Thr Gly Arg Gly Ser Pro Gly Arg Ala Ser Arg Gln Lys
1               5                   10                  15

Ile
```

<210> SEQ ID NO 66
<211> LENGTH: 5
<212> TYPE: PRT
<213> ORGANISM: Artificial Sequence
<220> FEATURE:
<223> OTHER INFORMATION: Synthetic or recombinant sequence

<400> SEQUENCE: 66

```
Gly Lys Arg Cys Asp
1               5
```

<210> SEQ ID NO 67
<211> LENGTH: 37
<212> TYPE: PRT
<213> ORGANISM: Artificial Sequence
<220> FEATURE:
<223> OTHER INFORMATION: Synthetic or recombinant sequence

<400> SEQUENCE: 67

```
Val Phe Gly Asp Ser Pro Ala Leu Ser Pro Arg Leu Glu Cys Ser Gly
1               5                   10                  15

Arg Ile Ser Ala His Cys Ser Leu Cys Leu Leu Gly Ser Ser Asp Ser
            20                  25                  30

Pro Thr Ser Ala Ser
        35
```

<210> SEQ ID NO 68
<211> LENGTH: 6
<212> TYPE: PRT
<213> ORGANISM: Artificial Sequence
<220> FEATURE:
<223> OTHER INFORMATION: Synthetic or recombinant sequence

<400> SEQUENCE: 68

```
Gly Pro Gly Pro Ser Arg
1               5
```

<210> SEQ ID NO 69
<211> LENGTH: 6
<212> TYPE: PRT
<213> ORGANISM: Artificial Sequence
<220> FEATURE:
<223> OTHER INFORMATION: Synthetic or recombinant sequence

<400> SEQUENCE: 69

```
Ala Thr Pro Thr Trp Lys
1               5
```

<210> SEQ ID NO 70
<211> LENGTH: 42
<212> TYPE: PRT

<213> ORGANISM: Artificial Sequence
<220> FEATURE:
<223> OTHER INFORMATION: Synthetic or recombinant sequence

<400> SEQUENCE: 70

Thr Leu Leu Gln Glu Gln Gly Thr Lys Thr Val Arg Gln Asn Leu Glu
1               5                   10                  15

Pro Leu Phe Glu Gln Tyr Ile Asn Asn Leu Arg Arg Gln Leu Asp Asn
            20                  25                  30

Ile Val Gly Glu Arg Gly Arg Leu Asp Ser
            35                  40

<210> SEQ ID NO 71
<211> LENGTH: 76
<212> TYPE: PRT
<213> ORGANISM: Artificial Sequence
<220> FEATURE:
<223> OTHER INFORMATION: Synthetic or recombinant sequence

<400> SEQUENCE: 71

Glu Ser Trp Tyr Gln Thr Lys Tyr Glu Glu Leu Gln Ile Thr Ala Gly
1               5                   10                  15

Arg His Gly Asp Asp Leu Arg Asn Thr Lys Gln Glu Ile Ala Glu Ile
            20                  25                  30

Asn Arg Met Ile Gln Arg Leu Arg Ser Glu Ile Asp His Val Lys Lys
        35                  40                  45

Gln Cys Ala Asn Leu Gln Ala Ala Ile Ala Asp Ala Glu Gln Arg Gly
    50                  55                  60

Glu Met Ala Leu Lys Asp Ala Lys Asn Lys Leu Glu
65                  70                  75

<210> SEQ ID NO 72
<211> LENGTH: 5
<212> TYPE: PRT
<213> ORGANISM: Artificial Sequence
<220> FEATURE:
<223> OTHER INFORMATION: Synthetic or recombinant sequence

<400> SEQUENCE: 72

Gly Arg Arg Leu Arg
1               5

<210> SEQ ID NO 73
<211> LENGTH: 40
<212> TYPE: PRT
<213> ORGANISM: Artificial Sequence
<220> FEATURE:
<223> OTHER INFORMATION: Synthetic or recombinant sequence

<400> SEQUENCE: 73

Leu Ala Arg Met Cys Val Pro Thr Leu Leu Leu Thr Asn Leu Arg Ala
1               5                   10                  15

Arg Leu Val Arg Lys Arg Glu Glu Leu Ser Asn Val Leu Ala Ala Met
            20                  25                  30

Lys Lys Ala Thr Ala Lys Lys Asp
        35                  40

<210> SEQ ID NO 74
<211> LENGTH: 44
<212> TYPE: PRT
<213> ORGANISM: Artificial Sequence
<220> FEATURE:
<223> OTHER INFORMATION: Synthetic or recombinant sequence

```
<400> SEQUENCE: 74

Arg Val Arg His Gly Val Arg Gly Pro Gly His Arg Asp Ser Arg Gly
1               5                   10                  15

Ser Gly Arg Asn Gly Arg His Pro Glu Arg Glu Gly Asp His Ala Lys
            20                  25                  30

Pro Glu Arg Pro Pro Gly Leu Leu Pro Gly Gln Gln
        35                  40

<210> SEQ ID NO 75
<211> LENGTH: 13
<212> TYPE: PRT
<213> ORGANISM: Artificial Sequence
<220> FEATURE:
<223> OTHER INFORMATION: Synthetic or recombinant sequence

<400> SEQUENCE: 75

Leu Leu Ser Phe Cys Cys Pro Gly Trp Ser Ser Val Ala
1               5                   10

<210> SEQ ID NO 76
<211> LENGTH: 31
<212> TYPE: PRT
<213> ORGANISM: Artificial Sequence
<220> FEATURE:
<223> OTHER INFORMATION: Synthetic or recombinant sequence

<400> SEQUENCE: 76

Leu Asp Asp Ser Ile Val Val Lys Leu Val Ser Pro Gly Ser Ala Leu
1               5                   10                  15

Pro Arg Ile Phe Gly Leu Ser Pro Glu Ser Leu Ser Ala Asp His
            20                  25                  30

<210> SEQ ID NO 77
<211> LENGTH: 38
<212> TYPE: PRT
<213> ORGANISM: Artificial Sequence
<220> FEATURE:
<223> OTHER INFORMATION: Synthetic or recombinant sequence

<400> SEQUENCE: 77

Ile Val Glu Glu Arg Lys Met His Trp Ser Pro Arg Thr Trp Ser Leu
1               5                   10                  15

Gly Asn Gln Phe Met Glu Arg Arg Gly Ser Arg Phe Arg Lys Glu Met
            20                  25                  30

Thr Lys Leu Ser Thr Glu
        35

<210> SEQ ID NO 78
<211> LENGTH: 8
<212> TYPE: PRT
<213> ORGANISM: Artificial Sequence
<220> FEATURE:
<223> OTHER INFORMATION: Synthetic or recombinant sequence

<400> SEQUENCE: 78

Thr Val Lys His Pro Val Cys Val
1               5

<210> SEQ ID NO 79
<211> LENGTH: 22
<212> TYPE: PRT
<213> ORGANISM: Artificial Sequence
<220> FEATURE:
```

<223> OTHER INFORMATION: Synthetic or recombinant sequence

<400> SEQUENCE: 79

Phe His Val Asn His Val Lys Arg Ser Arg Val Pro Leu Ser Val Gly
1               5                   10                  15
Asp His Thr Asn Ser Ser
            20

<210> SEQ ID NO 80
<211> LENGTH: 40
<212> TYPE: PRT
<213> ORGANISM: Artificial Sequence
<220> FEATURE:
<223> OTHER INFORMATION: Synthetic or recombinant sequence

<400> SEQUENCE: 80

Leu Ala Arg Met Cys Val Pro Thr Leu Leu Thr Asn Leu Arg Ala
1               5                   10                  15
Arg Leu Val Arg Lys Arg Glu Glu Leu Ser Asn Val Leu Ala Ala Met
            20                  25                  30
Lys Lys Ala Thr Ala Lys Lys Asp
        35                  40

<210> SEQ ID NO 81
<211> LENGTH: 41
<212> TYPE: PRT
<213> ORGANISM: Artificial Sequence
<220> FEATURE:
<223> OTHER INFORMATION: Synthetic or recombinant sequence

<400> SEQUENCE: 81

Arg Cys Val Leu Lys Ile Gly Glu His Thr Pro Ser Ala Leu Ala Ile
1               5                   10                  15
Met Glu Asn Ala Lys Cys Ser Gly Pro Leu Cys Gln Tyr Leu Pro Ala
            20                  25                  30
Glu Trp His Cys Ala His Arg Gly Ala
        35                  40

<210> SEQ ID NO 82
<211> LENGTH: 44
<212> TYPE: PRT
<213> ORGANISM: Artificial Sequence
<220> FEATURE:
<223> OTHER INFORMATION: Synthetic or recombinant sequence

<400> SEQUENCE: 82

Gly Gly Gly Gly Arg Ala Glu Arg Pro Ala Gly Leu Ala Gly Val Gln
1               5                   10                  15
Gly Gln Thr Gly Trp Val Ser Val Leu Lys Pro Pro Ala Leu Leu Pro
            20                  25                  30
Gln Leu Arg Ser Lys Val Lys Arg Leu Ile Arg Phe
        35                  40

<210> SEQ ID NO 83
<211> LENGTH: 82
<212> TYPE: PRT
<213> ORGANISM: Artificial Sequence
<220> FEATURE:
<223> OTHER INFORMATION: Synthetic or recombinant sequence

<400> SEQUENCE: 83

Ala Lys Gln Val Leu Leu Gly Arg Lys Val Val Val Val Arg Cys Glu
1               5                   10                  15

Gly Ile Asn Ile Ser Gly Asn Phe Tyr Thr Lys Gln Val Glu Val Pro
            20                  25                  30

Arg Phe Pro Pro Gln Ala Asp Glu His Gln Leu Leu Pro Arg Leu Leu
        35                  40                  45

Pro Leu Pro Gly Pro Gln Pro His Leu Leu Ala Asp Arg Ala Arg Tyr
    50                  55                  60

Ala Ala Pro Gln Asp Gln Ala Arg Pro Gly Arg Ser Gly Pro Pro Gln
65                  70                  75                  80

Gly Val

<210> SEQ ID NO 84
<211> LENGTH: 69
<212> TYPE: PRT
<213> ORGANISM: Artificial Sequence
<220> FEATURE:
<223> OTHER INFORMATION: Synthetic or recombinant sequence

<400> SEQUENCE: 84

Gly Asn Phe Tyr Arg Asn Lys Leu Lys Tyr Leu Ala Phe Leu Arg Lys
1               5                   10                  15

Arg Met Asn Thr Asn Pro Ser Arg Gly Pro Tyr His Phe Arg Ala Pro
            20                  25                  30

Ser Arg Ile Phe Trp Arg Thr Val Arg Gly Met Leu Pro His Lys Thr
        35                  40                  45

Lys Arg Gly Gln Ala Ala Leu Asp Arg Leu Lys Val Phe Asp Gly Ile
    50                  55                  60

Pro Pro Pro Thr Thr
65

<210> SEQ ID NO 85
<211> LENGTH: 41
<212> TYPE: PRT
<213> ORGANISM: Artificial Sequence
<220> FEATURE:
<223> OTHER INFORMATION: Synthetic or recombinant sequence

<400> SEQUENCE: 85

Val Gly Asp Glu Ala Gln Ser Lys Arg Gly Ile Leu Thr Leu Lys Tyr
1               5                   10                  15

Pro Ile Glu His Gly Ile Val Thr Thr Pro Ser Thr Thr Ser Cys Ala
            20                  25                  30

Trp Pro Arg Arg Ser Thr Arg Cys Cys
        35                  40

<210> SEQ ID NO 86
<211> LENGTH: 5
<212> TYPE: PRT
<213> ORGANISM: Artificial Sequence
<220> FEATURE:
<223> OTHER INFORMATION: Synthetic or recombinant sequence

<400> SEQUENCE: 86

Gln Ala Pro Arg Leu
1               5

<210> SEQ ID NO 87
<211> LENGTH: 28
<212> TYPE: PRT
<213> ORGANISM: Artificial Sequence
<220> FEATURE:
<223> OTHER INFORMATION: Synthetic or recombinant sequence

```
<400> SEQUENCE: 87

Gly Thr Cys Trp Arg Lys Trp His Arg Lys Cys Lys Leu Pro Ile Lys
1               5                   10                  15

Ser Thr Gly Leu Arg Arg Gln Ile Ile Pro Trp Gln
            20                  25

<210> SEQ ID NO 88
<211> LENGTH: 67
<212> TYPE: PRT
<213> ORGANISM: Artificial Sequence
<220> FEATURE:
<223> OTHER INFORMATION: Synthetic or recombinant sequence

<400> SEQUENCE: 88

Gly Phe Thr Thr Ala Ala Tyr Leu Arg Ile His Ala Val Lys Asp His
1               5                   10                  15

Gly Leu Gln Ala Pro Arg Ala Asp Arg Ile Leu Cys Lys Leu Cys Ser
            20                  25                  30

Val His Cys Lys Thr Pro Ala Gln Leu Ala Gly His Met Gln Thr His
        35                  40                  45

Leu Gly Gly Ala Ala Pro Pro Val Pro Gly Asp Ala Pro Gln Pro Gln
    50                  55                  60

Pro Thr Cys
65

<210> SEQ ID NO 89
<211> LENGTH: 34
<212> TYPE: PRT
<213> ORGANISM: Artificial Sequence
<220> FEATURE:
<223> OTHER INFORMATION: Synthetic or recombinant sequence

<400> SEQUENCE: 89

Arg Glu Glu Met Ser Thr Gln Trp Leu Pro Thr Tyr Val Pro Ile Pro
1               5                   10                  15

Pro Ser Cys His Lys Phe Pro Lys Asn Ser Gln Asn His Cys Ser Pro
            20                  25                  30

His Leu

<210> SEQ ID NO 90
<211> LENGTH: 12
<212> TYPE: PRT
<213> ORGANISM: Artificial Sequence
<220> FEATURE:
<223> OTHER INFORMATION: Synthetic or recombinant sequence

<400> SEQUENCE: 90

Tyr Phe Leu Ser Ser Ile Arg Phe Ile Ser Thr Phe
1               5                   10

<210> SEQ ID NO 91
<211> LENGTH: 8
<212> TYPE: PRT
<213> ORGANISM: Artificial Sequence
<220> FEATURE:
<223> OTHER INFORMATION: Synthetic or recombinant sequence

<400> SEQUENCE: 91

Arg Asn Pro Gln Gln Met Pro Leu
1               5
```

<210> SEQ ID NO 92
<211> LENGTH: 6
<212> TYPE: PRT
<213> ORGANISM: Artificial Sequence
<220> FEATURE:
<223> OTHER INFORMATION: Synthetic or recombinant sequence

<400> SEQUENCE: 92

Arg His Cys Thr Trp Leu
1               5

<210> SEQ ID NO 93
<211> LENGTH: 6
<212> TYPE: PRT
<213> ORGANISM: Artificial Sequence
<220> FEATURE:
<223> OTHER INFORMATION: Synthetic or recombinant sequence

<400> SEQUENCE: 93

Trp Arg Ile Phe Leu His
1               5

<210> SEQ ID NO 94
<211> LENGTH: 5
<212> TYPE: PRT
<213> ORGANISM: Artificial Sequence
<220> FEATURE:
<223> OTHER INFORMATION: Synthetic or recombinant sequence

<400> SEQUENCE: 94

Gly Leu Ala Asp Ser
1               5

<210> SEQ ID NO 95
<211> LENGTH: 19
<212> TYPE: PRT
<213> ORGANISM: Artificial Sequence
<220> FEATURE:
<223> OTHER INFORMATION: Synthetic or recombinant sequence

<400> SEQUENCE: 95

Glu Phe Ser Ser Gln Leu Trp Thr Leu Lys Glu Gly Ala Glu Val Ala
1               5                   10                  15

Pro Gly Gln

<210> SEQ ID NO 96
<211> LENGTH: 41
<212> TYPE: PRT
<213> ORGANISM: Artificial Sequence
<220> FEATURE:
<223> OTHER INFORMATION: Synthetic or recombinant sequence

<400> SEQUENCE: 96

Ser Pro Leu Leu His Trp Asp Gly Ser Ala Trp Ser Pro Pro Ala Leu
1               5                   10                  15

Trp Trp Thr Val Cys Glu Thr Gly Leu Gln Leu Gly Gly Val Gln Val
            20                  25                  30

Thr Thr Gly Glu Glu Gly Gly Asn Leu
        35                  40

<210> SEQ ID NO 97
<211> LENGTH: 58
<212> TYPE: PRT
<213> ORGANISM: Artificial Sequence
<220> FEATURE:
<223> OTHER INFORMATION: Synthetic or recombinant sequence

```
<400> SEQUENCE: 97

Val Val Val Val Lys Asp Arg Glu Thr Gln Arg Ser Arg Gly Phe Gly
1               5                   10                  15

Phe Ile Thr Phe Thr Asn Pro Asp Leu Trp Met Val Val Arg Ser Val
            20                  25                  30

Trp Ile Met Gln Ala Ser Leu Leu Gly Glu Pro Glu Glu Val Ala Leu
        35                  40                  45

Gly Pro Met Gly Val Val Ala Ala Thr Leu
    50                  55

<210> SEQ ID NO 98
<211> LENGTH: 65
<212> TYPE: PRT
<213> ORGANISM: Artificial Sequence
<220> FEATURE:
<223> OTHER INFORMATION: Synthetic or recombinant sequence

<400> SEQUENCE: 98

Leu Phe Leu Trp Leu Ser Ser Gln Ala Leu Thr Leu Arg Pro Cys Thr
1               5                   10                  15

Thr Ser Gly Thr Ser Ile Ser Gln Pro Pro Gly Ser Cys Phe Ala Pro
            20                  25                  30

Trp Asp Arg Thr His Arg Thr Trp Phe Arg Pro Leu Ser Thr Ser Ser
        35                  40                  45

Ala Arg Leu Asp His Pro Cys Ala Asp Arg Pro Thr Ser Ala Thr Arg
    50                  55                  60

Arg
65

<210> SEQ ID NO 99
<211> LENGTH: 13
<212> TYPE: PRT
<213> ORGANISM: Artificial Sequence
<220> FEATURE:
<223> OTHER INFORMATION: Synthetic or recombinant sequence

<400> SEQUENCE: 99

Lys Leu Val Gly Asn Ser Gln Lys Glu Cys Gly Val Ser
1               5                   10

<210> SEQ ID NO 100
<211> LENGTH: 87
<212> TYPE: PRT
<213> ORGANISM: Artificial Sequence
<220> FEATURE:
<223> OTHER INFORMATION: Synthetic or recombinant sequence

<400> SEQUENCE: 100

Gly Val Ser Gly Val Gly Gly Val Leu Val Val Thr Glu Gly Lys Leu
1               5                   10                  15

Arg His Arg Ala Thr Lys Leu Met Leu Gly His Pro Glu His Gln Gly
            20                  25                  30

Arg Ala Gly Asn Lys His Ser Cys Val Leu Asn Ser Thr Pro Cys Ser
        35                  40                  45

Leu Ser Ala Ser His Leu Thr Gln Gly Pro Cys Trp Leu Leu Thr Asp
    50                  55                  60

Ser Leu Gly Val Trp Leu Ala Ala Ile Leu Gln Asp Arg Ala Pro Pro
65                  70                  75                  80

Trp Pro Cys Pro His Gln Trp
```

<210> SEQ ID NO 101
<211> LENGTH: 29
<212> TYPE: PRT
<213> ORGANISM: Artificial Sequence
<220> FEATURE:
<223> OTHER INFORMATION: Synthetic or recombinant sequence

<400> SEQUENCE: 101

Met Asp Leu Lys Glu Gln Pro Gly Asn Thr Ile Ser Ala Gly Gln Glu
1               5                   10                  15

Asp Phe Pro Ser Val Leu Leu Glu Thr Ala Ala Ser Leu
            20                  25

<210> SEQ ID NO 102
<211> LENGTH: 21
<212> TYPE: PRT
<213> ORGANISM: Artificial Sequence
<220> FEATURE:
<223> OTHER INFORMATION: Synthetic or recombinant sequence

<400> SEQUENCE: 102

Arg Ala Ala Leu Val Leu Val Val Leu Leu Ile Ala Gly Gly Leu Phe
1               5                   10                  15

Met Phe Thr Tyr Lys
            20

<210> SEQ ID NO 103
<211> LENGTH: 22
<212> TYPE: PRT
<213> ORGANISM: Artificial Sequence
<220> FEATURE:
<223> OTHER INFORMATION: Synthetic or recombinant sequence

<400> SEQUENCE: 103

Val Arg Met Ala Arg Gly Gly Ala Ala Leu Gly Arg Glu Leu Ser Arg
1               5                   10                  15

Gly Ala Glu Gln Gly Arg
            20

<210> SEQ ID NO 104
<211> LENGTH: 58
<212> TYPE: PRT
<213> ORGANISM: Artificial Sequence
<220> FEATURE:
<223> OTHER INFORMATION: Synthetic or recombinant sequence

<400> SEQUENCE: 104

Lys Lys Leu Asn Gly Gly Arg His Val Gln Gly Ile Leu Arg Gly Phe
1               5                   10                  15

Asp Pro Phe Met Asn Leu Val Ile Asp Glu Cys Val Glu Met Ala Thr
            20                  25                  30

Ser Gly Gln Gln Asn Asn Ile Gly Met Val Val Ile Arg Gly Asn Ser
        35                  40                  45

Ile Ile Met Leu Glu Ala Leu Glu Arg Val
    50                  55

<210> SEQ ID NO 105
<211> LENGTH: 7
<212> TYPE: PRT
<213> ORGANISM: Artificial Sequence
<220> FEATURE:
<223> OTHER INFORMATION: Synthetic or recombinant sequence

<400> SEQUENCE: 105

Val Gly Leu Ala Pro Leu Pro
1               5

<210> SEQ ID NO 106
<211> LENGTH: 57
<212> TYPE: PRT
<213> ORGANISM: Artificial Sequence
<220> FEATURE:
<223> OTHER INFORMATION: Synthetic or recombinant sequence

<400> SEQUENCE: 106

Met Leu Leu Arg Arg Arg Gly Thr Pro Ser Ser Pro Cys Ala Arg Thr
1               5                   10                  15

Thr Thr Ala Phe Val Pro Trp Pro Ser Thr Thr Ala Ser Arg Leu Cys
            20                  25                  30

Ser Pro Pro Pro Arg Thr Ala Arg Ser Ser Ser Gly Thr Cys Arg Arg
        35                  40                  45

Arg Ser Arg Pro Arg Arg Met Arg Arg
    50                  55

<210> SEQ ID NO 107
<211> LENGTH: 33
<212> TYPE: PRT
<213> ORGANISM: Artificial Sequence
<220> FEATURE:
<223> OTHER INFORMATION: Synthetic or recombinant sequence

<400> SEQUENCE: 107

Arg Gly Leu Gln Asp Pro Cys His Val Val Ile Phe Phe Ile Glu Gly
1               5                   10                  15

Leu Ala Ala Ala Ala Ala Asn Ala Gly Pro Gly Ala Gly Ala Gly Glu
            20                  25                  30

Ala

<210> SEQ ID NO 108
<211> LENGTH: 9
<212> TYPE: PRT
<213> ORGANISM: Artificial Sequence
<220> FEATURE:
<223> OTHER INFORMATION: Synthetic or recombinant sequence

<400> SEQUENCE: 108

Ala Trp Thr Arg Phe Ala Met Arg Ala
1               5

<210> SEQ ID NO 109
<211> LENGTH: 11
<212> TYPE: PRT
<213> ORGANISM: Artificial Sequence
<220> FEATURE:
<223> OTHER INFORMATION: Synthetic or recombinant sequence

<400> SEQUENCE: 109

Val His Arg Ala Leu Arg Leu Ser Thr Arg Leu
1               5                   10

<210> SEQ ID NO 110
<211> LENGTH: 67
<212> TYPE: PRT
<213> ORGANISM: Artificial Sequence
<220> FEATURE:
<223> OTHER INFORMATION: Synthetic or recombinant sequence

<400> SEQUENCE: 110

Gly Thr Lys Thr Cys Glu Ala Glu Pro Gly Ala Val Val Arg Ala Val
1               5                   10                  15

His Gln Gln Pro Gln Glu Ala Ala Gly Gln His Arg Gly Gly Thr Gly
            20                  25                  30

Ser Ser Gly Leu Gly Ala Glu Lys His Ala Gly Pro Gly Gly Gly Pro
        35                  40                  45

Gln Glu Gln Thr Met Arg Met Lys Ser Thr Ser Ala Gln Gln Gln Arg
    50                  55                  60

Met Asn Leu
65

<210> SEQ ID NO 111
<211> LENGTH: 24
<212> TYPE: PRT
<213> ORGANISM: Artificial Sequence
<220> FEATURE:
<223> OTHER INFORMATION: Synthetic or recombinant sequence

<400> SEQUENCE: 111

Ser Cys Leu Leu Val Lys Ile Phe Leu Phe Ile Leu Met Phe Ile Ala
1               5                   10                  15

Met Val Ile Ser Val Tyr Pro Phe
            20

<210> SEQ ID NO 112
<211> LENGTH: 11
<212> TYPE: PRT
<213> ORGANISM: Artificial Sequence
<220> FEATURE:
<223> OTHER INFORMATION: Synthetic or recombinant sequence

<400> SEQUENCE: 112

Ser Leu Ile Ile Ile Lys Arg Tyr Gly His Phe
1               5                   10

<210> SEQ ID NO 113
<211> LENGTH: 23
<212> TYPE: PRT
<213> ORGANISM: Artificial Sequence
<220> FEATURE:
<223> OTHER INFORMATION: Synthetic or recombinant sequence

<400> SEQUENCE: 113

Thr Arg Tyr Gly Arg Cys Val His Cys Arg Glu Ile Val Leu Gln Gln
1               5                   10                  15

Pro Ser Gly His Arg Gln Pro
            20

<210> SEQ ID NO 114
<211> LENGTH: 23
<212> TYPE: PRT
<213> ORGANISM: Artificial Sequence
<220> FEATURE:
<223> OTHER INFORMATION: Synthetic or recombinant sequence

<400> SEQUENCE: 114

Glu Asp Arg Lys Arg Gly Cys Cys Pro Thr Ser Ser Leu Pro Ile
1               5                   10                  15

Ser Leu Arg Val Arg Leu Ser
            20

<210> SEQ ID NO 115
<211> LENGTH: 63
<212> TYPE: PRT
<213> ORGANISM: Artificial Sequence
<220> FEATURE:
<223> OTHER INFORMATION: Synthetic or recombinant sequence

<400> SEQUENCE: 115

His Thr Gly Val Tyr Pro Ile Leu Ser Arg Ser Leu Arg Gln Met Ala
1               5                   10                  15

Gln Gly Lys Asp Pro Thr Glu Trp His Val His Thr Cys Gly Leu Ala
            20                  25                  30

Asn Met Phe Ala Tyr His Thr Leu Gly Tyr Glu Asp Leu Asp Glu Leu
        35                  40                  45

Gln Lys Glu Pro Gln Pro Leu Val Phe Val Ile Glu Leu Leu Gln
    50                  55                  60

<210> SEQ ID NO 116
<211> LENGTH: 12
<212> TYPE: PRT
<213> ORGANISM: Artificial Sequence
<220> FEATURE:
<223> OTHER INFORMATION: Synthetic or recombinant sequence

<400> SEQUENCE: 116

Thr Gln Arg Leu Thr Gly Arg Pro Thr Trp Pro Arg
1               5                   10

<210> SEQ ID NO 117
<211> LENGTH: 10
<212> TYPE: PRT
<213> ORGANISM: Artificial Sequence
<220> FEATURE:
<223> OTHER INFORMATION: Synthetic or recombinant sequence

<400> SEQUENCE: 117

Val Trp Met Arg Ser Pro Leu Ser Thr Phe
1               5                   10

<210> SEQ ID NO 118
<211> LENGTH: 25
<212> TYPE: PRT
<213> ORGANISM: Artificial Sequence
<220> FEATURE:
<223> OTHER INFORMATION: Synthetic or recombinant sequence

<400> SEQUENCE: 118

Ser Leu Arg Lys Arg Gln Arg Thr Leu Ala Trp Lys His Thr Gly Arg
1               5                   10                  15

Glu Arg Asp Gln Ala Thr Val Ile Leu
            20                  25

<210> SEQ ID NO 119
<211> LENGTH: 29
<212> TYPE: PRT
<213> ORGANISM: Artificial Sequence
<220> FEATURE:
<223> OTHER INFORMATION: Synthetic or recombinant sequence

<400> SEQUENCE: 119

Cys His Gln Glu Thr Lys Val His Gln Lys His Pro Glu Asn Tyr Gln
1               5                   10                  15

Val Tyr Glu Asn Gly Ser Gly Ser Lys Ile Cys Pro Ser
            20                  25

```
<210> SEQ ID NO 120
<211> LENGTH: 24
<212> TYPE: PRT
<213> ORGANISM: Artificial Sequence
<220> FEATURE:
<223> OTHER INFORMATION: Synthetic or recombinant sequence

<400> SEQUENCE: 120

Ile Phe Phe Phe Phe Gly Ile His Leu Gly Ser Ile Phe Ile Leu Trp
1               5                   10                  15

His Gly Asn Leu Gln Arg Ile Lys
            20

<210> SEQ ID NO 121
<211> LENGTH: 13
<212> TYPE: PRT
<213> ORGANISM: Artificial Sequence
<220> FEATURE:
<223> OTHER INFORMATION: Synthetic or recombinant sequence

<400> SEQUENCE: 121

Gly Cys Cys Phe Phe Trp Trp Ser Val Tyr Gln Glu Gly
1               5                   10

<210> SEQ ID NO 122
<211> LENGTH: 57
<212> TYPE: PRT
<213> ORGANISM: Artificial Sequence
<220> FEATURE:
<223> OTHER INFORMATION: Synthetic or recombinant sequence

<400> SEQUENCE: 122

Ser Asn Gln Ala Ser Trp Arg Lys Ala Asn Leu Thr Cys Lys Ile Ala
1               5                   10                  15

Ile Asp Asn Leu Glu Lys Ala Glu Leu Leu Gln Gly Gly Asp Leu Leu
            20                  25                  30

Arg Gln Arg Pro Pro Lys Arg Ala Trp Pro Arg His Pro Val Pro Ser
        35                  40                  45

Leu Arg Ala Ser Trp Gly Ser Ala Gly
    50                  55

<210> SEQ ID NO 123
<211> LENGTH: 20
<212> TYPE: PRT
<213> ORGANISM: Artificial Sequence
<220> FEATURE:
<223> OTHER INFORMATION: Synthetic or recombinant sequence

<400> SEQUENCE: 123

Ala Pro Ser Cys Cys Gln Ala Thr Ser Ala Lys Gly Gly Gln Thr Gly
1               5                   10                  15

Pro Phe Gln Cys
            20

<210> SEQ ID NO 124
<211> LENGTH: 10
<212> TYPE: PRT
<213> ORGANISM: Artificial Sequence
<220> FEATURE:
<223> OTHER INFORMATION: Synthetic or recombinant sequence

<400> SEQUENCE: 124

Asp Pro Gly Ala Pro Glu Pro Trp Arg Gly
```

```
1               5                   10

<210> SEQ ID NO 125
<211> LENGTH: 4
<212> TYPE: PRT
<213> ORGANISM: Artificial Sequence
<220> FEATURE:
<223> OTHER INFORMATION: Synthetic or recombinant sequence

<400> SEQUENCE: 125

Ala Glu Arg Glu
1

<210> SEQ ID NO 126
<211> LENGTH: 4
<212> TYPE: PRT
<213> ORGANISM: Artificial Sequence
<220> FEATURE:
<223> OTHER INFORMATION: Synthetic or recombinant sequence

<400> SEQUENCE: 126

Ala Arg Arg Gly
1

<210> SEQ ID NO 127
<211> LENGTH: 7
<212> TYPE: PRT
<213> ORGANISM: Artificial Sequence
<220> FEATURE:
<223> OTHER INFORMATION: Synthetic or recombinant sequence

<400> SEQUENCE: 127

Val Ile Gln Arg Leu Leu Cys
1               5

<210> SEQ ID NO 128
<211> LENGTH: 11
<212> TYPE: PRT
<213> ORGANISM: Artificial Sequence
<220> FEATURE:
<223> OTHER INFORMATION: Synthetic or recombinant sequence

<400> SEQUENCE: 128

Gly Lys Asn Cys Asp Ser Gly Glu Glu Ser Lys
1               5                   10

<210> SEQ ID NO 129
<211> LENGTH: 4
<212> TYPE: PRT
<213> ORGANISM: Artificial Sequence
<220> FEATURE:
<223> OTHER INFORMATION: Synthetic or recombinant sequence

<400> SEQUENCE: 129

Arg Pro Arg Gly
1

<210> SEQ ID NO 130
<211> LENGTH: 27
<212> TYPE: PRT
<213> ORGANISM: Artificial Sequence
<220> FEATURE:
<223> OTHER INFORMATION: Synthetic or recombinant sequence

<400> SEQUENCE: 130

Ala Ala Cys Trp Thr Leu Ser Met Asp Thr Leu Leu Ala Leu Leu Ile
1               5                   10                  15
```

Lys Glu Pro Gly Leu Gly Pro Cys Trp Thr Cys
            20                  25

<210> SEQ ID NO 131
<211> LENGTH: 7
<212> TYPE: PRT
<213> ORGANISM: Artificial Sequence
<220> FEATURE:
<223> OTHER INFORMATION: Synthetic or recombinant sequence

<400> SEQUENCE: 131

Cys Arg Ser Cys Ser Thr Phe
1               5

<210> SEQ ID NO 132
<211> LENGTH: 5
<212> TYPE: PRT
<213> ORGANISM: Artificial Sequence
<220> FEATURE:
<223> OTHER INFORMATION: Synthetic or recombinant sequence

<400> SEQUENCE: 132

Gly Glu Arg Arg Glu
1               5

<210> SEQ ID NO 133
<211> LENGTH: 51
<212> TYPE: PRT
<213> ORGANISM: Artificial Sequence
<220> FEATURE:
<223> OTHER INFORMATION: Synthetic or recombinant sequence

<400> SEQUENCE: 133

Arg Asp Ser Ile Val Ala Glu Leu Asp Arg Glu Met Ser Arg Ser Val
1               5                   10                  15

Asp Val Thr Asn Thr Thr Phe Leu Leu Met Ala Ala Ser Ile Tyr Leu
            20                  25                  30

His Asp Gln Asn Pro Asp Ala Ala Leu Arg Ala Leu His Gln Gly Asp
        35                  40                  45

Ser Leu Glu
    50

<210> SEQ ID NO 134
<211> LENGTH: 11
<212> TYPE: PRT
<213> ORGANISM: Artificial Sequence
<220> FEATURE:
<223> OTHER INFORMATION: Synthetic or recombinant sequence

<400> SEQUENCE: 134

Leu Gln Thr Leu Glu Ile Lys Lys Val Leu Glu
1               5                   10

<210> SEQ ID NO 135
<211> LENGTH: 8
<212> TYPE: PRT
<213> ORGANISM: Artificial Sequence
<220> FEATURE:
<223> OTHER INFORMATION: Synthetic or recombinant sequence

<400> SEQUENCE: 135

Asp Lys Thr Phe Gln Arg Lys Tyr
1               5

```
<210> SEQ ID NO 136
<211> LENGTH: 8
<212> TYPE: PRT
<213> ORGANISM: Artificial Sequence
<220> FEATURE:
<223> OTHER INFORMATION: Synthetic or recombinant sequence

<400> SEQUENCE: 136

Ile Pro Lys Val Phe Leu Lys Ile
1               5

<210> SEQ ID NO 137
<211> LENGTH: 27
<212> TYPE: PRT
<213> ORGANISM: Artificial Sequence
<220> FEATURE:
<223> OTHER INFORMATION: Synthetic or recombinant sequence

<400> SEQUENCE: 137

Asp Pro Lys Gly Asn Ser Gly Thr Trp Arg Leu Tyr Gly Ser His Leu
1               5                   10                  15

Ser Cys Leu His Trp Trp Asn Lys Cys Ser Lys
            20                  25

<210> SEQ ID NO 138
<211> LENGTH: 18
<212> TYPE: PRT
<213> ORGANISM: Artificial Sequence
<220> FEATURE:
<223> OTHER INFORMATION: Synthetic or recombinant sequence

<400> SEQUENCE: 138

Lys Phe Lys Phe Glu Cys Asn Phe Arg Ser Tyr Glu Tyr Arg Asn Tyr
1               5                   10                  15

Tyr Leu

<210> SEQ ID NO 139
<211> LENGTH: 6
<212> TYPE: PRT
<213> ORGANISM: Artificial Sequence
<220> FEATURE:
<223> OTHER INFORMATION: Synthetic or recombinant sequence

<400> SEQUENCE: 139

Val Gly Asn Leu His Phe
1               5

<210> SEQ ID NO 140
<211> LENGTH: 16
<212> TYPE: PRT
<213> ORGANISM: Artificial Sequence
<220> FEATURE:
<223> OTHER INFORMATION: Synthetic or recombinant sequence

<400> SEQUENCE: 140

Gly Cys Gln Pro Asp His Gly Ala Gly Ala Trp Ala Ala Cys Val Pro
1               5                   10                  15

<210> SEQ ID NO 141
<211> LENGTH: 11
<212> TYPE: PRT
<213> ORGANISM: Artificial Sequence
<220> FEATURE:
<223> OTHER INFORMATION: Synthetic or recombinant sequence

<400> SEQUENCE: 141
```

```
Ile Pro Ala Leu Leu Leu Ala Ser Cys Leu Gly
1               5                   10
```

<210> SEQ ID NO 142
<211> LENGTH: 32
<212> TYPE: PRT
<213> ORGANISM: Artificial Sequence
<220> FEATURE:
<223> OTHER INFORMATION: Synthetic or recombinant sequence

<400> SEQUENCE: 142

```
Ser Cys Arg Thr His Pro Thr Pro Ser Leu Arg Ala Ala Trp Ser Pro
1               5                   10                  15

Gln Pro Trp Thr Arg Pro Gly Trp Arg Pro Arg Gly Arg Arg Cys
            20                  25                  30
```

<210> SEQ ID NO 143
<211> LENGTH: 17
<212> TYPE: PRT
<213> ORGANISM: Artificial Sequence
<220> FEATURE:
<223> OTHER INFORMATION: Synthetic or recombinant sequence

<400> SEQUENCE: 143

```
Ala Val Arg Trp Ser Ser Gly Thr Arg Met Ser Pro Ser Leu Pro Arg
1               5                   10                  15

Ser
```

<210> SEQ ID NO 144
<211> LENGTH: 64
<212> TYPE: PRT
<213> ORGANISM: Artificial Sequence
<220> FEATURE:
<223> OTHER INFORMATION: Synthetic or recombinant sequence

<400> SEQUENCE: 144

```
Leu Pro Tyr Leu Ile Asp Gly Ala His Lys Ile Thr Gln Ser Asn Ala
1               5                   10                  15

Ile Leu Cys Tyr Ile Ala Arg Lys His Asn Leu Cys Gly Glu Thr Glu
            20                  25                  30

Glu Glu Lys Ile Arg Val Asp Ile Leu Glu Asn Gln Ala Met Asp Val
        35                  40                  45

Ser Asn Gln Leu Ala Arg Val Cys Tyr Ser Pro Asp Phe Glu Lys Leu
    50                  55                  60
```

<210> SEQ ID NO 145
<211> LENGTH: 7
<212> TYPE: PRT
<213> ORGANISM: Artificial Sequence
<220> FEATURE:
<223> OTHER INFORMATION: Synthetic or recombinant sequence

<400> SEQUENCE: 145

```
Val Trp Pro Ser Cys Ser Thr
1               5
```

<210> SEQ ID NO 146
<211> LENGTH: 42
<212> TYPE: PRT
<213> ORGANISM: Artificial Sequence
<220> FEATURE:
<223> OTHER INFORMATION: Synthetic or recombinant sequence

<400> SEQUENCE: 146

```
Leu Ala Ile Ile Glu Tyr Leu Glu Glu Met Arg Pro Thr Pro Arg Leu
1               5                   10                  15

Leu Pro Gln Asp Pro Lys Lys Arg Ala Ser Val Arg Met Ile Ser Asp
                20                  25                  30

Leu Ile Ala Gly Gly Ile Gln Pro Leu Gln
            35                  40

<210> SEQ ID NO 147
<211> LENGTH: 55
<212> TYPE: PRT
<213> ORGANISM: Artificial Sequence
<220> FEATURE:
<223> OTHER INFORMATION: Synthetic or recombinant sequence

<400> SEQUENCE: 147

Gly Glu Gly Asp Ile His Glu Asn Val Asp Thr Asp Leu Pro Gly Ser
1               5                   10                  15

Leu Gly Gln Ser Glu Glu Lys Pro Val Pro Ala Ala Pro Val Pro Ser
                20                  25                  30

Pro Val Ala Pro Ala Pro Val Pro Ser Arg Arg Asn Pro Gly Gly
            35                  40                  45

Lys Ser Ser Leu Val Leu Gly
    50                  55

<210> SEQ ID NO 148
<211> LENGTH: 42
<212> TYPE: PRT
<213> ORGANISM: Artificial Sequence
<220> FEATURE:
<223> OTHER INFORMATION: Synthetic or recombinant sequence

<400> SEQUENCE: 148

Met Pro Trp Thr Ile Leu Pro Gly Arg Thr Asn Ser Thr Ile Pro Lys
1               5                   10                  15

Ser Ser Asn Lys Lys Thr Ser Gln Ala Thr Arg Gly Asp His Trp Lys
                20                  25                  30

Trp Ser Ser Ser Arg Pro Ile Val Gln Lys
            35                  40

<210> SEQ ID NO 149
<211> LENGTH: 29
<212> TYPE: PRT
<213> ORGANISM: Artificial Sequence
<220> FEATURE:
<223> OTHER INFORMATION: Synthetic or recombinant sequence

<400> SEQUENCE: 149

Met Ile Lys Lys Trp Leu Tyr Val Ile Cys Val Glu Asp His Val Ser
1               5                   10                  15

Glu Ile Arg Leu Tyr Ile Ser Lys Cys Trp Asp His Ala
                20                  25

<210> SEQ ID NO 150
<211> LENGTH: 7
<212> TYPE: PRT
<213> ORGANISM: Artificial Sequence
<220> FEATURE:
<223> OTHER INFORMATION: Synthetic or recombinant sequence

<400> SEQUENCE: 150

Cys Gln Trp Val Met Phe Gly
1               5
```

<210> SEQ ID NO 151
<211> LENGTH: 90
<212> TYPE: PRT
<213> ORGANISM: Artificial Sequence
<220> FEATURE:
<223> OTHER INFORMATION: Synthetic or recombinant sequence

<400> SEQUENCE: 151

```
Glu His Asp Pro Gly Pro Pro Arg Pro Gly Ala Ala Gly Pro Cys Gly
1               5                   10                  15

Gly Gly Arg Leu Leu Leu Thr Gln Pro Gly Gly Pro Ala Gly Gly Ser
            20                  25                  30

Gly Pro His Glu Thr Glu Trp Cys Leu Pro Leu His Gln Arg Arg Ala
        35                  40                  45

His Ser Ala Ala Cys Gly Arg Cys Arg Pro Pro Val Gln Gly Asp
50                  55                  60

Pro Glu Thr His Gln Gly Ala Arg Pro Arg Gln Arg Thr Ala Gly Pro
65                  70                  75                  80

Leu Pro Arg Pro Glu Leu Pro Pro Pro Leu
                85                  90
```

<210> SEQ ID NO 152
<211> LENGTH: 9
<212> TYPE: PRT
<213> ORGANISM: Artificial Sequence
<220> FEATURE:
<223> OTHER INFORMATION: Synthetic or recombinant sequence

<400> SEQUENCE: 152

```
Arg Lys Ala Gln Arg Tyr Thr Gly Gln
1               5
```

<210> SEQ ID NO 153
<211> LENGTH: 102
<212> TYPE: PRT
<213> ORGANISM: Artificial Sequence
<220> FEATURE:
<223> OTHER INFORMATION: Synthetic or recombinant sequence

<400> SEQUENCE: 153

```
Asp Leu Leu Leu Pro Gly Glu Val Glu Gln Asp Val Ser Thr Ser
1               5                   10                  15

Ile Pro Ser Cys Ile Pro Phe Val Ala Gln Pro Thr Cys Glu Val
            20                  25                  30

Lys Pro Lys Pro Ser Val Lys Arg Met Asp Lys Gln Thr Glu Glu Ile
        35                  40                  45

Leu Gly Asp Glu Val Gln Leu Phe Ser Leu Asp Glu Glu Phe Asp Tyr
50                  55                  60

Asp Asn Val Met Leu Thr Ser Lys Phe Ser Pro Ala Glu Ile Glu Asn
65                  70                  75                  80

Ile Lys Glu Leu Cys Lys Gln Gln Lys Arg Lys Asp Thr Ser Pro Asp
                85                  90                  95

Leu Glu Lys Ser Cys Asp
                100
```

<210> SEQ ID NO 154
<211> LENGTH: 5
<212> TYPE: PRT
<213> ORGANISM: Artificial Sequence
<220> FEATURE:
<223> OTHER INFORMATION: Synthetic or recombinant sequence

<400> SEQUENCE: 154

Gly Ser Ser Leu Leu
1               5

<210> SEQ ID NO 155
<211> LENGTH: 29
<212> TYPE: PRT
<213> ORGANISM: Artificial Sequence
<220> FEATURE:
<223> OTHER INFORMATION: Synthetic or recombinant sequence

<400> SEQUENCE: 155

Met Ile Lys Lys Trp Leu Tyr Val Ile Cys Val Glu Asp His Val Ser
1               5                   10                  15

Glu Ile Arg Pro Tyr Ile Ser Lys Cys Trp Asp His Ala
            20                  25

<210> SEQ ID NO 156
<211> LENGTH: 13
<212> TYPE: PRT
<213> ORGANISM: Artificial Sequence
<220> FEATURE:
<223> OTHER INFORMATION: Synthetic or recombinant sequence

<400> SEQUENCE: 156

Val Pro Ser Trp Lys Asn Arg Gln Gln Asn Ser Leu Glu
1               5                   10

<210> SEQ ID NO 157
<211> LENGTH: 9
<212> TYPE: PRT
<213> ORGANISM: Artificial Sequence
<220> FEATURE:
<223> OTHER INFORMATION: Synthetic or recombinant sequence

<400> SEQUENCE: 157

Cys Lys Thr Trp His Ser Ala Trp Val
1               5

<210> SEQ ID NO 158
<211> LENGTH: 81
<212> TYPE: PRT
<213> ORGANISM: Artificial Sequence
<220> FEATURE:
<223> OTHER INFORMATION: Synthetic or recombinant sequence

<400> SEQUENCE: 158

Val Ser Ala Cys Pro Ser Val Pro Gly His Ser Arg Pro Cys Trp Ala
1               5                   10                  15

Arg Pro Leu Ser Pro Leu Pro Ala Pro Ala Glu Val Pro Gly Pro Val
            20                  25                  30

Leu Pro Arg Gln Val Ala Gly Phe Val Trp Gly Gln Ser Gly Pro Ala
        35                  40                  45

Glu His Arg Gln His Leu Leu Leu Pro Gln Ser Gly Leu Ala Leu Pro
    50                  55                  60

Gly Val Cys Gly Ala Ala Ala Ala Pro Pro Gly Pro His Leu Pro Gly
65                  70                  75                  80

Gln

<210> SEQ ID NO 159
<211> LENGTH: 29
<212> TYPE: PRT

```
<213> ORGANISM: Artificial Sequence
<220> FEATURE:
<223> OTHER INFORMATION: Synthetic or recombinant sequence

<400> SEQUENCE: 159

Met Pro Ser Thr Ala Ser Pro Trp Ala Ala Ser Pro Leu Ser Cys Leu
1               5                   10                  15

Gln Thr Ser Phe Gln Arg Gln Gln Glu Thr Phe Met Leu
            20                  25

<210> SEQ ID NO 160
<211> LENGTH: 33
<212> TYPE: PRT
<213> ORGANISM: Artificial Sequence
<220> FEATURE:
<223> OTHER INFORMATION: Synthetic or recombinant sequence

<400> SEQUENCE: 160

Tyr Val Tyr Gln Ser Gln Tyr Cys Gly Phe Leu Gln Pro Glu Gln Asn
1               5                   10                  15

Cys His Pro Arg Glu Glu Gly Met Glu Phe Met Val Leu Ala Gln Lys
            20                  25                  30

Phe

<210> SEQ ID NO 161
<211> LENGTH: 9
<212> TYPE: PRT
<213> ORGANISM: Artificial Sequence
<220> FEATURE:
<223> OTHER INFORMATION: Synthetic or recombinant sequence

<400> SEQUENCE: 161

Cys Lys Thr Trp His Ser Ala Trp Val
1               5

<210> SEQ ID NO 162
<211> LENGTH: 14
<212> TYPE: PRT
<213> ORGANISM: Artificial Sequence
<220> FEATURE:
<223> OTHER INFORMATION: Synthetic or recombinant sequence

<400> SEQUENCE: 162

Arg Met Leu Gly Pro Arg Pro Pro Arg Ala Ala Arg Phe Arg
1               5                   10

<210> SEQ ID NO 163
<211> LENGTH: 52
<212> TYPE: PRT
<213> ORGANISM: Artificial Sequence
<220> FEATURE:
<223> OTHER INFORMATION: Synthetic or recombinant sequence

<400> SEQUENCE: 163

Lys Asn Ile Leu Val Arg Met Val Ser Glu Ala Gly Thr Gly Phe Cys
1               5                   10                  15

Phe Asn Thr Lys Arg Asn Arg Leu Arg Glu Lys Leu Thr Leu Leu His
            20                  25                  30

Tyr Asp Pro Val Val Lys Gln Arg Val Leu Phe Val Glu Lys Lys Lys
                35                  40                  45

Ile Arg Ser Leu
        50
```

```
<210> SEQ ID NO 164
<211> LENGTH: 6
<212> TYPE: PRT
<213> ORGANISM: Artificial Sequence
<220> FEATURE:
<223> OTHER INFORMATION: Synthetic or recombinant sequence

<400> SEQUENCE: 164

Ser Val Gly Ser Leu Ile
1               5

<210> SEQ ID NO 165
<211> LENGTH: 12
<212> TYPE: PRT
<213> ORGANISM: Artificial Sequence
<220> FEATURE:
<223> OTHER INFORMATION: Synthetic or recombinant sequence

<400> SEQUENCE: 165

Arg Gly Cys His Glu Glu Ser Trp Cys Gly Thr Gln
1               5                   10

<210> SEQ ID NO 166
<211> LENGTH: 18
<212> TYPE: PRT
<213> ORGANISM: Artificial Sequence
<220> FEATURE:
<223> OTHER INFORMATION: Synthetic or recombinant sequence

<400> SEQUENCE: 166

Glu Val Gly Val Gly Leu Pro Pro Gly Lys Trp Leu Ala Trp Pro Asn
1               5                   10                  15

Leu Thr

<210> SEQ ID NO 167
<211> LENGTH: 4
<212> TYPE: PRT
<213> ORGANISM: Artificial Sequence
<220> FEATURE:
<223> OTHER INFORMATION: Synthetic or recombinant sequence

<400> SEQUENCE: 167

Leu Phe Gln Leu
1

<210> SEQ ID NO 168
<211> LENGTH: 6
<212> TYPE: PRT
<213> ORGANISM: Artificial Sequence
<220> FEATURE:
<223> OTHER INFORMATION: Synthetic or recombinant sequence

<400> SEQUENCE: 168

Lys Leu Tyr Cys Ser Phe
1               5

<210> SEQ ID NO 169
<211> LENGTH: 5
<212> TYPE: PRT
<213> ORGANISM: Artificial Sequence
<220> FEATURE:
<223> OTHER INFORMATION: Synthetic or recombinant sequence

<400> SEQUENCE: 169

Leu Phe Leu Ile His
1               5
```

<210> SEQ ID NO 170
<211> LENGTH: 18
<212> TYPE: PRT
<213> ORGANISM: Artificial Sequence
<220> FEATURE:
<223> OTHER INFORMATION: Synthetic or recombinant sequence

<400> SEQUENCE: 170

Arg Cys Ala Ala Thr Ser Met Asp Asn Ser Met Thr Ser Lys Ser Cys
1               5                   10                  15

Ser Glu

<210> SEQ ID NO 171
<211> LENGTH: 5
<212> TYPE: PRT
<213> ORGANISM: Artificial Sequence
<220> FEATURE:
<223> OTHER INFORMATION: Synthetic or recombinant sequence

<400> SEQUENCE: 171

Arg Asn Ala Met Tyr
1               5

<210> SEQ ID NO 172
<211> LENGTH: 39
<212> TYPE: PRT
<213> ORGANISM: Artificial Sequence
<220> FEATURE:
<223> OTHER INFORMATION: Synthetic or recombinant sequence

<400> SEQUENCE: 172

Glu Asn Lys Ser Thr Asn Ser Arg Val Cys Glu Gly Lys Arg Cys Phe
1               5                   10                  15

His His Pro Asn Cys Phe Glu Gly Arg Glu His His His Gly Ala
            20                  25                  30

Pro Asp His Gly Val Cys Met
        35

<210> SEQ ID NO 173
<211> LENGTH: 27
<212> TYPE: PRT
<213> ORGANISM: Artificial Sequence
<220> FEATURE:
<223> OTHER INFORMATION: Synthetic or recombinant sequence

<400> SEQUENCE: 173

Ala Lys Phe Val Ser Tyr Cys Gly Ala Ser Asn Thr Arg Arg Ser Gly
1               5                   10                  15

Arg Cys Gln Phe Trp Ala Thr Ser Phe Arg Val
            20                  25

<210> SEQ ID NO 174
<211> LENGTH: 34
<212> TYPE: PRT
<213> ORGANISM: Artificial Sequence
<220> FEATURE:
<223> OTHER INFORMATION: Synthetic or recombinant sequence

<400> SEQUENCE: 174

Val Ser Gly Trp Ser Ser Asp Pro Cys Gly Ser Cys Arg Gln Val Cys
1               5                   10                  15

Ser Gly Asn Gln Arg Arg Trp Leu Trp Gly Pro Trp Ala Trp Ser Gln
            20                  25                  30

Leu Leu

<210> SEQ ID NO 175
<211> LENGTH: 11
<212> TYPE: PRT
<213> ORGANISM: Artificial Sequence
<220> FEATURE:
<223> OTHER INFORMATION: Synthetic or recombinant sequence

<400> SEQUENCE: 175

Arg Lys Leu Asn Ile Leu Met Leu Leu Gly His
1               5                   10

<210> SEQ ID NO 176
<211> LENGTH: 33
<212> TYPE: PRT
<213> ORGANISM: Artificial Sequence
<220> FEATURE:
<223> OTHER INFORMATION: Synthetic or recombinant sequence

<400> SEQUENCE: 176

Tyr Val Tyr Gln Ser Gln Tyr Cys Gly Phe Leu Gln Pro Glu Gln Asn
1               5                   10                  15

Cys His Pro Arg Glu Glu Gly Met Glu Phe Met Val Leu Ala Gln Lys
            20                  25                  30

Phe

<210> SEQ ID NO 177
<211> LENGTH: 7
<212> TYPE: PRT
<213> ORGANISM: Artificial Sequence
<220> FEATURE:
<223> OTHER INFORMATION: Synthetic or recombinant sequence

<400> SEQUENCE: 177

Gly Phe Val Phe Ala Pro Arg
1               5

<210> SEQ ID NO 178
<211> LENGTH: 35
<212> TYPE: PRT
<213> ORGANISM: Artificial Sequence
<220> FEATURE:
<223> OTHER INFORMATION: Synthetic or recombinant sequence

<400> SEQUENCE: 178

Tyr Ser Cys Glu Phe Gly Ser Ala Lys Tyr Tyr Ala Leu Cys Gly Phe
1               5                   10                  15

Gly Gly Val Leu Ser Cys Gly Leu Thr His Thr Ala Val Val Pro Leu
            20                  25                  30

Asp Leu Val
        35

<210> SEQ ID NO 179
<211> LENGTH: 7
<212> TYPE: PRT
<213> ORGANISM: Artificial Sequence
<220> FEATURE:
<223> OTHER INFORMATION: Synthetic or recombinant sequence

<400> SEQUENCE: 179

Phe Ile Asp Ala Val Trp Lys
1               5

-continued

<210> SEQ ID NO 180
<211> LENGTH: 18
<212> TYPE: PRT
<213> ORGANISM: Artificial Sequence
<220> FEATURE:
<223> OTHER INFORMATION: Synthetic or recombinant sequence

<400> SEQUENCE: 180

Arg Leu Ser Pro Ser Val Ser His Ser Ile Cys Arg Arg Gln Gln Phe
1               5                   10                  15

Gly Val

<210> SEQ ID NO 181
<211> LENGTH: 76
<212> TYPE: PRT
<213> ORGANISM: Artificial Sequence
<220> FEATURE:
<223> OTHER INFORMATION: Synthetic or recombinant sequence

<400> SEQUENCE: 181

Val Cys Glu Thr Gln Leu His Arg Leu Met Thr Lys Ser Pro Leu Ala
1               5                   10                  15

Phe Asp Thr Arg Pro Trp Asp Ser Gln Thr Leu Leu Trp Thr Pro Leu
                20                  25                  30

Gly Ser Gly Phe Cys Leu Thr Phe Pro Gly Gly Gly Leu Gly Gln Gly
            35                  40                  45

Gly His Glu Gly Leu Ser Leu Pro Lys Thr Gln Thr Pro Val Pro His
        50                  55                  60

Ser Val Leu Leu His Pro Pro His Leu His Cys
65                  70                  75

<210> SEQ ID NO 182
<211> LENGTH: 14
<212> TYPE: PRT
<213> ORGANISM: Artificial Sequence
<220> FEATURE:
<223> OTHER INFORMATION: Synthetic or recombinant sequence

<400> SEQUENCE: 182

Met Arg Glu Cys Ile Ser Val His Val Gly Gln Ala Gly Val
1               5                   10

<210> SEQ ID NO 183
<211> LENGTH: 26
<212> TYPE: PRT
<213> ORGANISM: Artificial Sequence
<220> FEATURE:
<223> OTHER INFORMATION: Synthetic or recombinant sequence

<400> SEQUENCE: 183

Glu Asp Glu Val Asp Met Leu Ser Asp Gly Cys Gly Ser Glu Glu Arg
1               5                   10                  15

Arg Ser Gln Ser Leu Pro Ala Met Ala Ala
                20                  25

<210> SEQ ID NO 184
<211> LENGTH: 32
<212> TYPE: PRT
<213> ORGANISM: Artificial Sequence
<220> FEATURE:
<223> OTHER INFORMATION: Synthetic or recombinant sequence

<400> SEQUENCE: 184

Asp Lys Asn Ile Arg Glu Leu Ser Leu Val Ser Met Lys Ser Leu Asn

```
                1               5                  10                  15
            Pro Val Thr Leu Cys Arg Glu Pro Pro Ala Thr Val Phe Gln Ala His
                            20                  25                  30

<210> SEQ ID NO 185
<211> LENGTH: 92
<212> TYPE: PRT
<213> ORGANISM: Artificial Sequence
<220> FEATURE:
<223> OTHER INFORMATION: Synthetic or recombinant sequence

<400> SEQUENCE: 185

Gly Phe Arg Asp Asp Phe Leu Gly Gly Arg Gly Gly Ser Arg Pro Gly
1               5                   10                  15

Asp Arg Arg Thr Gly Pro Pro Met Gly Ser Arg Phe Arg Asp Gly Pro
            20                  25                  30

Pro Leu Arg Gly Ser Asn Met Asp Phe Arg Glu Pro Thr Glu Glu Glu
        35                  40                  45

Arg Ala Gln Arg Pro Arg Leu Gln Leu Lys Pro Arg Thr Val Ala Thr
    50                  55                  60

Pro Leu Asn Gln Val Ala Asn Pro Asn Ser Ala Ile Phe Gly Gly Ala
65                  70                  75                  80

Arg Pro Arg Glu Glu Val Val Gln Lys Glu Gln Glu
                85                  90

<210> SEQ ID NO 186
<211> LENGTH: 14
<212> TYPE: PRT
<213> ORGANISM: Artificial Sequence
<220> FEATURE:
<223> OTHER INFORMATION: Synthetic or recombinant sequence

<400> SEQUENCE: 186

Ile Phe Phe His Leu Cys Val Met Ile Val Gln Glu Tyr Phe
1               5                   10

<210> SEQ ID NO 187
<211> LENGTH: 6
<212> TYPE: PRT
<213> ORGANISM: Artificial Sequence
<220> FEATURE:
<223> OTHER INFORMATION: Synthetic or recombinant sequence

<400> SEQUENCE: 187

Cys Pro Ala Glu Ile Lys
1               5

<210> SEQ ID NO 188
<211> LENGTH: 15
<212> TYPE: PRT
<213> ORGANISM: Artificial Sequence
<220> FEATURE:
<223> OTHER INFORMATION: Synthetic or recombinant sequence

<400> SEQUENCE: 188

Gln Phe Trp Cys Leu Trp Phe Cys Tyr Asp Lys Cys Phe Trp Asn
1               5                   10                  15

<210> SEQ ID NO 189
<211> LENGTH: 132
<212> TYPE: PRT
<213> ORGANISM: Artificial Sequence
<220> FEATURE:
<223> OTHER INFORMATION: Synthetic or recombinant sequence
```

<400> SEQUENCE: 189

Arg Tyr Thr Gln Ser Asn Gly Arg Arg Pro Phe Gly Ile Ser Ala Leu
1               5                   10                  15

Ile Val Gly Phe Asp Phe Asp Gly Thr Pro Arg Leu Tyr Gln Thr Asp
            20                  25                  30

Pro Ser Gly Thr Tyr His Ala Trp Lys Ala Asn Ala Ile Gly Arg Gly
        35                  40                  45

Ala Lys Ser Val Arg Glu Phe Leu Glu Lys Asn Tyr Thr Asp Glu Ala
50                  55                  60

Ile Glu Thr Asp Asp Leu Thr Ile Lys Leu Val Ile Lys Ala Leu Leu
65                  70                  75                  80

Glu Val Val Gln Ser Gly Gly Lys Asn Ile Glu Leu Ala Val Met Arg
                85                  90                  95

Arg Asp Gln Ser Leu Lys Ile Leu Asn Pro Glu Glu Ile Glu Lys Tyr
            100                 105                 110

Val Ala Glu Ile Glu Lys Glu Lys Glu Glu Asn Glu Lys Lys Lys Gln
        115                 120                 125

Lys Lys Ala Ser
    130

<210> SEQ ID NO 190
<211> LENGTH: 52
<212> TYPE: PRT
<213> ORGANISM: Artificial Sequence
<220> FEATURE:
<223> OTHER INFORMATION: Synthetic or recombinant sequence

<400> SEQUENCE: 190

Lys Tyr Gly Pro Ser His Thr Pro Ser Arg Ser Ser Arg Arg Ser Cys
1               5                   10                  15

Ala Cys Gln Ser Ser Pro Cys Ser Leu Ala Pro Gln Trp Phe Leu Ser
            20                  25                  30

Phe Ala Arg Met Glu Met Thr Asp Ser Asn Gly Pro Lys Leu Val Pro
        35                  40                  45

Thr Ser Ser Thr
    50

<210> SEQ ID NO 191
<211> LENGTH: 6
<212> TYPE: PRT
<213> ORGANISM: Artificial Sequence
<220> FEATURE:
<223> OTHER INFORMATION: Synthetic or recombinant sequence

<400> SEQUENCE: 191

Arg Pro Gly Pro Gly Pro
1               5

<210> SEQ ID NO 192
<211> LENGTH: 17
<212> TYPE: PRT
<213> ORGANISM: Artificial Sequence
<220> FEATURE:
<223> OTHER INFORMATION: Synthetic or recombinant sequence

<400> SEQUENCE: 192

Val Ser Glu Leu Ala Cys Ile Tyr Ser Ala Ser Phe Cys Thr Thr Met
1               5                   10                  15

Arg

<210> SEQ ID NO 193
<211> LENGTH: 34
<212> TYPE: PRT
<213> ORGANISM: Artificial Sequence
<220> FEATURE:
<223> OTHER INFORMATION: Synthetic or recombinant sequence

<400> SEQUENCE: 193

Val Gln Ala Asn Thr His Ser Gln Cys His Gln Thr Ala Met Phe Leu
1               5                   10                  15

His Ala Leu Arg Thr Gly Leu Ala Thr Arg Gly Asn Ala Thr Leu Phe
            20                  25                  30

Leu Leu

<210> SEQ ID NO 194
<211> LENGTH: 32
<212> TYPE: PRT
<213> ORGANISM: Artificial Sequence
<220> FEATURE:
<223> OTHER INFORMATION: Synthetic or recombinant sequence

<400> SEQUENCE: 194

Ser Pro Arg Ser Trp Ala Gly Pro Val Leu Arg Asp Ser Ala Arg Arg
1               5                   10                  15

Cys Ala Trp Asn Ser Trp Thr Thr Arg Ala Asp Pro Ser Ser Ala Met
            20                  25                  30

<210> SEQ ID NO 195
<211> LENGTH: 11
<212> TYPE: PRT
<213> ORGANISM: Artificial Sequence
<220> FEATURE:
<223> OTHER INFORMATION: Synthetic or recombinant sequence

<400> SEQUENCE: 195

Ala Thr Ser Thr Leu Gly Ala Ser Ser Ala Met
1               5                   10

<210> SEQ ID NO 196
<211> LENGTH: 13
<212> TYPE: PRT
<213> ORGANISM: Artificial Sequence
<220> FEATURE:
<223> OTHER INFORMATION: Synthetic or recombinant sequence

<400> SEQUENCE: 196

Val Leu Ala Ser Leu Pro Val Tyr Leu Leu Val Gly Leu
1               5                   10

<210> SEQ ID NO 197
<211> LENGTH: 13
<212> TYPE: PRT
<213> ORGANISM: Artificial Sequence
<220> FEATURE:
<223> OTHER INFORMATION: Synthetic or recombinant sequence

<400> SEQUENCE: 197

Val Leu Ala Leu Val Val Ser Val Gln Thr Gly Thr Val
1               5                   10

<210> SEQ ID NO 198
<211> LENGTH: 15
<212> TYPE: PRT
<213> ORGANISM: Artificial Sequence

```
<220> FEATURE:
<223> OTHER INFORMATION: Synthetic or recombinant sequence

<400> SEQUENCE: 198

Val Ser Asp Gly Val Ile Lys Gly Val Gln Arg His Glu Gly Ala
1               5                   10                  15

<210> SEQ ID NO 199
<211> LENGTH: 25
<212> TYPE: PRT
<213> ORGANISM: Artificial Sequence
<220> FEATURE:
<223> OTHER INFORMATION: Synthetic or recombinant sequence

<400> SEQUENCE: 199

Val His Gln Gly Pro Cys Trp Pro Pro Trp Ser Pro Trp Pro Ser Trp
1               5                   10                  15

Thr Ser Arg Cys Lys Arg Trp Trp Leu
            20                  25

<210> SEQ ID NO 200
<211> LENGTH: 22
<212> TYPE: PRT
<213> ORGANISM: Artificial Sequence
<220> FEATURE:
<223> OTHER INFORMATION: Synthetic or recombinant sequence

<400> SEQUENCE: 200

Trp Ala Ala Ser Pro Leu Ser Cys Leu Gln Thr Arg Ser Gln Arg Gln
1               5                   10                  15

Gln Lys Ile Phe Val Leu
            20

<210> SEQ ID NO 201
<211> LENGTH: 13
<212> TYPE: PRT
<213> ORGANISM: Artificial Sequence
<220> FEATURE:
<223> OTHER INFORMATION: Synthetic or recombinant sequence

<400> SEQUENCE: 201

Leu Gly Ala Ser Ser Leu Val Met Pro Gly Thr Leu Leu
1               5                   10

<210> SEQ ID NO 202
<211> LENGTH: 9
<212> TYPE: PRT
<213> ORGANISM: Artificial Sequence
<220> FEATURE:
<223> OTHER INFORMATION: Synthetic or recombinant sequence

<400> SEQUENCE: 202

Trp Thr Phe Leu Val Ile Pro Thr Trp
1               5

<210> SEQ ID NO 203
<211> LENGTH: 11
<212> TYPE: PRT
<213> ORGANISM: Artificial Sequence
<220> FEATURE:
<223> OTHER INFORMATION: Synthetic or recombinant sequence

<400> SEQUENCE: 203

Cys Gly Leu Gln Val Val Asp Pro Ile Phe His
1               5                   10
```

<210> SEQ ID NO 204
<211> LENGTH: 14
<212> TYPE: PRT
<213> ORGANISM: Artificial Sequence
<220> FEATURE:
<223> OTHER INFORMATION: Synthetic or recombinant sequence

<400> SEQUENCE: 204

Leu Gln Val Asp Val Gly Ile Tyr Leu Cys Trp Cys Leu Val
1               5                   10

<210> SEQ ID NO 205
<211> LENGTH: 16
<212> TYPE: PRT
<213> ORGANISM: Artificial Sequence
<220> FEATURE:
<223> OTHER INFORMATION: Synthetic or recombinant sequence

<400> SEQUENCE: 205

Val Leu Val Ser Ser Pro Ser Pro Thr Gln Ser Met Leu Gln Leu Pro
1               5                   10                  15

<210> SEQ ID NO 206
<211> LENGTH: 11
<212> TYPE: PRT
<213> ORGANISM: Artificial Sequence
<220> FEATURE:
<223> OTHER INFORMATION: Synthetic or recombinant sequence

<400> SEQUENCE: 206

Met Leu Arg Leu Met Met Asp Met Met Met Met
1               5                   10

<210> SEQ ID NO 207
<211> LENGTH: 14
<212> TYPE: PRT
<213> ORGANISM: Artificial Sequence
<220> FEATURE:
<223> OTHER INFORMATION: Synthetic or recombinant sequence

<400> SEQUENCE: 207

Leu Gln Val Asp Val Gly Ile Tyr Leu Cys Trp Cys Leu Val
1               5                   10

<210> SEQ ID NO 208
<211> LENGTH: 15
<212> TYPE: PRT
<213> ORGANISM: Artificial Sequence
<220> FEATURE:
<223> OTHER INFORMATION: Synthetic or recombinant sequence

<400> SEQUENCE: 208

Leu Val Ser Ser Pro Ser Pro Thr Gln Ser Met Leu Gln Leu Pro
1               5                   10                  15

<210> SEQ ID NO 209
<211> LENGTH: 11
<212> TYPE: PRT
<213> ORGANISM: Artificial Sequence
<220> FEATURE:
<223> OTHER INFORMATION: Synthetic or recombinant sequence

<400> SEQUENCE: 209

Leu Glu Val Val Ala Arg Phe His Arg Lys Lys
1               5                   10

```
<210> SEQ ID NO 210
<211> LENGTH: 11
<212> TYPE: PRT
<213> ORGANISM: Artificial Sequence
<220> FEATURE:
<223> OTHER INFORMATION: Synthetic or recombinant sequence

<400> SEQUENCE: 210

Trp Leu Met Ser Ser Arg Ser Glu Trp Val Asn
1               5                   10

<210> SEQ ID NO 211
<211> LENGTH: 24
<212> TYPE: PRT
<213> ORGANISM: Artificial Sequence
<220> FEATURE:
<223> OTHER INFORMATION: Synthetic or recombinant sequence

<400> SEQUENCE: 211

Val Ile Gln Arg Pro Ala Ala Thr Leu Arg Thr Thr Trp Ala Leu Ser
1               5                   10                  15

His Trp Leu Met Thr Val Lys Cys
            20

<210> SEQ ID NO 212
<211> LENGTH: 14
<212> TYPE: PRT
<213> ORGANISM: Artificial Sequence
<220> FEATURE:
<223> OTHER INFORMATION: Synthetic or recombinant sequence

<400> SEQUENCE: 212

Val Asp Glu Asn Trp Glu Gly Ser Leu Lys Ser Lys Leu Cys
1               5                   10

<210> SEQ ID NO 213
<211> LENGTH: 13
<212> TYPE: PRT
<213> ORGANISM: Artificial Sequence
<220> FEATURE:
<223> OTHER INFORMATION: Synthetic or recombinant sequence

<400> SEQUENCE: 213

Cys Glu Tyr Ser Thr Pro Thr Ser Met Gly Gly Gly Lys
1               5                   10

<210> SEQ ID NO 214
<211> LENGTH: 9
<212> TYPE: PRT
<213> ORGANISM: Artificial Sequence
<220> FEATURE:
<223> OTHER INFORMATION: Synthetic or recombinant sequence

<400> SEQUENCE: 214

Ser Leu Gln Ser Trp Tyr Leu Arg Leu
1               5

<210> SEQ ID NO 215
<211> LENGTH: 9
<212> TYPE: PRT
<213> ORGANISM: Artificial Sequence
<220> FEATURE:
<223> OTHER INFORMATION: Synthetic or recombinant sequence

<400> SEQUENCE: 215

Lys Ser Leu Gln Ser Trp Tyr Leu Arg
1               5
```

<210> SEQ ID NO 216
<211> LENGTH: 9
<212> TYPE: PRT
<213> ORGANISM: Artificial Sequence
<220> FEATURE:
<223> OTHER INFORMATION: Synthetic or recombinant sequence

<400> SEQUENCE: 216

Phe Leu Ser Pro Met Ser Gly Leu Leu
1               5

<210> SEQ ID NO 217
<211> LENGTH: 9
<212> TYPE: PRT
<213> ORGANISM: Artificial Sequence
<220> FEATURE:
<223> OTHER INFORMATION: Synthetic or recombinant sequence

<400> SEQUENCE: 217

Gln Ser Ala Cys Thr Gly Ile His Arg
1               5

<210> SEQ ID NO 218
<211> LENGTH: 9
<212> TYPE: PRT
<213> ORGANISM: Artificial Sequence
<220> FEATURE:
<223> OTHER INFORMATION: Synthetic or recombinant sequence

<400> SEQUENCE: 218

Gly Val Val Arg Pro Ile Leu Asp Val
1               5

<210> SEQ ID NO 219
<211> LENGTH: 9
<212> TYPE: PRT
<213> ORGANISM: Artificial Sequence
<220> FEATURE:
<223> OTHER INFORMATION: Synthetic or recombinant sequence

<400> SEQUENCE: 219

Val Val Arg Pro Ile Leu Asp Val Gly
1               5

<210> SEQ ID NO 220
<211> LENGTH: 9
<212> TYPE: PRT
<213> ORGANISM: Artificial Sequence
<220> FEATURE:
<223> OTHER INFORMATION: Synthetic or recombinant sequence

<400> SEQUENCE: 220

Gly Pro Gly Val Val Arg Pro Ile Leu
1               5

<210> SEQ ID NO 221
<211> LENGTH: 9
<212> TYPE: PRT
<213> ORGANISM: Artificial Sequence
<220> FEATURE:
<223> OTHER INFORMATION: Synthetic or recombinant sequence

<400> SEQUENCE: 221

Val Arg Pro Ile Leu Asp Val Gly Lys
1               5

<210> SEQ ID NO 222
<211> LENGTH: 9
<212> TYPE: PRT
<213> ORGANISM: Artificial Sequence
<220> FEATURE:
<223> OTHER INFORMATION: Synthetic or recombinant sequence

<400> SEQUENCE: 222

Arg Pro Ile Leu Asp Val Gly Lys Ile
1               5

<210> SEQ ID NO 223
<211> LENGTH: 9
<212> TYPE: PRT
<213> ORGANISM: Artificial Sequence
<220> FEATURE:
<223> OTHER INFORMATION: Synthetic or recombinant sequence

<400> SEQUENCE: 223

Lys Leu Ala Ala Glu Gly Leu Ala Pro
1               5

<210> SEQ ID NO 224
<211> LENGTH: 9
<212> TYPE: PRT
<213> ORGANISM: Artificial Sequence
<220> FEATURE:
<223> OTHER INFORMATION: Synthetic or recombinant sequence

<400> SEQUENCE: 224

Gly Thr Lys Leu Ala Ala Glu Gly Leu
1               5

<210> SEQ ID NO 225
<211> LENGTH: 14
<212> TYPE: PRT
<213> ORGANISM: Artificial Sequence
<220> FEATURE:
<223> OTHER INFORMATION: Synthetic or recombinant sequence

<400> SEQUENCE: 225

Val Ile Lys Ser Leu Gln Ser Trp Tyr Leu Arg Leu Val Ile
1               5                   10

<210> SEQ ID NO 226
<211> LENGTH: 24
<212> TYPE: PRT
<213> ORGANISM: Artificial Sequence
<220> FEATURE:
<223> OTHER INFORMATION: Synthetic or recombinant sequence

<400> SEQUENCE: 226

Phe Leu Ser Pro Met Ser Gly Leu Leu Ser Thr Thr Gln Gln Ser Ala
1               5                   10                  15

Cys Thr Gly Ile His Arg Thr Ser
            20

<210> SEQ ID NO 227
<211> LENGTH: 24
<212> TYPE: PRT
<213> ORGANISM: Artificial Sequence
<220> FEATURE:
<223> OTHER INFORMATION: Synthetic or recombinant sequence

<400> SEQUENCE: 227

Pro Ser Pro Gln Glu Thr Glu Phe Pro Gly Pro Gly Val Val Arg Pro

Ile Leu Asp Val Gly Lys Ile Ser
            20

<210> SEQ ID NO 228
<211> LENGTH: 12
<212> TYPE: PRT
<213> ORGANISM: Artificial Sequence
<220> FEATURE:
<223> OTHER INFORMATION: Synthetic or recombinant sequence

<400> SEQUENCE: 228

Gly Gln Asp Cys Tyr Arg Val Pro Val Thr Glu Asp
1               5                   10

<210> SEQ ID NO 229
<211> LENGTH: 15
<212> TYPE: PRT
<213> ORGANISM: Artificial Sequence
<220> FEATURE:
<223> OTHER INFORMATION: Synthetic or recombinant sequence

<400> SEQUENCE: 229

Ala Gly Leu Gly Thr Lys Leu Ala Ala Glu Gly Leu Ala Pro Asn
1               5                   10                  15

<210> SEQ ID NO 230
<211> LENGTH: 9
<212> TYPE: PRT
<213> ORGANISM: Artificial Sequence
<220> FEATURE:
<223> OTHER INFORMATION: Synthetic or recombinant sequence

<400> SEQUENCE: 230

Cys Leu Trp Phe Cys Tyr Asp Lys Cys
1               5

<210> SEQ ID NO 231
<211> LENGTH: 2040
<212> TYPE: DNA
<213> ORGANISM: Artificial Sequence
<220> FEATURE:
<223> OTHER INFORMATION: Synthetic or recombinant sequence

<400> SEQUENCE: 231

| | |
|---|---|
| atgaagattt tgtgggcaa tgtcgatggg gcggatacga caccggagga gttggcagct | 60 |
| ctcttcgcgc cctatggcac ggtcatgagc tgcgccgtca tgaaacagtt tgccttcgtg | 120 |
| cacatgcgcg agaacgctgg cgcggtgcgc gccatcgagg ccctgcatgg ccacgagctg | 180 |
| cgtccaggtc gcgcgctcgt ggtggagatg tcgcgcccga ggcccctgaa cacttggaag | 240 |
| attttcgtgg gcaatgtatc ggctgcatgt acaagtcagg aattgcgcag cctcttcgag | 300 |
| cgccgtggac gcgtcatcga gtgtgacgtg gtaaaaggct cttgtcagga tggtgaagct | 360 |
| gttcattgga atctgcccc gggaggccac agagcaggag atccgctcac tcttcgagca | 420 |
| gtacgggaag gtgctggaat gtgacatcat taagaattat ggctttgtgc acatagagga | 480 |
| caagacggcc gctgaggatg ccatacgcaa cctgcaccac tacaagctgc acggagtgaa | 540 |
| catcaatgtg gaagccagca agaataagag caaagcttca accaagttac acgtgggcaa | 600 |
| catcagcccc acttgtacca accaagagct tcgggccaag tttgaggagt acggcccagt | 660 |
| catcgaatgt gacatcgtga agattatgc ctttgtacac atggagcggg cagaggatgc | 720 |
| ggtggaggcc atcaggggcc tcgacaacac agagtttcaa ggcaaacgaa tgcatgtaca | 780 |

```
gttgtcaact agccggcttc ggactgcccc tgggatggga gaccagagtg gttgctatcg      840
gtgtggtaaa gaaggacatt ggtccaaaga gtgcccagta gaccgtacag ggcgtgtggc      900
agactttact gagcagtaca atgaacaata tggagcagtg cgcacacctt atactatggg      960
ttatggggag tccatgtatt acaacgatgc ctatggagca cttgactact ataagcgcta     1020
ccgcgtccga tcttacgaag ctgtggcggc ggcggctgca gcttccgcat acaattacgc     1080
agagcagacc atgtctcatc ttcctcaagt tcagagctca gctgtaccca gtcacctcaa     1140
ctccacttct gttgatcctt atgacagaca cctattgcag aactctggct ctgctgccac     1200
ctcagctgca atggctgctg ccgcttcctc ttcctattat ggaagggaca ggagcccact     1260
acgtcggaat gcggctgtgc ttcccgcagt ggagagggc tatggttatg gccagagag      1320 cgagatgtct caggcttcag cagcaactcg gaattctctg tatgacatgg cccggtatga     1380
gcgggagcag tatgtggacc gaacacggta ctcagccttt taaaaactgg aggtaggata     1440
attgcggact gaaccctcgg gctgcggtca tatatgagaa cttggtcctc gcggtcccct     1500
ttgccaggat gtttccattg cttcatgttt cagtaaacaa aggaatttgt gaccaactat     1560
gttttctttc ttaatttaat tcttctaagt tgacttttct ttcctcgatg ctagttgtct     1620
gtagcttttc actgttcctt ataccctcag cctctgaaca gccctaggta agggttatgc     1680
tgacatccct tttcctgtac agtagaagcc cctcttaatc ttgcttttct taggagttga     1740
gcccttctcc ctgccttcct gcagcatctc ctttcccttt aaaatgacca tgtagtggca     1800
agcaaccttt aactcttctg tcagtgctgg actcttagca ttgaagctgg tcttctgaag     1860
tcgctaggac cattgggttt tgttgttgtc ttggtttgat tttgttttgg ttttcggttt     1920
tgtctgacct gtgatcgtgg tacagcattt gctgaaattt agccttgttt tattccactc     1980
ctcccaattt ttttttgaaa aaaaaaaat  aaatgtttct aatacttaaa aaaaaaaaaa     2040
```

<210> SEQ ID NO 232
<211> LENGTH: 45
<212> TYPE: PRT
<213> ORGANISM: Artificial Sequence
<220> FEATURE:
<223> OTHER INFORMATION: Synthetic or recombinant sequence

<400> SEQUENCE: 232

Gly Arg Val Ile Glu Cys Asp Val Val Lys Gly Ser Cys Gln Asp Gly
1               5                   10                  15

Glu Ala Val His Trp Lys Ser Ala Pro Gly Gly His Arg Ala Gly Asp
            20                  25                  30

Pro Leu Thr Leu Arg Ala Val Arg Glu Gly Ala Gly Met
        35                  40                  45

<210> SEQ ID NO 233
<211> LENGTH: 1429
<212> TYPE: DNA
<213> ORGANISM: Artificial Sequence
<220> FEATURE:
<223> OTHER INFORMATION: Synthetic or recombinant sequence

<400> SEQUENCE: 233

```
atgaagatat tcgtgggcaa cgtcgacggg gcggatacga ctccggagga gctggcagcc       60
ctctttgcgc cctacggcac ggtcatgagc tgccgtcca tgaaacagtt cgccttcgtg       120
cacatgcgcg agaacgcggg cgcgctcgcg gccatcgaag ccctgcacgg ccacgagctg      180
cggccggggc gcgcgctcgt ggtggagatg tcgcgcccaa ggcctcttaa tacttggaag      240
```

```
attttcgtgg gcaatgtgtc ggctgcatgc acgagccagg aactgcgcag cctcttcgag    300
cgccgcggac gcgtcatcga gtgtgacgtg gtgaaaggct cttgtcagga tggtgaagct    360
gttcatcgga aaccttcccc gggaggctac agagcaggag attcgctcac tcttcgagca    420
gtatgggaag gtgctggaat gtgacatcat taagaattac ggctttgtgc acatagaaga    480
caagacggca gctgaggatg ccatacgcaa cctgcaccat tacaagcttc atggggtgaa    540
catcaacgtg gaagccagca agaataagag caaagcttca accaagttac acgtgggtaa    600
catcagcccc acttgtacca accaagagct tcgagccaag tttgaggagt atggtccggt    660
catcgaatgt gacatcgtga aagattatgc cttcgtacac atggagcggg cagaggatgc    720
agtggaggcc atcaggggcc ttgacaacac agagtttcaa ggcaaaagaa tgcatgtgca    780
gttgtccaca agccggcttc ggactgcccc tggtatggga ccagagtg gctgctatcg    840 gtgtgggaaa gaagggcact ggtccaaaga gtgcccagta gatcgtacgg tcgtgtggc    900 agactttact gagcagtata tgaacaata tggagcagtt cgaacacctt acaccatggg    960
ctacggggaa tccatgtatt acaacgatgc atatggagca ctcgactact ataagcgata   1020
ccgggtccgc tcttatgagg cagtagcagc ggcggcagcg gcttctgcat acaactacgc   1080
agagcagacc atgtcccatc tgcctcaagt ccaaagcaca actgtgacca gccacctcaa   1140
ctctacttct gttgatccct atgacagaca cctattgcca aactctggcg ctgctgccac   1200
ttcagctgct atggctgctg ctgcagccac cacttcctcc tactatggaa gggacaggag   1260
cccactgcgt cgtgctgcag ccatgctccc cacagttgga gagggctacg gttatgggcc   1320
agagagtgaa ttatctcagg cttccgcagc tacacggaat tctctgtatg acatggcccg   1380
gtatgaacgg gagcagtatg tggaccgagc ccggtactca gccttttaa              1429
```

<210> SEQ ID NO 234
<211> LENGTH: 45
<212> TYPE: PRT
<213> ORGANISM: Artificial Sequence
<220> FEATURE:
<223> OTHER INFORMATION: Synthetic or recombinant sequence

<400> SEQUENCE: 234

```
Gly Arg Val Ile Glu Cys Asp Val Val Lys Gly Ser Cys Gln Asp Gly
1               5                   10                  15

Glu Ala Val His Arg Lys Pro Ser Pro Gly Gly Tyr Arg Ala Gly Asp
            20                  25                  30

Ser Leu Thr Leu Arg Ala Val Trp Glu Gly Ala Gly Met
        35                  40                  45
```

<210> SEQ ID NO 235
<211> LENGTH: 1429
<212> TYPE: DNA
<213> ORGANISM: Artificial Sequence
<220> FEATURE:
<223> OTHER INFORMATION: Synthetic or recombinant sequence

<400> SEQUENCE: 235

```
atgaagatat tcgtgggaaa cgtcgatggg gcggatacaa cgccagagga gctagcggcc     60
ctcttcgcgc cctacggcac ggtcatgagc tgcgccgtca tgaaacagtt cgccttcgtg    120
cacatgcgcg agaacgcagg cgcgctcgcg gccatcgagg ccctgcacgg ccacgagctg    180
cggccggggc gcgcactcgt ggtggagatg tcgcgcccac ggcctcttaa cacttggaag    240
attttcgtgg gcaatgtgtc ggctgcgtgc acgagccagg aattgcgcag cctgttcgag    300
```

```
cgccgcggac gcgtcatcga gtgtgacgtg gtgaaaggcg cttatcagga tggtgaagct    360
gttcatcgga aacctgcccc gggaggccac agagcaggag atccgctcac tcttcgagca    420
gtatgggaag gtgctggagt gtgacatcat taagaactat ggctttgtgc acatagagga    480
caagacggcc gcggaggatg ccatacgcaa cctgcaccac tacaagctgc acggggtgaa    540
catcaacgtg gaagccagca agaataagag caaagcctca accaagttac acgtgggcaa    600
catcagtccc acctgtacaa accaagagct tcgggccaag tttgaggagt atggtccagt    660
catcgaatgt gacatcgtga agattatgc cttcgtacac atggagcggg cagaggatgc    720
agtggaagcc atcaggggcc ttgacaacac agagtttcaa ggcaaaagga tgcacgtgca    780
gttatccaca agccgacttc ggactgcccc tgggatggga gaccagagtg gctgctatcg    840
gtgtgggaaa gaggggcact ggtcaaaaga gtgtccagta gatcgtacag gtcgtgtggc    900
ggactttacc gagcagtata cgaacagta tggagcagtg cgcacgcctt acaccatggg    960
ctacggggaa tccatgtatt acaacgatgc gtatggagca ctcgactact ataagcgtta   1020
ccgggtccgc tcttatgagg cagtggcagc ggcagcagca gcttctgcgt acaactacgc   1080
ggagcagtcc atgtcccatc tgcctcaagt ccagagcaca gctgtgacca gtcacctcaa   1140
ctccacttct gttgatccct acgacagaca cctgttgccg aactcaggtg ctgctgccac   1200
ttcggctgct atggctgctg ccgctgccaa cacttcctcc tattatggaa gggacaggag   1260
cccctgcgt cgtgctgcag ctgtgctccc cacagttgga gagggctacg gttatgggcc   1320
agagagtgag ctgtctcagg cttcagcagc tgcacggaat tctctatatg acatggcccg   1380
gtatgagcgg gagcagtatg tggaccgagc gcggtactca gccttttaa               1429
```

<210> SEQ ID NO 236
<211> LENGTH: 45
<212> TYPE: PRT
<213> ORGANISM: Artificial Sequence
<220> FEATURE:
<223> OTHER INFORMATION: Synthetic or recombinant sequence

<400> SEQUENCE: 236

```
Gly Arg Val Ile Glu Cys Asp Val Val Lys Gly Ala Tyr Gln Asp Gly
1               5                   10                  15

Glu Ala Val His Arg Lys Pro Ala Pro Gly Gly His Arg Ala Gly Asp
            20                  25                  30

Pro Leu Thr Leu Arg Ala Val Trp Glu Gly Ala Gly Val
        35                  40                  45
```

<210> SEQ ID NO 237
<211> LENGTH: 1136
<212> TYPE: DNA
<213> ORGANISM: Artificial Sequence
<220> FEATURE:
<223> OTHER INFORMATION: Synthetic or recombinant sequence

<400> SEQUENCE: 237

```
atgccgacca attgcgccgc ggcgggctgt gctgctacct acaacaagca cattaacatc     60
agcttccaca ggtttccttt ggatcctaaa agaagaaaag aatgggttcg cctggttagg    120
cgcaaaaatt ttgtgccagg aaaacacact tttctttgct caaagcactt tgaagcctcc    180
tgttttgatc taacaggaca aacccgacga cttaaaatgg atgctgttcc aaccatttt     240
gatttttgta cccatgtaac tttcggcctg tttctccgtg gcgctggctg ttctccgtcg    300
tcgttcctgt tgtgatcgcc tgtaatggct ttaaaaagaa aagtctagat cacagtgggg    360
```

```
ctttaggagg gttggtggtc ggattcatct taaccatcgc aaatttcagc ttttttactt      420
ctttgatgac gtttttcctt tcatcttcaa aactcacaaa atggagagga aacataaaga      480
agcaactgga ctcagagtat aaggaaggag gacagaggaa ttgggtccag gtgttctgta      540
atggcgccgt gcccacagag ctggccctgc tctacatgat agagaacggc cccggggaaa      600
tgcccataga ttttccaag caacacactg cttcctggat gtgtttgtct ctcttggctg       660
cgctggccag ctcggctgga gacacctggg cttctgaagt tgctccagtt ctgagcaaaa      720
gctcacctcg gctaataaca acctgggaga agttccagt ggaaccaac ggaggagtca        780 cagcagtggg acttgcctcc agtctcctcg gcggtacctt tgtgggcctg gcctacttcc      840
ttacacagtt ggtgtttgtg aacgacttag acatctctgc tccgcagtgg cccattattg      900
catttggtgg tgtggctggg ttatttggat cactcgtgga ctcgttctta ggggcgacga      960
tgcagttctc tggtctggat gaacgcacag gcctggtggt gagtagcccg acgcaggaga     1020
cgaagcacat agcggggaaa ccgatcctgg ataacaacgc cgtgaatctc ttctcctccg     1080
tcttggtggc cctcctgctc cccacagccg cgtcggggtt ttggcccga gagtga         1136

<210> SEQ ID NO 238
<211> LENGTH: 29
<212> TYPE: PRT
<213> ORGANISM: Artificial Sequence
<220> FEATURE:
<223> OTHER INFORMATION: Synthetic or recombinant sequence

<400> SEQUENCE: 238

Phe Asp Phe Cys Thr His Ile Lys Ser Leu Val Thr Phe Gly Leu Phe
1               5                   10                  15

Leu Arg Gly Ala Gly Cys Ser Pro Ser Ser Phe Leu Leu
            20                  25

<210> SEQ ID NO 239
<211> LENGTH: 1148
<212> TYPE: DNA
<213> ORGANISM: Artificial Sequence
<220> FEATURE:
<223> OTHER INFORMATION: Synthetic or recombinant sequence

<400> SEQUENCE: 239
atgccgacca attgcgctgc ggcgggctgt gccactacct acaacaagca cattaacatc       60
agcttccaca ggtttccttt ggatcctaaa agaagaaaag aatgggttcg cctggttagg      120
cgcaaaaatt ttgtgccagg aaaacacact tttctttgtt caaagcactt tgaagcctcc      180
tgttttgacc taacaggaca aactcgacga cttaaaatgg atgctgttcc aaccattttt      240 gattttgta cccatataaa gtctatggta acttacgacc tatttctccg tggcgttggc       300
tgttttctgt tgttgttcct gttctgatcg tctctaatgg ccttaaaaag aaaagtctag      360
atcacagtgg ggctctagga gggctagtcg ttggatttat cctaaccatt gcaaatttca     420
gcttttttac ctctttgctg atgttttttct tgtcttcttc gaaactcact aaatggaagg     480
gagaagtgaa gaagcgtcta gattcagaat ataaggaagg tgggcaaagg aattgggttc      540
aggtgttctg taatggagct gtacccacag aactggccct gctgtacatg atagaaaatg     600 gccccggga atcccagtc gattttccca agcagtactc cgcttcctgg atgtgttgt        660 ctctcttggc tgcactggcc tgctctgctg gagacacatg gcttcagaa gttggcccag       720 ttctgagtaa aagttctcca agactgataa caacctggga gaaagttcca gttggtacca      780
```

```
atggaggagt tacagtggtg ggccttgtct ccagtctcct tggtggtacc tttgtgggca    840
ttgcatactt cctcacacag ctgattttg tgaatgattt agacatttct gccccgcagt    900
ggccaattat tgcatttggt ggtttagctg gattactagg atcaattgtg gactcatact    960
taggggctac aatgcagtat actgggttgg atgaaagcac tggcatggtg gtcaacagcc    1020
caacaaataa ggcaaggcac atagcaggga aacccattct tgataacaac gcagtgaatc    1080
tgttttcttc tgttcttatt gccctcttgc tcccaactgc tgcttggggt ttttggccca    1140
gggggtga                                                            1148
```

<210> SEQ ID NO 240
<211> LENGTH: 29
<212> TYPE: PRT
<213> ORGANISM: Artificial Sequence
<220> FEATURE:
<223> OTHER INFORMATION: Synthetic or recombinant sequence

<400> SEQUENCE: 240

Phe Asp Phe Cys Thr His Ile Lys Ser Met Val Thr Tyr Asp Leu Phe
1               5                   10                  15

Leu Arg Gly Val Gly Cys Phe Leu Leu Leu Phe Leu Phe
            20                  25

<210> SEQ ID NO 241
<211> LENGTH: 1148
<212> TYPE: DNA
<213> ORGANISM: Artificial Sequence
<220> FEATURE:
<223> OTHER INFORMATION: Synthetic or recombinant sequence

<400> SEQUENCE: 241

```
atgccgacca actgcgccgc ggcgggctgc gccactacct acgacaagca cattaacatc    60
agcttccaca ggtttccttt ggatcctaag agaagaaaag aatggattcg tctgcttagg    120
cgcaaaaatt ttgtgccagg aaaacacact tttctttgtt caaagcactt tgaagcctcc    180
tgttttgact aacaggaca aactcgacga cttaaaatgg atgctgttcc aaccattttt    240
gatttctgta cccatttaaa gtctatggca atttacagcc tatttctcct tggcgttggc    300
tgttctctgt cgtcgttcct gttttgatcg tctccaatgg ctttaaaaag aaaagtctag    360
accacagtgg ggccttagga gggcttgtgg ttggatttat cctaaccatt gcaaatttca    420
gcttttttac ctcttgctg atgttttcc tttcttcttc aaaactcact aaatggaagg    480
gagaaataaa gaagcgtctg gattcagaat acaaagaagg tgggcagagg aattgggttc    540
aggtgttctg caacggggct gtgcccacag agctggccct gctgtacatg atagaaaatg    600
gccccgggga gatcccgata gattttttcca agcagtacac cgcttcctgg atgtgtctgt    660
ctctcttggc tgcactggcc tgctctgctg gagacacctg gcttcagaa gtgggcccgg    720 ttctgagcaa aagcccgccg aggctaataa caacctggga aaaagttcca gttgggacca    780
atggaggggt tacagtagtg ggccttgtct ccagtctact tggcggtacc tttgtgggca    840
tcacctactt cctcacacag ttggtcttcg ttaatgattt agacatttct gctccccagt    900
ggccaattat tgcatttggg ggtctggctg gattactagg atcagttgtg gactcatatt    960
taggagctac aatgcaattt actggtttag acgaaagcac tggcatggtg gtcaacagcc    1020
cagcgaatga ggtgaagtac atagcgggga aacccattct tgataacaat gcagtgaacc    1080
tgttttcttc ggtcgttatt gccctcttac tcccaactgc tgcttggggt ttctggccca    1140
tggagtga                                                            1148
```

<210> SEQ ID NO 242
<211> LENGTH: 29
<212> TYPE: PRT
<213> ORGANISM: Artificial Sequence
<220> FEATURE:
<223> OTHER INFORMATION: Synthetic or recombinant sequence

<400> SEQUENCE: 242

Phe Asp Phe Cys Thr His Leu Lys Ser Met Ala Ile Tyr Ser Leu Phe
1               5                   10                  15

Leu Leu Gly Val Gly Cys Ser Leu Ser Ser Phe Leu Phe
            20                  25

<210> SEQ ID NO 243
<211> LENGTH: 14
<212> TYPE: PRT
<213> ORGANISM: Artificial Sequence
<220> FEATURE:
<223> OTHER INFORMATION: Synthetic or recombinant sequence

<400> SEQUENCE: 243

Glu Gly Lys Pro Leu Leu Gln Arg His Arg Leu Leu Asn Arg
1               5                   10

<210> SEQ ID NO 244
<211> LENGTH: 74
<212> TYPE: PRT
<213> ORGANISM: Artificial Sequence
<220> FEATURE:
<223> OTHER INFORMATION: Synthetic or recombinant sequence

<400> SEQUENCE: 244

Leu Thr Arg Gln Ile Ala Val Lys Thr Leu Glu Pro Gly His Gln Arg
1               5                   10                  15

Lys Lys Ile Ser Arg Gln Lys Asn Thr Gly Glu Lys Lys Met Pro Arg
            20                  25                  30

Gly Ser Val Gln Leu Ser Phe Cys Ser Leu Gln His Pro His Met Gly
        35                  40                  45

His Leu Phe Thr Pro His Asp Ala Ala Leu Gly Glu Ser Gln Gly Thr
    50                  55                  60

Gly Phe Lys Pro Leu Gly Met Gln Pro Val
65                  70

<210> SEQ ID NO 245
<211> LENGTH: 265
<212> TYPE: PRT
<213> ORGANISM: Artificial Sequence
<220> FEATURE:
<223> OTHER INFORMATION: Synthetic or recombinant sequence

<400> SEQUENCE: 245

Asn Leu Lys Asp Pro Ser Tyr Gly Trp Glu Ile Leu Asp Glu Phe Tyr
1               5                   10                  15

Asn Val Lys Phe Cys Ile Asp Ala Ser Gln Pro Asp Val Gly Ser Trp
            20                  25                  30

Leu Lys Tyr Ile Arg Phe Ala Gly Cys Tyr Asp Gln His Asn Leu Val
        35                  40                  45

Ala Cys Gln Ile Asn Asp Gln Ile Phe Tyr Arg Val Val Ala Asp Ile
    50                  55                  60

Ala Pro Gly Glu Glu Leu Leu Leu Phe Met Lys Ser Glu Asp Tyr Pro
65                  70                  75                  80

```
His Glu Thr Met Ala Pro Asp Ile His Glu Glu Arg Gln Tyr Arg Cys
                85                  90                  95

Glu Asp Cys Asp Gln Leu Phe Glu Ser Lys Ala Glu Leu Ala Asp His
            100                 105                 110

Gln Lys Phe Pro Cys Ser Thr Pro His Ser Ala Phe Ser Met Val Glu
        115                 120                 125

Glu Asp Phe Gln Gln Lys Leu Glu Ser Glu Asn Asp Leu Gln Glu Ile
130                 135                 140

His Thr Ile Gln Glu Cys Lys Glu Cys Asp Gln Val Phe Pro Asp Leu
145                 150                 155                 160

Gln Ser Leu Glu Lys His Met Leu Ser His Thr Glu Arg Glu Tyr
                165                 170                 175

Lys Cys Asp Gln Cys Pro Lys Ala Phe Asn Trp Lys Ser Asn Leu Ile
            180                 185                 190

Arg His Gln Met Ser His Asp Ser Gly Lys His Tyr Glu Cys Glu Asn
            195                 200                 205

Cys Ala Lys Val Phe Thr Asp Pro Ser Asn Leu Gln Arg His Ile Arg
        210                 215                 220

Ser Gln His Val Gly Ala Arg Ala His Ala Cys Pro Glu Cys Gly Lys
225                 230                 235                 240

Thr Phe Ala Thr Ser Ser Gly Leu Lys Gln His Lys His Ile His Ser
                245                 250                 255

Ser Val Lys Pro Phe Ile Cys Glu Val
            260                 265

<210> SEQ ID NO 246
<211> LENGTH: 134
<212> TYPE: PRT
<213> ORGANISM: Artificial Sequence
<220> FEATURE:
<223> OTHER INFORMATION: Synthetic or recombinant sequence

<400> SEQUENCE: 246

Asn Asp Trp Asp Ile Tyr Tyr Trp Ala Thr Gly Pro Glu Gly Pro Phe
1               5                   10                  15

Arg His Pro Gly Ala Arg Ala Ser Gly His His Gly Ala Gly Ala Gln
                20                  25                  30

Gly Ser Ala Ser Ala Pro Pro Ala Ala Gly Pro Gly Pro Ala Gly Ala
            35                  40                  45

Gly Glu Leu Pro Thr Trp Pro Thr Leu His Asp Val Gly Val Gln Phe
50                  55                  60

Gln Val Ser Gln Gly Pro Ser Arg Pro Ala Arg Phe Leu Ala Glu Glu
65                  70                  75                  80

Ile Asp Arg Arg Lys Gly Gly Glu Trp Leu His Gln Thr Val Pro Pro
                85                  90                  95

Glu Pro His Cys Leu Pro Thr Ala Leu Thr Gly Pro Pro Trp Gly Pro
            100                 105                 110

Cys Pro Pro Pro Arg Pro Glu Cys His Gln Val Arg Leu Pro Pro Gln
        115                 120                 125

Asp Ser Pro Thr Trp Arg
    130

<210> SEQ ID NO 247
<211> LENGTH: 45
<212> TYPE: PRT
<213> ORGANISM: Artificial Sequence
```

<220> FEATURE:
<223> OTHER INFORMATION: Synthetic or recombinant sequence

<400> SEQUENCE: 247

Gly Tyr Arg Ala Val Ala Leu Asp Leu Pro Ala His Ala Gln Arg
1               5                   10                  15

His Asp Gln Gln Gly Ser Arg Gly Gly Ala Pro Ile Gly Asp Ala Leu
            20                  25                  30

Pro Pro Val Pro Ala Tyr Pro His Cys Pro Ala Gln Ala
        35                  40                  45

<210> SEQ ID NO 248
<211> LENGTH: 45
<212> TYPE: PRT
<213> ORGANISM: Artificial Sequence
<220> FEATURE:
<223> OTHER INFORMATION: Synthetic or recombinant sequence

<400> SEQUENCE: 248

Gly Arg Val Ile Glu Cys Asp Val Val Lys Gly Ser Cys Gln Asp Gly
1               5                   10                  15

Glu Ala Val His Arg Lys Pro Ala Pro Gly Gly Tyr Arg Ala Gly Asp
            20                  25                  30

Ser Leu Thr Leu Arg Ala Val Trp Glu Gly Ala Gly Met
        35                  40                  45

<210> SEQ ID NO 249
<211> LENGTH: 30
<212> TYPE: PRT
<213> ORGANISM: Artificial Sequence
<220> FEATURE:
<223> OTHER INFORMATION: Synthetic or recombinant sequence

<400> SEQUENCE: 249

Leu Arg Lys Glu Gln Ile Leu Ala Val Ala Ser Leu Val Ser Ser Gln
1               5                   10                  15

Ser Ile His Pro Ser Trp Gly Gln Ser Pro Leu Ser Arg Ile
            20                  25                  30

<210> SEQ ID NO 250
<211> LENGTH: 44
<212> TYPE: PRT
<213> ORGANISM: Artificial Sequence
<220> FEATURE:
<223> OTHER INFORMATION: Synthetic or recombinant sequence

<400> SEQUENCE: 250

Leu Met Leu Glu Leu Gly Phe Ser Lys Val Leu Gly Asp Arg Glu Val
1               5                   10                  15

Gln Ser Arg Trp Ser Pro Gly Pro Arg Gly Asp Ser Thr Pro Val Arg
            20                  25                  30

Glu Met Glu Thr Asn His Pro Pro Ser Val Arg Gly
        35                  40

<210> SEQ ID NO 251
<211> LENGTH: 43
<212> TYPE: PRT
<213> ORGANISM: Artificial Sequence
<220> FEATURE:
<223> OTHER INFORMATION: Synthetic or recombinant sequence

<400> SEQUENCE: 251

Gln Leu Met Lys Ser Gln Leu Lys Ala Gly Tyr Pro Glu Tyr Met Ser

```
                1               5                  10                  15
Asn Asn Phe Pro Cys Asn Val Ser Cys Cys Phe Ser Leu Phe Pro Lys
                20                  25                  30

Asp Gln Asn Cys Phe Arg Asn Trp Arg His Ile
        35                  40
```

<210> SEQ ID NO 252
<211> LENGTH: 16
<212> TYPE: PRT
<213> ORGANISM: Artificial Sequence
<220> FEATURE:
<223> OTHER INFORMATION: Synthetic or recombinant sequence

<400> SEQUENCE: 252

```
Leu Phe Leu Thr Pro Glu Pro Gly Ala Glu Val Pro Leu Thr Gly Ala
1               5                  10                  15
```

<210> SEQ ID NO 253
<211> LENGTH: 38
<212> TYPE: PRT
<213> ORGANISM: Artificial Sequence
<220> FEATURE:
<223> OTHER INFORMATION: Synthetic or recombinant sequence

<400> SEQUENCE: 253

```
Trp Glu Glu Arg Arg Asn Ala Glu Ala Gln Ala Ser Arg Phe Phe Gln
1               5                  10                  15

Leu Ile Phe Thr Leu Thr Gly Pro Ser Ser Gln Leu Glu Asp Lys Gly
                20                  25                  30

Arg Ile Leu Gly Arg Leu
        35
```

<210> SEQ ID NO 254
<211> LENGTH: 33
<212> TYPE: PRT
<213> ORGANISM: Artificial Sequence
<220> FEATURE:
<223> OTHER INFORMATION: Synthetic or recombinant sequence

<400> SEQUENCE: 254

```
Gln Val Gln Ala Gln Gln Gln Ala Trp Gln Val Arg Ser Pro Ala Val
1               5                  10                  15

Gln Ser Pro Ala Lys Val Gln Pro Leu Cys Pro Ser Arg Ala Ala
                20                  25                  30

Arg
```

<210> SEQ ID NO 255
<211> LENGTH: 46
<212> TYPE: PRT
<213> ORGANISM: Artificial Sequence
<220> FEATURE:
<223> OTHER INFORMATION: Synthetic or recombinant sequence

<400> SEQUENCE: 255

```
Leu Ala Ala Ala Leu Thr Leu His Gly His Cys Leu Gln Cys Gln Ile
1               5                  10                  15

Val His Ser Cys Pro Leu Leu Glu Asn Gln Ile His Leu Ser Leu Lys
                20                  25                  30

Phe Pro Asp Tyr Phe Ile Lys Met Lys Pro Trp Arg Lys Ile
        35                  40                  45
```

<210> SEQ ID NO 256

-continued

```
<211> LENGTH: 18
<212> TYPE: PRT
<213> ORGANISM: Artificial Sequence
<220> FEATURE:
<223> OTHER INFORMATION: Synthetic or recombinant sequence

<400> SEQUENCE: 256

Lys His His Lys Tyr His Lys His Gly Lys Phe Leu Ala Phe Thr Pro
1               5                   10                  15

Asn Gln

<210> SEQ ID NO 257
<211> LENGTH: 13
<212> TYPE: PRT
<213> ORGANISM: Artificial Sequence
<220> FEATURE:
<223> OTHER INFORMATION: Synthetic or recombinant sequence

<400> SEQUENCE: 257

Val Ser Arg Val Gly Lys Ala Ile Asp Lys Asp Ser Leu
1               5                   10

<210> SEQ ID NO 258
<211> LENGTH: 17
<212> TYPE: PRT
<213> ORGANISM: Artificial Sequence
<220> FEATURE:
<223> OTHER INFORMATION: Synthetic or recombinant sequence

<400> SEQUENCE: 258

Val Asp Val Gly Gln Arg Leu Arg Arg Gly Ala Ser Asp Pro Cys Cys
1               5                   10                  15

Cys

<210> SEQ ID NO 259
<211> LENGTH: 11
<212> TYPE: PRT
<213> ORGANISM: Artificial Sequence
<220> FEATURE:
<223> OTHER INFORMATION: Synthetic or recombinant sequence

<400> SEQUENCE: 259

Ile Ser Ala Glu Tyr Asp Pro Ser Lys Leu Gly
1               5                   10

<210> SEQ ID NO 260
<211> LENGTH: 16
<212> TYPE: PRT
<213> ORGANISM: Artificial Sequence
<220> FEATURE:
<223> OTHER INFORMATION: Synthetic or recombinant sequence

<400> SEQUENCE: 260

Cys Leu Ala Asp Ala Val Val Lys Ile Gly Leu Trp Arg Pro Arg Ala
1               5                   10                  15

<210> SEQ ID NO 261
<211> LENGTH: 148
<212> TYPE: PRT
<213> ORGANISM: Artificial Sequence
<220> FEATURE:
<223> OTHER INFORMATION: Synthetic or recombinant sequence

<400> SEQUENCE: 261

Glu Asn Gly Gly Thr Tyr Val Ser Pro Pro Leu Pro Leu Gly Ala Ser
1               5                   10                  15
```

```
Gly Gly Phe Pro Ser Ala Thr Ala Asn Cys Phe Phe Arg Ser Lys Ser
            20                  25                  30

Phe Ala Thr Ser Ala Ala Thr Ser Phe Leu Ser Ala Phe Cys Ala Phe
        35                  40                  45

Ser Ser Arg Thr Met Phe Pro Cys Phe Val Thr Ser Ser Ile Ser Ala
    50                  55                  60

Cys Ile Cys Cys Gly Leu Ala Val Val Thr Val Ser Thr Thr Ala Gly
65                  70                  75                  80

Phe Gly Asp Val Phe Ala Trp Pro Pro Lys Arg Cys Leu Lys Leu
                85                  90                  95

Ser Ile Trp Ser Phe Ser Asn Phe Trp Asn Lys Gly Leu Thr Val Pro
            100                 105                 110

Ile Trp Cys Pro Ala Gly Lys Val His Arg Lys Phe Val Ser Arg Ile
        115                 120                 125

Leu Gln Ala Gly Gly Gly Ser Cys Ser Trp Ala Trp Ile Val Ala Leu
    130                 135                 140

Thr Val Gly Met
145

<210> SEQ ID NO 262
<211> LENGTH: 214
<212> TYPE: PRT
<213> ORGANISM: Artificial Sequence
<220> FEATURE:
<223> OTHER INFORMATION: Synthetic or recombinant sequence

<400> SEQUENCE: 262

Arg Thr Pro Glu Pro Asn Pro Val Thr Gly Ala Asp Leu Arg Pro Glu
1               5                   10                  15

Leu Pro Asp His Cys Ala Val Arg Ala Gly Arg Leu Leu Ala Ala Ala
                20                  25                  30

Gly Pro Arg Phe Pro Gly Ala Ala Thr Ala Ala Leu Asp Ala Ser Pro
            35                  40                  45

Val Arg Leu Gly Met Gly Arg Ala Ala Ser Ala Arg Pro Arg Leu Pro
        50                  55                  60

Val His Arg Gly Arg Gly Glu Arg Leu Gly Pro Gly Val Leu Phe Ser
65                  70                  75                  80

Leu Arg His Leu His Gly Val Cys His Ala Ala Leu Gly His Ala Gly
                85                  90                  95

Arg Arg Arg Arg Gly Pro Arg Leu Leu Thr Leu Ala Ser Ala Gly Pro
            100                 105                 110

Arg Ala Val Ser Trp Ala Thr Ala Gly Leu Thr Ala Cys Thr Ala Ala
        115                 120                 125

Ala Val Gly Ser Lys Arg Ser Ala Val Pro Val Arg Glu Arg Gly Arg
    130                 135                 140

Ser Val Pro Gln Gly Ala Asp Gly Ala Arg Pro Ala Gly His Val Pro
145                 150                 155                 160

Gly Gly Thr Gln Leu Pro Ala Leu Thr Pro Ala Ala Gly His Arg Glu
                165                 170                 175

Glu Ala Pro Gly Thr Pro Ser Leu Val His Pro Ser Cys Leu Pro Gly
            180                 185                 190

Pro Arg Asp Glu Gly Arg Asp His Gly Thr Ala Ala Gly Arg Thr Gly
        195                 200                 205

Val Thr Ala Arg Glu His
    210
```

<210> SEQ ID NO 263
<211> LENGTH: 28
<212> TYPE: PRT
<213> ORGANISM: Artificial Sequence
<220> FEATURE:
<223> OTHER INFORMATION: Synthetic or recombinant sequence

<400> SEQUENCE: 263

Leu Asp Ala Gln Ala Asp Glu Ala Val Leu Gly Phe Phe Ile Lys Gln
1               5                   10                  15

Lys Cys Ile Glu Gln Arg Glu Ser Arg Ser Leu Ser
            20                  25

<210> SEQ ID NO 264
<211> LENGTH: 65
<212> TYPE: PRT
<213> ORGANISM: Artificial Sequence
<220> FEATURE:
<223> OTHER INFORMATION: Synthetic or recombinant sequence

<400> SEQUENCE: 264

Lys Ser Ala Ser Met His Pro Tyr Gln Arg Val Leu Ser Gln Asp Gly
1               5                   10                  15

Gly Cys Cys Glu Leu Val Pro Arg Gly Asp Glu Ala Arg Arg Ser Pro
            20                  25                  30

Asp Pro Gly Leu Pro Ser Asp Gly Val Pro Leu Ala Asn Asp Leu His
        35                  40                  45

Ser Pro Asp Leu Arg Val Leu Arg Ser Leu Thr Trp Ala Ser His His
    50                  55                  60

Gly
65

<210> SEQ ID NO 265
<211> LENGTH: 39
<212> TYPE: PRT
<213> ORGANISM: Artificial Sequence
<220> FEATURE:
<223> OTHER INFORMATION: Synthetic or recombinant sequence

<400> SEQUENCE: 265

Asp His Thr Leu Gly Asn Ile Ile Lys Ser Arg Ala Cys Phe Pro Phe
1               5                   10                  15

Ala Phe Cys Arg Asp Cys Gln Phe Pro Glu Ala Ser Pro Ala Thr Leu
            20                  25                  30

Ser Val Gln Pro Ala Glu Leu
        35

<210> SEQ ID NO 266
<211> LENGTH: 33
<212> TYPE: PRT
<213> ORGANISM: Artificial Sequence
<220> FEATURE:
<223> OTHER INFORMATION: Synthetic or recombinant sequence

<400> SEQUENCE: 266

Gln Val Gln Ala Gln Gln Gln Ala Trp Gln Val Arg Ser Pro Ala Val
1               5                   10                  15

Gln Ser Pro Ala Lys Val Gln Pro Leu Cys Pro Ser Arg Arg Ala Ala
            20                  25                  30

Arg

```
<210> SEQ ID NO 267
<211> LENGTH: 131
<212> TYPE: PRT
<213> ORGANISM: Artificial Sequence
<220> FEATURE:
<223> OTHER INFORMATION: Synthetic or recombinant sequence

<400> SEQUENCE: 267

Gln Tyr Ile Phe Thr Glu Met Ala Ser Arg Pro Arg Gly Ala His Trp
1               5                   10                  15

Ala Gly Arg Asp Pro Glu Pro Gly Glu Gly Thr Arg Thr Arg Arg Ala
            20                  25                  30

Gly Ala Glu Arg Gly Arg His Leu Gly Ala His Val Gln Ala Phe Gly
        35                  40                  45

Gly Asp Met Pro Glu Ala Gly Gly Arg Arg Pro Gly Arg Gly Ala
    50                  55                  60

Val Leu Val Pro Pro His Gly Pro Arg Ala Ala Ala Pro Leu Arg Ala
65                  70                  75                  80

Gly Ala Gly Gln Leu Arg Ala Ala Arg Gly Pro Gly Ala Ala Thr
                85                  90                  95

His Gly Arg Glu Ala Arg Ser Arg Val Ala Leu Pro Ala Arg Leu Leu
            100                 105                 110

Gln Gly Gly Arg Ala Ala Ser Ala Ala Arg Leu Pro Arg Ser Ser Gly
        115                 120                 125

Val Gly Asp
    130

<210> SEQ ID NO 268
<211> LENGTH: 94
<212> TYPE: PRT
<213> ORGANISM: Artificial Sequence
<220> FEATURE:
<223> OTHER INFORMATION: Synthetic or recombinant sequence

<400> SEQUENCE: 268

Pro Tyr Ile Asn Ile Thr Ile Leu Lys Gly Leu Pro Ser Ser Ala Pro
1               5                   10                  15

Pro Cys Gly Cys Asn Gly Gly Pro Cys Ser Val Leu Ala Ser Ala Pro
            20                  25                  30

Pro His Pro Pro Ala Pro Gly Tyr Leu Leu Gly Ile Cys Ser Gly
        35                  40                  45

Glu Trp His Phe Pro Val His Met Leu Leu Gln Leu Glu Ser Gln His
    50                  55                  60

Leu Leu Cys Leu Glu Pro Arg Trp Gly Ser Ala Gly His Phe Leu Pro
65                  70                  75                  80

Ser Pro Cys Leu Ala Gly Gln Thr Ala Val Glu Pro Asn Leu
                85                  90

<210> SEQ ID NO 269
<211> LENGTH: 68
<212> TYPE: PRT
<213> ORGANISM: Artificial Sequence
<220> FEATURE:
<223> OTHER INFORMATION: Synthetic or recombinant sequence

<400> SEQUENCE: 269

Lys Leu Glu Glu Ala Gly Met Leu Glu Met Arg Pro Ser Thr Pro Cys
1               5                   10                  15

Leu His Gly Ala Ala Leu His Leu His Ser Gly His Gly Ser Gly Ser
```

```
                    20                  25                  30

Arg Leu Thr Asn Ser Ser Cys Phe Pro Gly Thr Arg Arg Leu Leu Ala
            35                  40                  45

Leu Gln Phe Thr Gln Gln Thr Gly Thr Val Gly His Pro Thr Trp Gln
        50                  55                  60

Pro Val Ile Arg
65

<210> SEQ ID NO 270
<211> LENGTH: 67
<212> TYPE: PRT
<213> ORGANISM: Artificial Sequence
<220> FEATURE:
<223> OTHER INFORMATION: Synthetic or recombinant sequence

<400> SEQUENCE: 270

Lys Glu Tyr Leu Glu Cys Arg Met Glu Arg Ser Arg Leu Gly Leu Leu
1               5                   10                  15

His Ser Gly Arg Leu His Leu Pro Glu Leu Leu Gly Asn Pro Pro Glu
            20                  25                  30

Tyr Pro Pro Gly Gln Gln Gly Glu Val Arg Pro Pro Gly Arg Leu Gly
        35                  40                  45

Gly Gly Pro Ser Gly Val His Gly Leu Pro Arg Glu Arg Arg Arg Glu
    50                  55                  60

Ser Gln Val
65

<210> SEQ ID NO 271
<211> LENGTH: 30
<212> TYPE: PRT
<213> ORGANISM: Artificial Sequence
<220> FEATURE:
<223> OTHER INFORMATION: Synthetic or recombinant sequence

<400> SEQUENCE: 271

Ile Asn Lys Ile Asn Met Lys Asp Leu Val Arg Asn Leu Arg Lys Lys
1               5                   10                  15

Leu Gln His Gly Lys Met Asp Ser Lys Ala Pro Met Ser Cys
            20                  25                  30

<210> SEQ ID NO 272
<211> LENGTH: 27
<212> TYPE: PRT
<213> ORGANISM: Artificial Sequence
<220> FEATURE:
<223> OTHER INFORMATION: Synthetic or recombinant sequence

<400> SEQUENCE: 272

Thr Met Thr Gly Met Leu Tyr Lys Cys Thr Val Ser Glu Met Ala Leu
1               5                   10                  15

Asp Ser Pro Phe Cys Val Leu Leu Ser Gly Ser
            20                  25

<210> SEQ ID NO 273
<211> LENGTH: 26
<212> TYPE: PRT
<213> ORGANISM: Artificial Sequence
<220> FEATURE:
<223> OTHER INFORMATION: Synthetic or recombinant sequence

<400> SEQUENCE: 273

Ile Ile Met Lys Asp Val Pro Asp Trp Lys Gly Leu Gly Ala Ala Ala
```

```
                1               5                   10                  15
Pro Thr Cys Arg His Gly Lys Ser Gly Ala
            20                  25

<210> SEQ ID NO 274
<211> LENGTH: 25
<212> TYPE: PRT
<213> ORGANISM: Artificial Sequence
<220> FEATURE:
<223> OTHER INFORMATION: Synthetic or recombinant sequence

<400> SEQUENCE: 274

Pro Ala Leu Val Lys Gly Thr Leu Pro Gln Tyr Pro Val Gln Pro Glu
1               5                   10                  15

Glu Glu Pro Lys Ala Leu Ser Thr Ser
            20                  25

<210> SEQ ID NO 275
<211> LENGTH: 16
<212> TYPE: PRT
<213> ORGANISM: Artificial Sequence
<220> FEATURE:
<223> OTHER INFORMATION: Synthetic or recombinant sequence

<400> SEQUENCE: 275

Gln Leu Pro Ala Leu Tyr Glu Met Thr Val Ser Asn Ser Cys Thr Ser
1               5                   10                  15

<210> SEQ ID NO 276
<211> LENGTH: 16
<212> TYPE: PRT
<213> ORGANISM: Artificial Sequence
<220> FEATURE:
<223> OTHER INFORMATION: Synthetic or recombinant sequence

<400> SEQUENCE: 276

Asp Ile Tyr Lys Gln Ile Arg Ala Asn Lys Val Ser Val Trp Arg Gln
1               5                   10                  15

<210> SEQ ID NO 277
<211> LENGTH: 22
<212> TYPE: PRT
<213> ORGANISM: Artificial Sequence
<220> FEATURE:
<223> OTHER INFORMATION: Synthetic or recombinant sequence

<400> SEQUENCE: 277

Arg Thr Ser Ala Leu Ala Glu Arg Thr His Ser Ile Gly His Ile Ser
1               5                   10                  15

Thr Met Leu Met Ala Phe
            20

<210> SEQ ID NO 278
<211> LENGTH: 25
<212> TYPE: PRT
<213> ORGANISM: Artificial Sequence
<220> FEATURE:
<223> OTHER INFORMATION: Synthetic or recombinant sequence

<400> SEQUENCE: 278

Leu Lys Gly His Tyr Ala Ile Thr Arg Lys Val Tyr Gln Pro Gln Ser
1               5                   10                  15

Leu His Val Ser Lys Ser Ser Arg Lys
            20                  25
```

```
<210> SEQ ID NO 279
<211> LENGTH: 17
<212> TYPE: PRT
<213> ORGANISM: Artificial Sequence
<220> FEATURE:
<223> OTHER INFORMATION: Synthetic or recombinant sequence

<400> SEQUENCE: 279

Pro Tyr Val Thr Leu Lys Arg Arg Arg Ala Ala Pro Ser Gly Leu Gly
1               5                   10                  15

Leu

<210> SEQ ID NO 280
<211> LENGTH: 25
<212> TYPE: PRT
<213> ORGANISM: Artificial Sequence
<220> FEATURE:
<223> OTHER INFORMATION: Synthetic or recombinant sequence

<400> SEQUENCE: 280

Leu Ala Thr Leu Asp Pro Pro His Thr Val Gln Thr Trp Met Arg Arg
1               5                   10                  15

His Arg Leu Val Pro Val His Tyr Arg
            20                  25

<210> SEQ ID NO 281
<211> LENGTH: 51
<212> TYPE: PRT
<213> ORGANISM: Artificial Sequence
<220> FEATURE:
<223> OTHER INFORMATION: Synthetic or recombinant sequence

<400> SEQUENCE: 281

Pro Ala Arg Pro Ala Pro Ala Ser Ser Glu Lys Arg Cys Ser Ile Phe
1               5                   10                  15

Arg Leu Arg Lys Thr Thr Arg Ala Gln Trp Arg Leu Pro His Phe Phe
            20                  25                  30

Ser Ser Ser Cys Trp Ser Ser Arg Arg Lys Ala Gly Ser Val Ala Phe
        35                  40                  45

Trp Met Pro
    50

<210> SEQ ID NO 282
<211> LENGTH: 20
<212> TYPE: PRT
<213> ORGANISM: Artificial Sequence
<220> FEATURE:
<223> OTHER INFORMATION: Synthetic or recombinant sequence

<400> SEQUENCE: 282

Leu His Pro Glu Asp Phe Pro Glu Glu Asp Val Tyr Cys Cys Gly Ala
1               5                   10                  15

Glu Arg Arg Gly
            20

<210> SEQ ID NO 283
<211> LENGTH: 22
<212> TYPE: PRT
<213> ORGANISM: Artificial Sequence
<220> FEATURE:
<223> OTHER INFORMATION: Synthetic or recombinant sequence

<400> SEQUENCE: 283
```

```
Cys Cys Pro Arg Leu Lys Ile Leu Arg Leu Ser Ala Leu Ser Val Ile
1               5                   10                  15

Arg Phe Ile Cys Gly Phe
            20
```

<210> SEQ ID NO 284
<211> LENGTH: 16
<212> TYPE: PRT
<213> ORGANISM: Artificial Sequence
<220> FEATURE:
<223> OTHER INFORMATION: Synthetic or recombinant sequence

<400> SEQUENCE: 284

```
Leu Leu Ser Leu Leu Pro Ser Asp Asn Ser Leu Ala Ser Lys Gly Pro
1               5                   10                  15
```

<210> SEQ ID NO 285
<211> LENGTH: 23
<212> TYPE: PRT
<213> ORGANISM: Artificial Sequence
<220> FEATURE:
<223> OTHER INFORMATION: Synthetic or recombinant sequence

<400> SEQUENCE: 285

```
Val Ser Val Asp Gly Tyr Met Asn Met Gln Gln Asp Phe His Leu His
1               5                   10                  15

Leu Gly Asn Ile Glu Thr Lys
            20
```

<210> SEQ ID NO 286
<211> LENGTH: 13
<212> TYPE: PRT
<213> ORGANISM: Artificial Sequence
<220> FEATURE:
<223> OTHER INFORMATION: Synthetic or recombinant sequence

<400> SEQUENCE: 286

```
Gly Asp Val Tyr Pro Val Tyr Gln Pro Val Asp Arg Pro
1               5                   10
```

<210> SEQ ID NO 287
<211> LENGTH: 17
<212> TYPE: PRT
<213> ORGANISM: Artificial Sequence
<220> FEATURE:
<223> OTHER INFORMATION: Synthetic or recombinant sequence

<400> SEQUENCE: 287

```
Lys Pro Gly Lys Val Asp Val Lys Thr Asp Thr Ser Ser Ser Asn Ser
1               5                   10                  15

Trp
```

<210> SEQ ID NO 288
<211> LENGTH: 15
<212> TYPE: PRT
<213> ORGANISM: Artificial Sequence
<220> FEATURE:
<223> OTHER INFORMATION: Synthetic or recombinant sequence

<400> SEQUENCE: 288

```
Gly Ser Ile Thr Gly Pro Ala His Trp Glu Gln Pro Val Ser Ser
1               5                   10                  15
```

<210> SEQ ID NO 289
<211> LENGTH: 19

<212> TYPE: PRT
<213> ORGANISM: Artificial Sequence
<220> FEATURE:
<223> OTHER INFORMATION: Synthetic or recombinant sequence

<400> SEQUENCE: 289

Ile Val Leu Gln Ile Phe Leu Arg Leu Phe Glu Thr Asn Thr Asp Thr
1               5                   10                  15

Leu Leu Val

<210> SEQ ID NO 290
<211> LENGTH: 21
<212> TYPE: PRT
<213> ORGANISM: Artificial Sequence
<220> FEATURE:
<223> OTHER INFORMATION: Synthetic or recombinant sequence

<400> SEQUENCE: 290

Ala Val Leu Leu Met Cys Gln Met Tyr Gln Pro Trp Met Cys Lys Lys
1               5                   10                  15

Tyr Tyr Arg Leu Leu
            20

<210> SEQ ID NO 291
<211> LENGTH: 21
<212> TYPE: PRT
<213> ORGANISM: Artificial Sequence
<220> FEATURE:
<223> OTHER INFORMATION: Synthetic or recombinant sequence

<400> SEQUENCE: 291

Ala Val Leu Leu Met Cys Gln Leu Tyr Gln Pro Trp Met Cys Lys Glu
1               5                   10                  15

Tyr Tyr Arg Leu Leu
            20

<210> SEQ ID NO 292
<211> LENGTH: 21
<212> TYPE: PRT
<213> ORGANISM: Artificial Sequence
<220> FEATURE:
<223> OTHER INFORMATION: Synthetic or recombinant sequence

<400> SEQUENCE: 292

Ala Val Leu Leu Met Cys Gln Met Tyr Gln Pro Trp Met Cys Glu Glu
1               5                   10                  15

Tyr Tyr Arg Leu Leu
            20

<210> SEQ ID NO 293
<211> LENGTH: 21
<212> TYPE: PRT
<213> ORGANISM: Artificial Sequence
<220> FEATURE:
<223> OTHER INFORMATION: Synthetic or recombinant sequence

<400> SEQUENCE: 293

Ile Pro Arg Met Gln Pro Gln Ala Ser Ala Asn Pro Cys Gln Leu Leu
1               5                   10                  15

Lys Pro Met Val Ala
            20

<210> SEQ ID NO 294
<211> LENGTH: 21

```
<212> TYPE: PRT
<213> ORGANISM: Artificial Sequence
<220> FEATURE:
<223> OTHER INFORMATION: Synthetic or recombinant sequence

<400> SEQUENCE: 294

Ile Pro Arg Met Gln Pro Gln Ala Ser Ala Asn His Cys Gln Leu Leu
1               5                   10                  15

Lys Val Met Val Ala
            20

<210> SEQ ID NO 295
<211> LENGTH: 21
<212> TYPE: PRT
<213> ORGANISM: Artificial Sequence
<220> FEATURE:
<223> OTHER INFORMATION: Synthetic or recombinant sequence

<400> SEQUENCE: 295

Ile Pro Arg Met Gln Pro Gln Ala Ser Ala Asn Pro Cys Gln Leu Leu
1               5                   10                  15

Lys Pro Met Val Ala
            20

<210> SEQ ID NO 296
<211> LENGTH: 27
<212> TYPE: PRT
<213> ORGANISM: Artificial Sequence
<220> FEATURE:
<223> OTHER INFORMATION: Synthetic or recombinant sequence

<400> SEQUENCE: 296

Thr Ala Ile Ile Gly Pro Asn Gly Ser Gly Cys Cys Gly Ile Tyr Cys
1               5                   10                  15

His Glu Glu Pro Gln Arg Glu Asp Ser Ser Ile
            20                  25

<210> SEQ ID NO 297
<211> LENGTH: 27
<212> TYPE: PRT
<213> ORGANISM: Artificial Sequence
<220> FEATURE:
<223> OTHER INFORMATION: Synthetic or recombinant sequence

<400> SEQUENCE: 297

Thr Ala Ile Ile Gly Pro Asn Gly Ser Gly Cys Ser Gly Val Tyr Cys
1               5                   10                  15

His Glu Glu Pro Gln Gly Glu Asp Ser Ser Val
            20                  25

<210> SEQ ID NO 298
<211> LENGTH: 27
<212> TYPE: PRT
<213> ORGANISM: Artificial Sequence
<220> FEATURE:
<223> OTHER INFORMATION: Synthetic or recombinant sequence

<400> SEQUENCE: 298

Thr Ala Ile Ile Gly Pro Asn Gly Ser Gly Cys Cys Arg Ile Tyr Cys
1               5                   10                  15

His Glu Glu Pro Gln Arg Glu Asp Ser Ser Ile
            20                  25

<210> SEQ ID NO 299
```

<211> LENGTH: 17
<212> TYPE: PRT
<213> ORGANISM: Artificial Sequence
<220> FEATURE:
<223> OTHER INFORMATION: Synthetic or recombinant sequence

<400> SEQUENCE: 299

Phe Asp Phe Cys Thr His Ile Lys Ser Leu Gly Trp Trp Ser Asp Ser
1               5                   10                  15

Ser

<210> SEQ ID NO 300
<211> LENGTH: 18
<212> TYPE: PRT
<213> ORGANISM: Artificial Sequence
<220> FEATURE:
<223> OTHER INFORMATION: Synthetic or recombinant sequence

<400> SEQUENCE: 300

Gly Leu Gln Ile Phe Leu Arg Leu Leu Gly Thr Ser Thr Gly Thr Leu
1               5                   10                  15

Leu Ala

<210> SEQ ID NO 301
<211> LENGTH: 16
<212> TYPE: PRT
<213> ORGANISM: Artificial Sequence
<220> FEATURE:
<223> OTHER INFORMATION: Synthetic or recombinant sequence

<400> SEQUENCE: 301

Ile Ala Pro Glu Val Leu Leu Arg Lys Gly Thr Thr Phe His Gly Gln
1               5                   10                  15

<210> SEQ ID NO 302
<211> LENGTH: 17
<212> TYPE: PRT
<213> ORGANISM: Artificial Sequence
<220> FEATURE:
<223> OTHER INFORMATION: Synthetic or recombinant sequence

<400> SEQUENCE: 302

Gln Ser Val Trp Ile Arg Asn Ile Gln Leu Ala Ser Arg Asn Arg Leu
1               5                   10                  15

Pro

<210> SEQ ID NO 303
<211> LENGTH: 16
<212> TYPE: PRT
<213> ORGANISM: Artificial Sequence
<220> FEATURE:
<223> OTHER INFORMATION: Synthetic or recombinant sequence

<400> SEQUENCE: 303

Gly Arg Val Ile Glu Cys Asp Val Val Lys Gly Gly Met Cys Val Gly
1               5                   10                  15

<210> SEQ ID NO 304
<211> LENGTH: 34
<212> TYPE: PRT
<213> ORGANISM: Artificial Sequence
<220> FEATURE:
<223> OTHER INFORMATION: Synthetic or recombinant sequence

<400> SEQUENCE: 304

```
Lys Pro Gly Lys Ile Asp Met Lys Thr Asp Ser Asn Arg Thr Pro Thr
1               5                   10                  15

Thr Leu Ser Ala Trp Ser Leu Asp Pro Gly Trp Ser Leu Gly Gly
            20                  25                  30

Arg Leu

<210> SEQ ID NO 305
<211> LENGTH: 17
<212> TYPE: PRT
<213> ORGANISM: Artificial Sequence
<220> FEATURE:
<223> OTHER INFORMATION: Synthetic or recombinant sequence

<400> SEQUENCE: 305

Lys Pro Gly Lys Ile Asp Met Lys Thr Asp Thr Ser Ser Asn Ser
1               5                   10                  15

Trp

<210> SEQ ID NO 306
<211> LENGTH: 17
<212> TYPE: PRT
<213> ORGANISM: Artificial Sequence
<220> FEATURE:
<223> OTHER INFORMATION: Synthetic or recombinant sequence

<400> SEQUENCE: 306

Leu Leu Ser Leu Leu Pro Ser Asp Asn Ser Arg Leu Thr Ser Lys Gly
1               5                   10                  15

Pro

<210> SEQ ID NO 307
<211> LENGTH: 26
<212> TYPE: PRT
<213> ORGANISM: Artificial Sequence
<220> FEATURE:
<223> OTHER INFORMATION: Synthetic or recombinant sequence

<400> SEQUENCE: 307

Lys Pro Gly Lys Ile Asp Val Lys Thr Asp Ser Asn Arg Thr Pro Thr
1               5                   10                  15

Thr Gln Ser Ala Trp Ser Leu Asp Leu Gly
            20                  25

<210> SEQ ID NO 308
<211> LENGTH: 12
<212> TYPE: PRT
<213> ORGANISM: Artificial Sequence
<220> FEATURE:
<223> OTHER INFORMATION: Synthetic or recombinant sequence

<400> SEQUENCE: 308

Lys Ser Ala Ser Met His Pro Tyr Gln Arg Val Pro
1               5                   10

<210> SEQ ID NO 309
<211> LENGTH: 16
<212> TYPE: PRT
<213> ORGANISM: Artificial Sequence
<220> FEATURE:
<223> OTHER INFORMATION: Synthetic or recombinant sequence

<400> SEQUENCE: 309

Tyr Thr Gln Glu Gln Phe Trp Ala Val Lys Leu Thr Lys Arg Gly Ala
1               5                   10                  15
```

<210> SEQ ID NO 310
<211> LENGTH: 59
<212> TYPE: PRT
<213> ORGANISM: Artificial Sequence
<220> FEATURE:
<223> OTHER INFORMATION: Synthetic or recombinant sequence

<400> SEQUENCE: 310

Thr Leu Cys Met Glu Val Met Leu Arg Trp Asn Thr Arg Glu Leu Gly
1               5                   10                  15

Tyr Leu Tyr Leu Gln Leu Cys Phe Leu Asn Thr His Phe Leu His Thr
            20                  25                  30

Ser Gln Glu Glu Lys Leu Leu Thr Leu Gly Arg Phe Leu Thr Trp Thr
        35                  40                  45

Ser Arg Cys Gly Ser Phe Val Ile Arg Pro Leu
    50                  55

<210> SEQ ID NO 311
<211> LENGTH: 33
<212> TYPE: PRT
<213> ORGANISM: Artificial Sequence
<220> FEATURE:
<223> OTHER INFORMATION: Synthetic or recombinant sequence

<400> SEQUENCE: 311

Ile Cys Met Ser Pro Pro Leu Leu Trp Ala Thr Leu Gln Ala Pro Glu
1               5                   10                  15

Thr Thr Ser Ala Ala Cys Lys Ala Ser Tyr Arg Pro Glu Gly Leu Tyr
            20                  25                  30

Leu

<210> SEQ ID NO 312
<211> LENGTH: 24
<212> TYPE: PRT
<213> ORGANISM: Artificial Sequence
<220> FEATURE:
<223> OTHER INFORMATION: Synthetic or recombinant sequence

<400> SEQUENCE: 312

Tyr Phe Ser Cys Asp Lys Arg Cys Ile Lys His Tyr Ala Gly Asn Lys
1               5                   10                  15

Ser Leu Leu Thr Phe Ser Gly Tyr
            20

<210> SEQ ID NO 313
<211> LENGTH: 20
<212> TYPE: PRT
<213> ORGANISM: Artificial Sequence
<220> FEATURE:
<223> OTHER INFORMATION: Synthetic or recombinant sequence

<400> SEQUENCE: 313

Lys Lys Ser Cys Pro Arg Tyr Asp Pro Thr Leu Ile Ser Leu Leu Tyr
1               5                   10                  15

Gln Cys Val Ser
            20

<210> SEQ ID NO 314
<211> LENGTH: 32
<212> TYPE: PRT
<213> ORGANISM: Artificial Sequence
<220> FEATURE:

<223> OTHER INFORMATION: Synthetic or recombinant sequence

<400> SEQUENCE: 314

Phe Leu Phe Pro Ala Phe Ser Cys Met Pro Asp Leu Phe Ile Thr Phe
1               5                   10                  15
Leu Val Thr Asn Thr Leu Leu Tyr Phe Ile Gln Phe Ser Leu Pro Cys
            20                  25                  30

<210> SEQ ID NO 315
<211> LENGTH: 34
<212> TYPE: PRT
<213> ORGANISM: Artificial Sequence
<220> FEATURE:
<223> OTHER INFORMATION: Synthetic or recombinant sequence

<400> SEQUENCE: 315

Ser Ala Gly Thr Glu Ser Asp Pro Ser Glu Glu Gln Ile Cys Glu Ala
1               5                   10                  15
Glu Gly Arg Pro Glu Gly His Phe Arg Gly Val Leu Thr Tyr Leu Pro
            20                  25                  30
Leu Leu

<210> SEQ ID NO 316
<211> LENGTH: 49
<212> TYPE: PRT
<213> ORGANISM: Artificial Sequence
<220> FEATURE:
<223> OTHER INFORMATION: Synthetic or recombinant sequence

<400> SEQUENCE: 316

Leu Ser Lys Thr Pro Ser Lys Lys Cys Ser Leu Arg Met Asn Thr Lys
1               5                   10                  15
Phe Tyr Arg Ser Phe Thr Ser Leu Lys Ser Leu Ile Val Thr Phe Leu
            20                  25                  30
Arg Met Val Trp Trp Met Leu Leu Arg Leu Glu Pro Ile Ser Trp Lys
        35                  40                  45
Ile

<210> SEQ ID NO 317
<211> LENGTH: 46
<212> TYPE: PRT
<213> ORGANISM: Artificial Sequence
<220> FEATURE:
<223> OTHER INFORMATION: Synthetic or recombinant sequence

<400> SEQUENCE: 317

His Ile Gln Gly Gln Ala Glu Ala Gly Ala Val Pro Gly Arg Ala Leu
1               5                   10                  15
Ala Cys Trp Asp Leu Ser Ala Pro Val Leu Pro Phe Thr Trp Asp Glu
            20                  25                  30
Gly Val Glu Ile Tyr Arg Gly Pro Asn Thr Val Val Leu Leu
        35                  40                  45

<210> SEQ ID NO 318
<211> LENGTH: 17
<212> TYPE: PRT
<213> ORGANISM: Artificial Sequence
<220> FEATURE:
<223> OTHER INFORMATION: Synthetic or recombinant sequence

<400> SEQUENCE: 318

Phe Pro Pro Pro Gly Arg Cys Gly Leu Ser Ser Leu Asp Ser His Gly 1               5                   10                  15

Leu

<210> SEQ ID NO 319
<211> LENGTH: 54
<212> TYPE: PRT
<213> ORGANISM: Artificial Sequence
<220> FEATURE:
<223> OTHER INFORMATION: Synthetic or recombinant sequence

<400> SEQUENCE: 319

His Pro Gln Val Cys Pro Pro Gln Gly Tyr Leu Gly Gln Val Met Glu
1               5                   10                  15

Gln Gly Gln Pro His Pro Leu His Pro His Ser Leu Gln His Arg Ala
            20                  25                  30

Pro Ile Val Gly Val Pro Gly Pro Gln Ala Trp Leu Leu Pro Leu Leu
        35                  40                  45

Glu Pro Asn Ser Gly Lys
    50

<210> SEQ ID NO 320
<211> LENGTH: 29
<212> TYPE: PRT
<213> ORGANISM: Artificial Sequence
<220> FEATURE:
<223> OTHER INFORMATION: Synthetic or recombinant sequence

<400> SEQUENCE: 320

Lys Lys Arg Ala Ser Pro Leu Leu Gly Arg Thr Pro Leu Ala Thr Arg
1               5                   10                  15

Ile Arg Glu Thr Leu Ala His His Leu Cys Tyr Gln Lys
            20                  25

<210> SEQ ID NO 321
<211> LENGTH: 24
<212> TYPE: PRT
<213> ORGANISM: Artificial Sequence
<220> FEATURE:
<223> OTHER INFORMATION: Synthetic or recombinant sequence

<400> SEQUENCE: 321

Ile Pro Ser Trp Gly Arg Ser Phe Tyr Cys Gly Asn Val Leu Pro Ser
1               5                   10                  15

Tyr His Ser Glu Trp Trp Gln Leu
            20

<210> SEQ ID NO 322
<211> LENGTH: 29
<212> TYPE: PRT
<213> ORGANISM: Artificial Sequence
<220> FEATURE:
<223> OTHER INFORMATION: Synthetic or recombinant sequence

<400> SEQUENCE: 322

Gly Leu Phe His Ala Arg Ile Ser Val Gln Glu Gln Tyr Gln Gly Glu
1               5                   10                  15

Leu Pro Leu Leu Gly Gly Lys Cys Gly Glu Arg Ser Leu
            20                  25

<210> SEQ ID NO 323
<211> LENGTH: 25
<212> TYPE: PRT
<213> ORGANISM: Artificial Sequence

```
<220> FEATURE:
<223> OTHER INFORMATION: Synthetic or recombinant sequence

<400> SEQUENCE: 323

Gly Val Asn Gly Ala Arg Arg Asn Ser Arg Ile Gly Glu Phe Arg Lys
1               5                   10                  15

Val Thr Ile Phe Leu Thr Ala Arg Val
            20                  25

<210> SEQ ID NO 324
<211> LENGTH: 52
<212> TYPE: PRT
<213> ORGANISM: Artificial Sequence
<220> FEATURE:
<223> OTHER INFORMATION: Synthetic or recombinant sequence

<400> SEQUENCE: 324

Val Thr Ala Gly Tyr Gln Glu Glu Met Glu Ala Ser Ala Cys Gly
1               5                   10                  15

Ala Lys Gly Pro Gly Leu Ala Pro Trp Pro Pro Ser Trp Leu Ala Leu
            20                  25                  30

Gln Asp Ser Leu Leu Cys Val Val Ala Leu Ala Asp Leu Arg Arg
        35                  40                  45

Lys Ser Cys Cys
    50

<210> SEQ ID NO 325
<211> LENGTH: 18
<212> TYPE: PRT
<213> ORGANISM: Artificial Sequence
<220> FEATURE:
<223> OTHER INFORMATION: Synthetic or recombinant sequence

<400> SEQUENCE: 325

Ser Leu Ser Leu Ser Phe Leu His Arg Trp Met Asp Lys Thr Val Gly
1               5                   10                  15

Thr Ile

<210> SEQ ID NO 326
<211> LENGTH: 59
<212> TYPE: PRT
<213> ORGANISM: Artificial Sequence
<220> FEATURE:
<223> OTHER INFORMATION: Synthetic or recombinant sequence

<400> SEQUENCE: 326

Thr Leu Cys Met Glu Val Met Leu Arg Trp Asn Thr Arg Glu Leu Gly
1               5                   10                  15

Tyr Leu Tyr Leu Gln Leu Cys Phe Leu Asn Thr His Phe Leu His Thr
            20                  25                  30

Ser Gln Glu Glu Lys Leu Leu Thr Leu Gly Arg Phe Leu Thr Trp Thr
        35                  40                  45

Ser Arg Cys Gly Ser Phe Val Ile Arg Pro Leu
    50                  55

<210> SEQ ID NO 327
<211> LENGTH: 37
<212> TYPE: PRT
<213> ORGANISM: Artificial Sequence
<220> FEATURE:
<223> OTHER INFORMATION: Synthetic or recombinant sequence

<400> SEQUENCE: 327
```

Arg Val Tyr Ser Lys Leu Glu Asn Gln Lys Ala Ala Lys Glu Gly Gly
1               5                   10                  15

Asn Thr Gln Val Lys Arg Lys Gly Gly His Arg Ala Ser Ala Phe Ser
                20                  25                  30

Lys Gln Ser Arg Arg
        35

<210> SEQ ID NO 328
<211> LENGTH: 33
<212> TYPE: PRT
<213> ORGANISM: Artificial Sequence
<220> FEATURE:
<223> OTHER INFORMATION: Synthetic or recombinant sequence

<400> SEQUENCE: 328

Ala Lys Glu Gln Ala Ala Ala Glu Ala Ala Glu Glu Gln Ala Ala Ala
1               5                   10                  15

Cys Arg Cys Gly Ser Gln Pro Val Ser Leu Cys Gln Cys Gln Lys Ile
                20                  25                  30

Leu

<210> SEQ ID NO 329
<211> LENGTH: 42
<212> TYPE: PRT
<213> ORGANISM: Artificial Sequence
<220> FEATURE:
<223> OTHER INFORMATION: Synthetic or recombinant sequence

<400> SEQUENCE: 329

Arg Gln Lys Lys Ile Arg Pro Pro Lys Lys Arg Ser Ile Gln Gly
1               5                   10                  15

Gln Arg Gln Lys Pro Pro Arg Asp His Arg Cys Glu Cys Asp Gln Leu
                20                  25                  30

Phe Cys Phe Phe Trp Trp Gly Gly Asn Pro
        35                  40

<210> SEQ ID NO 330
<211> LENGTH: 43
<212> TYPE: PRT
<213> ORGANISM: Artificial Sequence
<220> FEATURE:
<223> OTHER INFORMATION: Synthetic or recombinant sequence

<400> SEQUENCE: 330

Leu Leu Cys Val Val Phe Gly Lys Phe Val Ile Pro Arg Ser Thr Phe
1               5                   10                  15

Arg His Thr Gly Cys His Ser Glu Tyr Phe Val Phe Asn Phe Trp Thr
                20                  25                  30

Phe Tyr Phe Asn Pro Cys Ser Cys Ile Ser Glu
        35                  40

<210> SEQ ID NO 331
<211> LENGTH: 25
<212> TYPE: PRT
<213> ORGANISM: Artificial Sequence
<220> FEATURE:
<223> OTHER INFORMATION: Synthetic or recombinant sequence

<400> SEQUENCE: 331

Leu Lys Ser Ala Pro Leu Gln Ala Thr Thr Thr Leu Lys Leu Ile Pro
1               5                   10                  15

```
Val Met Arg Gly Thr Ala Thr Glu Leu
        20                  25
```

<210> SEQ ID NO 332
<211> LENGTH: 12
<212> TYPE: PRT
<213> ORGANISM: Artificial Sequence
<220> FEATURE:
<223> OTHER INFORMATION: Synthetic or recombinant sequence

<400> SEQUENCE: 332

```
Val Leu Pro Asn Leu Pro Ser Gln Ser Ser Thr Phe
1               5                   10
```

<210> SEQ ID NO 333
<211> LENGTH: 24
<212> TYPE: PRT
<213> ORGANISM: Artificial Sequence
<220> FEATURE:
<223> OTHER INFORMATION: Synthetic or recombinant sequence

<400> SEQUENCE: 333

```
Ser Ala Ser Thr Glu Ser Asn Ser Ser Glu Lys Gln Ile Cys Lys Ala
1               5                   10                  15

Glu Gly Arg Leu Glu Lys Cys Leu
            20
```

<210> SEQ ID NO 334
<211> LENGTH: 30
<212> TYPE: PRT
<213> ORGANISM: Artificial Sequence
<220> FEATURE:
<223> OTHER INFORMATION: Synthetic or recombinant sequence

<400> SEQUENCE: 334

```
Gln Ser Arg Ile Pro Ser Lys Lys Cys Ser Leu Arg Lys Ser Thr Lys
1               5                   10                  15

Ser Tyr Lys Ser Cys Thr Asn Leu Arg Asn Leu Ala Pro Thr
            20                  25                  30
```

<210> SEQ ID NO 335
<211> LENGTH: 85
<212> TYPE: PRT
<213> ORGANISM: Artificial Sequence
<220> FEATURE:
<223> OTHER INFORMATION: Synthetic or recombinant sequence

<400> SEQUENCE: 335

```
Pro Pro His Pro Gln Val Cys Pro Leu Arg Gly Ser Gln Leu Gln Arg
1               5                   10                  15

Thr Glu Gln Gly Glu Asp His Pro Leu His Pro Leu Ser Arg Gln His
            20                  25                  30

Arg Ala Leu Val Val Gly Glu Leu Gly Pro Gln Ala Trp Pro Gln Leu
        35                  40                  45

Leu Leu Glu Pro Asn Ser Gly Lys Ser Ala Ser Arg Arg Pro Gln
    50                  55                  60

Gly Gly Pro Gln Pro Pro Lys Leu Arg Val Val Glu Ala Glu Val Gly
65                  70                  75                  80

Asp Ser Trp Lys Arg
            85
```

<210> SEQ ID NO 336
<211> LENGTH: 24

```
<212> TYPE: PRT
<213> ORGANISM: Artificial Sequence
<220> FEATURE:
<223> OTHER INFORMATION: Synthetic or recombinant sequence

<400> SEQUENCE: 336

Ile Pro Cys Trp Gly Arg Pro Phe Tyr Cys Gly Asn Val Leu Pro Ser
1               5                   10                  15

Tyr His Ser Glu Trp Trp Gln Leu
            20

<210> SEQ ID NO 337
<211> LENGTH: 11
<212> TYPE: PRT
<213> ORGANISM: Artificial Sequence
<220> FEATURE:
<223> OTHER INFORMATION: Synthetic or recombinant sequence

<400> SEQUENCE: 337

Lys Glu Gly Leu Leu His Ala Gly Ile Pro Val
1               5                   10

<210> SEQ ID NO 338
<211> LENGTH: 8
<212> TYPE: PRT
<213> ORGANISM: Artificial Sequence
<220> FEATURE:
<223> OTHER INFORMATION: Synthetic or recombinant sequence

<400> SEQUENCE: 338

Arg Val Asn Ser Asp Leu Glu Asn
1               5

<210> SEQ ID NO 339
<211> LENGTH: 23
<212> TYPE: PRT
<213> ORGANISM: Artificial Sequence
<220> FEATURE:
<223> OTHER INFORMATION: Synthetic or recombinant sequence

<400> SEQUENCE: 339

Leu Leu Cys Val Val Phe Gly Lys Phe Val Ile Ser Arg Ser Thr Phe
1               5                   10                  15

Arg His Thr Ser Cys Tyr Ser
            20

<210> SEQ ID NO 340
<211> LENGTH: 24
<212> TYPE: PRT
<213> ORGANISM: Artificial Sequence
<220> FEATURE:
<223> OTHER INFORMATION: Synthetic or recombinant sequence

<400> SEQUENCE: 340

Leu Lys Leu Ala Pro Leu Gln Val Thr Thr Thr Leu Lys Leu Ile Leu
1               5                   10                  15

Val Met Leu Glu Ile Val Thr Glu
            20

<210> SEQ ID NO 341
<211> LENGTH: 11
<212> TYPE: PRT
<213> ORGANISM: Artificial Sequence
<220> FEATURE:
<223> OTHER INFORMATION: Synthetic or recombinant sequence
```

```
<400> SEQUENCE: 341

Lys Leu Leu Asn Leu Ser Cys Gln Ser Cys Thr
1               5                   10

<210> SEQ ID NO 342
<211> LENGTH: 30
<212> TYPE: PRT
<213> ORGANISM: Artificial Sequence
<220> FEATURE:
<223> OTHER INFORMATION: Synthetic or recombinant sequence

<400> SEQUENCE: 342

Gln Ser Arg Ile Pro Ser Lys Lys Cys Ser Leu Arg Lys Ser Thr Lys
1               5                   10                  15

Ser Tyr Lys Ser Cys Thr Ser Leu Lys Ser Leu Val Pro Thr
            20                  25                  30

<210> SEQ ID NO 343
<211> LENGTH: 79
<212> TYPE: PRT
<213> ORGANISM: Artificial Sequence
<220> FEATURE:
<223> OTHER INFORMATION: Synthetic or recombinant sequence

<400> SEQUENCE: 343

His Pro Leu Val Cys Pro Ser Gln Gly Ala Leu Arg Gln Gly Thr Glu
1               5                   10                  15

Gln Gly Glu Ala His Pro Leu Arg Pro Leu Ser Pro Gln His Lys Ala
            20                  25                  30

Pro Val Val Gly Glu Gln Gly Pro Pro Val Leu Gln Gln Pro Leu Pro
        35                  40                  45

Glu Pro Asn Ser Gly Lys Ser Ala Ser Lys Arg Arg Pro Gln Gly Gly
    50                  55                  60

Pro Gln Ser Leu Lys Gln Arg Ala Leu Glu Ala Arg Ala Gly Gly
65                  70                  75

<210> SEQ ID NO 344
<211> LENGTH: 24
<212> TYPE: PRT
<213> ORGANISM: Artificial Sequence
<220> FEATURE:
<223> OTHER INFORMATION: Synthetic or recombinant sequence

<400> SEQUENCE: 344

Val Pro Gly Arg Gly Arg Pro Phe Tyr Cys Gly Asn Val Leu Pro Ser
1               5                   10                  15

Tyr His Ser Glu Trp Trp Gln Leu
            20

<210> SEQ ID NO 345
<211> LENGTH: 11
<212> TYPE: PRT
<213> ORGANISM: Artificial Sequence
<220> FEATURE:
<223> OTHER INFORMATION: Synthetic or recombinant sequence

<400> SEQUENCE: 345

Lys Lys Gly Leu Leu Asp Ala Arg Ile Pro Val
1               5                   10

<210> SEQ ID NO 346
<211> LENGTH: 32
<212> TYPE: PRT
```

<213> ORGANISM: Artificial Sequence
<220> FEATURE:
<223> OTHER INFORMATION: Synthetic or recombinant sequence

<400> SEQUENCE: 346

Arg Val Tyr Ser Glu Leu Glu Asn Gln Lys Ala Ala Lys Glu Gly Gly
1               5                   10                  15

Asn Phe Gln Val Lys Gly Lys Ser Arg Glu Pro Ile Ser Thr Leu Ser
            20                  25                  30

<210> SEQ ID NO 347
<211> LENGTH: 23
<212> TYPE: PRT
<213> ORGANISM: Artificial Sequence
<220> FEATURE:
<223> OTHER INFORMATION: Synthetic or recombinant sequence

<400> SEQUENCE: 347

Leu Leu Cys Val Val Ser Gly Lys Phe Val Val Ser Arg Ser Thr Phe
1               5                   10                  15

Arg His Thr Gly Cys Tyr Ser
            20

<210> SEQ ID NO 348
<211> LENGTH: 12
<212> TYPE: PRT
<213> ORGANISM: Artificial Sequence
<220> FEATURE:
<223> OTHER INFORMATION: Synthetic or recombinant sequence

<400> SEQUENCE: 348

Ile Leu Leu Asn Leu Ser Ser Glu Ser Cys Thr Phe
1               5                   10

<210> SEQ ID NO 349
<211> LENGTH: 11
<212> TYPE: PRT
<213> ORGANISM: Artificial Sequence
<220> FEATURE:
<223> OTHER INFORMATION: Synthetic or recombinant sequence

<400> SEQUENCE: 349

Met Asp Val Thr Val Ser Glu Leu Leu Glu Asn
1               5                   10

<210> SEQ ID NO 350
<211> LENGTH: 11
<212> TYPE: PRT
<213> ORGANISM: Artificial Sequence
<220> FEATURE:
<223> OTHER INFORMATION: Synthetic or recombinant sequence

<400> SEQUENCE: 350

Met Phe Arg Ala Ala Ala Pro Gly Gln Leu Ser
1               5                   10

<210> SEQ ID NO 351
<211> LENGTH: 11
<212> TYPE: PRT
<213> ORGANISM: Artificial Sequence
<220> FEATURE:
<223> OTHER INFORMATION: Synthetic or recombinant sequence

<400> SEQUENCE: 351

Met Pro Ala Gly Pro Val Gln Ala Val Pro Ser
1               5                   10

```
<210> SEQ ID NO 352
<211> LENGTH: 11
<212> TYPE: PRT
<213> ORGANISM: Artificial Sequence
<220> FEATURE:
<223> OTHER INFORMATION: Synthetic or recombinant sequence

<400> SEQUENCE: 352

Met Ala Ser Trp Gly Gly Glu Lys Arg Gly Leu
1               5                   10

<210> SEQ ID NO 353
<211> LENGTH: 11
<212> TYPE: PRT
<213> ORGANISM: Artificial Sequence
<220> FEATURE:
<223> OTHER INFORMATION: Synthetic or recombinant sequence

<400> SEQUENCE: 353

Met Thr Leu Arg Leu Leu Val Ala Ala Leu Ala
1               5                   10

<210> SEQ ID NO 354
<211> LENGTH: 11
<212> TYPE: PRT
<213> ORGANISM: Artificial Sequence
<220> FEATURE:
<223> OTHER INFORMATION: Synthetic or recombinant sequence

<400> SEQUENCE: 354

Met Ala Thr Gln Gln Lys Ala Ser Asp Glu Gly
1               5                   10

<210> SEQ ID NO 355
<211> LENGTH: 11
<212> TYPE: PRT
<213> ORGANISM: Artificial Sequence
<220> FEATURE:
<223> OTHER INFORMATION: Synthetic or recombinant sequence

<400> SEQUENCE: 355

Met Thr Pro Val Arg Met Gln His Ser Leu Arg
1               5                   10

<210> SEQ ID NO 356
<211> LENGTH: 11
<212> TYPE: PRT
<213> ORGANISM: Artificial Sequence
<220> FEATURE:
<223> OTHER INFORMATION: Synthetic or recombinant sequence

<400> SEQUENCE: 356

Met Thr Pro Val Arg Met Gln His Ser Leu Arg
1               5                   10

<210> SEQ ID NO 357
<211> LENGTH: 11
<212> TYPE: PRT
<213> ORGANISM: Artificial Sequence
<220> FEATURE:
<223> OTHER INFORMATION: Synthetic or recombinant sequence

<400> SEQUENCE: 357

Met Gly Ser Lys Ile Tyr Ser Tyr Glu Phe Val
1               5                   10
```

```
<210> SEQ ID NO 358
<211> LENGTH: 11
<212> TYPE: PRT
<213> ORGANISM: Artificial Sequence
<220> FEATURE:
<223> OTHER INFORMATION: Synthetic or recombinant sequence

<400> SEQUENCE: 358

Met Glu Glu Asp Glu Phe Ile Gly Glu Lys Val
1               5                   10

<210> SEQ ID NO 359
<211> LENGTH: 12
<212> TYPE: PRT
<213> ORGANISM: Artificial Sequence
<220> FEATURE:
<223> OTHER INFORMATION: Synthetic or recombinant sequence

<400> SEQUENCE: 359

Met Ala Glu Gly Ser Arg Ile Pro Gln Ala Gly Phe
1               5                   10

<210> SEQ ID NO 360
<211> LENGTH: 12
<212> TYPE: PRT
<213> ORGANISM: Artificial Sequence
<220> FEATURE:
<223> OTHER INFORMATION: Synthetic or recombinant sequence

<400> SEQUENCE: 360

Met Ala Ser Lys Lys Arg Glu Val Gln Leu Ile Ile
1               5                   10

<210> SEQ ID NO 361
<211> LENGTH: 12
<212> TYPE: PRT
<213> ORGANISM: Artificial Sequence
<220> FEATURE:
<223> OTHER INFORMATION: Synthetic or recombinant sequence

<400> SEQUENCE: 361

Met Asp Ala Pro Lys Ala Gly Tyr Ala Phe Glu Ile
1               5                   10

<210> SEQ ID NO 362
<211> LENGTH: 12
<212> TYPE: PRT
<213> ORGANISM: Artificial Sequence
<220> FEATURE:
<223> OTHER INFORMATION: Synthetic or recombinant sequence

<400> SEQUENCE: 362

Met Ala Ser Val Thr Leu Ser Glu Ala Glu Ser Ala
1               5                   10

<210> SEQ ID NO 363
<211> LENGTH: 12
<212> TYPE: PRT
<213> ORGANISM: Artificial Sequence
<220> FEATURE:
<223> OTHER INFORMATION: Synthetic or recombinant sequence

<400> SEQUENCE: 363

Met Ser Asp Val Glu Glu Asn Asn Phe Glu Val Phe
1               5                   10
```

<210> SEQ ID NO 364
<211> LENGTH: 12
<212> TYPE: PRT
<213> ORGANISM: Artificial Sequence
<220> FEATURE:
<223> OTHER INFORMATION: Synthetic or recombinant sequence

<400> SEQUENCE: 364

Met Gly Asp Glu Met Asp Ala Met Ile Pro Ala Pro
1               5                   10

<210> SEQ ID NO 365
<211> LENGTH: 12
<212> TYPE: PRT
<213> ORGANISM: Artificial Sequence
<220> FEATURE:
<223> OTHER INFORMATION: Synthetic or recombinant sequence

<400> SEQUENCE: 365

Met Ala Phe Gly Glu Val Glu His Thr Asp Asp Ala
1               5                   10

<210> SEQ ID NO 366
<211> LENGTH: 12
<212> TYPE: PRT
<213> ORGANISM: Artificial Sequence
<220> FEATURE:
<223> OTHER INFORMATION: Synthetic or recombinant sequence

<400> SEQUENCE: 366

Met Arg Ala Arg Leu Arg Phe Leu Pro Ser Asp Cys
1               5                   10

<210> SEQ ID NO 367
<211> LENGTH: 12
<212> TYPE: PRT
<213> ORGANISM: Artificial Sequence
<220> FEATURE:
<223> OTHER INFORMATION: Synthetic or recombinant sequence

<400> SEQUENCE: 367

Met Val Met Gly Leu Gly Val Leu Leu Leu His Leu
1               5                   10

<210> SEQ ID NO 368
<211> LENGTH: 12
<212> TYPE: PRT
<213> ORGANISM: Artificial Sequence
<220> FEATURE:
<223> OTHER INFORMATION: Synthetic or recombinant sequence

<400> SEQUENCE: 368

Met Ala Gly Gln Phe Arg Ser Tyr Val Trp Trp Ser
1               5                   10

<210> SEQ ID NO 369
<211> LENGTH: 13
<212> TYPE: PRT
<213> ORGANISM: Artificial Sequence
<220> FEATURE:
<223> OTHER INFORMATION: Synthetic or recombinant sequence

<400> SEQUENCE: 369

Met Leu Arg Val Leu Cys Leu Leu Arg Pro Asp Leu Pro
1               5                   10

<210> SEQ ID NO 370

```
<211> LENGTH: 13
<212> TYPE: PRT
<213> ORGANISM: Artificial Sequence
<220> FEATURE:
<223> OTHER INFORMATION: Synthetic or recombinant sequence

<400> SEQUENCE: 370

Met Ala Thr Leu Lys Glu Lys Leu Ile Ala Gly Ser Phe
1               5                   10

<210> SEQ ID NO 371
<211> LENGTH: 13
<212> TYPE: PRT
<213> ORGANISM: Artificial Sequence
<220> FEATURE:
<223> OTHER INFORMATION: Synthetic or recombinant sequence

<400> SEQUENCE: 371

Met Asp Gln Cys Val Thr Val Glu Arg Glu Asp Ser Leu
1               5                   10

<210> SEQ ID NO 372
<211> LENGTH: 13
<212> TYPE: PRT
<213> ORGANISM: Artificial Sequence
<220> FEATURE:
<223> OTHER INFORMATION: Synthetic or recombinant sequence

<400> SEQUENCE: 372

Met Tyr Phe Leu Asn Asp Ala Leu Cys Ala Gly Lys Gln
1               5                   10

<210> SEQ ID NO 373
<211> LENGTH: 13
<212> TYPE: PRT
<213> ORGANISM: Artificial Sequence
<220> FEATURE:
<223> OTHER INFORMATION: Synthetic or recombinant sequence

<400> SEQUENCE: 373

Met Ala Glu Arg Gly Gly Trp Arg Glu Ala Asp Ser Arg
1               5                   10

<210> SEQ ID NO 374
<211> LENGTH: 13
<212> TYPE: PRT
<213> ORGANISM: Artificial Sequence
<220> FEATURE:
<223> OTHER INFORMATION: Synthetic or recombinant sequence

<400> SEQUENCE: 374

Met Gly Gly Gly Pro Ala Arg Glu Lys Gly Pro Thr Leu
1               5                   10

<210> SEQ ID NO 375
<211> LENGTH: 13
<212> TYPE: PRT
<213> ORGANISM: Artificial Sequence
<220> FEATURE:
<223> OTHER INFORMATION: Synthetic or recombinant sequence

<400> SEQUENCE: 375

Met Ala Val Ala Arg Ala Gly Val Leu Gly Asp Arg Pro
1               5                   10

<210> SEQ ID NO 376
<211> LENGTH: 14
```

```
<212> TYPE: PRT
<213> ORGANISM: Artificial Sequence
<220> FEATURE:
<223> OTHER INFORMATION: Synthetic or recombinant sequence

<400> SEQUENCE: 376

Met Ala Ala Lys Thr Pro Ser Ser Glu Glu Leu Cys Trp Pro
1               5                   10

<210> SEQ ID NO 377
<211> LENGTH: 14
<212> TYPE: PRT
<213> ORGANISM: Artificial Sequence
<220> FEATURE:
<223> OTHER INFORMATION: Synthetic or recombinant sequence

<400> SEQUENCE: 377

Met Ala Asp Glu Ala Thr Arg Arg Val Val Gly Asn Pro His
1               5                   10

<210> SEQ ID NO 378
<211> LENGTH: 14
<212> TYPE: PRT
<213> ORGANISM: Artificial Sequence
<220> FEATURE:
<223> OTHER INFORMATION: Synthetic or recombinant sequence

<400> SEQUENCE: 378

Met Ala Glu Glu Gln Glu Phe Thr Gln Leu Arg Asp Gln Val
1               5                   10

<210> SEQ ID NO 379
<211> LENGTH: 14
<212> TYPE: PRT
<213> ORGANISM: Artificial Sequence
<220> FEATURE:
<223> OTHER INFORMATION: Synthetic or recombinant sequence

<400> SEQUENCE: 379

Met Ser Ala Ser Leu Val Arg Ala Thr Val Asp Ser Gln Arg
1               5                   10

<210> SEQ ID NO 380
<211> LENGTH: 14
<212> TYPE: PRT
<213> ORGANISM: Artificial Sequence
<220> FEATURE:
<223> OTHER INFORMATION: Synthetic or recombinant sequence

<400> SEQUENCE: 380

Met Pro His Ile Asp Asn Asp Val Lys Leu Gly Ala Asp Lys
1               5                   10

<210> SEQ ID NO 381
<211> LENGTH: 14
<212> TYPE: PRT
<213> ORGANISM: Artificial Sequence
<220> FEATURE:
<223> OTHER INFORMATION: Synthetic or recombinant sequence

<400> SEQUENCE: 381

Met Ala Ser Ala Lys Ser Leu Asp Arg Trp Phe Cys Thr Glu
1               5                   10

<210> SEQ ID NO 382
<211> LENGTH: 14
<212> TYPE: PRT
```

```
<213> ORGANISM: Artificial Sequence
<220> FEATURE:
<223> OTHER INFORMATION: Synthetic or recombinant sequence

<400> SEQUENCE: 382

Met Arg Thr Gly Ser Arg Ala Pro Ser Glu Val Ser Arg Val
1               5                   10

<210> SEQ ID NO 383
<211> LENGTH: 14
<212> TYPE: PRT
<213> ORGANISM: Artificial Sequence
<220> FEATURE:
<223> OTHER INFORMATION: Synthetic or recombinant sequence

<400> SEQUENCE: 383

Met Arg Arg Pro Arg Leu Pro Ala Gln Ala Val Leu Glu Met
1               5                   10

<210> SEQ ID NO 384
<211> LENGTH: 14
<212> TYPE: PRT
<213> ORGANISM: Artificial Sequence
<220> FEATURE:
<223> OTHER INFORMATION: Synthetic or recombinant sequence

<400> SEQUENCE: 384

Met Tyr Phe His Lys Lys Pro Pro Ala Leu Gly Met Cys Phe
1               5                   10

<210> SEQ ID NO 385
<211> LENGTH: 14
<212> TYPE: PRT
<213> ORGANISM: Artificial Sequence
<220> FEATURE:
<223> OTHER INFORMATION: Synthetic or recombinant sequence

<400> SEQUENCE: 385

Met Lys Phe Gly Cys Leu Ser Phe Arg Gln Leu Gln Asn Pro
1               5                   10

<210> SEQ ID NO 386
<211> LENGTH: 14
<212> TYPE: PRT
<213> ORGANISM: Artificial Sequence
<220> FEATURE:
<223> OTHER INFORMATION: Synthetic or recombinant sequence

<400> SEQUENCE: 386

Met Lys Phe Gly Cys Leu Ser Phe Arg Gln Leu Gln Asn Pro
1               5                   10

<210> SEQ ID NO 387
<211> LENGTH: 15
<212> TYPE: PRT
<213> ORGANISM: Artificial Sequence
<220> FEATURE:
<223> OTHER INFORMATION: Synthetic or recombinant sequence

<400> SEQUENCE: 387

Met Ala Ala Ala Lys Val Ala Leu Thr Lys Leu Gly Trp Leu Arg
1               5                   10                  15

<210> SEQ ID NO 388
<211> LENGTH: 15
<212> TYPE: PRT
<213> ORGANISM: Artificial Sequence
```

```
<220> FEATURE:
<223> OTHER INFORMATION: Synthetic or recombinant sequence

<400> SEQUENCE: 388

Met His Ser Trp Glu Arg Leu Ala Val Leu Thr Leu Thr Arg Ser
1               5                   10                  15

<210> SEQ ID NO 389
<211> LENGTH: 7
<212> TYPE: PRT
<213> ORGANISM: Artificial Sequence
<220> FEATURE:
<223> OTHER INFORMATION: Synthetic or recombinant sequence

<400> SEQUENCE: 389

Met Lys Ile Ser Phe Glu Val
1               5

<210> SEQ ID NO 390
<211> LENGTH: 15
<212> TYPE: PRT
<213> ORGANISM: Artificial Sequence
<220> FEATURE:
<223> OTHER INFORMATION: Synthetic or recombinant sequence

<400> SEQUENCE: 390

Met Leu Gly Phe Ile Thr Arg Pro Pro His Gln Pro Val Ser Ser
1               5                   10                  15

<210> SEQ ID NO 391
<211> LENGTH: 15
<212> TYPE: PRT
<213> ORGANISM: Artificial Sequence
<220> FEATURE:
<223> OTHER INFORMATION: Synthetic or recombinant sequence

<400> SEQUENCE: 391

Met Leu Ser Arg Leu Leu Lys Glu His Gln Gly Phe Leu Val Trp
1               5                   10                  15

<210> SEQ ID NO 392
<211> LENGTH: 16
<212> TYPE: PRT
<213> ORGANISM: Artificial Sequence
<220> FEATURE:
<223> OTHER INFORMATION: Synthetic or recombinant sequence

<400> SEQUENCE: 392

Met Ser Glu Ser Glu Leu Gly Arg Lys Trp Leu Trp Arg Pro Arg Ala
1               5                   10                  15

<210> SEQ ID NO 393
<211> LENGTH: 16
<212> TYPE: PRT
<213> ORGANISM: Artificial Sequence
<220> FEATURE:
<223> OTHER INFORMATION: Synthetic or recombinant sequence

<400> SEQUENCE: 393

Met Gln Arg Thr Gly Gly Gly Ala Pro Arg Val Pro Leu Thr Gly Ala
1               5                   10                  15

<210> SEQ ID NO 394
<211> LENGTH: 16
<212> TYPE: PRT
<213> ORGANISM: Artificial Sequence
<220> FEATURE:
```

<223> OTHER INFORMATION: Synthetic or recombinant sequence

<400> SEQUENCE: 394

Met Met Ala Ile Arg Glu Leu Lys Val Cys Cys Arg Glu Asn Tyr Pro
1               5                   10                  15

<210> SEQ ID NO 395
<211> LENGTH: 16
<212> TYPE: PRT
<213> ORGANISM: Artificial Sequence
<220> FEATURE:
<223> OTHER INFORMATION: Synthetic or recombinant sequence

<400> SEQUENCE: 395

Met Trp Arg Ala Glu Gly Lys Trp Leu Pro Gly Met Lys Ala Thr Gly
1               5                   10                  15

<210> SEQ ID NO 396
<211> LENGTH: 16
<212> TYPE: PRT
<213> ORGANISM: Artificial Sequence
<220> FEATURE:
<223> OTHER INFORMATION: Synthetic or recombinant sequence

<400> SEQUENCE: 396

Met Gln His Arg Glu Val Arg Val Lys Cys Asn Thr Glu Lys Ser Ala
1               5                   10                  15

<210> SEQ ID NO 397
<211> LENGTH: 16
<212> TYPE: PRT
<213> ORGANISM: Artificial Sequence
<220> FEATURE:
<223> OTHER INFORMATION: Synthetic or recombinant sequence

<400> SEQUENCE: 397

Met Ala Ser Ala Ser Cys Ser Pro Gly Arg Trp Asn Asn Pro Lys Phe
1               5                   10                  15

<210> SEQ ID NO 398
<211> LENGTH: 16
<212> TYPE: PRT
<213> ORGANISM: Artificial Sequence
<220> FEATURE:
<223> OTHER INFORMATION: Synthetic or recombinant sequence

<400> SEQUENCE: 398

Met Val Gln Pro Ile Ile His Leu Gly Tyr Leu Ala Ser Lys Gly Pro
1               5                   10                  15

<210> SEQ ID NO 399
<211> LENGTH: 16
<212> TYPE: PRT
<213> ORGANISM: Artificial Sequence
<220> FEATURE:
<223> OTHER INFORMATION: Synthetic or recombinant sequence

<400> SEQUENCE: 399

Met Lys Ile Phe Val Gly Asn Val Asp Gly Gly Gly Met Cys Val Gly
1               5                   10                  15

<210> SEQ ID NO 400
<211> LENGTH: 17
<212> TYPE: PRT
<213> ORGANISM: Artificial Sequence
<220> FEATURE:
<223> OTHER INFORMATION: Synthetic or recombinant sequence

<400> SEQUENCE: 400

Met Phe Pro Gly Ser Leu Ser Arg Gly Arg His Asp Val Ala Ile Lys
1               5                   10                  15

Ser

<210> SEQ ID NO 401
<211> LENGTH: 17
<212> TYPE: PRT
<213> ORGANISM: Artificial Sequence
<220> FEATURE:
<223> OTHER INFORMATION: Synthetic or recombinant sequence

<400> SEQUENCE: 401

Met Ala Ser Val Thr Leu Ser Glu Ala Glu Cys Cys Glu His Lys Asp
1               5                   10                  15

Val

<210> SEQ ID NO 402
<211> LENGTH: 17
<212> TYPE: PRT
<213> ORGANISM: Artificial Sequence
<220> FEATURE:
<223> OTHER INFORMATION: Synthetic or recombinant sequence

<400> SEQUENCE: 402

Met Arg Thr Thr Lys Val Tyr Lys Leu Val Leu Trp Ser Gly Val Ser
1               5                   10                  15

Leu

<210> SEQ ID NO 403
<211> LENGTH: 17
<212> TYPE: PRT
<213> ORGANISM: Artificial Sequence
<220> FEATURE:
<223> OTHER INFORMATION: Synthetic or recombinant sequence

<400> SEQUENCE: 403

Met Ala Ala Ser Gly Ser Gly Met Ala Gln Val Thr Met Gly Lys Ala
1               5                   10                  15

Ala

<210> SEQ ID NO 404
<211> LENGTH: 17
<212> TYPE: PRT
<213> ORGANISM: Artificial Sequence
<220> FEATURE:
<223> OTHER INFORMATION: Synthetic or recombinant sequence

<400> SEQUENCE: 404

Met Ala Ala Leu Met Thr Pro Gly Thr Gly Ala Ser Asp Pro Cys Cys
1               5                   10                  15

Cys

<210> SEQ ID NO 405
<211> LENGTH: 17
<212> TYPE: PRT
<213> ORGANISM: Artificial Sequence
<220> FEATURE:
<223> OTHER INFORMATION: Synthetic or recombinant sequence

<400> SEQUENCE: 405

Met Ala Gly Leu Lys Arg Arg Ala Ser Gln Ala Pro Ser Gly Leu Gly

-continued

```
                1               5                  10                 15
Leu

<210> SEQ ID NO 406
<211> LENGTH: 17
<212> TYPE: PRT
<213> ORGANISM: Artificial Sequence
<220> FEATURE:
<223> OTHER INFORMATION: Synthetic or recombinant sequence

<400> SEQUENCE: 406

Met Ala Ala Leu Met Thr Pro Gly Thr Gly Ala Ser Asp Pro Cys Cys
1               5                   10                  15
Cys

<210> SEQ ID NO 407
<211> LENGTH: 17
<212> TYPE: PRT
<213> ORGANISM: Artificial Sequence
<220> FEATURE:
<223> OTHER INFORMATION: Synthetic or recombinant sequence

<400> SEQUENCE: 407

Met Trp Asn Ala Ala Leu Pro Gly Pro Thr His Gly Cys Leu Leu Ile
1               5                   10                  15
Pro

<210> SEQ ID NO 408
<211> LENGTH: 18
<212> TYPE: PRT
<213> ORGANISM: Artificial Sequence
<220> FEATURE:
<223> OTHER INFORMATION: Synthetic or recombinant sequence

<400> SEQUENCE: 408

Met Arg Leu Thr His Ile Cys Cys Cys Glu Arg Arg Lys Cys Arg
1               5                   10                  15
Asn His

<210> SEQ ID NO 409
<211> LENGTH: 18
<212> TYPE: PRT
<213> ORGANISM: Artificial Sequence
<220> FEATURE:
<223> OTHER INFORMATION: Synthetic or recombinant sequence

<400> SEQUENCE: 409

Met Trp Asn Pro Asn Ala Gly Gly Pro Pro Phe Leu Ala Phe Thr Pro
1               5                   10                  15
Asn Gln

<210> SEQ ID NO 410
<211> LENGTH: 18
<212> TYPE: PRT
<213> ORGANISM: Artificial Sequence
<220> FEATURE:
<223> OTHER INFORMATION: Synthetic or recombinant sequence

<400> SEQUENCE: 410

Met Ala Asn Glu Thr Leu Phe Ser Ser Pro Ser Leu Met Pro Met Gln
1               5                   10                  15
Val Thr
```

<210> SEQ ID NO 411
<211> LENGTH: 18
<212> TYPE: PRT
<213> ORGANISM: Artificial Sequence
<220> FEATURE:
<223> OTHER INFORMATION: Synthetic or recombinant sequence

<400> SEQUENCE: 411

Met Ser Arg Pro Gln Leu Arg Arg Trp Arg Lys Phe Pro Arg Gln Leu
1               5                   10                  15

Gln Thr

<210> SEQ ID NO 412
<211> LENGTH: 18
<212> TYPE: PRT
<213> ORGANISM: Artificial Sequence
<220> FEATURE:
<223> OTHER INFORMATION: Synthetic or recombinant sequence

<400> SEQUENCE: 412

Met Ala Ala Ser Ala Phe Ala Gly Ala Val Ser Arg Gly Phe Gly Gly
1               5                   10                  15

Arg Gly

<210> SEQ ID NO 413
<211> LENGTH: 19
<212> TYPE: PRT
<213> ORGANISM: Artificial Sequence
<220> FEATURE:
<223> OTHER INFORMATION: Synthetic or recombinant sequence

<400> SEQUENCE: 413

Met Pro Pro Ala Ala Pro Ala Arg Leu Ala Val Asp Gly Arg Met Ala
1               5                   10                  15

Thr Trp Met

<210> SEQ ID NO 414
<211> LENGTH: 19
<212> TYPE: PRT
<213> ORGANISM: Artificial Sequence
<220> FEATURE:
<223> OTHER INFORMATION: Synthetic or recombinant sequence

<400> SEQUENCE: 414

Leu Pro Thr Gly Phe Val Ala Pro Ile Leu Lys Ser Leu Gly Leu Lys
1               5                   10                  15

Met Met Leu

<210> SEQ ID NO 415
<211> LENGTH: 19
<212> TYPE: PRT
<213> ORGANISM: Artificial Sequence
<220> FEATURE:
<223> OTHER INFORMATION: Synthetic or recombinant sequence

<400> SEQUENCE: 415

Met Ser Gln Val Lys Ser Ser Tyr Ser Tyr Met Glu Met Cys Gly Met
1               5                   10                  15

His Met Ser

<210> SEQ ID NO 416
<211> LENGTH: 19
<212> TYPE: PRT

<213> ORGANISM: Artificial Sequence
<220> FEATURE:
<223> OTHER INFORMATION: Synthetic or recombinant sequence

<400> SEQUENCE: 416

Met Asn Gly Lys Arg Pro Ala Glu Pro Gly Pro Arg Lys Lys Leu Ser
1               5                   10                  15

Pro Leu Ala

<210> SEQ ID NO 417
<211> LENGTH: 19
<212> TYPE: PRT
<213> ORGANISM: Artificial Sequence
<220> FEATURE:
<223> OTHER INFORMATION: Synthetic or recombinant sequence

<400> SEQUENCE: 417

Met Ser Asn Pro Gly Gly Arg Arg Asn Gly Val Leu Ser Arg Val Met
1               5                   10                  15

Thr Thr Pro

<210> SEQ ID NO 418
<211> LENGTH: 22
<212> TYPE: PRT
<213> ORGANISM: Artificial Sequence
<220> FEATURE:
<223> OTHER INFORMATION: Synthetic or recombinant sequence

<400> SEQUENCE: 418

Met Ser Lys Pro His Ser Glu Ala Gly Thr Gly Ser Ala Asn Ile Gln
1               5                   10                  15

Glu Glu Glu Val Cys Arg
            20

<210> SEQ ID NO 419
<211> LENGTH: 22
<212> TYPE: PRT
<213> ORGANISM: Artificial Sequence
<220> FEATURE:
<223> OTHER INFORMATION: Synthetic or recombinant sequence

<400> SEQUENCE: 419

Met Ala Gly Arg Pro Gly Ser Gln Glu Gln Ser Ile Gly His Ile Ser
1               5                   10                  15

Thr Met Leu Met Ala Phe
            20

<210> SEQ ID NO 420
<211> LENGTH: 22
<212> TYPE: PRT
<213> ORGANISM: Artificial Sequence
<220> FEATURE:
<223> OTHER INFORMATION: Synthetic or recombinant sequence

<400> SEQUENCE: 420

Met Gly Asn Ser Ala Leu Arg Ala His Val Ser Ala Leu Ser Val Ile
1               5                   10                  15

Arg Phe Ile Cys Gly Phe
            20

<210> SEQ ID NO 421
<211> LENGTH: 23
<212> TYPE: PRT
<213> ORGANISM: Artificial Sequence

```
<220> FEATURE:
<223> OTHER INFORMATION: Synthetic or recombinant sequence

<400> SEQUENCE: 421

Met Lys Lys Arg Lys Glu Leu Asn Ala Leu Arg Cys Leu Gly Glu Thr
1               5                   10                  15

Val Cys Glu Gln Arg Ile His
            20

<210> SEQ ID NO 422
<211> LENGTH: 23
<212> TYPE: PRT
<213> ORGANISM: Artificial Sequence
<220> FEATURE:
<223> OTHER INFORMATION: Synthetic or recombinant sequence

<400> SEQUENCE: 422

Met Gly Asp Lys Ile Trp Leu Pro Phe Pro Ile Lys Leu Tyr Pro Thr
1               5                   10                  15

Ser Ser Lys Thr Thr Lys Glu
            20

<210> SEQ ID NO 423
<211> LENGTH: 23
<212> TYPE: PRT
<213> ORGANISM: Artificial Sequence
<220> FEATURE:
<223> OTHER INFORMATION: Synthetic or recombinant sequence

<400> SEQUENCE: 423

Met Arg Thr Leu Pro Leu Arg Phe Ala Gly Tyr Phe Asn Ser Arg Pro
1               5                   10                  15

His Leu Cys Pro Ala Gly Ser
            20

<210> SEQ ID NO 424
<211> LENGTH: 23
<212> TYPE: PRT
<213> ORGANISM: Artificial Sequence
<220> FEATURE:
<223> OTHER INFORMATION: Synthetic or recombinant sequence

<400> SEQUENCE: 424

Met Glu Ala Ala Arg Arg Pro Arg Leu Gly Tyr Phe Asn Ser Arg Pro
1               5                   10                  15

His Leu Cys Pro Ala Gly Ser
            20

<210> SEQ ID NO 425
<211> LENGTH: 23
<212> TYPE: PRT
<213> ORGANISM: Artificial Sequence
<220> FEATURE:
<223> OTHER INFORMATION: Synthetic or recombinant sequence

<400> SEQUENCE: 425

Met Ser Leu Pro Leu Asn Pro Lys Pro Phe Gln Asp Phe His Leu His
1               5                   10                  15

Leu Gly Asn Ile Glu Thr Lys
            20

<210> SEQ ID NO 426
<211> LENGTH: 24
<212> TYPE: PRT
```

-continued

```
<213> ORGANISM: Artificial Sequence
<220> FEATURE:
<223> OTHER INFORMATION: Synthetic or recombinant sequence

<400> SEQUENCE: 426

Met Ser Ala Glu Val Ile His Gln Val Glu Asp Ile Leu Leu Ser Ala
1               5                   10                  15

Gly Arg Ala Asp Leu Leu Ala Val
            20

<210> SEQ ID NO 427
<211> LENGTH: 24
<212> TYPE: PRT
<213> ORGANISM: Artificial Sequence
<220> FEATURE:
<223> OTHER INFORMATION: Synthetic or recombinant sequence

<400> SEQUENCE: 427

Met Ser Thr Leu Leu Leu Asn Leu Asp Phe Gly Ser Ala Ala Lys Ala
1               5                   10                  15

Ala Asp Gly Cys Arg Thr Gly Gly
            20

<210> SEQ ID NO 428
<211> LENGTH: 21
<212> TYPE: PRT
<213> ORGANISM: Artificial Sequence
<220> FEATURE:
<223> OTHER INFORMATION: Synthetic or recombinant sequence

<400> SEQUENCE: 428

Met Ala Trp Trp Lys Ala Trp Asp Ser Gly Ile Leu Pro Leu Arg Asn
1               5                   10                  15

Ala Leu Leu Leu Gly
            20

<210> SEQ ID NO 429
<211> LENGTH: 25
<212> TYPE: PRT
<213> ORGANISM: Artificial Sequence
<220> FEATURE:
<223> OTHER INFORMATION: Synthetic or recombinant sequence

<400> SEQUENCE: 429

Met Glu Glu Gly Asn Asn Asn Glu Glu Val Val Tyr Gln Pro Gln Ser
1               5                   10                  15

Leu His Val Ser Lys Ser Ser Arg Lys
            20                  25

<210> SEQ ID NO 430
<211> LENGTH: 25
<212> TYPE: PRT
<213> ORGANISM: Artificial Sequence
<220> FEATURE:
<223> OTHER INFORMATION: Synthetic or recombinant sequence

<400> SEQUENCE: 430

Met Arg Arg Ser Ala Ala Pro Ser Gln Leu Gln Thr Trp Met Arg Arg
1               5                   10                  15

His Arg Leu Val Pro Val His Tyr Arg
            20                  25

<210> SEQ ID NO 431
<211> LENGTH: 25
```

```
<212> TYPE: PRT
<213> ORGANISM: Artificial Sequence
<220> FEATURE:
<223> OTHER INFORMATION: Synthetic or recombinant sequence

<400> SEQUENCE: 431

Met Arg Gly Arg Arg Gly Arg Pro Pro Lys Ser Phe Leu Pro Leu Ser
1               5                   10                  15

His Asn His Val His Gln Arg Glu Cys
            20                  25

<210> SEQ ID NO 432
<211> LENGTH: 26
<212> TYPE: PRT
<213> ORGANISM: Artificial Sequence
<220> FEATURE:
<223> OTHER INFORMATION: Synthetic or recombinant sequence

<400> SEQUENCE: 432

Met Gln Glu Pro Arg Arg Val Thr Pro Cys Gly Leu Gly Ala Ala Ala
1               5                   10                  15

Pro Thr Cys Arg His Gly Lys Ser Gly Ala
            20                  25

<210> SEQ ID NO 433
<211> LENGTH: 26
<212> TYPE: PRT
<213> ORGANISM: Artificial Sequence
<220> FEATURE:
<223> OTHER INFORMATION: Synthetic or recombinant sequence

<400> SEQUENCE: 433

Met Lys Gln Leu Pro Val Leu Glu Pro Gly Thr Gly Phe His Arg Val
1               5                   10                  15

Ser Gln Asp Gly Leu Asp Leu Leu Thr Ser
            20                  25

<210> SEQ ID NO 434
<211> LENGTH: 26
<212> TYPE: PRT
<213> ORGANISM: Artificial Sequence
<220> FEATURE:
<223> OTHER INFORMATION: Synthetic or recombinant sequence

<400> SEQUENCE: 434

Met Ala Gly Ile Lys Ala Leu Ile Ser Leu Arg Val Gln Met Ser Ala
1               5                   10                  15

Ser Gly Thr Tyr Pro Ser Ser Pro Gly Leu
            20                  25

<210> SEQ ID NO 435
<211> LENGTH: 27
<212> TYPE: PRT
<213> ORGANISM: Artificial Sequence
<220> FEATURE:
<223> OTHER INFORMATION: Synthetic or recombinant sequence

<400> SEQUENCE: 435

Met Leu Gly Trp Ile Lys Arg Leu Ile Arg Ser Leu Pro Ala Gly Phe
1               5                   10                  15

Ile Gln Pro His Val Ser Lys His Cys Leu Gly
            20                  25

<210> SEQ ID NO 436
```

```
<211> LENGTH: 27
<212> TYPE: PRT
<213> ORGANISM: Artificial Sequence
<220> FEATURE:
<223> OTHER INFORMATION: Synthetic or recombinant sequence

<400> SEQUENCE: 436

Met Glu Gly Gly Gly Gly Ser Gly Asn Lys Val Ser Glu Met Ala Leu
1               5                   10                  15

Asp Ser Pro Phe Cys Val Leu Leu Ser Gly Ser
            20                  25

<210> SEQ ID NO 437
<211> LENGTH: 28
<212> TYPE: PRT
<213> ORGANISM: Artificial Sequence
<220> FEATURE:
<223> OTHER INFORMATION: Synthetic or recombinant sequence

<400> SEQUENCE: 437

Met Val Glu Leu Met Phe Pro Leu Leu Leu Trp Gln Arg Trp Arg Arg
1               5                   10                  15

Ser Tyr Val Met His Pro Cys Leu Ser Glu Thr Pro
            20                  25

<210> SEQ ID NO 438
<211> LENGTH: 28
<212> TYPE: PRT
<213> ORGANISM: Artificial Sequence
<220> FEATURE:
<223> OTHER INFORMATION: Synthetic or recombinant sequence

<400> SEQUENCE: 438

Met Ala Gly Glu Gln Lys Pro Ser Ser Asn Val Glu Thr Gly Phe His
1               5                   10                  15

Leu Val Ser Gln Asp Gly Leu Asp Leu Leu Thr Ser
            20                  25

<210> SEQ ID NO 439
<211> LENGTH: 29
<212> TYPE: PRT
<213> ORGANISM: Artificial Sequence
<220> FEATURE:
<223> OTHER INFORMATION: Synthetic or recombinant sequence

<400> SEQUENCE: 439

Met Glu Leu Asn Ser Leu Leu Ile Leu Leu Ser Arg Gln Gly Gly Ser
1               5                   10                  15

Glu Asp Pro Ala Gly Ala Ala Glu Ser Asp Gly Trp Ile
            20                  25

<210> SEQ ID NO 440
<211> LENGTH: 30
<212> TYPE: PRT
<213> ORGANISM: Artificial Sequence
<220> FEATURE:
<223> OTHER INFORMATION: Synthetic or recombinant sequence

<400> SEQUENCE: 440

Met Ala Val Tyr Val Gly Met Leu Arg Leu Arg Asn Leu Arg Lys Lys
1               5                   10                  15

Leu Gln His Gly Lys Met Asp Ser Lys Ala Pro Met Ser Cys
            20                  25                  30
```

<210> SEQ ID NO 441
<211> LENGTH: 31
<212> TYPE: PRT
<213> ORGANISM: Artificial Sequence
<220> FEATURE:
<223> OTHER INFORMATION: Synthetic or recombinant sequence

<400> SEQUENCE: 441

Met Gln Pro Gln Ser Val Leu His Ser Gly Ser Ile Val Phe Glu Ala
1               5                   10                  15

Arg Gly Asp Lys Ala Glu Ile Arg Asp Gly Ala Leu Gln Gln Gly
            20                  25                  30

<210> SEQ ID NO 442
<211> LENGTH: 32
<212> TYPE: PRT
<213> ORGANISM: Artificial Sequence
<220> FEATURE:
<223> OTHER INFORMATION: Synthetic or recombinant sequence

<400> SEQUENCE: 442

Met Ala Ala Gln Arg Arg Ser Leu Leu Gln Thr Phe Ala Thr Arg Ser
1               5                   10                  15

Tyr Cys Thr His Gln Leu His Leu Pro Thr Leu Cys Leu Gln Asn Leu
            20                  25                  30

<210> SEQ ID NO 443
<211> LENGTH: 33
<212> TYPE: PRT
<213> ORGANISM: Artificial Sequence
<220> FEATURE:
<223> OTHER INFORMATION: Synthetic or recombinant sequence

<400> SEQUENCE: 443

Met Ala Glu Ala Ser Ser Ala Asn Leu Gly Val Arg Ser Pro Ala Val
1               5                   10                  15

Gln Ser Pro Ala Lys Val Gln Pro Leu Cys Pro Ser Arg Arg Ala Ala
            20                  25                  30

Arg

<210> SEQ ID NO 444
<211> LENGTH: 33
<212> TYPE: PRT
<213> ORGANISM: Artificial Sequence
<220> FEATURE:
<223> OTHER INFORMATION: Synthetic or recombinant sequence

<400> SEQUENCE: 444

Met Ala Glu Ala Ser Ser Ala Asn Leu Gly Val Arg Ser Pro Ala Val
1               5                   10                  15

Gln Ser Pro Ala Lys Val Gln Pro Leu Cys Pro Ser Arg Arg Ala Ala
            20                  25                  30

Arg

<210> SEQ ID NO 445
<211> LENGTH: 33
<212> TYPE: PRT
<213> ORGANISM: Artificial Sequence
<220> FEATURE:
<223> OTHER INFORMATION: Synthetic or recombinant sequence

<400> SEQUENCE: 445

Met Ala Glu Ala Ser Ser Ala Asn Leu Gly Val Arg Ser Pro Ala Val
1               5                   10                  15

Gln Ser Pro Ala Lys Val Gln Pro Leu Cys Pro Ser Arg Arg Ala Ala
            20                  25                  30

Arg

<210> SEQ ID NO 446
<211> LENGTH: 37
<212> TYPE: PRT
<213> ORGANISM: Artificial Sequence
<220> FEATURE:
<223> OTHER INFORMATION: Synthetic or recombinant sequence

<400> SEQUENCE: 446

Met Lys Lys Ile Arg Ile Cys His Ile Phe Lys Cys Trp Thr Pro Trp
1               5                   10                  15

Ser Ala Met Ser Thr Leu Ser Cys Ser Met Pro Ser Ala Thr Ile Trp
            20                  25                  30

Trp Ala Gly Glu Ser
        35

<210> SEQ ID NO 447
<211> LENGTH: 37
<212> TYPE: PRT
<213> ORGANISM: Artificial Sequence
<220> FEATURE:
<223> OTHER INFORMATION: Synthetic or recombinant sequence

<400> SEQUENCE: 447

Met Asp Arg Phe Val Trp Thr Ser Gly Leu Cys Phe Trp Gly Lys Lys
1               5                   10                  15

Ser Gln Ser Gly Arg Glu Lys Gly His Glu Glu Thr Lys Asp Leu Gly
            20                  25                  30

Phe Cys Gln Ser Glu
        35

<210> SEQ ID NO 448
<211> LENGTH: 38
<212> TYPE: PRT
<213> ORGANISM: Artificial Sequence
<220> FEATURE:
<223> OTHER INFORMATION: Synthetic or recombinant sequence

<400> SEQUENCE: 448

Met Ala Arg Phe Trp Val Cys Val Ala Gly Phe Gln Gly Gly Leu Gln
1               5                   10                  15

Ser Ser Ser Cys Tyr Asp Ile Phe Leu Trp Asn Asn Pro Arg Lys Ser
            20                  25                  30

Ile Ser Gln Arg Lys Thr
        35

<210> SEQ ID NO 449
<211> LENGTH: 38
<212> TYPE: PRT
<213> ORGANISM: Artificial Sequence
<220> FEATURE:
<223> OTHER INFORMATION: Synthetic or recombinant sequence

<400> SEQUENCE: 449

Met Leu Gly Trp Ile Lys Arg Leu Ile Arg Val Pro Ser Ser Trp Leu
1               5                   10                  15

Tyr Ser Ala Pro Arg Val Gln Leu Ser Gly Ile Ala Leu Tyr Trp
            20                  25                  30

-continued

Lys Thr Trp Pro Ile Leu
        35

<210> SEQ ID NO 450
<211> LENGTH: 38
<212> TYPE: PRT
<213> ORGANISM: Artificial Sequence
<220> FEATURE:
<223> OTHER INFORMATION: Synthetic or recombinant sequence

<400> SEQUENCE: 450

Met Arg Tyr Asn Glu Lys Glu Leu Gln Ala Thr Glu Thr Pro Arg Asp
1               5                   10                  15

Pro Arg Gln Ala Cys Pro Ala Ser Gln Gly Met Leu Arg Ala Met Asp
            20                  25                  30

Ser Arg Glu Ile Gln Lys
        35

<210> SEQ ID NO 451
<211> LENGTH: 39
<212> TYPE: PRT
<213> ORGANISM: Artificial Sequence
<220> FEATURE:
<223> OTHER INFORMATION: Synthetic or recombinant sequence

<400> SEQUENCE: 451

Met Leu Gln Gln Asp Ser Asn Asp Asp Thr Glu Pro Ser Glu Met Ser
1               5                   10                  15

Cys Thr Arg Asn Phe Lys Arg Glu Phe Ser Ala Gly Arg Arg Gly Arg
            20                  25                  30

Gln Asp Ile Arg Thr Arg Ile
        35

<210> SEQ ID NO 452
<211> LENGTH: 39
<212> TYPE: PRT
<213> ORGANISM: Artificial Sequence
<220> FEATURE:
<223> OTHER INFORMATION: Synthetic or recombinant sequence

<400> SEQUENCE: 452

Met Glu Glu Ile Pro Ala Gln Glu Ala Ala Asp Phe Gln Phe Pro Ser
1               5                   10                  15

Leu Met Gly Ser Pro Ser Trp Asn Arg Ile Tyr Arg Ser Leu Ile Trp
            20                  25                  30

Lys Leu Arg Leu Glu Lys Ser
        35

<210> SEQ ID NO 453
<211> LENGTH: 40
<212> TYPE: PRT
<213> ORGANISM: Artificial Sequence
<220> FEATURE:
<223> OTHER INFORMATION: Synthetic or recombinant sequence

<400> SEQUENCE: 453

Met Val Ala Arg Pro Leu His Ser Thr Glu Arg Leu Pro Thr Thr Arg
1               5                   10                  15

Thr Leu Ala Tyr Phe Leu Lys Ile Glu Glu Lys Lys Glu Asp Arg Lys
            20                  25                  30

Arg Arg Thr Gln Arg Tyr Thr Lys
        35                  40

```
<210> SEQ ID NO 454
<211> LENGTH: 41
<212> TYPE: PRT
<213> ORGANISM: Artificial Sequence
<220> FEATURE:
<223> OTHER INFORMATION: Synthetic or recombinant sequence

<400> SEQUENCE: 454

Met Ser Val Ser Val Leu Ala Pro Ala Gly Ser Pro Ala Pro Ser Arg
1               5                   10                  15

Gly His Pro Pro Ala Leu Ala Arg Ala Ser Arg Arg Asn Leu Ala Thr
            20                  25                  30

Ser Cys Ala Leu Val Leu Trp Ala Ala
        35                  40

<210> SEQ ID NO 455
<211> LENGTH: 41
<212> TYPE: PRT
<213> ORGANISM: Artificial Sequence
<220> FEATURE:
<223> OTHER INFORMATION: Synthetic or recombinant sequence

<400> SEQUENCE: 455

Met Thr Glu Gln Met Thr Leu Arg Gly Thr Val Arg Pro Gly Trp Ser
1               5                   10                  15

Ala Val Val Arg Ser Arg Leu Thr Ala Ser Ser Ala Ser Arg Val His
            20                  25                  30

Thr Ile Leu Leu Pro Gln Pro Pro Glu
        35                  40

<210> SEQ ID NO 456
<211> LENGTH: 43
<212> TYPE: PRT
<213> ORGANISM: Artificial Sequence
<220> FEATURE:
<223> OTHER INFORMATION: Synthetic or recombinant sequence

<400> SEQUENCE: 456

Met Ile Pro Pro Gln Glu Ala Ser Ala Arg Ile Ser Pro Gly His Glu
1               5                   10                  15

His Asp Phe Arg Val Lys His Leu Ser Glu Ala Leu Asn Asp Lys His
            20                  25                  30

Gly Pro Leu Ala Gly Glu Tyr Arg Ser Pro Ala
        35                  40

<210> SEQ ID NO 457
<211> LENGTH: 43
<212> TYPE: PRT
<213> ORGANISM: Artificial Sequence
<220> FEATURE:
<223> OTHER INFORMATION: Synthetic or recombinant sequence

<400> SEQUENCE: 457

Met Ser Met Asp Val Thr Phe Leu Gly Thr Tyr Pro Glu Tyr Met Ser
1               5                   10                  15

Asn Asn Phe Pro Cys Asn Val Ser Cys Cys Phe Ser Leu Phe Pro Lys
            20                  25                  30

Asp Gln Asn Cys Phe Arg Asn Trp Arg His Ile
        35                  40

<210> SEQ ID NO 458
<211> LENGTH: 44
```

```
<212> TYPE: PRT
<213> ORGANISM: Artificial Sequence
<220> FEATURE:
<223> OTHER INFORMATION: Synthetic or recombinant sequence

<400> SEQUENCE: 458

Met Leu Ser Leu Arg Val Pro Leu Ala Pro Leu Gly Asp Arg Glu Val
1               5                   10                  15

Gln Ser Arg Trp Ser Pro Gly Pro Arg Gly Asp Ser Thr Pro Val Arg
            20                  25                  30

Glu Met Glu Thr Asn His Pro Pro Ser Val Arg Gly
        35                  40

<210> SEQ ID NO 459
<211> LENGTH: 44
<212> TYPE: PRT
<213> ORGANISM: Artificial Sequence
<220> FEATURE:
<223> OTHER INFORMATION: Synthetic or recombinant sequence

<400> SEQUENCE: 459

Met Gly Ser Ser Ala Val Gln Ser Gln Leu Trp His Phe Ser Thr Pro
1               5                   10                  15

Leu Glu Pro Met Pro Arg Arg Asn Lys Gly Cys Ala Ala Ser Pro Trp
            20                  25                  30

Leu Thr Gln Trp Pro Arg Pro Arg Lys Ser Gln Arg
        35                  40

<210> SEQ ID NO 460
<211> LENGTH: 44
<212> TYPE: PRT
<213> ORGANISM: Artificial Sequence
<220> FEATURE:
<223> OTHER INFORMATION: Synthetic or recombinant sequence

<400> SEQUENCE: 460

Met Arg Ala Arg Leu Arg Phe Leu Pro Ser Thr Gly Leu Arg Cys Ser
1               5                   10                  15

Leu Leu Cys Leu Asp Arg Pro Gly Arg Ala Arg Pro His Leu His His
            20                  25                  30

Thr Gln Cys Glu Glu Gly Leu Gly Thr His His Ser
        35                  40

<210> SEQ ID NO 461
<211> LENGTH: 45
<212> TYPE: PRT
<213> ORGANISM: Artificial Sequence
<220> FEATURE:
<223> OTHER INFORMATION: Synthetic or recombinant sequence

<400> SEQUENCE: 461

Met Lys Ile Phe Val Gly Asn Val Asp Gly Ser Cys Gln Asp Gly
1               5                   10                  15

Glu Ala Val His Arg Lys Pro Ala Pro Gly Gly Tyr Arg Ala Gly Asp
            20                  25                  30

Ser Leu Thr Leu Arg Ala Val Trp Glu Gly Ala Gly Met
        35                  40                  45

<210> SEQ ID NO 462
<211> LENGTH: 46
<212> TYPE: PRT
<213> ORGANISM: Artificial Sequence
<220> FEATURE:
```

<223> OTHER INFORMATION: Synthetic or recombinant sequence

<400> SEQUENCE: 462

Met Ala Gly Ile Ile Lys Lys Gln Ile Leu Asn Ile Leu Phe Glu Cys
1               5                   10                  15

Lys Glu Glu Phe Leu Trp Lys Thr Ala Gly Arg Leu Leu Glu Asp Thr
            20                  25                  30

Val Thr Leu Ile Cys Leu Thr Thr Ala Tyr Arg Leu Gln Ala
        35                  40                  45

<210> SEQ ID NO 463
<211> LENGTH: 46
<212> TYPE: PRT
<213> ORGANISM: Artificial Sequence
<220> FEATURE:
<223> OTHER INFORMATION: Synthetic or recombinant sequence

<400> SEQUENCE: 463

Met Leu Arg Glu Glu Ala Thr Lys Lys Ser Gly Ser Ile Asp Ile Gln
1               5                   10                  15

Gly Cys Gly His Arg Ile Leu Ser Gly Gly Val Glu Met Pro Gly Pro
            20                  25                  30

Cys Ser Glu Asp Ser Ile Gln Arg Cys Asp Val Gly Glu Leu
        35                  40                  45

<210> SEQ ID NO 464
<211> LENGTH: 46
<212> TYPE: PRT
<213> ORGANISM: Artificial Sequence
<220> FEATURE:
<223> OTHER INFORMATION: Synthetic or recombinant sequence

<400> SEQUENCE: 464

Met Ala Val Leu Trp Arg Leu Ser Ala Val Cys Leu Gln Cys Gln Ile
1               5                   10                  15

Val His Ser Cys Pro Leu Leu Glu Asn Gln Ile His Leu Ser Leu Lys
            20                  25                  30

Phe Pro Asp Tyr Phe Ile Lys Met Lys Pro Trp Arg Lys Ile
        35                  40                  45

<210> SEQ ID NO 465
<211> LENGTH: 46
<212> TYPE: PRT
<213> ORGANISM: Artificial Sequence
<220> FEATURE:
<223> OTHER INFORMATION: Synthetic or recombinant sequence

<400> SEQUENCE: 465

Met Ser Ser Glu Glu Gly Lys Leu Phe Val Leu Gly Gly Gly Gly Gln
1               5                   10                  15

Arg Gln Thr Glu Pro Gly Arg Leu Gly Gly Asp Asp Trp Ser Cys Met
            20                  25                  30

Arg Pro Arg Ser His Leu Trp Met Val Asp Leu Pro Trp Ala
        35                  40                  45

<210> SEQ ID NO 466
<211> LENGTH: 47
<212> TYPE: PRT
<213> ORGANISM: Artificial Sequence
<220> FEATURE:
<223> OTHER INFORMATION: Synthetic or recombinant sequence

<400> SEQUENCE: 466

```
Met Glu Glu Gly Asn Asn Glu Glu Val Gly Leu Ala Ser Ala His
1               5                  10                  15

Pro Ser Trp Ala Ser Arg Gly His Cys Ser Thr Thr Thr Gly Pro Cys
            20                  25                  30

Ala Pro Ala Ser Pro Pro Ser Arg Ser Trp Ala Trp Ala Pro Pro
            35                  40                  45

<210> SEQ ID NO 467
<211> LENGTH: 47
<212> TYPE: PRT
<213> ORGANISM: Artificial Sequence
<220> FEATURE:
<223> OTHER INFORMATION: Synthetic or recombinant sequence

<400> SEQUENCE: 467

Met Ala Glu His Pro Pro Leu Leu Asp Thr Asn Arg Leu Pro Phe Gly
1               5                  10                  15

Ala Ser Lys Lys Gln Ser Ala Ile Gly Gln Glu Lys Asn Gly Ile Glu
            20                  25                  30

Ala Asp Phe Gln Gln Gln Val Leu Trp Gly Ile Ala Glu Ser Phe
            35                  40                  45

<210> SEQ ID NO 468
<211> LENGTH: 51
<212> TYPE: PRT
<213> ORGANISM: Artificial Sequence
<220> FEATURE:
<223> OTHER INFORMATION: Synthetic or recombinant sequence

<400> SEQUENCE: 468

Met Gly Ser Gln Pro Pro Leu Gly Ser Pro Lys Arg Cys Ser Ile Phe
1               5                  10                  15

Arg Leu Arg Lys Thr Thr Arg Ala Gln Trp Arg Leu Pro His Phe Phe
            20                  25                  30

Ser Ser Ser Cys Trp Ser Ser Arg Arg Lys Ala Gly Ser Val Ala Phe
            35                  40                  45

Trp Met Pro
    50

<210> SEQ ID NO 469
<211> LENGTH: 52
<212> TYPE: PRT
<213> ORGANISM: Artificial Sequence
<220> FEATURE:
<223> OTHER INFORMATION: Synthetic or recombinant sequence

<400> SEQUENCE: 469

Met Ala Gln Asn Leu Lys Asp Leu Ala Gly Ala Leu Arg Gly Pro Ala
1               5                  10                  15

Arg His Arg Thr Leu Gln Gly Glu His Pro Ala Leu Val Leu Gln Pro
            20                  25                  30

Leu Gln Arg Thr Leu Arg Pro Leu Tyr Leu Trp Trp Leu Leu Arg Gln
            35                  40                  45

Gln Glu Gln Leu
    50

<210> SEQ ID NO 470
<211> LENGTH: 53
<212> TYPE: PRT
<213> ORGANISM: Artificial Sequence
<220> FEATURE:
```

<223> OTHER INFORMATION: Synthetic or recombinant sequence

<400> SEQUENCE: 470

Met Ser Ser Ser Glu Glu Val Ser Trp Ile Ser Ser Cys Ser Arg His
1               5                   10                  15

Pro Asp Val Pro Leu Leu Pro Arg Arg Arg Pro Phe Cys Arg Met His
            20                  25                  30

Phe Arg Leu Arg Glu Val Tyr His Gln Gln Leu Ile Pro Val His Gly
        35                  40                  45

Asp His His Leu Leu
    50

<210> SEQ ID NO 471
<211> LENGTH: 55
<212> TYPE: PRT
<213> ORGANISM: Artificial Sequence
<220> FEATURE:
<223> OTHER INFORMATION: Synthetic or recombinant sequence

<400> SEQUENCE: 471

Met Ala Lys Arg Arg Arg Pro Lys Lys Arg Asp Ser Gln Arg His Phe
1               5                   10                  15

Trp Asn Ile Ser Gly Lys Asn Cys Arg Thr Gln Val Ile Leu Pro Ser
            20                  25                  30

Ser Gly Arg Leu Leu Glu Ile Ile Leu Glu Ala Phe Trp Gln Glu Leu
        35                  40                  45

Asn Leu Phe Leu Leu Leu Leu
    50                  55

<210> SEQ ID NO 472
<211> LENGTH: 57
<212> TYPE: PRT
<213> ORGANISM: Artificial Sequence
<220> FEATURE:
<223> OTHER INFORMATION: Synthetic or recombinant sequence

<400> SEQUENCE: 472

Met Pro Lys Gly Lys Lys Ala Lys Gly Lys Leu Ser His Pro Pro Gly
1               5                   10                  15

Pro Gly Gly Val Pro Gly Ala Leu Met Glu Cys Gln Leu His Pro Gly
            20                  25                  30

Gly His Pro Phe Pro Ala Pro Gly Ala Glu Ala Gln Gly Trp Arg Pro
        35                  40                  45

Val Trp Asp Val Arg Pro Trp Arg Ala
    50                  55

<210> SEQ ID NO 473
<211> LENGTH: 61
<212> TYPE: PRT
<213> ORGANISM: Artificial Sequence
<220> FEATURE:
<223> OTHER INFORMATION: Synthetic or recombinant sequence

<400> SEQUENCE: 473

Met Arg Gly Gln Thr Glu Glu Val Val Ala Ser Ala Ser Trp Ala Val
1               5                   10                  15

Pro Ser Thr Cys Cys Phe Arg Ser Cys Lys Pro Leu Leu Ala Met Ala
            20                  25                  30

Ser Gly Tyr Leu Trp Ser Arg Gln Glu Gln Leu Glu Arg Arg Trp Ile
        35                  40                  45

```
Leu Pro Arg Val Ala Met Pro Ser Ala Ser Ser Gly Phe
    50                  55                  60
```

<210> SEQ ID NO 474
<211> LENGTH: 62
<212> TYPE: PRT
<213> ORGANISM: Artificial Sequence
<220> FEATURE:
<223> OTHER INFORMATION: Synthetic or recombinant sequence

<400> SEQUENCE: 474

```
Met Ala Glu Ala Ser Ser Ala Asn Leu Gly Cys Glu Ala Gln Arg Cys
1               5                   10                  15

Arg Val Gln Gln Arg Cys Ser Leu Cys Val Gln Ala Gly Gly Gln Arg
            20                  25                  30

Gly Ser Glu Glu Thr Gln Ala Leu Pro Val Ser Met Ala Gly Ser Pro
        35                  40                  45

Ser Pro Leu Pro Gly Ser Pro Gly Ala Gln Glu Gly Val
    50                  55                  60
```

<210> SEQ ID NO 475
<211> LENGTH: 63
<212> TYPE: PRT
<213> ORGANISM: Artificial Sequence
<220> FEATURE:
<223> OTHER INFORMATION: Synthetic or recombinant sequence

<400> SEQUENCE: 475

```
Met Arg Ala Arg Leu Arg Phe Leu Pro Ser Glu Ala Glu Glu Ala Trp
1               5                   10                  15

Thr Leu Ala His Thr Asp Pro Gly Thr Asp Glu Gln Gly Cys Leu His
            20                  25                  30

Pro His Leu Ala Val His Leu Leu Pro Gly Ala Gln Gly Ala Met Gly
        35                  40                  45

Tyr Trp Thr Ala Val Leu Asn Ile Ala Val Ala Gln Val His Asp
    50                  55                  60
```

<210> SEQ ID NO 476
<211> LENGTH: 64
<212> TYPE: PRT
<213> ORGANISM: Artificial Sequence
<220> FEATURE:
<223> OTHER INFORMATION: Synthetic or recombinant sequence

<400> SEQUENCE: 476

```
Met Ala Leu Asn Gly Ala Glu Val Asp Asp Gly Gly Ala Ala Ala Val
1               5                   10                  15

Gly His Val Leu Val Val Pro Ala Val Gly Pro Val Arg Val Asn Pro
            20                  25                  30

Gly Leu Gln Thr Pro Val Pro Arg Pro Glu Leu Leu Pro Gly Pro Val
        35                  40                  45

Ile Leu Pro Pro Phe Gly Gln Leu Leu Pro Thr Gly Cys Gly Pro Val
    50                  55                  60
```

<210> SEQ ID NO 477
<211> LENGTH: 65
<212> TYPE: PRT
<213> ORGANISM: Artificial Sequence
<220> FEATURE:
<223> OTHER INFORMATION: Synthetic or recombinant sequence

<400> SEQUENCE: 477

```
Met Gly Asn Ser Ala Leu Arg Ala His Val Met Leu His Gly Gln
1               5                  10                  15

Thr Gln Arg Pro Gln His Leu Leu Ser Ser Val Lys Val Phe Ser Val
                20                  25                  30

Ser Leu Met Ser Leu Phe Ile Trp Ser Lys Pro Ser Ser Met Arg Phe
            35                  40                  45

Ser Cys Ser Phe Cys Ser Ser Ile Val Met Val Leu Ile Pro Ala
        50                  55                  60

Ser
65
```

<210> SEQ ID NO 478
<211> LENGTH: 68
<212> TYPE: PRT
<213> ORGANISM: Artificial Sequence
<220> FEATURE:
<223> OTHER INFORMATION: Synthetic or recombinant sequence

<400> SEQUENCE: 478

```
Met Asp Pro Ala Ser Arg Gly Cys Leu Gly Arg Pro Ser Thr Pro Cys
1               5                  10                  15

Leu His Gly Ala Ala Leu His Leu His Ser Gly His Gly Ser Gly Ser
                20                  25                  30

Arg Leu Thr Asn Ser Ser Cys Phe Pro Gly Thr Arg Arg Leu Leu Ala
            35                  40                  45

Leu Gln Phe Thr Gln Gln Thr Gly Thr Val Gly His Pro Thr Trp Gln
        50                  55                  60

Pro Val Ile Arg
65
```

<210> SEQ ID NO 479
<211> LENGTH: 69
<212> TYPE: PRT
<213> ORGANISM: Artificial Sequence
<220> FEATURE:
<223> OTHER INFORMATION: Synthetic or recombinant sequence

<400> SEQUENCE: 479

```
Met Val Arg Tyr Ser Leu Asp Pro Glu Asn Leu Arg Ser Ser Ser Leu
1               5                  10                  15

Gly Lys Trp Cys Ala Phe Leu Val Ser Ser Phe Gln Phe Cys Ser Gly
                20                  25                  30

Ser Thr Lys Asn Ser Trp Ser His Ile Tyr Thr Leu Trp Phe Pro Pro
            35                  40                  45

Ser Leu Val Val Tyr Gly Leu Arg Lys Gln Tyr Lys Asn Pro Met Ile
        50                  55                  60

Gln Thr Lys Ala Lys
65
```

<210> SEQ ID NO 480
<211> LENGTH: 74
<212> TYPE: PRT
<213> ORGANISM: Artificial Sequence
<220> FEATURE:
<223> OTHER INFORMATION: Synthetic or recombinant sequence

<400> SEQUENCE: 480

```
Met Glu Ala Thr Arg Arg Arg Gln His Leu Arg Lys Trp Arg Ala Gly
1               5                  10                  15

Phe Leu His Phe Ser Asp His Tyr Ala His Ala Asn Lys Thr Arg Arg
```

```
                    20                  25                  30

Pro Lys Glu Arg Asn Ser Ser His Val Asp Gly Gln Gly Glu
            35                  40                  45

Glu Arg Leu Arg His Gly Val Arg Pro Ala Val Lys Thr His Glu Ser
        50                  55                  60

Gly Gly Glu Ala His Pro Gln Gly Ser Gly
65                  70

<210> SEQ ID NO 481
<211> LENGTH: 77
<212> TYPE: PRT
<213> ORGANISM: Artificial Sequence
<220> FEATURE:
<223> OTHER INFORMATION: Synthetic or recombinant sequence

<400> SEQUENCE: 481

Met Ser Ser Pro Leu Gln Arg Ala Val Gly Leu Asp Tyr Val Asp Met
1               5                   10                  15

Glu Ile His Leu Pro Leu Ser Thr Ala Pro Leu Pro Ala Pro Leu Pro
                20                  25                  30

Ser Pro Pro Leu His Asp Asp Val Trp Leu Gly Asp Asn His Thr Pro
            35                  40                  45

Gln Lys Leu Asp Gly Cys Ser Ser Pro Thr Ser His Pro Arg Met Leu
        50                  55                  60

Ser Ser His Gln Gly Pro Val Ala Ala Thr Pro Pro Gly
65                  70                  75

<210> SEQ ID NO 482
<211> LENGTH: 81
<212> TYPE: PRT
<213> ORGANISM: Artificial Sequence
<220> FEATURE:
<223> OTHER INFORMATION: Synthetic or recombinant sequence

<400> SEQUENCE: 482

Met Val Arg Glu Thr Arg His Leu Trp Val Phe Trp Asn Pro Gly Ala
1               5                   10                  15

Glu Asp His Val Gly Gly Cys Asp Leu Gly Gly Leu Pro Gly Tyr Gln
                20                  25                  30

Glu Leu Trp Gly Gln Gly Gly Gly Pro Leu Leu His Pro Gly His Arg
            35                  40                  45

Gln His Pro Val Pro Gly Gln Ser Gly Pro Phe Arg Ala Pro Val Cys
        50                  55                  60

Asn Asp Arg Cys Leu Pro Gly Pro Cys Ala His His Asp His Arg Gly
65                  70                  75                  80

Ala

<210> SEQ ID NO 483
<211> LENGTH: 92
<212> TYPE: PRT
<213> ORGANISM: Artificial Sequence
<220> FEATURE:
<223> OTHER INFORMATION: Synthetic or recombinant sequence

<400> SEQUENCE: 483

Met Pro Thr Gly Asp Phe Asp Ser Lys Pro Pro Trp Ser Phe Ser Ile
1               5                   10                  15

Ser Leu Cys Cys Arg Gln His Thr Phe Leu Met Glu Val Pro Gly Cys
                20                  25                  30
```

-continued

```
Trp Arg Ser Leu Gly Ala Trp Lys Ser Ser Leu Met Phe Thr Arg Pro
         35                  40                  45

Thr Leu Trp Pro His Ser Glu Arg Ile Thr Leu Ala Asn Pro Met Pro
 50                  55                  60

Gly Cys Ala Leu Val Asp Leu Met Ser Leu Ser Gln Thr Ser Ala Ala
 65                  70                  75                  80

Ser Ser Gly Cys Leu Thr Arg Val Gly Met Ser Leu
                 85                  90
```

<210> SEQ ID NO 484
<211> LENGTH: 94
<212> TYPE: PRT
<213> ORGANISM: Artificial Sequence
<220> FEATURE:
<223> OTHER INFORMATION: Synthetic or recombinant sequence

<400> SEQUENCE: 484

```
Met Gln Trp Leu Arg Val Arg Glu Ser Pro Leu Pro Ser Ser Ala Pro
 1               5                  10                  15

Pro Cys Gly Cys Asn Gly Gly Pro Cys Ser Val Leu Ala Ser Ala Pro
                 20                  25                  30

Pro His Pro Pro Ala Pro Gly Tyr Leu Leu Gly Ile Cys Ser Gly
         35                  40                  45

Glu Trp His Phe Pro Val His Met Leu Leu Gln Leu Glu Ser Gln His
 50                  55                  60

Leu Leu Cys Leu Glu Pro Arg Trp Gly Ser Gly His Phe Leu Pro
 65                  70                  75                  80

Ser Pro Cys Leu Ala Gly Gln Thr Ala Val Glu Pro Asn Leu
                 85                  90
```

<210> SEQ ID NO 485
<211> LENGTH: 106
<212> TYPE: PRT
<213> ORGANISM: Artificial Sequence
<220> FEATURE:
<223> OTHER INFORMATION: Synthetic or recombinant sequence

<400> SEQUENCE: 485

```
Met Ala His Ala Ala Ser Gln Leu Lys Lys Ser Gly Cys Val Ile Ala
 1               5                  10                  15

Ile Leu Gly Lys Arg Cys Ser Arg Pro Trp Thr Trp Arg Gly Arg
                 20                  25                  30

Thr Pro Ser Thr Arg His Ile Cys Ser Trp Cys Thr Met Val Ser Gly
         35                  40                  45

Thr Ser Ala Ala Ala Pro Gln Gly Pro Arg Ala Ser Pro Ala Ala Leu
 50                  55                  60

Ala Thr Trp Gln Pro Pro Trp Lys Ser Ser Ile Ala Val Thr Met
 65                  70                  75                  80

Asp Leu Ala Asp Ser Leu Ser Phe Val Asp Leu Glu Glu Leu Leu Ala
                 85                  90                  95

Val Ala Gln His Ile Gln His Trp Phe Leu
                 100                 105
```

<210> SEQ ID NO 486
<211> LENGTH: 130
<212> TYPE: PRT
<213> ORGANISM: Artificial Sequence
<220> FEATURE:
<223> OTHER INFORMATION: Synthetic or recombinant sequence

<400> SEQUENCE: 486

Met Ala Val Pro Gly Asp Ala Ala Arg Val Glu Gln Asp Cys Gln Trp
1               5                   10                  15

Arg Leu Pro Gln Arg Pro Pro Gly Ala Glu Pro Gln Pro His Arg Ala
            20                  25                  30

Arg Cys Gly Pro His His Glu Pro Ala Arg Gln Pro Pro Val His Leu
        35                  40                  45

Pro Pro Gln Pro Trp Pro Gly Ala Ala Pro Arg Thr Asp Gln Glu Gln
    50                  55                  60

Pro Gly Arg Gln Gln Ala Ser Arg Pro Leu Ala His Thr Asp Pro Gly
65                  70                  75                  80

Gly Ala Ala Glu Pro Ala Leu Arg Asp His Leu Cys Leu Gly Trp
                85                  90                  95

Arg Pro Gln Leu Gln Pro Leu Ala Leu Pro His Arg Ala Gln Arg Leu
            100                 105                 110

Cys Arg Ala Arg Ala Cys Gln Leu Pro Glu Ala Thr Glu Arg Cys His
        115                 120                 125

His Leu
    130

<210> SEQ ID NO 487
<211> LENGTH: 136
<212> TYPE: PRT
<213> ORGANISM: Artificial Sequence
<220> FEATURE:
<223> OTHER INFORMATION: Synthetic or recombinant sequence

<400> SEQUENCE: 487

Met Ser Ala Gln Cys Cys Ala Gly Gln Leu Ala Thr Lys Val Pro Thr
1               5                   10                  15

Ser Arg Ala Ser Ser Ala Gly Ala Gly Pro Ser Ser Gly Ser Arg Trp
            20                  25                  30

Pro Pro Ala Gly Tyr Ala Cys Cys Cys Thr Cys Val Arg Trp Ser Leu
        35                  40                  45

Pro Ser Ala Ala Pro Pro Gly Ser Ser Leu Cys Asp Asp Ile Gly Gly
    50                  55                  60

Pro Leu Gly Phe Val Gly Leu Gln Pro Gly Lys Cys His Leu Leu Asn
65                  70                  75                  80

Ser Val Pro Gly Ala Gly Thr Gly Ala Leu Cys Leu Ser Gly Ser Glu
                85                  90                  95

Lys Ala Leu Arg Leu His Ser Gly Thr Ser Ser Leu Leu Phe Pro Pro
            100                 105                 110

Ser Tyr Phe Gly Lys Phe Ser Ser Arg Ser Ser His Val Phe Ser Ile
        115                 120                 125

Gln Leu Ser Cys His Ser Phe Ser
    130                 135

<210> SEQ ID NO 488
<211> LENGTH: 148
<212> TYPE: PRT
<213> ORGANISM: Artificial Sequence
<220> FEATURE:
<223> OTHER INFORMATION: Synthetic or recombinant sequence

<400> SEQUENCE: 488

Met Ala Ala Glu Ser Leu Pro Phe Ser Phe Leu Pro Leu Gly Ala Ser
1               5                   10                  15

```
Gly Gly Phe Pro Ser Ala Thr Ala Asn Cys Phe Phe Arg Ser Lys Ser
            20                  25                  30

Phe Ala Thr Ser Ala Ala Thr Ser Phe Leu Ser Ala Phe Cys Ala Phe
            35                  40                  45

Ser Ser Arg Thr Met Phe Pro Cys Phe Val Thr Ser Ser Ile Ser Ala
            50                  55                  60

Cys Ile Cys Cys Gly Leu Ala Val Val Thr Val Ser Thr Thr Ala Gly
65                  70                  75                  80

Phe Gly Asp Val Phe Ala Trp Pro Pro Lys Arg Cys Leu Lys Leu
                85                  90                  95

Ser Ile Trp Ser Phe Ser Asn Phe Trp Asn Lys Gly Leu Thr Val Pro
            100                 105                 110

Ile Trp Cys Pro Ala Gly Lys Val His Arg Lys Phe Val Ser Arg Ile
            115                 120                 125

Leu Gln Ala Gly Gly Gly Ser Cys Ser Trp Ala Trp Ile Val Ala Leu
            130                 135                 140

Thr Val Gly Met
145

<210> SEQ ID NO 489
<211> LENGTH: 177
<212> TYPE: PRT
<213> ORGANISM: Artificial Sequence
<220> FEATURE:
<223> OTHER INFORMATION: Synthetic or recombinant sequence

<400> SEQUENCE: 489

Met Arg Glu Val Gln Lys Asp Gln Arg Ser Pro Phe Ser Thr Ser His
1               5                   10                  15

Ser Cys Val Phe Pro Gln Pro Gly Lys His Ile Asn Pro Ser Ala Phe
            20                  25                  30

Thr Pro Gly Asn Lys Glu Thr Lys Pro Asp Tyr Gly Gly Lys Gly Asp
            35                  40                  45

Lys Lys Asp Pro Gly Thr Leu Lys Arg Glu Arg Val Arg Phe Arg Asn
50                  55                  60

Arg Gln Asp Trp Thr Leu Arg Asp Val Leu Cys Gln His Lys Gly Leu
65                  70                  75                  80

Ala His Thr Asp Thr Arg Asp Arg Gly Glu Thr Ala Asp Lys Trp Arg
            85                  90                  95

Tyr Lys Asp Leu Glu Gly Gln Leu Leu Ser Pro His Pro Thr Cys Pro
            100                 105                 110

Glu Gly Lys Lys Thr Gln Pro Glu Arg Lys Gly Ile Gly Ser Ala Leu
            115                 120                 125

Arg Ser Gly Gln Ala Val Asp Leu Trp Arg Tyr Ser Glu Ser Trp Ser
            130                 135                 140

Cys Ser Thr Pro Leu Leu Tyr Cys Ser Pro Val Lys Arg Glu Arg
145                 150                 155                 160

Ala Gly Arg Lys Ser Ser Ser Arg Lys Leu Ser Trp Glu Pro Asn
                165                 170                 175

Phe

<210> SEQ ID NO 490
<211> LENGTH: 214
<212> TYPE: PRT
<213> ORGANISM: Artificial Sequence
<220> FEATURE:
<223> OTHER INFORMATION: Synthetic or recombinant sequence
```

<400> SEQUENCE: 490

Met Ser Cys Val Lys Leu Trp Pro Ser Gly Ala Asp Leu Arg Pro Glu
1               5                   10                  15

Leu Pro Asp His Cys Ala Val Arg Ala Gly Arg Leu Leu Ala Ala Ala
            20                  25                  30

Gly Pro Arg Phe Pro Gly Ala Ala Thr Ala Leu Asp Ala Ser Pro
        35                  40                  45

Val Arg Leu Gly Met Gly Arg Ala Ala Ser Ala Arg Pro Arg Leu Pro
50                  55                  60

Val His Arg Gly Arg Gly Glu Arg Leu Gly Pro Gly Val Leu Phe Ser
65                  70                  75                  80

Leu Arg His Leu His Gly Val Cys His Ala Ala Leu Gly His Ala Gly
                85                  90                  95

Arg Arg Arg Arg Gly Pro Arg Leu Leu Thr Leu Ala Ser Ala Gly Pro
            100                 105                 110

Arg Ala Val Ser Trp Ala Thr Ala Gly Leu Thr Ala Cys Thr Ala Ala
            115                 120                 125

Ala Val Gly Ser Lys Arg Ser Ala Val Pro Val Arg Glu Arg Gly Arg
130                 135                 140

Ser Val Pro Gln Gly Ala Asp Gly Ala Arg Pro Ala Gly His Val Pro
145                 150                 155                 160

Gly Gly Thr Gln Leu Pro Ala Leu Thr Pro Ala Ala Gly His Arg Glu
                165                 170                 175

Glu Ala Pro Gly Thr Pro Ser Leu Val His Pro Ser Cys Leu Pro Gly
            180                 185                 190

Pro Arg Asp Glu Gly Arg Asp His Gly Thr Ala Ala Gly Arg Thr Gly
            195                 200                 205

Val Thr Ala Arg Glu His
            210

<210> SEQ ID NO 491
<211> LENGTH: 48
<212> TYPE: PRT
<213> ORGANISM: Artificial Sequence
<220> FEATURE:
<223> OTHER INFORMATION: Synthetic or recombinant sequence

<400> SEQUENCE: 491

Pro Cys Thr Gly Leu Ser Leu His Pro Met Ala Pro Arg Ile Trp Ser
1               5                   10                  15

Arg Trp Ser Phe Pro Ala Gly Arg Cys Gln Asp Arg Pro Asn Lys His
            20                  25                  30

Val Trp Pro Pro Gln Lys Lys Lys Lys Lys Lys Lys Lys Lys Lys Lys
            35                  40                  45

<210> SEQ ID NO 492
<211> LENGTH: 9
<212> TYPE: PRT
<213> ORGANISM: Artificial Sequence
<220> FEATURE:
<223> OTHER INFORMATION: Synthetic or recombinant sequence

<400> SEQUENCE: 492

Cys Phe Thr Ser Ser Pro Leu Arg Trp
1               5

<210> SEQ ID NO 493

```
<211> LENGTH: 28
<212> TYPE: PRT
<213> ORGANISM: Artificial Sequence
<220> FEATURE:
<223> OTHER INFORMATION: Synthetic or recombinant sequence

<400> SEQUENCE: 493

Leu Leu Leu Gln Leu Arg Pro Gly Ser Arg Pro Phe Pro Val Thr Tyr
1               5                   10                  15

Val Ser Val Thr Gly Arg Gln Pro Tyr Lys Ser Trp
            20                  25

<210> SEQ ID NO 494
<211> LENGTH: 50
<212> TYPE: PRT
<213> ORGANISM: Artificial Sequence
<220> FEATURE:
<223> OTHER INFORMATION: Synthetic or recombinant sequence

<400> SEQUENCE: 494

Leu Leu Arg Ser Arg His Ser Thr Arg Ile Leu Pro Thr Ala Ala Gly
1               5                   10                  15

Leu Arg Leu Arg Ala Cys Thr Arg Ser Ser Met Arg Ser Cys Arg Ala
            20                  25                  30

Trp Leu Gly Ser Thr Gly Met Thr Cys Gly Ala Gln Arg Leu Arg Ser
        35                  40                  45

Leu Arg
    50

<210> SEQ ID NO 495
<211> LENGTH: 8
<212> TYPE: PRT
<213> ORGANISM: Artificial Sequence
<220> FEATURE:
<223> OTHER INFORMATION: Synthetic or recombinant sequence

<400> SEQUENCE: 495

Gly Gly Pro Arg Arg Ile Trp Ser
1               5

<210> SEQ ID NO 496
<211> LENGTH: 18
<212> TYPE: PRT
<213> ORGANISM: Artificial Sequence
<220> FEATURE:
<223> OTHER INFORMATION: Synthetic or recombinant sequence

<400> SEQUENCE: 496

Arg Ser Val Lys Trp Ser Pro Asn Thr Met Gln Met Gly Arg Thr Pro
1               5                   10                  15

Met Pro

<210> SEQ ID NO 497
<211> LENGTH: 32
<212> TYPE: PRT
<213> ORGANISM: Artificial Sequence
<220> FEATURE:
<223> OTHER INFORMATION: Synthetic or recombinant sequence

<400> SEQUENCE: 497

Gly Leu Trp Leu Phe Arg Pro Gln Asn Val Leu Gln Met Pro Gln Ser
1               5                   10                  15

Ile Leu Leu Gln Gln Gly Ala Ser Asp Pro Arg Leu Glu Ile Gly Thr
            20                  25                  30
```

<210> SEQ ID NO 498
<211> LENGTH: 9
<212> TYPE: PRT
<213> ORGANISM: Artificial Sequence
<220> FEATURE:
<223> OTHER INFORMATION: Synthetic or recombinant sequence

<400> SEQUENCE: 498

Phe Gly Lys Ala His Gly Ala Ser Trp
1               5

<210> SEQ ID NO 499
<211> LENGTH: 24
<212> TYPE: PRT
<213> ORGANISM: Artificial Sequence
<220> FEATURE:
<223> OTHER INFORMATION: Synthetic or recombinant sequence

<400> SEQUENCE: 499

Cys Ser Ala Gln Ala Arg Asn Arg Ser Glu Asp Glu Thr Gln Pro Leu
1               5                   10                  15

Pro Leu Gly Thr Leu Leu Ala Phe
            20

<210> SEQ ID NO 500
<211> LENGTH: 21
<212> TYPE: PRT
<213> ORGANISM: Artificial Sequence
<220> FEATURE:
<223> OTHER INFORMATION: Synthetic or recombinant sequence

<400> SEQUENCE: 500

Lys Glu Gly Val Leu Leu Gln Val Thr Asn Glu Glu Val Val Asn His
1               5                   10                  15

Arg Val Phe Lys Lys
            20

<210> SEQ ID NO 501
<211> LENGTH: 14
<212> TYPE: PRT
<213> ORGANISM: Artificial Sequence
<220> FEATURE:
<223> OTHER INFORMATION: Synthetic or recombinant sequence

<400> SEQUENCE: 501

Val Pro Thr Ala Cys Cys Arg Cys Cys Phe Cys Trp Asp Val
1               5                   10

<210> SEQ ID NO 502
<211> LENGTH: 10
<212> TYPE: PRT
<213> ORGANISM: Artificial Sequence
<220> FEATURE:
<223> OTHER INFORMATION: Synthetic or recombinant sequence

<400> SEQUENCE: 502

Gly Val Arg Gln Trp Gln His Leu Gln Pro
1               5                   10

<210> SEQ ID NO 503
<211> LENGTH: 61
<212> TYPE: PRT
<213> ORGANISM: Artificial Sequence
<220> FEATURE:
<223> OTHER INFORMATION: Synthetic or recombinant sequence

<400> SEQUENCE: 503

Leu Pro Cys Ser Ser Leu Thr Ser Tyr Trp Glu Met Leu Trp Leu Trp
1               5                   10                  15

Leu His Asp Trp Arg Arg Arg Gln Gly Gln Arg Cys Ser Phe Trp Val
            20                  25                  30

Thr Gln Pro Thr Ala Ala Ala Trp Met Cys Trp Val Leu Ser Lys
        35                  40                  45

Leu Glu Leu Arg Leu Ser Tyr Ile Leu Ala Leu Pro Ala
    50                  55                  60

<210> SEQ ID NO 504
<211> LENGTH: 31
<212> TYPE: PRT
<213> ORGANISM: Artificial Sequence
<220> FEATURE:
<223> OTHER INFORMATION: Synthetic or recombinant sequence

<400> SEQUENCE: 504

Gly Trp Pro Gly His Val Met Gly Ser Gln Arg Arg Gln Thr Pro Leu
1               5                   10                  15

His Ala Arg Trp Trp Gly His His Gln Arg Pro Val Leu Gln Pro
            20                  25                  30

<210> SEQ ID NO 505
<211> LENGTH: 12
<212> TYPE: PRT
<213> ORGANISM: Artificial Sequence
<220> FEATURE:
<223> OTHER INFORMATION: Synthetic or recombinant sequence

<400> SEQUENCE: 505

Ile Arg Glu Leu Cys His Arg Tyr Leu Pro Gln Pro
1               5                   10

<210> SEQ ID NO 506
<211> LENGTH: 22
<212> TYPE: PRT
<213> ORGANISM: Artificial Sequence
<220> FEATURE:
<223> OTHER INFORMATION: Synthetic or recombinant sequence

<400> SEQUENCE: 506

Asn Cys Pro Val Trp Arg His Asn Pro Cys Leu Ala Ser Trp Met Ser
1               5                   10                  15

Trp Arg Cys Trp Lys Ser
            20

<210> SEQ ID NO 507
<211> LENGTH: 22
<212> TYPE: PRT
<213> ORGANISM: Artificial Sequence
<220> FEATURE:
<223> OTHER INFORMATION: Synthetic or recombinant sequence

<400> SEQUENCE: 507

Val Gly Ser Met Pro Lys Glu Leu Leu Gly Glu Ser Ser Ser Ser Met
1               5                   10                  15

Ile Phe Glu Glu Arg Gly
            20

<210> SEQ ID NO 508
<211> LENGTH: 15

```
<212> TYPE: PRT
<213> ORGANISM: Artificial Sequence
<220> FEATURE:
<223> OTHER INFORMATION: Synthetic or recombinant sequence

<400> SEQUENCE: 508

Glu Ile Pro Glu Arg Asn Gln Gly Pro Val Ala Ala Ile Arg Ser
1               5                   10                  15

<210> SEQ ID NO 509
<211> LENGTH: 20
<212> TYPE: PRT
<213> ORGANISM: Artificial Sequence
<220> FEATURE:
<223> OTHER INFORMATION: Synthetic or recombinant sequence

<400> SEQUENCE: 509

Glu Gly Val Leu Leu Gln Val Thr Asn Glu Glu Val Val Asn His Arg
1               5                   10                  15

Val Phe Lys Lys
            20

<210> SEQ ID NO 510
<211> LENGTH: 17
<212> TYPE: PRT
<213> ORGANISM: Artificial Sequence
<220> FEATURE:
<223> OTHER INFORMATION: Synthetic or recombinant sequence

<400> SEQUENCE: 510

Cys Cys Gly Ile Tyr Cys His Glu Glu Pro Gln Arg Glu Asp Ser Ser
1               5                   10                  15

Ile

<210> SEQ ID NO 511
<211> LENGTH: 20
<212> TYPE: PRT
<213> ORGANISM: Artificial Sequence
<220> FEATURE:
<223> OTHER INFORMATION: Synthetic or recombinant sequence

<400> SEQUENCE: 511

Ala Gly Asp Ala Val Leu Gly Ala His Thr Gln Arg Pro Cys Val Val
1               5                   10                  15

Gly Gly Ser Gly
            20

<210> SEQ ID NO 512
<211> LENGTH: 15
<212> TYPE: PRT
<213> ORGANISM: Artificial Sequence
<220> FEATURE:
<223> OTHER INFORMATION: Synthetic or recombinant sequence

<400> SEQUENCE: 512

Pro Leu Arg Arg Pro Cys Thr Arg Ser Cys Trp Gly Gln Gly Ser
1               5                   10                  15

<210> SEQ ID NO 513
<211> LENGTH: 9
<212> TYPE: PRT
<213> ORGANISM: Artificial Sequence
<220> FEATURE:
<223> OTHER INFORMATION: Synthetic or recombinant sequence

<400> SEQUENCE: 513
```

```
Cys Gln Arg Cys Pro Leu Cys Trp Pro
1               5
```

<210> SEQ ID NO 514
<211> LENGTH: 36
<212> TYPE: PRT
<213> ORGANISM: Artificial Sequence
<220> FEATURE:
<223> OTHER INFORMATION: Synthetic or recombinant sequence

<400> SEQUENCE: 514

```
Ser Leu Pro Pro Asn Pro Ser Ala Ala Arg Glu Thr Lys Gly Ile Ser
1               5                   10                  15

Pro Ile Lys Asp Ser Lys Cys Val Phe Pro Arg Thr Ser Pro Gly Lys
            20                  25                  30

Asp Pro Leu Pro
        35
```

<210> SEQ ID NO 515
<211> LENGTH: 30
<212> TYPE: PRT
<213> ORGANISM: Artificial Sequence
<220> FEATURE:
<223> OTHER INFORMATION: Synthetic or recombinant sequence

<400> SEQUENCE: 515

```
Phe Ser Leu Lys Met Ser Ser Tyr Pro Leu Leu Gly Leu Ile Met Lys
1               5                   10                  15

Gly Asn Ser Phe His Asn Val Ile Pro Val Asn Ala Leu Thr
            20                  25                  30
```

<210> SEQ ID NO 516
<211> LENGTH: 30
<212> TYPE: PRT
<213> ORGANISM: Artificial Sequence
<220> FEATURE:
<223> OTHER INFORMATION: Synthetic or recombinant sequence

<400> SEQUENCE: 516

```
Gly Leu Leu Trp Cys Ala Ala Val His His Gly Glu Trp Gly Gln Arg
1               5                   10                  15

Leu Arg Gly Cys Gly Val Trp Glu Thr Pro Arg Thr Glu Gly
            20                  25                  30
```

<210> SEQ ID NO 517
<211> LENGTH: 28
<212> TYPE: PRT
<213> ORGANISM: Artificial Sequence
<220> FEATURE:
<223> OTHER INFORMATION: Synthetic or recombinant sequence

<400> SEQUENCE: 517

```
Gly Asp Gly Gly Ser Gly Ser Lys Gly Arg Pro Val Glu Gln Thr Glu
1               5                   10                  15

Val Phe Leu Cys Ile Ser Lys Pro Ser Ser Phe Leu
            20                  25
```

<210> SEQ ID NO 518
<211> LENGTH: 62
<212> TYPE: PRT
<213> ORGANISM: Artificial Sequence
<220> FEATURE:
<223> OTHER INFORMATION: Synthetic or recombinant sequence

<400> SEQUENCE: 518

Leu Pro Gln Gln Asp Leu Trp His Leu Gln Phe His Gln Gly Leu Pro
1               5                   10                  15

Arg Arg Cys His Pro Val Cys Ala Glu Pro Pro His Val Gln Leu
            20                  25                  30      Leu

Cys Pro Ala His Trp Gly Ala Pro Ser Phe Pro Thr Ser Trp Ser Gln
            35                  40                  45

Leu His Leu His Ser Asn Cys Arg Gly Pro Gly Cys Ser Arg
        50                  55                  60

<210> SEQ ID NO 519
<211> LENGTH: 56
<212> TYPE: PRT
<213> ORGANISM: Artificial Sequence
<220> FEATURE:
<223> OTHER INFORMATION: Synthetic or recombinant sequence

<400> SEQUENCE: 519

Ala Gly Pro Ser Pro Gly Thr Trp Thr Val Arg Thr Pro Ala Ala
1               5                   10                  15

Arg Arg Pro Ala Cys Ala Gly Ser Ala Arg Arg Cys Arg Ala Ala Arg
            20                  25                  30

Gly Arg Ala Val Ala Pro Arg Phe Glu Ser Cys Ser Ser Met Leu Pro
            35                  40                  45

Gly Thr Gly Thr Arg Arg Pro Cys
        50                  55

<210> SEQ ID NO 520
<211> LENGTH: 35
<212> TYPE: PRT
<213> ORGANISM: Artificial Sequence
<220> FEATURE:
<223> OTHER INFORMATION: Synthetic or recombinant sequence

<400> SEQUENCE: 520

Gly Ile Gly Ala Val Cys Met Asp Trp Trp Ala Ala Ala Pro Pro Gly
1               5                   10                  15

Glu Cys Ala Pro Arg Pro Gly Cys Ala Ala His Cys Gly His Arg
            20                  25                  30

Leu Leu His
        35

<210> SEQ ID NO 521
<211> LENGTH: 28
<212> TYPE: PRT
<213> ORGANISM: Artificial Sequence
<220> FEATURE:
<223> OTHER INFORMATION: Synthetic or recombinant sequence

<400> SEQUENCE: 521

Gly Val Gly Gly Gly Ile Leu Pro Pro Glu Thr Pro Pro Val Ser Ala
1               5                   10                  15

Trp Gly Glu Leu Cys Pro Pro Ala Trp Leu His Leu
            20                  25

<210> SEQ ID NO 522
<211> LENGTH: 39
<212> TYPE: PRT
<213> ORGANISM: Artificial Sequence
<220> FEATURE:
<223> OTHER INFORMATION: Synthetic or recombinant sequence

<400> SEQUENCE: 522

Val Ser Pro Gly Val Ser Glu Leu Arg Arg Asn Ser Lys Lys Tyr Gly
1               5                   10                  15

Lys Ala Gly Glu Ala Val Trp Phe Ser Ser Asp Pro Pro Val Leu Phe
                20                  25                  30

Phe His Phe Leu Arg Thr Glu
                35

<210> SEQ ID NO 523
<211> LENGTH: 23
<212> TYPE: PRT
<213> ORGANISM: Artificial Sequence
<220> FEATURE:
<223> OTHER INFORMATION: Synthetic or recombinant sequence

<400> SEQUENCE: 523

Leu His Ala Arg Ala Pro Gly Pro Arg Gly Pro Pro Leu Leu Cys Pro
1               5                   10                  15

Cys Cys Leu Arg Val Ser His
                20

<210> SEQ ID NO 524
<211> LENGTH: 15
<212> TYPE: PRT
<213> ORGANISM: Artificial Sequence
<220> FEATURE:
<223> OTHER INFORMATION: Synthetic or recombinant sequence

<400> SEQUENCE: 524

Cys Leu Gln Lys His Leu Pro Val Ala Leu Ser Thr Ser Leu Cys
1               5                   10                  15

<210> SEQ ID NO 525
<211> LENGTH: 13
<212> TYPE: PRT
<213> ORGANISM: Artificial Sequence
<220> FEATURE:
<223> OTHER INFORMATION: Synthetic or recombinant sequence

<400> SEQUENCE: 525

Ile Ser Val Ser Ile Met Trp Thr Gln Arg Arg Lys Leu
1               5                   10

<210> SEQ ID NO 526
<211> LENGTH: 42
<212> TYPE: PRT
<213> ORGANISM: Artificial Sequence
<220> FEATURE:
<223> OTHER INFORMATION: Synthetic or recombinant sequence

<400> SEQUENCE: 526

Ser His Ser Gln Ser Gly Gly Pro Arg His Pro Gly Gly Thr Arg Arg
1               5                   10                  15

Lys Ala Met Gly Ser Gln Cys Pro Glu Leu Gln Gly Gly Pro Glu Pro
                20                  25                  30

Gln Arg Pro Ser Ser Arg Arg Arg Glu Ile
                35                  40

<210> SEQ ID NO 527
<211> LENGTH: 12
<212> TYPE: PRT
<213> ORGANISM: Artificial Sequence
<220> FEATURE:
<223> OTHER INFORMATION: Synthetic or recombinant sequence

```
<400> SEQUENCE: 527

Ser Pro Lys Leu Pro Leu Val Arg Arg Trp Met Gln
1               5                   10

<210> SEQ ID NO 528
<211> LENGTH: 12
<212> TYPE: PRT
<213> ORGANISM: Artificial Sequence
<220> FEATURE:
<223> OTHER INFORMATION: Synthetic or recombinant sequence

<400> SEQUENCE: 528

Gly Ala Lys Pro Gly Gly Leu Ala Leu Gly Ala Val
1               5                   10

<210> SEQ ID NO 529
<211> LENGTH: 35
<212> TYPE: PRT
<213> ORGANISM: Artificial Sequence
<220> FEATURE:
<223> OTHER INFORMATION: Synthetic or recombinant sequence

<400> SEQUENCE: 529

Cys Tyr Gln His Pro Phe Pro Lys Lys Ser Gln Phe Pro Gly Ala Tyr
1               5                   10                  15

Trp Thr Ser Phe Glu Gly Glu Glu Gly Ser Gly Gln Leu Thr Leu
            20                  25                  30

Pro Gly Pro
        35

<210> SEQ ID NO 530
<211> LENGTH: 15
<212> TYPE: PRT
<213> ORGANISM: Artificial Sequence
<220> FEATURE:
<223> OTHER INFORMATION: Synthetic or recombinant sequence

<400> SEQUENCE: 530

Leu Leu Ser Ser His His Pro Leu Lys Arg Arg Asn Leu Glu Pro
1               5                   10                  15

<210> SEQ ID NO 531
<211> LENGTH: 11
<212> TYPE: PRT
<213> ORGANISM: Artificial Sequence
<220> FEATURE:
<223> OTHER INFORMATION: Synthetic or recombinant sequence

<400> SEQUENCE: 531

Ser Pro Ser Gln Ala Met Trp Ala Thr Arg Met
1               5                   10

<210> SEQ ID NO 532
<211> LENGTH: 22
<212> TYPE: PRT
<213> ORGANISM: Artificial Sequence
<220> FEATURE:
<223> OTHER INFORMATION: Synthetic or recombinant sequence

<400> SEQUENCE: 532

His Phe Pro Ala Cys Gln Leu Leu Pro Leu Cys Asp Leu Ile Ser Ser
1               5                   10                  15

Ala Leu Pro Tyr Val Glu
            20
```

<210> SEQ ID NO 533
<211> LENGTH: 44
<212> TYPE: PRT
<213> ORGANISM: Artificial Sequence
<220> FEATURE:
<223> OTHER INFORMATION: Synthetic or recombinant sequence

<400> SEQUENCE: 533

Cys Leu Gln Asn Trp Trp Tyr Trp Tyr Cys Ser Cys Trp Pro Ser Gly
1               5                   10                  15

Asp Trp Cys Ser Gln Thr Arg Tyr Gly Gly His Leu Cys Ser Ser Gln
            20                  25                  30

Arg Tyr Asn Gly Ser Lys Ile Cys Arg Asn Ala Pro
        35                  40

<210> SEQ ID NO 534
<211> LENGTH: 40
<212> TYPE: PRT
<213> ORGANISM: Artificial Sequence
<220> FEATURE:
<223> OTHER INFORMATION: Synthetic or recombinant sequence

<400> SEQUENCE: 534

Arg His Glu Lys Cys Cys Asn Trp Lys Gln Gln Ala Glu Ser Gln Ser
1               5                   10                  15

His Cys Phe Arg Ser Cys Ser Lys Ile Val Val Leu Ala Ser Ala Arg
            20                  25                  30

Asn Leu Lys His Arg Ala Glu Asn
        35                  40

<210> SEQ ID NO 535
<211> LENGTH: 36
<212> TYPE: PRT
<213> ORGANISM: Artificial Sequence
<220> FEATURE:
<223> OTHER INFORMATION: Synthetic or recombinant sequence

<400> SEQUENCE: 535

Gln Phe Arg Thr Pro Gly Trp Pro Leu Lys Ala Leu Ala Gly Arg Gly
1               5                   10                  15

Trp Pro Glu Asp Ala Ser Pro Gly Gln Glu Pro Ser Lys Gly Ala Gly
            20                  25                  30

Arg Gly Trp Ala
        35

<210> SEQ ID NO 536
<211> LENGTH: 41
<212> TYPE: PRT
<213> ORGANISM: Artificial Sequence
<220> FEATURE:
<223> OTHER INFORMATION: Synthetic or recombinant sequence

<400> SEQUENCE: 536

Trp Pro Gln Leu Leu Leu Glu Pro Asn Ser Gly Lys Ser Ala Ser Arg
1               5                   10                  15

Arg Arg Pro Gln Gly Gly Pro Gln Pro Pro Lys Leu Arg Val Val Glu
            20                  25                  30

Ala Glu Val Gly Asp Ser Trp Lys Arg
        35                  40

<210> SEQ ID NO 537

```
<211> LENGTH: 19
<212> TYPE: PRT
<213> ORGANISM: Artificial Sequence
<220> FEATURE:
<223> OTHER INFORMATION: Synthetic or recombinant sequence

<400> SEQUENCE: 537

Pro Ala Ser Gly Gly Ser Asp Leu Val Asn His Ser Phe Leu Cys Lys
1               5                   10                  15

Trp His Pro

<210> SEQ ID NO 538
<211> LENGTH: 9
<212> TYPE: PRT
<213> ORGANISM: Artificial Sequence
<220> FEATURE:
<223> OTHER INFORMATION: Synthetic or recombinant sequence

<400> SEQUENCE: 538

Cys Leu Leu Leu Gly Ala Val Thr Leu
1               5

<210> SEQ ID NO 539
<211> LENGTH: 26
<212> TYPE: PRT
<213> ORGANISM: Artificial Sequence
<220> FEATURE:
<223> OTHER INFORMATION: Synthetic or recombinant sequence

<400> SEQUENCE: 539

Ala Ala Ala Ala Ala His His His Ser Pro Arg Pro Ala Ala Leu Arg
1               5                   10                  15

His Pro Gln Glu Glu Thr Gly Cys Val Pro
            20                  25

<210> SEQ ID NO 540
<211> LENGTH: 38
<212> TYPE: PRT
<213> ORGANISM: Artificial Sequence
<220> FEATURE:
<223> OTHER INFORMATION: Synthetic or recombinant sequence

<400> SEQUENCE: 540

Asp His Gly Gly Val Gly Arg Cys Ser Asn Val Leu Pro Trp Glu Glu
1               5                   10                  15

Gly Asp Ser Gln Arg His Lys Ala Arg Lys Ser Ala Leu Arg Ala Gln
            20                  25                  30

Gly Arg Ala Glu Asp Cys
        35

<210> SEQ ID NO 541
<211> LENGTH: 12
<212> TYPE: PRT
<213> ORGANISM: Artificial Sequence
<220> FEATURE:
<223> OTHER INFORMATION: Synthetic or recombinant sequence

<400> SEQUENCE: 541

Thr Ser Ala Ser Gln Ile Gln Ala Ile Leu Val Pro
1               5                   10

<210> SEQ ID NO 542
<211> LENGTH: 19
<212> TYPE: PRT
<213> ORGANISM: Artificial Sequence
```

```
<220> FEATURE:
<223> OTHER INFORMATION: Synthetic or recombinant sequence

<400> SEQUENCE: 542

Gly Leu Met Ala Ser Asp Tyr Ser Glu Glu Val Ala Thr Ser Glu Lys
1               5                   10                  15

Phe Pro Phe

<210> SEQ ID NO 543
<211> LENGTH: 37
<212> TYPE: PRT
<213> ORGANISM: Artificial Sequence
<220> FEATURE:
<223> OTHER INFORMATION: Synthetic or recombinant sequence

<400> SEQUENCE: 543

Gln Glu Asn Cys Ser Asn Pro Gly Gly Arg Gly Cys Ser Asp Pro Arg
1               5                   10                  15

Ser Cys His Phe Thr Pro Ala Trp Ala Lys Glu Gln Asn Ala Ile Ser
            20                  25                  30

Lys Asn Ile His Ile
        35

<210> SEQ ID NO 544
<211> LENGTH: 15
<212> TYPE: PRT
<213> ORGANISM: Artificial Sequence
<220> FEATURE:
<223> OTHER INFORMATION: Synthetic or recombinant sequence

<400> SEQUENCE: 544

Val Lys Gly Val Leu His Ser Leu Thr Ala Ala Gly Gln Thr His
1               5                   10                  15

<210> SEQ ID NO 545
<211> LENGTH: 9
<212> TYPE: PRT
<213> ORGANISM: Artificial Sequence
<220> FEATURE:
<223> OTHER INFORMATION: Synthetic or recombinant sequence

<400> SEQUENCE: 545

Asp Ser Cys Gly Ile Val Asn Ser Tyr
1               5

<210> SEQ ID NO 546
<211> LENGTH: 66
<212> TYPE: PRT
<213> ORGANISM: Artificial Sequence
<220> FEATURE:
<223> OTHER INFORMATION: Synthetic or recombinant sequence

<400> SEQUENCE: 546

Asn Cys Pro Val Trp Arg His Asn Pro Cys Leu Ala Ser Trp Met Ser
1               5                   10                  15

Trp Arg Cys Trp Lys Ser Asp Glu Val Phe Ala Leu Pro Leu Ala His
            20                  25                  30

Leu Leu Gln Thr Gln Asn Gln Gly Tyr Thr His Phe Cys Arg Gly Gly
        35                  40                  45

His Phe Arg Tyr Thr Leu Pro Val Phe Leu His Gly Pro His Arg Val
    50                  55                  60

Trp Gly
65
```

<210> SEQ ID NO 547
<211> LENGTH: 56
<212> TYPE: PRT
<213> ORGANISM: Artificial Sequence
<220> FEATURE:
<223> OTHER INFORMATION: Synthetic or recombinant sequence

<400> SEQUENCE: 547

Leu Thr Ala Val Ile Thr Glu Phe Ala Leu Gln Leu Ala Pro Gly
1               5                   10                  15

Thr Tyr Gln Pro Arg Leu Ala Gly Leu Thr Cys Ser Gly Ala Glu Gly
            20                  25                  30

Leu Ala Arg Pro Lys Gln Pro Leu Ala Ser Pro Cys Gln Ala Ser Ser
        35                  40                  45

Thr Pro Gly Leu Asn Lys Gly Leu
    50                  55

<210> SEQ ID NO 548
<211> LENGTH: 20
<212> TYPE: PRT
<213> ORGANISM: Artificial Sequence
<220> FEATURE:
<223> OTHER INFORMATION: Synthetic or recombinant sequence

<400> SEQUENCE: 548

Lys His Gln Ala Met Asp His His Gly Val Pro Gly Arg Arg Leu Ser
1               5                   10                  15

Thr Gly Leu Ala
            20

<210> SEQ ID NO 549
<211> LENGTH: 64
<212> TYPE: PRT
<213> ORGANISM: Artificial Sequence
<220> FEATURE:
<223> OTHER INFORMATION: Synthetic or recombinant sequence

<400> SEQUENCE: 549

Pro Arg Ala Ala Val Ser Gly Ile Gln Gln Trp Trp Asn Gly Arg Gln
1               5                   10                  15

Asn Trp Lys Arg Lys Lys Glu Lys Met Ser Ser Arg Leu Ala Gly Ala
            20                  25                  30

Phe Arg Val Leu Trp Arg Ala Val Ser Thr Ala Ser Ile Arg Arg His
        35                  40                  45

Ile Gln Val Ala Pro Arg Pro Leu Gln Ala Gly Pro Ala Met Gly Pro
    50                  55                  60

<210> SEQ ID NO 550
<211> LENGTH: 14
<212> TYPE: PRT
<213> ORGANISM: Artificial Sequence
<220> FEATURE:
<223> OTHER INFORMATION: Synthetic or recombinant sequence

<400> SEQUENCE: 550

Leu Ile Val Gly Gly Gly Ala Pro Asp Arg Lys Gly Phe Gln
1               5                   10

<210> SEQ ID NO 551
<211> LENGTH: 13
<212> TYPE: PRT
<213> ORGANISM: Artificial Sequence
<220> FEATURE:
<223> OTHER INFORMATION: Synthetic or recombinant sequence

<400> SEQUENCE: 551

Gly Val Arg Cys Leu Ile His Ser Ile His Gly Phe Leu
1               5                   10

<210> SEQ ID NO 552
<211> LENGTH: 117
<212> TYPE: PRT
<213> ORGANISM: Artificial Sequence
<220> FEATURE:
<223> OTHER INFORMATION: Synthetic or recombinant sequence

<400> SEQUENCE: 552

Val Ala Ala Arg Ala Trp Ala Gln Pro Pro Leu Pro Gly Ala Glu Cys
1               5                   10                  15

Gly His Arg Arg Glu Gly Ala Thr Leu Ala Gly His Arg Gly Arg Pro
                20                  25                  30

Ala Ala Ala His Arg Gly Leu Arg Pro Gly His Ala Ala Ala Ala Thr
            35                  40                  45

Glu His Gln Ala Gln Glu Ala Ser Pro Arg Gly Asp Arg Gly Arg
        50                  55                  60

His Gly Ser Gly Leu Leu Gln Leu His Arg Asp Ser Arg Gly Ser Gly
65                  70                  75                  80

Arg Asn Gly Arg His Pro Glu Arg Glu Gly Asp His Ala Lys Pro Glu
                85                  90                  95

Arg Pro Pro Gly Leu Leu Pro Gln Ser Glu Glu Pro Gly Asp Arg
            100                 105                 110

Glu Pro Glu Ala Gly
        115

<210> SEQ ID NO 553
<211> LENGTH: 45
<212> TYPE: PRT
<213> ORGANISM: Artificial Sequence
<220> FEATURE:
<223> OTHER INFORMATION: Synthetic or recombinant sequence

<400> SEQUENCE: 553

Glu Gln Asn Pro Gly Ala Leu Gly Glu Gly Thr Pro Gly Gln Arg
1               5                   10                  15

Leu Glu Pro Leu Leu Gln Asp His Arg Gly Pro Glu Gly Ser Asp Leu
                20                  25                  30

Arg Lys Tyr Cys Gly Gln Cys Pro His Arg Ser Ala Asp
            35                  40                  45

<210> SEQ ID NO 554
<211> LENGTH: 17
<212> TYPE: PRT
<213> ORGANISM: Artificial Sequence
<220> FEATURE:
<223> OTHER INFORMATION: Synthetic or recombinant sequence

<400> SEQUENCE: 554

Ser Gly Lys Thr Ser Ser Ile Leu Cys Arg Arg Gly Arg Trp Arg Trp
1               5                   10                  15

Ser

<210> SEQ ID NO 555
<211> LENGTH: 39

```
<212> TYPE: PRT
<213> ORGANISM: Artificial Sequence
<220> FEATURE:
<223> OTHER INFORMATION: Synthetic or recombinant sequence

<400> SEQUENCE: 555

His Phe Pro Asp Gly Glu Val Thr Ala Glu Arg Cys Gly His Leu Ala
1               5                   10                  15

Phe Pro Tyr Pro Leu Pro Phe Pro Ser Pro Ser Ser Tyr Ser Phe
            20                  25                  30

His Val Pro Phe Gln Thr Glu
        35

<210> SEQ ID NO 556
<211> LENGTH: 14
<212> TYPE: PRT
<213> ORGANISM: Artificial Sequence
<220> FEATURE:
<223> OTHER INFORMATION: Synthetic or recombinant sequence

<400> SEQUENCE: 556

Gly Thr Ile Val Val Gln Trp Gly Pro Ser Trp Cys Leu Thr
1               5                   10

<210> SEQ ID NO 557
<211> LENGTH: 22
<212> TYPE: PRT
<213> ORGANISM: Artificial Sequence
<220> FEATURE:
<223> OTHER INFORMATION: Synthetic or recombinant sequence

<400> SEQUENCE: 557

Thr Thr Asn Pro Ser Arg Ile Ser Leu Pro Ser Trp Val Trp Met Asn
1               5                   10                  15

Phe Leu Arg Lys Thr Ser
            20

<210> SEQ ID NO 558
<211> LENGTH: 53
<212> TYPE: PRT
<213> ORGANISM: Artificial Sequence
<220> FEATURE:
<223> OTHER INFORMATION: Synthetic or recombinant sequence

<400> SEQUENCE: 558

Trp Ser Cys Ser Ser Ile Thr Gly Ala Ala Gly Asn Leu Asn Thr Thr
1               5                   10                  15

Ser Trp Ser Thr Arg Leu Trp Pro Asn Gly Arg Arg Lys Lys Leu Ser
            20                  25                  30

Ser Gly Trp Ser Trp Ala Leu Gly His Leu Phe Thr Gly Lys Gly
        35                  40                  45

Phe Tyr Leu Asn Glu
    50

<210> SEQ ID NO 559
<211> LENGTH: 10
<212> TYPE: PRT
<213> ORGANISM: Artificial Sequence
<220> FEATURE:
<223> OTHER INFORMATION: Synthetic or recombinant sequence

<400> SEQUENCE: 559

Gly Ser Ala Asp Arg Asp Asp Gly Lys Val
1               5                   10
```

<210> SEQ ID NO 560
<211> LENGTH: 79
<212> TYPE: PRT
<213> ORGANISM: Artificial Sequence
<220> FEATURE:
<223> OTHER INFORMATION: Synthetic or recombinant sequence

<400> SEQUENCE: 560

Asp Ala Ala Phe Phe Met Ser Pro Lys Leu Arg Trp Trp Gln Glu Met
1               5                   10                  15

Ala Thr Glu Arg Gly Leu Phe Gly Leu Glu Ile Pro Ile Ile Leu Lys
            20                  25                  30

Glu Leu Arg Val Gln Gly Thr Leu Val His Cys Pro Thr Arg His Leu
        35                  40                  45

Ser Gln Arg Arg Gly Pro Gly Arg Gln Arg Gly Asn Ser Leu Pro Glu
    50                  55                  60

Pro Ser Ser Met Leu Thr Cys Pro Gln Gln Pro His Arg Ala Thr
65                  70                  75

<210> SEQ ID NO 561
<211> LENGTH: 122
<212> TYPE: PRT
<213> ORGANISM: Artificial Sequence
<220> FEATURE:
<223> OTHER INFORMATION: Synthetic or recombinant sequence

<400> SEQUENCE: 561

Phe Pro Ala Ala Pro Gly Leu Gln Gly Cys Pro Arg Thr Gly Pro Ser
1               5                   10                  15

Gln Pro Ser Met Gln Leu Pro Ser Tyr Pro Glu Asp Gly Ser Gly Leu
            20                  25                  30

Ser Arg Gly His Lys Asp Val Arg Pro Gly Pro Pro Gly Gln Glu Arg
        35                  40                  45

Val Gln Val Leu Arg Ala Cys Ala Pro Gln Pro Gln His Gln Val Asp
    50                  55                  60

Cys Ser Ala Val Gly Gly Pro Val Ala Ala Arg Glu Lys Pro Pro Val
65                  70                  75                  80

Ser Arg Leu Gly Ser Ala His Gln Gly Leu Pro Thr Ser Ala Phe Glu
                85                  90                  95

Gly Ala Cys His Ala Leu Gly Asp Pro Gly Ile Phe Thr Gly Leu Glu
            100                 105                 110

Ala Gly Asp Arg Thr Val Ser Val Pro Gly
        115                 120

<210> SEQ ID NO 562
<211> LENGTH: 16
<212> TYPE: PRT
<213> ORGANISM: Artificial Sequence
<220> FEATURE:
<223> OTHER INFORMATION: Synthetic or recombinant sequence

<400> SEQUENCE: 562

Leu Leu Gln Pro Pro Phe Val Phe Ile Pro Pro Gly Cys Val Met Leu
1               5                   10                  15

<210> SEQ ID NO 563
<211> LENGTH: 10
<212> TYPE: PRT
<213> ORGANISM: Artificial Sequence
<220> FEATURE:

<223> OTHER INFORMATION: Synthetic or recombinant sequence

<400> SEQUENCE: 563

Gly Phe Trp Ser Arg Phe Pro Pro Pro Trp
1               5                   10

<210> SEQ ID NO 564
<211> LENGTH: 22
<212> TYPE: PRT
<213> ORGANISM: Artificial Sequence
<220> FEATURE:
<223> OTHER INFORMATION: Synthetic or recombinant sequence

<400> SEQUENCE: 564

Gly Pro Arg Gly His Ala Gly Glu Gly Gly Arg Gln Ser Cys Gly Arg
1               5                   10                  15

Pro Val Leu Arg Gly Arg
            20

<210> SEQ ID NO 565
<211> LENGTH: 9
<212> TYPE: PRT
<213> ORGANISM: Artificial Sequence
<220> FEATURE:
<223> OTHER INFORMATION: Synthetic or recombinant sequence

<400> SEQUENCE: 565

Asp Ser Cys Gly Ile Val Asn Ser Tyr
1               5

<210> SEQ ID NO 566
<211> LENGTH: 64
<212> TYPE: PRT
<213> ORGANISM: Artificial Sequence
<220> FEATURE:
<223> OTHER INFORMATION: Synthetic or recombinant sequence

<400> SEQUENCE: 566

Ile Val Gly Pro Gly Pro Lys Pro Glu Ala Ser Ala Lys Leu Pro Ser
1               5                   10                  15

Arg Pro Ala Asp Asn Tyr Asp Asn Phe Val Leu Pro Glu Leu Pro Ser
            20                  25                  30

Val Pro Asp Thr Leu Pro Thr Ala Ser Ala Gly Ala Ser Thr Ser Ala
        35                  40                  45

Ser Glu Asp Ile Asp Phe Asp Asp Leu Ser Arg Phe Glu Glu Leu
    50                  55                  60

<210> SEQ ID NO 567
<211> LENGTH: 36
<212> TYPE: PRT
<213> ORGANISM: Artificial Sequence
<220> FEATURE:
<223> OTHER INFORMATION: Synthetic or recombinant sequence

<400> SEQUENCE: 567

Arg Cys Gln Pro Asp Arg His Ser His Ile Trp Ala Leu Arg Trp Pro
1               5                   10                  15

Trp Trp Ser Trp Cys Gln His Gln Trp Gln Leu Trp Cys Leu Trp Phe
            20                  25                  30

Leu Leu Gln Val
        35

<210> SEQ ID NO 568

```
<211> LENGTH: 34
<212> TYPE: PRT
<213> ORGANISM: Artificial Sequence
<220> FEATURE:
<223> OTHER INFORMATION: Synthetic or recombinant sequence

<400> SEQUENCE: 568

Glu Thr Pro Ser Asp Ser Asp His Lys Lys Lys Lys Lys Lys Lys Glu
1               5                   10                  15

Glu Asp Pro Glu Arg Lys Arg Lys Lys Glu Lys Lys Lys Lys Lys Lys
            20                  25                  30

Val Glu

<210> SEQ ID NO 569
<211> LENGTH: 14
<212> TYPE: PRT
<213> ORGANISM: Artificial Sequence
<220> FEATURE:
<223> OTHER INFORMATION: Synthetic or recombinant sequence

<400> SEQUENCE: 569

Ala Gly Asn Val Arg Ser Asn Ser Arg Pro Ser Ile Gln Arg
1               5                   10

<210> SEQ ID NO 570
<211> LENGTH: 13
<212> TYPE: PRT
<213> ORGANISM: Artificial Sequence
<220> FEATURE:
<223> OTHER INFORMATION: Synthetic or recombinant sequence

<400> SEQUENCE: 570

Leu His Trp Gly Ser Thr Lys Val His Leu Leu Leu Ile
1               5                   10

<210> SEQ ID NO 571
<211> LENGTH: 8
<212> TYPE: PRT
<213> ORGANISM: Artificial Sequence
<220> FEATURE:
<223> OTHER INFORMATION: Synthetic or recombinant sequence

<400> SEQUENCE: 571

Gly Gly Pro Arg Arg Ile Trp Ser
1               5

<210> SEQ ID NO 572
<211> LENGTH: 16
<212> TYPE: PRT
<213> ORGANISM: Artificial Sequence
<220> FEATURE:
<223> OTHER INFORMATION: Synthetic or recombinant sequence

<400> SEQUENCE: 572

Ala Lys Phe Cys Pro Thr Phe Asn Lys Ser Met Glu Glu Gln Gly Lys
1               5                   10                  15

<210> SEQ ID NO 573
<211> LENGTH: 49
<212> TYPE: PRT
<213> ORGANISM: Artificial Sequence
<220> FEATURE:
<223> OTHER INFORMATION: Synthetic or recombinant sequence

<400> SEQUENCE: 573

Asp Tyr Arg Arg Leu Pro Pro Gly Pro Ala Asn Phe Phe Cys Ile Phe
```

```
                1               5                  10                  15
Ser Arg Asp Gly Val Ser Pro Cys Tyr Pro Gly Trp Ser Pro Ser Pro
                20                  25                  30

Asp Leu Val Met Ser Pro Leu Arg Ser Pro Lys Val Leu Gly Leu Gln
            35                  40                  45

Ala

<210> SEQ ID NO 574
<211> LENGTH: 72
<212> TYPE: PRT
<213> ORGANISM: Artificial Sequence
<220> FEATURE:
<223> OTHER INFORMATION: Synthetic or recombinant sequence

<400> SEQUENCE: 574

Cys Asp Leu Asn Ser Leu Cys Ile Phe Val Ala Ile Phe His Thr Lys
1               5                  10                  15

Cys Phe Lys Cys Gly Glu Ser Ile Lys His Leu Tyr Ser Gly Leu Trp
                20                  25                  30

Met Val Val Arg Ser Val Trp Ile Met Gln Ala Ser Leu Leu Gly Glu
            35                  40                  45

Pro Glu Glu Val Ala Leu Gly Pro Met Gly Val Val Ala Ala Thr Leu
        50                  55                  60

Glu Val Val Gly Thr Arg Ala Met
65                  70

<210> SEQ ID NO 575
<211> LENGTH: 45
<212> TYPE: PRT
<213> ORGANISM: Artificial Sequence
<220> FEATURE:
<223> OTHER INFORMATION: Synthetic or recombinant sequence

<400> SEQUENCE: 575

Gly Val Ala Gly Ile Met Thr Val Asp Leu Glu Gly Met Asp Met Asp
1               5                  10                  15

Met Asp Val Pro Glu Thr Ile Met Ala Glu Thr Arg Val Val Met Thr
                20                  25                  30

Ala Thr Gln Glu Glu Ile Thr Glu Thr Ile Met Thr Thr
            35                  40                  45

<210> SEQ ID NO 576
<211> LENGTH: 11
<212> TYPE: PRT
<213> ORGANISM: Artificial Sequence
<220> FEATURE:
<223> OTHER INFORMATION: Synthetic or recombinant sequence

<400> SEQUENCE: 576

Gly Leu Phe Val Phe Pro Ile Tyr Cys Leu Cys
1               5                  10

<210> SEQ ID NO 577
<211> LENGTH: 12
<212> TYPE: PRT
<213> ORGANISM: Artificial Sequence
<220> FEATURE:
<223> OTHER INFORMATION: Synthetic or recombinant sequence

<400> SEQUENCE: 577

Glu Val Trp Arg His Leu Leu Gly Arg Pro His Ser
1               5                  10
```

<210> SEQ ID NO 578
<211> LENGTH: 8
<212> TYPE: PRT
<213> ORGANISM: Artificial Sequence
<220> FEATURE:
<223> OTHER INFORMATION: Synthetic or recombinant sequence

<400> SEQUENCE: 578

Gly Ile Phe Glu Leu Phe Ile Leu
1               5

<210> SEQ ID NO 579
<211> LENGTH: 12
<212> TYPE: PRT
<213> ORGANISM: Artificial Sequence
<220> FEATURE:
<223> OTHER INFORMATION: Synthetic or recombinant sequence

<400> SEQUENCE: 579

Ser Pro Cys Pro Ser Ser Pro Pro Ser Gln Pro Trp
1               5                   10

<210> SEQ ID NO 580
<211> LENGTH: 25
<212> TYPE: PRT
<213> ORGANISM: Artificial Sequence
<220> FEATURE:
<223> OTHER INFORMATION: Synthetic or recombinant sequence

<400> SEQUENCE: 580

Val Leu Ser Asp Leu Gly Cys Ala Ala Gly Lys Ser Asp Asp Pro Gln
1               5                   10                  15

Leu Trp Gly His Ser His Ile Thr Gly
            20                  25

<210> SEQ ID NO 581
<211> LENGTH: 13
<212> TYPE: PRT
<213> ORGANISM: Artificial Sequence
<220> FEATURE:
<223> OTHER INFORMATION: Synthetic or recombinant sequence

<400> SEQUENCE: 581

His Gln Ala Leu Gly Ala Val Pro Ser Cys Glu Gly Val
1               5                   10

<210> SEQ ID NO 582
<211> LENGTH: 22
<212> TYPE: PRT
<213> ORGANISM: Artificial Sequence
<220> FEATURE:
<223> OTHER INFORMATION: Synthetic or recombinant sequence

<400> SEQUENCE: 582

Arg Tyr Gly Arg Cys Val His Cys Arg Glu Ile Val Leu Gln Gln Pro
1               5                   10                  15

Ser Gly His Arg Gln Pro
            20

<210> SEQ ID NO 583
<211> LENGTH: 22
<212> TYPE: PRT
<213> ORGANISM: Artificial Sequence
<220> FEATURE:
<223> OTHER INFORMATION: Synthetic or recombinant sequence

<400> SEQUENCE: 583

Asp Arg Lys Arg Gly Cys Cys Pro Thr Ser Ser Ser Leu Pro Ile Ser
1               5                   10                  15

Leu Arg Val Arg Leu Ser
            20

<210> SEQ ID NO 584
<211> LENGTH: 18
<212> TYPE: PRT
<213> ORGANISM: Artificial Sequence
<220> FEATURE:
<223> OTHER INFORMATION: Synthetic or recombinant sequence

<400> SEQUENCE: 584

Met Thr Ser Leu Leu Ser Ser His His Pro Leu Lys Arg Arg Asn Leu
1               5                   10                  15

Glu Pro

<210> SEQ ID NO 585
<211> LENGTH: 41
<212> TYPE: PRT
<213> ORGANISM: Artificial Sequence
<220> FEATURE:
<223> OTHER INFORMATION: Synthetic or recombinant sequence

<400> SEQUENCE: 585

Gly Asp Gln Gln Pro Asp Arg Thr Gln Ala Gly Leu Lys Ser Val Ser
1               5                   10                  15

Gln Val Glu Asp Val Phe Arg Glu Leu Ile Gly Thr Gln Lys Thr Arg
            20                  25                  30

Thr Gly Cys Phe Pro Pro Ser Gly Ser
            35                  40

<210> SEQ ID NO 586
<211> LENGTH: 25
<212> TYPE: PRT
<213> ORGANISM: Artificial Sequence
<220> FEATURE:
<223> OTHER INFORMATION: Synthetic or recombinant sequence

<400> SEQUENCE: 586

Val Gln Met Lys Met Met Lys Ser Ser Ser Asp Pro Leu Asp Ile Lys
1               5                   10                  15

Lys Asp Val Leu Leu Pro Ala Trp Asn
            20                  25

<210> SEQ ID NO 587
<211> LENGTH: 28
<212> TYPE: PRT
<213> ORGANISM: Artificial Sequence
<220> FEATURE:
<223> OTHER INFORMATION: Synthetic or recombinant sequence

<400> SEQUENCE: 587

Gly Phe Ala Ala Ser Trp Leu Phe Lys Lys Pro Arg Pro Ser Glu Cys
1               5                   10                  15

His Thr Val Ile Phe Lys Glu Glu Ser Tyr Met Asn
            20                  25